(12) United States Patent
Anderson et al.

(10) Patent No.: US 9,770,455 B2
(45) Date of Patent: *Sep. 26, 2017

(54) ADMINISTRATION OF AN ANTI-OBESITY COMPOUND TO INDIVIDUALS WITH RENAL IMPAIRMENT

(71) Applicant: Arena Pharmaceuticals, Inc., San Diego, CA (US)

(72) Inventors: Christen M. Anderson, Encinitas, CA (US); William R. Shanahan, Del Mar, CA (US)

(73) Assignee: Arena Pharmaceuticals, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/398,997

(22) Filed: Jan. 5, 2017

(65) Prior Publication Data

US 2017/0216307 A1    Aug. 3, 2017

Related U.S. Application Data

(63) Continuation of application No. 14/671,151, filed on Mar. 27, 2015, now abandoned, which is a continuation of application No. 13/511,639, filed as application No. PCT/US2011/049936 on Aug. 31, 2011, now Pat. No. 8,999,970.

(60) Provisional application No. 61/403,149, filed on Sep. 10, 2010, provisional application No. 61/402,628, filed on Sep. 1, 2010.

(51) Int. Cl.
*A61K 31/55* (2006.01)
*A61K 9/00* (2006.01)

(52) U.S. Cl.
CPC ............ *A61K 31/55* (2013.01); *A61K 9/0053* (2013.01)

(58) Field of Classification Search
CPC ..................................................... A61K 31/55
USPC .................................................... 514/217.01
See application file for complete search history.

(56) References Cited

U.S. PATENT DOCUMENTS

| | | |
|---|---|---|
| 2,900,415 A | 8/1959 | Biel |
| 3,652,543 A | 3/1972 | Hoegerle |
| 3,716,639 A | 2/1973 | Hoegerle |
| 3,795,683 A | 3/1974 | Brossi et al. |
| 4,108,989 A | 8/1978 | Holden |
| 4,111,957 A | 9/1978 | Holden et al. |
| 4,210,729 A | 7/1980 | Hermans et al. |
| 4,210,749 A | 7/1980 | Shetty |
| 4,233,117 A | 11/1980 | Shetty |
| 4,477,378 A | 10/1984 | Gold et al. |
| 4,541,954 A | 9/1985 | Borowski et al. |
| 4,584,293 A | 4/1986 | Reiffen et al. |
| 4,737,495 A | 4/1988 | Bomhard et al. |
| 4,762,845 A | 8/1988 | Chu et al. |
| 4,957,914 A | 9/1990 | Clark et al. |
| 4,988,690 A | 1/1991 | Effland et al. |
| 5,015,639 A | 5/1991 | Berger et al. |
| 5,098,911 A | 3/1992 | Ibrahim |
| 5,178,786 A | 1/1993 | Jahnke et al. |
| 5,247,080 A | 9/1993 | Berger et al. |
| 5,275,915 A | 1/1994 | Kojima et al. |
| 5,362,728 A | 11/1994 | Asberom et al. |
| 5,387,685 A | 2/1995 | Powell et al. |
| 5,397,793 A | 3/1995 | Shaber et al. |
| 5,412,119 A | 5/1995 | Brussee et al. |
| 5,422,355 A | 6/1995 | White et al. |
| 5,677,297 A | 10/1997 | Waldeck et al. |
| 5,691,362 A | 11/1997 | McCormick et al. |

(Continued)

FOREIGN PATENT DOCUMENTS

| | | |
|---|---|---|
| AU | 515 236 | 3/1981 |
| CA | 1090797 | 12/1980 |

(Continued)

OTHER PUBLICATIONS

"Arena Pharmaceuticals Announces Results of its Phase 1 b Safety Study for its Novel Anti-Obesity Compound," Press Release, Nov. 30, 2004, 2 pages.

(Continued)

*Primary Examiner* — Raymond Henley, III

(74) *Attorney, Agent, or Firm* — Fish & Richardson P.C.

(57) ABSTRACT

The present disclosure relates to methods for weight management in an individual in need thereof by determining the level of renal sufficiency of the individual and prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a level of renal sufficiency selected from the group consisting of: no renal impairment, mild renal impairment, and moderate renal impairment. In addition, the disclosure relates to a method for selecting an individual for treatment with (R)-8-chloro-1-methyl-2,3,4,5-tetrahydro-1H-3-benzazepine or a pharmaceutically acceptable salt, solvate or hydrate thereof from a plurality of individuals in need of weight management by determining the level of renal sufficiency of the individual and selecting the individual for treatment with (R)-8-chloro-1-methyl-2,3,4,5-tetrahydro-1H-3-benzazepine or a pharmaceutically acceptable salt, solvate or hydrate thereof if the individual has a level of renal sufficiency selected from the group consisting of: no renal impairment, mild renal impairment, and moderate renal impairment.

6 Claims, 14 Drawing Sheets

(56) References Cited

U.S. PATENT DOCUMENTS

| | | |
|---|---|---|
| 5,750,520 A | 5/1998 | Danilewicz et al. |
| 5,856,503 A | 1/1999 | Aebi et al. |
| 5,861,393 A | 1/1999 | Danilewicz et al. |
| 5,908,830 A | 6/1999 | Smith et al. |
| 5,925,651 A | 7/1999 | Hutchinson |
| 5,939,415 A | 8/1999 | Laufer et al. |
| 5,942,535 A | 8/1999 | Laufer et al. |
| 5,958,543 A | 9/1999 | Teng et al. |
| 5,958,943 A | 9/1999 | Laufer et al. |
| 6,087,346 A | 7/2000 | Glennon et al. |
| 6,218,385 B1 | 4/2001 | Adam et al. |
| 6,900,313 B2 | 5/2005 | Wasserscheid et al. |
| 6,953,787 B2 | 10/2005 | Smith et al. |
| 6,972,295 B2 | 12/2005 | Hagmann et al. |
| 7,105,523 B2 | 9/2006 | Stasch et al. |
| 7,157,445 B2 | 1/2007 | Sanderink et al. |
| 7,157,466 B2 | 1/2007 | McClure et al. |
| 7,173,037 B2 | 2/2007 | Alonso-Alija et al. |
| 7,211,591 B2 | 5/2007 | Tajima et |
| 7,229,991 B2 | 6/2007 | Merla et al. |
| 7,230,024 B2 | 6/2007 | Carpino et al. |
| 7,232,823 B2 | 6/2007 | Carpino et al. |
| 7,514,422 B2 | 4/2009 | Smith et al. |
| 7,608,616 B1 | 10/2009 | Cartt |
| 7,704,993 B2 | 4/2010 | Smith et al. |
| 7,858,319 B2 | 12/2010 | Hetherington et al. |
| 7,977,329 B2 | 7/2011 | Smith et al. |
| 8,153,621 B2 | 4/2012 | Behan et al. |
| 8,168,624 B2 | 5/2012 | Agarwal et al. |
| 8,168,782 B2 | 5/2012 | Weigl et al. |
| 8,207,158 B2 | 6/2012 | Smith et al. |
| 8,273,734 B1 | 9/2012 | Smith et al. |
| 8,299,241 B2 | 10/2012 | Gharbaoui et al. |
| 8,367,657 B2 | 2/2013 | Wolgast et al. |
| 8,999,970 B2 * | 4/2015 | Anderson .............. A61K 31/55 436/98 |
| 2003/0105106 A1 | 6/2003 | Chiang et al. |
| 2003/0225057 A1 | 12/2003 | Smith et al. |
| 2004/0097483 A1 | 5/2004 | Zeng et al. |
| 2004/0101575 A1 | 5/2004 | Hinz |
| 2005/0020573 A1 | 1/2005 | Smith et al. |
| 2007/0060568 A1 | 3/2007 | Smith et al. |
| 2007/0275949 A1 | 11/2007 | Smith et al. |
| 2008/0009478 A1 | 1/2008 | Smith et al. |
| 2008/0045502 A1 | 2/2008 | Wolgast et al. |
| 2008/0255093 A1 | 10/2008 | Tam et al. |
| 2009/0143576 A1 | 6/2009 | Weigl et al. |
| 2010/0004223 A1 | 1/2010 | Agarwal et al. |
| 2010/0173894 A1 | 7/2010 | Brian et al. |
| 2010/0305316 A1 | 12/2010 | Gharbaoui et al. |
| 2011/0015438 A1 | 1/2011 | Carlos et al. |
| 2012/0135982 A1 | 5/2012 | Smith et al. |
| 2012/0142967 A1 | 6/2012 | De Mattei et al. |
| 2012/0252786 A1 | 10/2012 | Behan et al. |
| 2012/0252787 A1 | 10/2012 | Anderson et al. |
| 2012/0252788 A1 | 10/2012 | Smith et al. |
| 2012/0264743 A1 | 10/2012 | Agarwal et al. |
| 2015/0196567 A1 | 7/2015 | Anderson et al. |

FOREIGN PATENT DOCUMENTS

| | | |
|---|---|---|
| CA | 2197789 | 8/1995 |
| CA | 2325741 | 10/1999 |
| CH | 500194 | 12/1970 |
| CN | 102126988 | 7/2011 |
| DE | 1914456 | 6/1971 |
| DE | 3315106 | 11/1983 |
| DE | 3418270 | 11/1985 |
| DE | 1944121 | 10/2003 |
| EP | 0002765 | 7/1979 |
| EP | 07070 | 7/1979 |
| EP | 0027695 | 10/1980 |
| EP | 080779 | 6/1983 |
| EP | 096838 | 12/1983 |
| EP | 0161350 | 11/1985 |
| EP | 0174118 | 3/1986 |
| EP | 0204349 | 12/1986 |
| EP | 0245997 | 11/1987 |
| EP | 0285287 | 10/1988 |
| EP | 0331130 | 9/1989 |
| EP | 0285919 | 10/1994 |
| EP | 0987235 | 3/2000 |
| EP | 1074549 | 2/2001 |
| EP | 1411881 | 4/2004 |
| EP | 1838677 | 9/2009 |
| FR | 2518544 | 6/1983 |
| GB | 1196229 | 6/1970 |
| GB | 1221324 | 2/1971 |
| GB | 1225053 | 3/1971 |
| GB | 1247306 | 9/1971 |
| GB | 1268243 | 3/1972 |
| GB | 1542317 | 3/1979 |
| GB | 2133401 | 7/1984 |
| GP | 1599705 | 10/1981 |
| JP | 62-267250 | 11/1987 |
| JP | 2-502723 | 8/1990 |
| JP | 05-339263 | 12/1993 |
| JP | 6-62574 | 8/1994 |
| JP | 06-298746 | 10/1994 |
| JP | 08-134048 | 5/1996 |
| JP | 09-030960 | 2/1997 |
| JP | 02-987258 | 3/1997 |
| JP | 2000-44533 | 2/2000 |
| JP | 2001-76413 | 3/2001 |
| JP | 2001-89472 | 4/2001 |
| NL | 7807819 | 1/1980 |
| SU | 1238732 | 6/1986 |
| WO | WO 88/07526 | 10/1988 |
| WO | WO 88/07858 | 10/1988 |
| WO | WO 91/19698 | 12/1991 |
| WO | WO 93/00094 | 1/1993 |
| WO | WO 93/03015 | 2/1993 |
| WO | WO 93/16977 | 9/1993 |
| WO | WO 95/13274 | 5/1995 |
| WO | WO 96/04271 | 2/1996 |
| WO | WO 96/05194 | 2/1996 |
| WO | WO 96/33993 | 10/1996 |
| WO | WO 97/24364 | 7/1997 |
| WO | WO 98/06701 | 2/1998 |
| WO | WO 98/40385 | 9/1998 |
| WO | WO 99/24411 | 5/1999 |
| WO | WO 02/40471 | 5/2002 |
| WO | WO 02/48124 | 6/2002 |
| WO | WO 02/074746 | 9/2002 |
| WO | WO 03/000663 | 1/2003 |
| WO | WO 03/027068 | 4/2003 |
| WO | WO 03/057161 | 7/2003 |
| WO | WO 03/062205 | 7/2003 |
| WO | WO 03/062392 | 7/2003 |
| WO | WO 03/086306 | 10/2003 |
| WO | WO 2004/037788 | 5/2004 |
| WO | WO 2005/003096 | 1/2005 |
| WO | WO 2005/016902 | 2/2005 |
| WO | WO 2005/019179 | 3/2005 |
| WO | WO 2005/019180 | 3/2005 |
| WO | WO 2005/042490 | 5/2005 |
| WO | WO 2005/042491 | 5/2005 |
| WO | WO 2005/082859 | 9/2005 |
| WO | WO 2006/006933 | 1/2006 |
| WO | WO 2006/013209 | 2/2006 |
| WO | WO 2006/043710 | 4/2006 |
| WO | WO 2006/069363 | 6/2006 |
| WO | WO 2006/071740 | 7/2006 |
| WO | WO 2007/120517 | 10/2007 |
| WO | WO 2008/070111 | 6/2008 |
| WO | WO 2008/153632 | 12/2008 |
| WO | WO 2008/156707 | 12/2008 |
| WO | WO 2009/080691 | 7/2009 |
| WO | WO 2009/097416 | 8/2009 |
| WO | WO 2009/111004 | 9/2009 |
| WO | WO 2010/148207 | 12/2010 |
| WO | WO 2012/030927 | 3/2012 |

(56) References Cited

FOREIGN PATENT DOCUMENTS

| WO | WO 2012/030938 | 3/2012 |
|----|----------------|--------|
| WO | WO 2012/030951 | 3/2012 |
| WO | WO 2012/030953 | 3/2012 |

OTHER PUBLICATIONS

"Arena Pharmaceuticals' APD356 Selected as Winner of CONNECT's Most Innovative New Product Award in the Biotechnology Research and Development Category," Press Release, Arena Pharmaceuticals, Inc., 3 pages (Dec. 12, 2005).
"Arena Pharmaceuticals Completes Enrollment with 3,182 Patients in Lorcaserin Phase 3 Bloom Trial for Obesity," Press Release, Arena Pharmaceuticals, Inc., 3 pages (Feb. 5, 2007).
"Arena Pharmaceuticals Continues Phase 3 BLOOM Obesity Trial Following Independent Echocardiographic Data Safety Monitoring Board Review," Press Release, Arena Pharmaceuticals, Inc., 3 pages (Sep. 11, 2007).
"Arena Pharmaceuticals Enters into Strategic Agreements for the Manufacture of Pharmaceutical Material, Including Lorcaserin," Press Release, Arena Pharmaceuticals, Inc., 3 pages (Dec. 18, 2007).
"Arena Pharmaceuticals Initiates Clinical Trial of Novel Anti-Obesity Drug," Press Release, Feb. 24, 2004, 1 page.
"Arena Pharmaceuticals Initiates Lorcaserin Phase 3 Obesity Clinical Trial," Press Release, Arena Pharmaceuticals, Inc., 3 pages (Sep. 12, 2006).
"Arena Pharmaceuticals Initiates Phase 1 b Clinical Trial of Novel Anti-Obesity Drug," Press Release, Jul. 26, 2004, 1 page.
"Arena Pharmaceuticals Initiates Phase 2 Efficacy Study for its Novel Anti-Obesity Compound," Press Release, Dec. 22, 2004, 2 pages.
"Arena Pharmaceuticals Initiates Second and Third Pivotal Trials Evaluating Lorcaserin for the Treatment of Obesity," Press Release, Arena Pharmaceuticals, Inc., 4 pages (Dec. 13, 2007).
"Arena Pharmaceuticals' Lorcaserin for Obesity Passes Major Safety Milestone," Press Release, Arena Pharmaceuticals, Inc., 4 pages (Mar. 17, 2008).
"Arena Pharmaceuticals' Lorcaserin Hydrochloride Phase 2b Study Results Demonstrate Significant Weight Loss and Positive Effect on BMI and Waist and Hip Circumference in Obese Patients," Press Release, Arena Pharmaceuticals, Inc., 4 pages (Jun. 12, 2006).
"Arena Pharmaceuticals Provides APD356 Obesity and APD125 Insomnia Clinical Program Updates," Press Release, Arena Pharmaceuticals, Inc., 3 pages (Mar. 29, 2006).
"Arena Pharmaceuticals Reports Successful Phase 1 a Safety and Clinical Pharmacology Trial Results of Novel Anti-Obesity Compound," Press Release, Jul. 14, 2004, 2 pages.
"Arena's APD356 Phase 2a Clinical Trial Data Presented at the 2005 NAASO Annual Meeting," Press Release, Arena Pharmaceuticals, Inc., 3 pages (Oct. 18, 2005).
Bays, "Lorcaserin and Adiposopathy: 5-HT 2c Agonism as a Treatment for 'Sick Fat' and Metabolic Disease," Expert Rev. Cardiovasc. Ther., Nov. 2009, 7: 1429-1445.
Berge et al., Pharmaceutical Salts, Journal of Pharmaceutical Sciences, vol. 66, No. 1, Jan. 1977, 1-19.
Dhurandhar et al., "Initial weight loss as a predictor of response to obesity drugs," International Journal of Obesity, 1999, 23: 1333-1336.
Gould, "Salt selection for basic drugs," International Journal of Pharmaceutics, 1986, 33: 201-217.
"Guidance for Industry, Pharmacokinetics in Patients with Impaired Renal Function—Study Design, Data Analysis, and Impact on Dosing and Labeling", FDA (1998).
Pi-Sunyer et al., "Clinical guidelines on the identification, evaluation, and treatment of overweight and obesity in adults: the evidence report," NIH, Sep. 1998, 6 (Suppl. 2): p. SIS.
"Arena Pharmaceuticals Announces Assessment of Echocardiograms Indicates No Apparent APD356 Effect on Heart Valves or Pulmonary Artery Pressure in Phase 2a Trial," Press Release, Arena Pharmaceuticals, Inc., 3 pages (Aug. 25, 2005).
"Arena Pharmaceuticals Announces Initiation of Phase 2b Clinical Trial of its Novel Anti-Obesity Compound," Press Release, Arena Pharmaceuticals, Inc., 3 pages (Jun. 23, 2005).
"Arena Pharmaceuticals Announces Locaserin Phase 2b Clinical Trial Results Published in Obesity," Press Release, Arena Pharmaceuticals, Inc., 3 pages (Dec. 8, 2008).
"Arena Pharmaceuticals Announces Positive Phase 2 Clinical Trial Results of Novel Anti-Obesity Compound," Press Release, Arena Pharmaceuticals, Inc., 4 pages (May 11, 2005).
"Arena Pharmaceuticals Announces Positive Phase 2b Clinical Trial Results of Novel Anti-Obesity Compound," Press Release, Arena Pharmaceuticals, Inc., 5 pages (Dec. 13, 2005).
"FDA approves Belviq to treat some overweight or obese adults," Home Healthcare Nurse vol. 30, No. 8, Jan. 1, 2012 (Jan. 1, 2012), pp. 443-444.
Abdelghany and Pauli, "Lorcaserin: A novel, selective 5-HT2C-receptor agonist for the treatment of obesity.", Formulary Journal (Jun. 1, 2010).
Anderson et al., "Dose Selection and Design of Phase 3 Clinical Trials: Efficacy and Safety of Lorcaserin for Weight Management," presented at the Obesity Society, 2008.
Anderson et al., "Lorcaserin, a Selective 5-HT2c Agonist, Is Efficacious for Weight Loss across Patient Subgroups", Diabetes, vol. 59, No. Suppl. 1, Jun. 1, 2010 (Jun. 1, 2010 ), p. A482.
Anderson, Pharmacokinetic Properties of Lorcaserin in Subjects with Renal Impairment. Jul. 27, 2009. www.clinicaltrials.gov/ct2/show/NCT00828438?term=lorcaserin&rank=8.
Arena Pharmaceuticals Research & Development Day, Powerpoint presentations from Meeting, 141 pages, Dec. 15, 2008.
Arena Pharmaceuticals Research & Development Day, Powerpoint presentations from Meeting, 182 pages, Nov. 9, 2006.
Arena Pharmaceuticals Research & Development Day, Transcript of Meeting, 36 pages, Dec. 15, 2008.
Arena Pharmaceuticals Research & Development Day, Transcript of Meeting, 36 pages, Nov. 9, 2006.
Bai et al., "The Use of Lorcaserin in the Management of Obesity: A Critical Appraisal," Drug Design, Development & Therapy, 2011, 1-7.
Barnes, Pharmacological Strategies for Relapse Prevention in Schizophrenia, Psychiatry, 3(10):37-40 (2004).
Barnett, "Review on Dopamine Receptors," Drugs of the Future, 1986, 11(1): 49-56.
'ClinicalTrials.gov' [Online]. "BLOOM: Behavioral Modification and Lorcaserin for Overweight and Obesity Management," Oct. 2006, [retrieved on Aug. 29, 2016]. Retrieved from Internet: URL<https://clinicaltrials.gov/ct2/show/study/NCT00395135>, 3 pages.
BELVIQ Prescribing Information Jun. 2012.
Bickerdike, "5-HT2C Receptor Agonists as Potential Drugs for the Treatment of Obesity," Current Topics in Medicinal Chemistry, 2003, 3:885-897.
Binetti et al., "Behavior Disorders in Alzheimer Disease: A Transcultural Perspective.," Arch Neurol., 1998, 55:539-544.
Bjenning et al., "Chronic Oral Administration of APD356 Significantly Reduces Body Weight and Fat Mass in Obesity-Prone (010) Male and Female Rats," presented at the European Conference on Obesity, Prague, 2004.
Bjenning et al., "Increased Sensitivity in Female Obesity-Prone Rats to the Weight-loss Effect o APO 356 A Selective 5-HT2c Agonist," presented at the Annual North American Association for the Study of Obesity, Las Vegas,NV, 2004.
Brittain, Polymorphism in Pharmaceutical Solids, "Generation of Polymorphs, Hydrates, Solvates, and Amorphous Solids," 1999, Chapter 5, 183-219.
Brooks et al., "Obstructive Sleep Apnea in Obese Noninsulin-Dependent Diabetic Patients: Effect of Continuous Positive Airway Pressure Treatment on Insulin Responsiveness," Journal of Clinical Endocrinology and Metabolism, 1994, 79: 1681-1685.
Callahan et al., "Fluoxetine Increases the Anorectic and Long-Term Dopamine-Depleting Effects of Phentermine," Synapse, 2000, 38(4):471-6.

(56) References Cited

OTHER PUBLICATIONS

Cerny et al., "Kinetics of N-Carbamoyl Glucuronide Formation," presented at N. American ISSX, 2008.
Cerny et al., "Formation of N-Carbamoyl Glucuronide Metabolite of Lorcaserin." Drug Metab Rev 2008, 40(Suppl. 3): Abst 92.
Chahal et al, IDdb Meeting Report, May 17-18, 2000.
Chang et al., "Dopamine Receptor Binding Properties of Some 2,3,4,5-Tetrahydro-1 H-3-Benzazepine-7-ols With Non-Aromatic Substituents In The 5-Position", Bioorganic & Med. Chem. Letters, 1992, 2(5):399-402.
Chen et al., "Metabolism and Disposition of Lorcaserin, A Novel Selective Serotonin 5-HT2C Receptor Agonist, in Rats, Mice, Monkeys and Humans," presented at the European ISSX, 2008.
Chen et al., "Metabolism, Pharmacokinetics, & Excretion of Lorcaserin, A Novel Selective Serotonin 5-HT2C Receptor Agonist, in Healthy Male Volunteers," presented at N. American ISSX, 2008.
Chen et al., "Metabolism and Disposition of Lorcaserin, A Novel Selective Serotonin 5-HT2C Receptor Agonist, in Rats, Mice, Monkeys and Humans." Drug Metab Rev, 2008, 40(Suppl. 1 ): Abst 185.
Chen et al., "Metabolism, Pharmacokinetics, and Excretion of Lorcaserin, A Novel Selective Serotonin 5-HT2C Receptor Agonist, In Healthy Male Volunteers." Drug Metab Rev, 2008, 40(Suppl. 3): Abst 281.
Cheng, "Fen/Phen and Valvular Heart Disease: The Final Link Has Now Been Established," Circulation, 2000, 102:e180.
Clinical Trial NCT00768612. "Study Evaluating Safety and Tolerability of Vabicaserin in Patients With Sudden Worsening of Schizophrenia Study," (2008).
Cole et al., "Establishing a standard definition for child overweight and obesity worldwide: international survey," BMJ, May 2000, 1-6.
Connolly et al., "Selections from Current Literature: Pharmacological Treatment of Obesity," Family Practice, 1998, 15(1):88-93.
Deady, et al., "Synthesis of some tetrahydro-2-and 3-benzazepines, and of hexahydro-3-benzazocine," Journal of the Chemical Society, Perkins Transactions L 1973, pp. 782-783.
Deurenberg et al., "Body mass index and percent body fat: a meta analysis among different ethnic groups," International Journal of Obesity, 1998, 22: 1164-1171.
Dhonnchadha et al., "Anxiolytic-Like Effects Of "5-HT2 Ligands on Three Mouse Models of Anxiety," Behav. Brain Res., 2003, 140:203-214.
Di Chiara et al., "Reward System and Addiction: What Dopamine Does and Doesn't Do", Current Opinion in Pharmacology, 2007, 7:69-76.
Di Chiara G., "Nucleus accumbens shell and core dopamine: differential role in behavior and addiction." (2002) Behavioural Brain Research, 137: 75-414.
Di Giovanni et al., "Serotonin/dopamine interaction—Focus on 5-HT2c receptor, a new target of psychotropic drugs," Indian Journal of Experimental Biology, 2002, 40:1344-1352.
Di Matteo et al., "Role of 5-HT2c Receptors in the Control of Central Dopamine Function," Trends in Pharmacological Sciences, 22(5):229-232 (2001).
Diagnostic and Statistical Manual of Mental Disorders, 4th edition, Text Revision, Washington, DC, American Psychiatric Association, 2000.
Endocrinologic and Metabolic Drugs Advisory Committee Meeting United States Food & Drug Administration Center for Drug Evaluation and Research, May 2012.
Faull and Lee, "Prescribing in renal disease," Australian Prescriber, 2007, 30:17-20.
FDA "Guidance for Industry: Pharmacokinetics in Patients with Impaired Renal Function-Study Design, Data Analysis, and Impact on Dosing and Labeling," May 1998, 19 pages.
FDA Briefing Document: Lorcaserin Hydrochloride Tablets, 10 mg, United States Food & Drug Administration Endocrinologic and Metabolic Drugs Advisory Committee Meeting, May 2012.
FDA "Guidance for Industry," May 1992, 4 pages.
Fidler et al., "A One-Year Randomized Trial of Lorcaserin for Weight Loss in Obese and Overweight Adults: The BLOSSOM Trial", Journal of Clinical Endocrinology & Metabolism, Oct. 2011, 96(10): 3067-3077.
Fidler et al., "Changes in Glucose Tolerance and Cardiovascular Risk Factors after 52 Weeks of Treatment with Lorcaserin", Diabetes, Jun. 2010, 59(1):A484-A485.
Flannery-Schroeder, "Reducing Anxiety to Prevent Depression," Am. J. Prev. Med. 31 (6S1):S136-S142 (2006).
Frankel et al., "Brain Serotonin Transporter distribution in Subjects With Impulsive Aggressivity: A Positron Emission Study With [11 C]McN 5652." Am. J. Psychiatry, 2005, 162:915-923.
Fuchs et al., "Total Synthesis of (±)-Lennoxamine and (+)-Aphanorphine by Intramolecular Electrophilic Aromatic Substitution Reactions of 2-Amidoacroleins", Organic Letters, 2001, 3(24):3923-5.
Gallant et al., "U-22,394A: a controlled evaluation in chronic schizophrenic patients," Current Therapy Research, 1967, 9(11):579-81.
Gamber et al., "Pharmacokinetics of a series of 6-chloro-2, 3, 4, 5-tetrahydro-3-substituted—1 H-3-benzazepines in rats," Drug Metab. Disposition, 1988, 16:367-372.
Gardent et al., "Sur quelques de l'amino-2-bromo-4 1 H benzazepine-3 et de ses derives," Bull Soc. Chim. France, 1968, 2:600-605.
Garrison, "Defining Obesity: An Adventure in Cardiovascular Disease Epidemiology," J. Nutritional Biochem., 1998, 9(9):493-500.
Gault et al., "Predicting Glomerular Function from Adjusted Serum Creatinine," Nephron, 1992, 62: 249-256.
Gerace et al., "Predictors of Weight Increases over 7 Years in Fire Fighters and Paramedics," Preventive Medicine, 1996, 25:593-600.
Gobert et al., "Serotonin2c Receptors Tonically Suppress the Activity of Mesocortical Dopaminergic and Adrenergic, But Not Serotonergic, Pathways: A Combined Dialysis and Electrophysiological Analysis in the Rat," Synapse, 2000, 36:205-221.
Goldenberg, "Pharmaceutical approval update", P & T Pharmacy and Therapeutics Journal, Sep. 2012, 37(9): 499-502.
Griesser, "Polymorphism in the Pharmaceutical Industry," ed. Rolf Hilfiker, Wiley,VCH Verlag GmbH & Co.: pp. 211-233 (2006).
Grottick et al.,"Lorcaserin: A Selective 5-HT2c Agonist for Weight Management," presented at the Annual North American Association for the Study of Obesity, 2007.
FDA, "Guidance for Industry: Pharmacokinetics in Patients with Impaired Renal Function-Study Design, Data Analysis, and Impact on Dosing and Labeling," Draft Guidance, Mar. 2010, 21 pages.
Guillory, "Polymorphism in Pharmaceutical Solids," ed. Harry G. Brittain, Marcel Dekker, Inc., vol. 95: pp. 202-209 (1999).
Halford et al., "Serotonergic Drugs: Effects on Appetite Expression and Use for the Treatment of Obesity," Drugs, 2007, 67(1):27-55.
Halford, "Obesity Drugs in Clinical Development," Current Opinion in Investigational Drugs, 2006, 7(4):312-318.
Hassine-Coniac, et al., "Preparation et proprietes d'aldehydes dans la serie de la benzazepine-3", Bulletin de La Societe Chimique de France, 11 :3985-92 (1971) French Lang Only.
Hazebroucq "Acces a des 1-H, tetrahydro-2, 3, 4, 5 benzazepines-3 one-1 eta des hexahydro imidazo isoquinoleines," Ann. Chim. (1966) pp. 221-254.
Heisler et al., "Activation of Central Melanocortin Pathways by Fenfluramine," Science, 2002, 297:609- 611.
Hester et al., "Azepinoindoles. I. Hexahyclroazepino[4,5-b)indoles," J. Med. Chem, 1968, 11 (1):101-106.
Higgins et al, "Serotonin and drug reward: focus on 5-HT2c receptors," European Journal of Pharmacology, 2003, 480:151-162.
Hill and Peters, "Environmental Contributions to the Obesity Epidemic," Science, May 29, 1998, 280: 1371-1374.
Hitzig, "Combined Serotonin and Dopamine Indirect Agonistscorrectalcohol Craving and Alcohol-Associated Neuroses," Journal of Substance Abuse Treatment, 1994, 11(5):489-90.
Im et al., "Positive Allosteric Modulator of the Human 5-HT2C Receptor," MolecularPharmacology, 64: 78-84 (2003).
International search report for international application No. PCT/US2003/11076 dated Oct. 16, 2003.

(56) References Cited

OTHER PUBLICATIONS

International search report for international application No. PCT/US2011/049936 dated Nov. 10, 2011.
Isaac, "The 5-HT2C Receptor As A Potential Therapeutic Target for the Design of Antiobesity and Antiepileptic Drugs," Drugs of the Future, 2001, 26(4), 383-393.
Jandacek, "APD-356 (Arena)", Current Opinion in Investigational Drugs, 2005, 6(10): 1051-1056.
Jenck et al., "Antiaversive effects of 5-HT2c receptor agonists and fluoxetine in a model of panic-like anxiety in rats," European Neuropsychopharmacology, 1998, 8:161.
Jensen et al., "Potential Role of New Therapies in Modifying Cardiovascular Risk in Overweight Patients with Metabolic Risk Facts", Obesity 14, 2006, (Suppl. 3):143S-149S.
Kaplan et al., "Preventing Childhood Obesity: Health in the Balance, Executive Summary", http://www.nap.edu/catalog/11015.html, 2005, 41 pages.
Karasu et al., 2000, Practice Guideline for the Treatment of Patients with MajorDepressive Disorder.
Klein, "Outcome Success in Obesity," Obesity Res., 2001, 9(suppl. 4):354S-358S.
Lacivita et al., "Selective Agents for Serotonin2C (5-HTC2C) Receptor," Current Topics in Medicinal Chemistry, 2006, 6: 1927-1970.
Ladd et al., "Synthesis and Dopaminergic Binding of 2-Aryldopamine Analogues: Phenethylamines, 3-Benzazepines, and 9-(Aminomethyl)flourenes", J. Med. Chem., 1986, 29(10):1904-1912.
Lam, Levitt AJ, 1999, (eds) Canadian Consensus Guidelines for the Treatment of Seasonal Affective Disorder, Clinical & Academic Publishing, Vancouver, BC, Canada.
Lanteri et al., "Drugs of abuse specifically sensitive noradrenergic and serotonergic neurons via a non-dopaminergic mechanism," Neuropsychopharmacology, 2008, 33(7):1724-1734.
Lennon et al., "Azabenzocycloheptenones. Part XVIII. Amines and amino-ketones of the tetrahydro-3-benzazepine-1-one series," J. Chem. Soc. Perkin Transacts., 1975, 7:622-626.
Loke et al., "Appetite Suppressants and Valvular Heart Disease—A Systematic Review," BMC Clinical Pharmacology, 2002, 2(6):1-10.
Lorcaserin for Weight Management, United States Food & Drug Administration Center for Drug Evaluation & Research, May 2012.
Macdonald, et al., "Design and Synthesis of trans-3-(2-(4-((3-(3-(5-methyl-1,2,4-oxad iazolyl) )- phenyl )carboxamido )cyclohexyl )ethyl)-7 -methylsu lfonyl-2,3,4,5-tetrahyd ro-1 H—3-benzazepine (SB-414796): A Potent and Selective Dopamine D3 Receptor Antagonist", J. Med. Chem., 2003, 46(23):4952-64.
Martin et al.,"5HT2C Receptor Agonists Pharmacological Characteristics and Therapeutic Potential," J. Pharmacol. Exp. Therap., 1998, 286(2):913-924.
Menzahgi et al., "APD356, A Selective 5-HT2c Receptor Agonist As a Potential Novel Treatment for Obesity," presented at the 33rd Annual Society of Neuroscience Meeting New Orleans, LA, 2003.
Millan et al., "5HT2C Receptors Mediate Penile Erections in Rats: Actions of Novel and Selective Agonists and Antagonists." Eur. J. Pharmacol., 1997, 325:9-12.
Millan et al., "Serotonin (5-HT)2C receptors tonically inhibit dopamine (DA) and noradrenaline (NA), but not 5-HT, release in the frontal cortex in vivo," Neuropharmalogy, 1998, 37(7):953-955.
Moline et al., "Postpartum Depression: A Guide for Patients and Families," Expert Consensus Guidelines Series—Treatment of Depression in Woman, Mar. 2001: 112-113.
Morgan et al, "Pharmacokinetic Properties, Metabolism and Tolerability of Lorcaserin in Healthy Volunteers," Oct. 3-7, 2008, Annual Meeting of the Obesity Society, 846.
Morris et al., "Theoretical approaches to physical transformations of active pharmaceutical ingredients during manufacturing processes," Advanced Drug Delivery Reviews, 2001, 48: 91-114.
Morrow, "Insurers Find Small Gains in Weight Control With Belviq", Managed Care, Aug. 2012, 21(8): 45-46.

Muller et al., "Intracellular 5-HT2c-receptor dephosphorylation: a new target for treating drug addiction," Trends in Pharmacological Sciences, 2006, 27(9):455-58.
Nagase et al., "An anhydrous polymorphic form of trehalose," Carbohydrate Research, 2002, 337(2): 167-173 (Abstract).
National Institute on Drug Abuse, Proceedings of the 41st Annual Scientific Meeting, 1979, 356-401.
Navarro-Vazquez et al., "A study of aryl radical cyclization in enaminone esters", J. Org. Chem., 2002, 67:3213-20.
Niendam et al., "Neurocognitive Performance and Functional Disability in the Psychosis Prodrome," Schizophrenia Research, 2006, 84:100-111.
O'Neil et al., "Early Weight Loss with Naltrexone SR/Bupropion SR Combination Therapy for Obesity Predicts Long-term Weight Loss," Obesity, Nov. 2009, 17(2): 5109-5110.
O'Neil et al., "Randomized Placebo-Controlled Clinical Trial of Lorcaserin for Weight Loss in Type 2 Diabetes Mellitus: The BLOOM-OM Study", Obesity, Jul. 2012, 20(7): 1426-1436.
Orito et al., Hokkaido Daigaku Kogakubu Kenkyu Hokoku, 1979, 96: 41-44.
Orito et al., "Benzolactams-1: Alkylation of 1,2,4,5-tetrahydro-3-methyl-3H-3-benzazepin-2-one with sodium hydride and alkyl halide," Tetrahedron, 1980, 36:1017-1021, Pergamon Press Ltd.
Orito et al., "Synthetic Studies of Heterocyclic Compounds I: Alkylation and Acylation of 1, 2, 4, 5-tetrahydro-3-methyl-3H-3-benzepin-2-one", Bulletin of the Faculty of Engineering, Hokkaido University (Hokkaido Kogakubu Kenkyu Hokuko), 1979, 96(54):41-4.
Onto et al., "Total Synthesis of Pseudo Type of Proto pine Alkaloids", Heterocycles, 1980, 14(1):11-4.
Orlistat Prescribing Information Jan. 2012.
Pauvert et al., "Silver Nitrate-Promoted Ring Enlargement of 1-Tribromomethyl-1,2-dihydro- and 1-Tribromomethyl-1,2,3,4-tetrahydro-isoquinoline Derivatives: Application to the Synthesis of the Anti-Antianginal Zatebradine," Tetrahedron Letters, 2003, 44:4203-6, Pergamon Press Ltd.
Pawan et al., "Preliminary study on the effects of fenfluramine derivative, 'S992' in man," British Journal of Pharmacology, 41 (2): 416P-417P (1971) (CAPLUS abstract).
PCT/US2011/049936 Int'l Search Report-Written Opinion, (Mar. 30, 2012).
PCT/US2011/049936, Article 34 Demand and amended claims (Feb. 13, 2012).
Pecherer et al., "The Synthesis of Some 7- and 7,8-substituted 2,3,4,5-tetrahydro-1 H-3-benzazepines," J. Heterocyclic Chemistry, 1971, 8(5):779-783.
Perrone et al., "Serum Creatinine as an Index of Renal Function: New Insights into Old Concepts," Clinical Chemistry, 1992, 38(10): 1933-1953.
Perry et al., "Prospective Study of Risk Factors for Development of Non-Insulin Dependent Diabetes in Middle Aged British Men," BMJ, 1995, 310:560-4.
Pfeiffer et al., "Dopaminergic Activity of Substituted 6-Chloro-1-phenyl-2,3,4,5-tetrahydro-1 H-3-benzazepines," J. Med. Chem., 1982, 25(4):352-8.
'ClinicalTrials.gov' [Online]. "Pharmacokinetc Properties of Lorcaserin in Subjects With Renal Impairment," Jan. 2009, [retrieved on Aug. 29, 2016]. Retrieved from Internet: URL<https://clinicaltrials.gov/ct2/show/study/NCT00828438>, 3 pages.
Piesla et al, Schizophrenia Research, 2001, 49:95.
Pi-Sunyer, "Symposium on 'Body weight regulation and obesity: metabolic and clinical aspects' 1$^{st}$ Plenary Session: 'Obesity'," Proceedings of the Nutrition Society, 2000, 59: 505-509.
Porras et al., "5-HT2a and 5-HT2c/2b Receptor Subtypes Modulate Dopamine ReleaseInduced in Vivo by Amphetamine and Morphine in Both the Rat Nucleus Accumbensand Striatum," Neuropsychopharmacology, 2002, 26: 311-324.
Prous Science Integrity entry 156186, 2007.
Prous Science Integrity entry 354056, 2007.
Faull et al., "Prescribing in renal disease," Australian Prescriber, Feb. 2007, 30(1): 17-20.
Remington's Pharmaceutical Sciences, 20th ed., Lippincott Williams & Wilkins, Philadelphia, PA, 2000, 710-712.

(56) References Cited

OTHER PUBLICATIONS

Rigalleau et al., "Estimation of Glomerular Filtration Rate in Diabetic Subjects," Diabetes Care, Apr. 2005, 28(4): 838-843.
Rosenzweig-Lipson et al., "Vabicaserin: Effects of A Novel 5HT2C Agaonist on Medial Prefrontal Cortex Neurotransmission, Cognition and Sensorimotor Gating," 29th ECNP Congress, Vienna, Austria, 2007.
Roth et al., "Anorectic Efficacy of the Fenfluramine/Phentermine Combination in Rats: Additivity or Synergy?" Eur. J. Pharmacol., 1999, 373(2-3):127-34.
Rothman et al., "Evidence of Possible Involvement of 5-HT2B Receptors in the Cardiac Valvulopathy Associated with Fenfluramine and Other Serotonergic Medications," Circulation, 2000, 2836-41.
Rothman, "Treatment of Alcohol and Cocaine Addiction by the Combination of Pemoline and Fenfluramine: A Preliminary Case Series," Journal of Substance Abuse Treatment, 1995, 12(6):449-53.
Rowland et al., "Acute Anorectic Effect of Single and Combined Drugs in Mice Using a Non deprivation Protocol," Psychopharmacology (Berl), 2001, 157(2):193-6.
Rowland et al., "Anorectic Effect of Dehydroepiandrosterone Combined with Dexfenfluramine or Thionisoxetine," Eur. J. Pharmacol., 2001, 419(1):61-4.
Rowland et al., "Comparison of Either Norepinephrine-uptake Inhibitors or Phentermine Combined with Serotonergic Agents on Food Intake in Rats," Psychopharmacology (Berl), 2000, 149(1): 77-83.
Rowland et al., "Effects of the Cannabinoid Receptor Antagonist SR 141716, Alone and in Combination with Dexfenfluramine or Naloxone, on Food Intake in Rats," Psychopharmacology (Berl), 2001, 159(1):111-6.
Sadeque et al., "Formation Kinetics of Lorcaserin Sulfamate," presented at N. American ISSX, 2008.
Sadeque et al., "Formation Kinetics of Lorcaserin Sulfamate." Drug Metab Rev, 2008, 40(Suppl. 3): Abst 95.
Schaffner et al., "Preventing Severe Mental Illnesses—New Prospects and Ethical Challenges," Schizophrenia Research, 2001, 51 :3-15.
Schlademan et al., "Synthesis of oxo- and 1-hydroxy-azobenzocycloalkanes," J. Chem. Soc. Perkin Transacts., 1972, 2:213-215.
Sibutramine Prescribing Information, Aug. 2012.
Silverstone, "Appetite Suppressants: a Review." Drugs. 43:6, 1992, Abstract.
Smith et al., "APD-356, An Orally-Active Selective 5HT2c Agonist, Reduces Body Weight in Obese Adult Men and Women," Diabetes 55 [Supp/1 ]:80, 2006.
Smith et al., "Discovery and Sar of New Benzazepines as Potent and Selective 5HT2c Receptor Agonists for the Treatment of Obesity," Bioorganic & Medicinal Chemistry Letters, 2005, 15(5): 1467-1470.
Smith et al., "Effect of APD356, a Selective 5-HT2c Agonist, on Weight Loss in a 4 Week Study of Healthy Obese Patients," presented at the Annual North American Association for the Study of Obesity, 2005.
Smith et al., "Lorcaserin (APD356), a Selective 5-HT2c Agonist, Safely Induces Weight-Loss in a 12 Week Study of Healthy Obese Patients," presented at American Diabetes Association, 2006.
Smith et al., "Lorcaserin (APD356), a Selective 5-HT$_{2C}$ Agonist, Reduces Body Weight in Obese Men and Women," Obesity Journal, Mar. 2009, 17(3): 494-503.
Smith et al., "Multicenter, Placebo-Controlled Trial of Lorcaserin for Weight Management.", New England Journal of Medicine, Jul. 2010, 36(3): 245-256.
Smith, "5-HT2C Receptor Agonists for the Treatment of Obesity," Presentation, Arena Pharmaceuticals, Inc., Jul. 28, 2010, 30 pages.
Smith, "Discovery of Lorcaserin (APD356): A Selective 5HT2C Agonist for the Treatment of Obesity," Presentation, Arena Pharmaceuticals, Inc., 2006.
Smith et al, Discovery and structure—activity relationship of (1 R)-8-chloro-2,3,4,5-tetrahydro-1-methyl-1 H-3-benzazepine (lorcaserin), in a selective serotonin 5-HT2c receptor agonist for the treatment of obesity, retreived from the internet on Dec. 21, 2007 <URL:http:pubs.acs.orq/joumals/imcmar/index.html>.
Smith et al., "Discovery and Structure—Activity Relationship of (1 R)-8-Chloro-2,3,4,5-tetrahydro-1-methyl-1 H-3-benzazepine (Lorcaserin), a Selective Serotonin 5-HT2c Receptor Agonist for the Treatment of Obesity," J. Med. Chem., 2008, 51 :305-313.
Sussman et al., "Effects of Nefazodone on Body Weight: A Pooled Analysis of Selective Serotonin Reuptake Inhibitor- and Imipramine-Controlled Trails," J. Clin. Psychiatry, 2001, 62:4:256-60.
Tecott et al., "Eating Disorder and Epilepsy in Mice Lacking 5-HT2C Serotonin Receptors." Nature, 1996, 374:542-546.
Tietze et al., "Efficient Synthesis of 2,3,4,5-tetrahydro-1 H-3-benzazepines by intermolecular heck Reaction," Institut fur Organische Chemie der Universtat Gottingen, Tammannstrasse 2, D-3400 Gottingen, Germany, received Jan. 29, 1993.
Tohda et al., "Molecular Pathopharmacology of 5-HT2C Receptors and the RNA Editing in The Brain." J. Pharma. Science, 2006, 100: 427-432.
Tsuang et al., Towards the Prevention of Schizophrenia, 8245 Biol. Psychiatry, 2000, 48:349-356.
Usmani et al., "Identification of Human Liver Cytochrome P450 isoforms Involved in the Metabolism of Lorcaserin," presented at N. American ISSX, 2008.
Usmani et al., "Identification of Human Liver Cytochrome P450 Isoforms Involved in The Metabolism of Lorcaserin," Drug Metab Rev, 2008, 40(Suppl. 3): Abst 273.
Van Oekelen et al., "5-HT2A and 5-HT2C receptors and their atypical regulation properties," Life Sciences, 2003, 72:2429-2449.
Veyrat-Follet et al., "The pharmacokinetics of idraparinux, a long-acting indirect factor Xa inhibitor: population pharmacokinetic analysis from Phase III clinical trials," Journal of Thrombosis and Haemostasis, 2009, 7: 559-565.
Vink et al., "Risk Factors for Anxiety and Depression in the Elderly: A Review", J. Affect. Disord., 2007, doi: 10.1016/j.jad.2007.06.005, 16 pages.
Wang et al. "The use of lorcaserin in the management of obesity: a critical appraisal." Drug Design, Devel. & Therapy, Dec. 2010.
Wang et al., "Lorcaserin Hydrochloride", Drugs of the Future, Jan. 2007, 32(9): 766.
Wang et al., "The Use of Lorcaserin in the Management of Obesity: A Critical Appraisal", Drug Design, Development and Therapy, Dec. 2010, p. 1.
Wang et al. "Lorcaserin hydrochloride." Drugs of the Future vol., Jan. 2007, 32:9 p. 766.
Webb, "APD356, A Potential New Treatment for Obesity," Presentation, Arena Pharmaceuticals, Inc., Aug. 11, 2005, 43 pages.
Wellman et al., "Synergistic Interactions Between Fenfluramine and Phentermine," Int. J. Obes., 1999, 23(7):723-32.
Williams, Chemistry Demystified, 2003, 123.
Winkler, "Obesity and Hemostasis" Archives of Gynecology & Obst., 1997, 261 (1 ):25-29.
Wise, "Addiction becomes a brain disease," Neuron, 2000, 26: 27-33.
Wisner et al., "Clinical practice. Postpartum depression," N. Engl. J. Med., 2002, 34 7(3): 194-199.
Woods et al., "Annual Report: Evaluation of New Compounds for Opioid Activity," National Institute on Drug Abuse, Proceedings of the 41st Annual Scientific Meeting, 1979, 356-401.
Xu et al., "In Vivo Metabolism of Lorcaserin in Preclinical Species," presented at N. American ISSX, 2008.
Xu et al., "In Vivo Metabolism of Lorcaserin, A Novel Selective Serotonin 5-HT2C Receptor Agonist, In Preclinical Species." Drug Metab Rev, 2008, 40(Suppl. 3): Abst 310.
Yoshinaga et al., "Prevention of Mildly Overweight Children from Development of More Overweight Condition," Prevention Medicine, 2004, 38:172-174.
Detailed Factual and Legal Basis for Paragraph IV Certification regarding U.S. Pat. No. 6,953,787; 7,514,422; 7,977,329; 8,207,158; 8,273,734; 8,367,657; 8,946,207; 8,546,379; 8,575,149;

(56) References Cited

OTHER PUBLICATIONS 8,168,624; 8,697,686; 8,980,881; 8,999,970; and 9,169,213, Included in Generic Pharmaceutical Company's Notice Letter dated Aug. 19, 2016, 233 pages [redacted].

Detailed Factual and Legal Basis for Paragraph IV Certification Regarding U.S. Pat. No. 8,168,624; 8,999,970; and 9,169,213, Included in Generic Pharmaceutical Company's Notice Letter dated Aug. 24, 2016, 65 pages [redacted].

Detailed Factual and Legal Basis for Paragraph IV Certification Regarding U.S. Pat. No. 8,168,624; 8,697,686; 8,980,881; 8,999,970; and 9,169,213, Included in Generic Pharmaceutical Company's Notice Letter dated Sep. 1, 2016, 90 pages [redacted].

Detailed Factual and Legal Basis for Paragraph IV Certification Regarding U.S. Pat. No. 8,168,624; 8,697,686; 9,980,881; 8,999,970; and 9,169,213, Included in Generic Pharmaceutical Company's Notice Letter dated Sep. 7, 2016, 87 pages [redacted].

Detailed Factual and Legal Basis for Paragraph IV Certification Regarding U.S. Pat. No. 6,953,787; 7,514,422; 7,977,329; 8,168,624; 8,207,158; 8,273,734; 8,367,657; 8,546,379; 8,575,149; 8,697,686; 8,946,207; 8,980,881; 8,999,970; and 9,169,213, Included in Generic Pharmaceutical Company's Notice Letter dated Feb. 21, 2017, 103 pages [redacted].

\* cited by examiner

Renal Clearance of Lorcaserin as a Function of Creatinine Clearance

Calculation using Ideal Body Weight

| Parameter | |
|---|---|
| N | 32 |
| Spearman r | -0.3730 |
| 95% confidence interval | -0.6450 to 0.01711 |
| P value (two-tailed) | 0.0355 |

Calculation using Actual Body Weight

| Parameter | |
|---|---|
| N | 32 |
| Spearman r | -0.2649 |
| 95% confidence interval | -0.5691 to 0.1031 |
| P value (two-tailed) | 0.1429 |

ADMINISTRATION OF AN ANTI-OBESITY COMPOUND TO INDIVIDUALS WITH RENAL IMPAIRMENT

CROSS-REFERENCE TO RELATED APPLICATIONS

This application is a continuation of U.S. patent application Ser. No. 14/671,151 filed Mar. 27, 2015, now abandoned, which is a continuation of U.S. patent application Ser. No. 13/511,639 filed May 23, 2012, now U.S. Pat. No. 8,999,970, which is a 35 USC 371 of International Application No. PCT/US2011/049936 filed Aug. 31, 2011, and claims benefit of U.S. Provisional Application No. 61/403,149 filed Sep. 10, 2010 and 61/402,628 filed Sep. 1, 2010.

Provided herein are methods useful in the prophylaxis or treatment of obesity in different populations of individuals, including those with renal impairment. In the methods provided herein, lorcaserin is prescribed or administered to an individual in need of treatment if they do not have severe renal impairment or end stage renal disease (ESRD).

CONCURRENTLY FILED APPLICATIONS RELATED TO (R)-8-CHLORO-1-METHYL-2,3,4,5-TETRAHYDRO-1H-3-BENZAZEPINE

The following United States provisional applications are related to (R)-8-chloro-1-methyl-2,3,4,5-tetrahydro-1H-3-benzazepine: 61/402,578; 61/403,143; 61/402,580; 61/402,628; 61/403,149; 61/402,589; 61/402,611; 61/402,565; 61/403,185; each of which is incorporated herein by reference in its entirety.

The following applications are related to (R)-8-chloro-1-methyl-2,3,4,5-tetrahydro-1H-3-benzazepine and have the same filing date as the subject application: a PCT application which claims priority to U.S. provisional applications 61/402,578 and 61/403,1439; a PCT application which claims priority to U.S. provisional application 61/402,580; a PCT application which claims priority to U.S. provisional application 61/402,589; a PCT application which claims priority to U.S. provisional application 61/402,611; and a PCT application which claims priority to U.S. provisional applications 61/402,565 and 61/403,185; each of which is incorporated herein by reference in its entirety.

BACKGROUND

Obesity is a life-threatening disorder in which there is an increased risk of morbidity and mortality arising from concomitant diseases such as type II diabetes, hypertension, stroke, cancer and gallbladder disease.

Obesity is now a major healthcare issue in the Western World and increasingly in some third world countries. The increase in numbers of obese people is due largely to the increasing preference for high fat content foods but also the decrease in activity in most people's lives. Currently about 30% of the population of the USA is now considered obese.

Whether someone is classified as overweight or obese is generally determined on the basis of their body mass index (BMI) which is calculated by dividing body weight (kg) by height squared ($m^2$). Thus, the units of BMI are $kg/m^2$ and it is possible to calculate the BMI range associated with minimum mortality in each decade of life. Overweight is defined as a BMI in the range 25-30 $kg/m^2$, and obesity as a BMI greater than 30 $kg/m^2$ (see table below).

| CLASSIFICATION OF WEIGHT BY BODY MASS INDEX (BMI) | |
|---|---|
| BMI | CLASSIFICATION |
| <18.5 | Underweight |
| 18.5-24.9 | Normal |
| 25.0-29.9 | Overweight |
| 30.0-34.9 | Obesity (Class I) |
| 35.0-39.9 | Obesity (Class II) |
| >40 | Extreme Obesity (Class III) |

As the BMI increases there is an increased risk of death from a variety of causes that are independent of other risk factors. The most common diseases associated with obesity are cardiovascular disease (particularly hypertension), diabetes (obesity aggravates the development of diabetes), gall bladder disease (particularly cancer) and diseases of reproduction. The strength of the link between obesity and specific conditions varies. One of the strongest is the link with type 2 diabetes. Excess body fat underlies 64% of cases of diabetes in men and 77% of cases in women (Seidell, Semin Vasc Med 5:3-14 (2005)). Research has shown that even a modest reduction in body weight can correspond to a significant reduction in the risk of developing coronary heart disease.

There are problems however with the BMI definition in that it does not take into account the proportion of body mass that is muscle in relation to fat (adipose tissue). To account for this, obesity can also be defined on the basis of body fat content: greater than 25% in males and greater than 30% in females.

Obesity considerably increases the risk of developing cardiovascular diseases as well. Coronary insufficiency, atheromatous disease, and cardiac insufficiency are at the forefront of the cardiovascular complications induced by obesity. It is estimated that if the entire population had an ideal weight, the risk of coronary insufficiency would decrease by 25% and the risk of cardiac insufficiency and of cerebral vascular accidents would decrease by 35%. The incidence of coronary diseases is doubled in subjects less than 50 years of age who are 30% overweight. The diabetes patient faces a 30% reduced lifespan. After age 45, people with diabetes are about three times more likely than people without diabetes to have significant heart disease and up to five times more likely to have a stroke. These findings emphasize the inter-relations between risks factors for diabetes and coronary heart disease and the potential value of an integrated approach to the prevention of these conditions based on the prevention of obesity (Perry, I. J., et al., *BMJ* 310, 560-564 (1995)).

Diabetes has also been implicated in the development of kidney disease, eye diseases and nervous system problems. Kidney disease, also called nephropathy, occurs when the kidney's "filter mechanism" is damaged and protein leaks into urine in excessive amounts and eventually the kidney fails. Diabetes is also a leading cause of damage to the retina at the back of the eye and increases risk of cataracts and glaucoma. Finally, diabetes is associated with nerve damage, especially in the legs and feet, which interferes with the ability to sense pain and contributes to serious infections. Taken together, diabetes complications are one of the nation's leading causes of death.

The first line of treatment is to offer diet and life style advice to patients such as reducing the fat content of their diet and increasing their physical activity. However, many patients find this difficult and need additional help from drug therapy to maintain results from these efforts.

Most currently marketed products have been unsuccessful as treatments for obesity because of a lack of efficacy or unacceptable side-effect profiles. The most successful drug so far was the indirectly acting 5-hydroxytryptamine (5-HT) agonist d-fenfluramine (Redux™) but reports of cardiac valve defects in up to one third of patients led to its withdrawal by the FDA in 1998.

In addition, two drugs have been launched in the USA and Europe: Orlistat (Xenical™), a drug that prevents absorption of fat by the inhibition of pancreatic lipase, and Sibutramine (Reductil™), a 5-HT/noradrenaline re-uptake inhibitor. However, side effects associated with these products may limit their long-term utility. Treatment with Xenical™ is reported to induce gastrointestinal distress in some patients, while Sibutramine has been associated with raised blood pressure in some patients.

Serotonin (5-HT) neurotransmission plays an important role in numerous physiological processes both in physical and in psychiatric disorders. 5-HT has been implicated in the regulation of feeding behavior. 5-HT is believed to work by inducing a feeling of satiety, such that a subject with enhanced 5-HT stops eating earlier and fewer calories are consumed. It has been shown that a stimulatory action of 5-HT on the 5-HT$_{2C}$ receptor plays an important role in the control of eating and in the anti-obesity effect of d-fenfluramine. As the 5-HT$_{2C}$ receptor is expressed in high density in the brain (notably in the limbic structures, extrapyramidal pathways, thalamus and hypothalamus i.e. PVN and DMH, and predominantly in the choroid plexus) and is expressed in low density or is absent in peripheral tissues, a selective 5-HT$_{2C}$ receptor agonist can be a more effective and safe anti-obesity agent. Also, 5-HT$_{2C}$ knockout mice are overweight with cognitive impairment and susceptibility to seizure.

It is believed that the 5-HT$_{2C}$ receptor may play a role in obsessive compulsive disorder, some forms of depression, and epilepsy. Accordingly, agonists can have anti-panic properties, and properties useful for the treatment of sexual dysfunction.

In sum, the 5-HT$_{2C}$ receptor is a receptor target for the treatment of obesity and psychiatric disorders, and it can be seen that there is a need for selective 5-HT$_{2C}$ agonists which safely decrease food intake and body weight.

Compounds and formulations presented herein can comprise the selective 5-HT$_{2C}$-receptor agonist (R)-8-chloro-1-methyl-2,3,4,5-tetrahydro-1H-3-benzazepine (Compound 1), and are useful for, inter alia, weight management, including weight loss and the maintenance of weight loss. Compound 1 is disclosed in PCT patent publication WO2003/086303, which is incorporated herein by reference in its entirety.

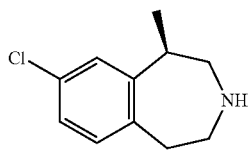

Various synthetic routes to (R)-8-chloro-1-methyl-2,3,4,5-tetrahydro-1H-3-benzazepine, its related salts, enantiomers, crystalline forms, and intermediates, have been reported in WO 2005/019179, WO2006/069363, WO2007/120517, WO2008/070111, and WO2009/111004 each of which is incorporated herein by reference in its entirety.

Combinations of (R)-8-Chloro-1-methyl-2,3,4,5-tetrahydro-1H-3-benzazepine with other agents, including without limitation, phentermine, and uses of such combinations in therapy are described in WO2006/071740, which is incorporated herein by reference in its entirety.

(R)-8-Chloro-1-methyl-2,3,4,5-tetrahydro-1H-3-benzazepine hydrochloride (lorcaserin hydrochloride) is an agonist of the 5-HT$_{2C}$ receptor and shows effectiveness at reducing obesity in animal models and humans. In December 2009, Arena Pharmaceuticals submitted a New Drug Application, or NDA, for lorcascrin to the FDA. The NDA submission is based on an extensive data package from lorcaserin's clinical development program that includes 18 clinical trials totaling 8,576 patients. The pivotal phase 3 clinical trial program evaluated nearly 7,200 patients treated for up to two years, and showed that lorcaserin consistently produced significant weight loss with excellent tolerability. About two-thirds of patients achieved at least 5% weight loss and over one-third achieved at least 10% weight loss. On average, patients lost 17 to 18 pounds or about 8% of their weight. Secondary endpoints, including body composition, lipids, cardiovascular risk factors and glycemic parameters improved compared to placebo. In addition, heart rate and blood pressure went down. Lorcaserin did not increase the risk of cardiac valvulopathy. Lorcaserin improved quality of life, and there was no signal for depression or suicidal ideation. The only adverse event that exceeded the placebo rate by 5% was generally mild or moderate, transient headache. Based on a normal BMI of 25, patients in the first phase 3 trial lost about one-third of their excess body weight. The average weight loss was 35 pounds or 16% of body weight for the top quartile of patients in the second phase 3 trial.

Applicants have disclosed herein the interaction of renal sufficiency with the pharmacokinetics, tolerability and safety of lorcaserin in a formal pharmacokinetic study in subjects with renal impairment and in the populations studied in phase 2 and phase 3 clinical studies.

Renal sufficiency can be measured by several methods. For example, measuring creatinine clearance in an individual using serum creatinine level and a timed urine collection gives an estimate of glomerular filtration rate, which is the unit measure of kidney function. An individual can be classified as having normal renal function if the creatinine clearance rate is greater than 80 mL/min. Mild renal impairment is defined as a creatinine clearance rate of 51-80 mL/min, moderate renal impairment is 31-50 mL/min, and severe renal impairment is less than or equal to 30 mL/min. A further level of renal impairment is an individual who requires hemodialysis (end stage renal disease).

There exists a need for safely treating individuals who are in need of treatment with lorcaserin, including individuals with renal impairment. The present disclosure satisfies this need and provides related advantages as well.

SUMMARY (R)-8-chloro-1-methyl-2,3,4,5-tetrahydro-1H-3-benzazepine hydrochloride (lorcaserin) is eliminated primarily by liver metabolism, whereas the resulting major metabolites M1 (lorcaserin sulfamate) and M5 (N-carbamoyl glucuronide of lorcaserin) are eliminated by urinary excretion.

Applicants have found that the maximum concentration ($C_{max}$) of the M1 and M5 metabolites of lorcaserin can be quite variable in individuals with severe renal impairment or ESRD. For example, four hours after administration of lorcaserin, the mean plasma concentration of the M1 metabolite in a group of eight individuals with severe renal impairment was 99.5 ng/mL (Table 13 for day 1, 4 hours). However, one of the eight individuals with severe renal impairment, subject 3285-009, had a mean plasma concentration of 542 ng/mL of M1 four hours after administration of lorcaserin (Table 13 for subject 3285-009 at day 1, 4 hours). Thus, this individual had a level of M1 that was five times the mean level for the severe renal impairment group.

To better assess the potential implications of M1 and M5 levels in patients, steady state exposures (i.e. the state of equilibrium obtained at the end of a certain number of dosings) following lorcaserin 10 mg twice daily (BID) dosing were modeled using simulations and noncompartmental analysis based on data from pharmacokinetic studies with once daily (QD) dosing. The modeled steady state $C_{max}$ for metabolite M1 in the severe renal impairment group was 1090 ng/mL (Table 8); however, given the individual variability seen with this metabolite, it is possible that a particular individual with severe renal impairment would reach a level of five times this amount (i.e., over 5000 ng/mL) according to the model. Applicants are not aware of any toxicity associated with metabolite M1 or M5; however, some of the levels of these metabolites observed in the severe renal impairment group are higher than those levels that have been analyzed in human clinical trials. In addition, a level of over 5000 ng/mL of M1 in a severe renal impairment individual is approximately the $C_{max}$ in monkeys at the no observable adverse event level (NOAEL) dose of lorcaserin (Table 9 M1 $C_{max}$ is 5.01 t 2.16 µg/mL for monkeys at the 2 mg/kg dose of lorcaserin). Therefore, there is no margin between exposure levels at the NOAEL dose and projected exposure levels in some individuals with severe renal impairment. Since some of the levels of M1 observed in the severe renal impairment group are higher than those levels that have been analyzed in human clinical trials, lorcaserin is contraindicated for individuals with severe renal impairment and for individuals with ESRD given the currently available data.

It should be noted that in the study results to date (as of the filing of the first priority document of the subject application), the incidence of adverse events due to lorcaserin was not related to the severity of renal impairment of the individual (Example 6). However, given possible widespread use of lorcaserin in humans, in an abundance of caution given the currently available data, lorcascrin is contraindicated for individuals with severe renal impairment and for individuals with ESRD.

In a first aspect, a method for weight management in an individual in need thereof, comprising a) determining the level of renal sufficiency of the individual, and b) prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a level of renal sufficiency selected from the group consisting of: no renal impairment, mild renal impairment, and moderate renal impairment is disclosed.

In a second aspect, a method for weight management in an individual in need thereof, comprising: a) determining the level of renal sufficiency of the individual, and b) prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual does not have severe renal impairment or end stage renal disease (ESRD) is disclosed.

In a third aspect, a method for weight management in an individual in need thereof, comprising: a) determining the level of renal sufficiency of the individual, and b) prescribing or administering a reduced dosage regimen of (R)-8-chloro-1-methyl-2,3,4,5-tetrahydro-1H-3-benzazepine or a pharmaceutically acceptable salt, solvate or hydrate thereof to the individual provided that the individual has renal impairment is disclosed.

In a fourth aspect, a method for weight management in an individual in need thereof, comprising: a) determining an approximate serum creatinine concentration for the individual, and b) prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual provided that the individual has an approximate serum creatinine concentration of:

(i) less than 4.9 mg/dL for an 18-20 year old man,
(ii) less than 3.5 mg/dL for an 18-20 year old woman,
(iii) less than 4.5 mg/dL for a 21-30 year old man,
(iv) less than 3.2 mg/dL for a 21-30 year old woman,
(v) less than 4.1 mg/dL for a 31-40 year old man,
(vi) less than 2.9 mg/dL for a 31-40 year old woman,
(viii) less than 2.7 mg/dL for a 41-50 year old woman,
(ix) less than 3.3 mg/dL for a 51-60 year old man,
(x) less than 2.4 mg/dL for a 51-60 year old woman,
(xi) less than 3.0 mg/dL for a man over 60 years old, or
(xii) less than 2.0 mg/dL for a woman over 60 years old
is disclosed.

In a fifth aspect, a method for weight management in an individual in need thereof, comprising: a) determining a creatinine clearance rate using the Cockcroft-Gault equation for the individual, and b) prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a creatinine clearance rate of greater than about 80 mL/minute using the Cockcroft-Gault equation is disclosed.

In a sixth aspect, a method for weight management in an individual in need thereof, comprising: a) determining a creatinine clearance rate using the Cockcroft-Gault equation for the individual, and b) prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a creatinine clearance rate of greater than about 50 mL/minute using the Cockcroft-Gault equation is disclosed.

In a seventh aspect, a method for weight management in an individual in need thereof, comprising: a) determining a creatinine clearance rate using the Cockcroft-Gault equation for the individual, and b) prescribing or administering a therapeutically effective amount of (R)-8-chloro-1-methyl-2,3,4,5-tetrahydro-H-3-benzazepine or a pharmaceutically acceptable salt, solvate or hydrate thereof to the individual, provided that the individual has a creatinine clearance rate of greater than about 30 mL/minute using the Cockcroft-Gault equation is disclosed.

In an eighth aspect, a method for reducing the risk of an adverse event in an individual in need of weight management, comprising: a) determining the level of renal sufficiency of the individual, and b) prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a level of renal sufficiency selected from the group consisting of: no renal impairment, mild renal impairment, and moderate renal impairment is disclosed.

In a ninth aspect, a method for reducing the risk of an adverse event in an individual in need of weight management, comprising: a) determining the level of renal sufficiency of the individual, and b) prescribing or administering a reduced dosage regimen of (R)-8-chloro-1-methyl-2,3,4,5-tetrahydro-1H-3-benzazepine or a pharmaceutically acceptable salt, solvate or hydrate thereof to the individual provided that the individual has renal impairment is disclosed.

In a tenth aspect, a method for reducing the risk of an adverse event in an individual in need of weight management, comprising: a) determining an approximate serum creatinine concentration for the individual, and b) prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual provided that the individual has an approximate serum creatinine concentration of:

(i) less than 4.9 mg/dL for an 18-20 year old man,
(ii) less than 3.5 mg/dL for an 18-20 year old woman,
(iii) less than 4.5 mg/dL for a 21-30 year old man,
(iv) less than 3.2 mg/dL for a 21-30 year old woman,
(v) less than 4.1 mg/dL for a 31-40 year old man,
(vi) less than 2.9 mg/dL for a 31-40 year old woman,
(vii) less than 3.7 mg/dL for a 41-50 year old man,
(viii) less than 2.7 mg/dL for a 41-50 year old woman,
(ix) less than 3.3 mg/dL for a 51-60 year old man,
(x) less than 2.4 mg/dL for a 51-60 year old woman,
(xi) less than 3.0 mg/dL for a man over 60 years old, or
(xii) less than 2.0 mg/dL for a woman over 60 years old is disclosed.

In an eleventh aspect, a method for selecting an individual for treatment with (R)-8-chloro-1-methyl-2,3,4,5-tetrahydro-1H-3-benzazepine or a pharmaceutically acceptable salt, solvate or hydrate thereof from a plurality of individuals in need of weight management, comprising: a) determining the level of renal sufficiency of the individual; and b) selecting the individual for treatment with (R)-8-chloro-1-methyl-2,3,4,5-tetrahydro-H-3-benzazepine or a pharmaceutically acceptable salt, solvate or hydrate thereof if the individual has a level of renal sufficiency selected from the group consisting of: no renal impairment, mild renal impairment, and moderate renal impairment is disclosed.

In a twelfth aspect, a method for selecting an individual for treatment with (R)-8-chloro-1-methyl-2,3,4,5-tetrahydro-1H-3-benzazepine or a pharmaceutically acceptable salt, solvate or hydrate thereof from a plurality of individuals in need of weight management, comprising: a) determining an approximate serum creatinine concentration for the individual, and b) selecting the individual for treatment with (R)-8-chloro-1-methyl-2,3,4,5-tetrahydro-1H-3-benzazepine or a pharmaceutically acceptable salt, solvate or hydrate thereof if the individual has an approximate serum creatinine concentration of:

(i) less than 4.9 mg/dL for an 18-20 year old man,
(ii) less than 3.5 mg/dL for an 18-20 year old woman,
(iii) less than 4.5 mg/dL for a 21-30 year old man,
(iv) less than 3.2 mg/dL for a 21-30 year old woman,
(v) less than 4.1 mg/dL for a 31-40 year old man,
(vi) less than 2.9 mg/dL for a 31-40 year old woman,
(vii) less than 3.7 mg/dL for a 41-50 year old man,
(viii) less than 2.7 mg/dL for a 41-50 year old woman,
(ix) less than 3.3 mg/dL for a 51-60 year old man,
(x) less than 2.4 mg/dL for a 51-60 year old woman,
(xi) less than 3.0 mg/dL for a man over 60 years old, or
(xii) less than 2.0 mg/dL for a woman over 60 years old is disclosed In a thirteenth aspect, a compound for use in a method of weight management in an individual, said method comprising prescribing or administering said compound to said individual, wherein said individual has previously been determined to have a level of renal sufficiency selected from the group consisting of: no renal impairment, mild renal impairment, and moderate renal impairment; wherein said compound is (R)-8-chloro-1-methyl-2,3,4,5-tetrahydro-1H-3-benzazepine or a pharmaceutically acceptable salt, solvate or hydrate thereof is disclosed.

In a fourteenth aspect, a compound for use in a method of weight management in an individual, said method comprising prescribing or administering said compound at a dosage level appropriate for the level of renal sufficiency of said individual, wherein said individual has previously been determined to have a level of renal sufficiency selected from the group consisting of: no renal impairment, mild renal impairment, moderate renal impairment, severe renal impairment and ESRD; wherein said compound is (R)-8-chloro-1-methyl-2,3,4,5-tetrahydro-1H-3-benzazepine or a pharmaceutically acceptable salt, solvate or hydrate thereof is disclosed In a fifteenth aspect, a compound for use in a method of weight management in an individual, said method comprising determining the level of renal sufficiency of said individual and prescribing or administering said compound at a dosage level appropriate for the level of renal sufficiency of said individual, wherein said individual has a level of renal sufficiency selected from the group consisting of: no renal impairment, mild renal impairment, moderate renal impairment, severe renal impairment and ESRD; wherein said compound is (R)-8-chloro-1-methyl-2,3,4,5-tetrahydro-1H-3-benzazepine or a pharmaceutically acceptable salt, solvate or hydrate thereof is disclosed.

In a sixteenth aspect, a low dosage formulation of a compound for use in a method of weight management in an individual, said method comprising prescribing or administering said low dosage formulation of the compound to said individual, wherein said individual has previously been determined to have renal impairment; wherein said compound is R)-8-chloro-1-methyl-2,3,4,5-tetrahydro-1H-3-benzazepine or a pharmaceutically acceptable salt, solvate or hydrate thereof is disclosed.

In a seventeenth aspect, a low dosage formulation of a compound for use in a method of weight management in an individual, wherein said low dosage reduces or prevents a toxic event in said individual to said compound, wherein said individual has previously been determined to have renal impairment; and wherein said compound is (R)-8-chloro-1-methyl-2,3,4,5-tetrahydro-1H-3-benzazepine or a pharmaceutically acceptable salt, solvate or hydrate thereof is disclosed.

In the first through seventeenth aspects, the following embodiments, for example and without limitation, are envisioned. In some embodiments, said weight management comprises weight loss. In some embodiments, said weight management comprises maintenance of weight loss. In some embodiments, said weight management further comprises prescribing or administering a reduced-calorie diet. In some embodiments, said weight management further comprises prescribing or administering a program of regular exercise. In some embodiments, said weight management further comprises prescribing or administering both a reduced-calorie diet and a program of regular exercise. In some embodiments, said individual is an individual with an initial body mass index ≥30 kg/m². In some embodiments, said individual is an individual with an initial body mass index ≥27 kg/m² in the presence of at least one weight related comorbid condition. In some embodiments, said weight related comorbid condition is selected from the group consisting of: hypertension, dyslipidemia, cardiovascular disease, glucose intolerance and sleep apnea. In some embodiments, the methods of the first through seventeenth aspects further comprise prescribing or administering phentermine to said individual. In some embodiments, the Cockcroft-Gault equation is used to determine the level of renal sufficiency of the individual. In some embodiments, the individual's ideal body weight is used in the Cockcroft-Gault equation and in some embodiments the individual's actual body weight is used in the Cockcroft-Gault equation. In some embodiments, the individual's serum creatinine concentration is used to determine the level of renal sufficiency of the individual.

In an eighteenth aspect, a method for decreasing food intake in an individual in need thereof, comprising a) determining the level of renal sufficiency of the individual, and b) prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a level of renal sufficiency selected from the group consisting of: no renal impairment, mild renal impairment, and moderate renal impairment is disclosed.

In a nineteenth aspect, a method for decreasing food intake in an individual in need thereof, comprising: a) determining the level of renal sufficiency of the individual, and b) prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual does not have severe renal impairment or end stage renal disease (ESRD) is disclosed.

In a twentieth aspect, a method for decreasing food intake in an individual in need thereof, comprising: a) determining the level of renal sufficiency of the individual, and b) prescribing or administering a reduced dosage regimen of (R)-8-chloro-1-methyl-2,3,4,5-tetrahydro-1H-3-benzazepine or a pharmaceutically acceptable salt, solvate or hydrate thereof to the individual provided that the individual has renal impairment is disclosed.

In a twenty first aspect, a method for decreasing food intake in an individual in need thereof, comprising: a) determining an approximate serum creatinine concentration for the individual, and b) prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual provided that the individual has an approximate serum creatinine concentration of:

(i) less than 4.9 mg/dL for an 18-20 year old man,
(ii) less than 3.5 mg/dL for an 18-20 year old woman,
(iii) less than 4.5 mg/dL for a 21-30 year old man,
(iv) less than 3.2 mg/dL for a 21-30 year old woman,
(v) less than 4.1 mg/dL for a 31-40 year old man,
(vi) less than 2.9 mg/dL for a 31-40 year old woman,
(viii) less than 2.7 mg/dL for a 41-50 year old woman,
(ix) less than 3.3 mg/dL for a 51-60 year old man,
(x) less than 2.4 mg/dL for a 51-60 year old woman,
(xi) less than 3.0 mg/dL for a man over 60 years old, or
(xii) less than 2.0 mg/dL for a woman over 60 years old is disclosed In a twenty second aspect, a method for decreasing food intake in an individual in need thereof, comprising: a) determining a creatinine clearance rate using the Cockcroft-Gault equation for the individual, and b) prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a creatinine clearance rate of greater than about 80 mL/minute using the Cockcroft-Gault equation is disclosed.

In a twenty third aspect, a method for decreasing food intake in an individual in need thereof, comprising: a) determining a creatinine clearance rate using the Cockcroft-Gault equation for the individual, and b) prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a creatinine clearance rate of greater than about 50 mL/minute using the Cockcroft-Gault equation is disclosed.

In a twenty fourth aspect, a method for decreasing food intake in an individual in need thereof, comprising: a) determining a creatinine clearance rate using the Cockcroft-Gault equation for the individual, and b) prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a creatinine clearance rate of greater than about 30 mL/minute using the Cockcroft-Gault equation is disclosed.

In an twenty fifth aspect, a method for reducing the risk of an adverse event in an individual in need of decreasing food intake, comprising: a) determining the level of renal sufficiency of the individual, and b) prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a level of renal sufficiency selected from the group consisting of: no renal impairment, mild renal impairment, and moderate renal impairment is disclosed.

In a twenty sixth aspect, a method for reducing the risk of an adverse event in an individual in need of decreasing food intake, comprising: a) determining the level of renal sufficiency of the individual, and b) prescribing or administering a reduced dosage regimen of (R)-8-chloro-1-methyl-2,3,4,5-tetrahydro-1H-3-benzazepine or a pharmaceutically acceptable salt, solvate or hydrate thereof to the individual provided that the individual has renal impairment is disclosed.

In a twenty seventh aspect, a method for reducing the risk of an adverse event in an individual in need of decreasing food intake, comprising: a) determining an approximate serum creatinine concentration for the individual, and b) prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual provided that the individual has an approximate serum creatinine concentration of:

(i) less than 4.9 mg/dL for an 18-20 year old man,
(ii) less than 3.5 mg/dL for an 18-20 year old woman,
(iii) less than 4.5 mg/dL for a 21-30 year old man,
(iv) less than 3.2 mg/dL for a 21-30 year old woman,
(v) less than 4.1 mg/dL for a 31-40 year old man, (vi) less than 2.9 mg/dL for a 31-40 year old woman,
(vii) less than 3.7 mg/dL for a 41-50 year old man,
(viii) less than 2.7 mg/dL for a 41-50 year old woman,
(ix) less than 3.3 mg/dL for a 51-60 year old man,
(x) less than 2.4 mg/dL for a 51-60 year old woman,
(xi) less than 3.0 mg/dL for a man over 60 years old, or
(xii) less than 2.0 mg/dL for a woman over 60 years old
is disclosed In a twenty eighth aspect, a method for selecting an individual for treatment with (R)-8-chloro-1-methyl-2,3,4,5-tetrahydro-1H-3-benzazepine or a pharmaceutically acceptable salt, solvate or hydrate thereof from a plurality of individuals in need of decreasing food intake, comprising: a) determining the level of renal sufficiency of the individual; and b) selecting the individual for treatment with (R)-8-chloro-1-methyl-2,3,4,5-tetrahydro-1H-3-benzazepine or a pharmaceutically acceptable salt, solvate or hydrate thereof if the individual has a level of renal sufficiency selected from the group consisting of: no renal impairment, mild renal impairment, and moderate renal impairment is disclosed.

In a twenty ninth aspect, a method for selecting an individual for treatment with (R)-8-chloro-1-methyl-2,3,4,5-tetrahydro-1H-3-benzazepine or a pharmaceutically acceptable salt, solvate or hydrate thereof from a plurality of individuals in need of decreasing food intake, comprising: a) determining an approximate serum creatinine concentration for the individual, and b) selecting the individual for treatment with (R)-8-chloro-1-methyl-2,3,4,5-tetrahydro-1H-3-benzazepine or a pharmaceutically acceptable salt, solvate or hydrate thereof if the individual has an approximate serum creatinine concentration of:
(i) less than 4.9 mg/dL for an 18-20 year old man,
(ii) less than 3.5 mg/dL for an 18-20 year old woman,
(iii) less than 4.5 mg/dL for a 21-30 year old man,
(iv) less than 3.2 mg/dL for a 21-30 year old woman,
(v) less than 4.1 mg/dL for a 31-40 year old man,
(vi) less than 2.9 mg/dL for a 31-40 year old woman,
(vii) less than 3.7 mg/dL for a 41-50 year old man,
(viii) less than 2.7 mg/dL for a 41-50 year old woman,
(ix) less than 3.3 mg/dL for a 51-60 year old man,
(x) less than 2.4 mg/dL for a 51-60 year old woman,
(xi) less than 3.0 mg/dL for a man over 60 years old, or
(xii) less than 2.0 mg/dL for a woman over 60 years old
is disclosed In a thirtieth aspect, a compound for use in a method of decreasing food intake in an individual, said method comprising prescribing or administering said compound to said individual, wherein said individual has previously been determined to have a level of renal sufficiency selected from the group consisting of: no renal impairment, mild renal impairment, and moderate renal impairment; wherein said compound is (R)-8-chloro-1-methyl-2,3,4,5-tetrahydro-1H-3-benzazepine or a pharmaceutically acceptable salt, solvate or hydrate thereof is disclosed.

In a thirty first aspect, a compound for use in a method of decreasing food intake in an individual, said method comprising prescribing or administering said compound at a dosage level appropriate for the level of renal sufficiency of said individual, wherein said individual has previously been determined to have a level of renal sufficiency selected from the group consisting of: no renal impairment, mild renal impairment, moderate renal impairment, severe renal impairment and ESRD; wherein said compound is (R)-8-chloro-1-methyl-2,3,4,5-tetrahydro-1H-3-benzazepine or a pharmaceutically acceptable salt, solvate or hydrate thereof is disclosed.

In a thirty second aspect, a compound for use in a method of decreasing food intake in an individual, said method comprising determining the level of renal sufficiency of said individual and prescribing or administering said compound at a dosage level appropriate for the level of renal sufficiency of said individual, wherein said individual has a level of renal sufficiency selected from the group consisting of: no renal impairment, mild renal impairment, moderate renal impairment, severe renal impairment and ESRD; wherein said compound is (R)-8-chloro-1-methyl-2,3,4,5-tetrahydro-1H-3-benzazepine or a pharmaceutically acceptable salt, solvate or hydrate thereof is disclosed.

In a thirty third aspect, a low dosage formulation of a compound for use in a method of decreasing food intake in an individual, said method comprising prescribing or administering said low dosage formulation of the compound to said individual, wherein said individual has previously been determined to have renal impairment; and wherein said compound is (R)-8-chloro-1-methyl-2,3,4,5-tetrahydro-H-3-benzazepine or a pharmaceutically acceptable salt, solvate or hydrate thereof is disclosed.

In a thirty fourth aspect, a low dosage formulation of a compound for use in decreasing food intake in an individual, wherein said low dosage reduces or prevents a toxic event in said individual to said compound, wherein said individual has previously been determined to have renal impairment; and wherein said compound is (R)-8-chloro-1-methyl-2,3,4,5-tetrahydro-1H-3-benzazepine or a pharmaceutically acceptable salt, solvate or hydrate thereof is disclosed.

In the eighteenth through thirty fourth aspects, the following embodiments, for example and without limitation, are envisioned. In some embodiments, said individual in need of decreasing food intake is an individual with an initial body mass index ≥30 kg/m$^2$. In some embodiments, said individual in need of decreasing food intake is an individual with an initial body mass index ≥27 kg/m$^2$ in the presence of at least one weight related comorbid condition. In some embodiments, said weight related comorbid condition is selected from the group consisting of: hypertension, dyslipidemia, cardiovascular disease, glucose intolerance and sleep apnea. In some embodiments, the methods of the eighteenth through thirty forth aspects further comprise prescribing or administering phentermine to said individual. In some embodiments, the Cockcroft-Gault equation is used to determine the level of renal sufficiency of the individual. In some embodiments, the individual's ideal body weight is used in the Cockcroft-Gault equation and in some embodiments the individual's actual body weight is used in the Cockcroft-Gault equation. In some embodiments, the individual's serum creatinine concentration is used to determine the level of renal sufficiency of the individual.

In a thirty fifth aspect, a method for inducing satiety in an individual in need thereof, comprising a) determining the level of renal sufficiency of the individual, and b) prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a level of renal sufficiency selected from the group consisting of: no renal impairment, mild renal impairment, and moderate renal impairment is disclosed.

In a thirty sixth aspect, a method for inducing satiety in an individual in need thereof, comprising: a) determining the level of renal sufficiency of the individual, and b) prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual does not have severe renal impairment or end stage renal disease (ESRD) is disclosed.

In a thirty seventh aspect, a method for inducing satiety in an individual in need thereof, comprising: a) determining the level of renal sufficiency of the individual, and b) prescribing or administering a reduced dosage regimen of (R)-8-chloro-1-methyl-2,3,4,5-tetrahydro-1H-3-benzazepine or a pharmaceutically acceptable salt, solvate or hydrate thereof to the individual provided that the individual has renal impairment is disclosed.

In a thirty eighth aspect, a method for inducing satiety in an individual in need thereof, comprising: a) determining an approximate serum creatinine concentration for the individual, and b) prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual provided that the individual has an approximate serum creatinine concentration of:
  (i) less than 4.9 mg/dL for an 18-20 year old man,
  (ii) less than 3.5 mg/dL for an 18-20 year old woman,
  (iii) less than 4.5 mg/dL for a 21-30 year old man,
  (iv) less than 3.2 mg/dL for a 21-30 year old woman,
  (v) less than 4.1 mg/dL for a 31-40 year old man,
  (vi) less than 2.9 mg/dL for a 31-40 year old woman,
  (viii) less than 2.7 mg/dL for a 41-50 year old woman,
  (ix) less than 3.3 mg/dL for a 51-60 year old man,
  (x) less than 2.4 mg/dL for a 51-60 year old woman,
  (xi) less than 3.0 mg/dL for a man over 60 years old, or
  (xii) less than 2.0 mg/dL for a woman over 60 years old
is disclosed In a thirty ninth aspect, a method for inducing satiety in an individual in need thereof, comprising: a) determining a creatinine clearance rate using the Cockcroft-Gault equation for the individual, and b) prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a creatinine clearance rate of greater than about 80 mL/minute using the Cockcroft-Gault equation is disclosed.

In a fortieth aspect, a method for inducing satiety in an individual in need thereof, comprising: a) determining a creatinine clearance rate using the Cockcroft-Gault equation for the individual, and b) prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a creatinine clearance rate of greater than about 50 mL/minute using the Cockcroft-Gault equation is disclosed.

In a forty first aspect, a method for inducing satiety in an individual in need thereof, comprising: a) determining a creatinine clearance rate using the Cockcroft-Gault equation for the individual, and b) prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a creatinine clearance rate of greater than about 30 mL/minute using the Cockcroft-Gault equation is disclosed.

In an forty second aspect, a method for reducing the risk of an adverse event in an individual in need of inducing satiety, comprising: a) determining the level of renal sufficiency of the individual, and b) prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a level of renal sufficiency selected from the group consisting of: no renal impairment, mild renal impairment, and moderate renal impairment is disclosed.

In a forty third aspect, a method for reducing the risk of an adverse event in an individual in need of inducing satiety, comprising: a) determining the level of renal sufficiency of the individual, and b) prescribing or administering a reduced dosage regimen of (R)-8-chloro-1-methyl-2,3,4,5-tetrahydro-1H-3-benzazepine or a pharmaceutically acceptable salt, solvate or hydrate thereof to the individual provided that the individual has renal impairment is disclosed.

In a forty fourth aspect, a method for reducing the risk of an adverse event in an individual in need of inducing satiety, comprising: a) determining an approximate serum creatinine concentration for the individual, and b) prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual provided that the individual has an approximate serum creatinine concentration of:
  (i) less than 4.9 mg/dL for an 18-20 year old man,
  (ii) less than 3.5 mg/dL for an 18-20 year old woman,
  (iii) less than 4.5 mg/dL for a 21-30 year old man,
  (iv) less than 3.2 mg/dL for a 21-30 year old woman,
  (v) less than 4.1 mg/dL for a 31-40 year old man,
  (vi) less than 2.9 mg/dL for a 31-40 year old woman,
  (vii) less than 3.7 mg/dL for a 41-50 year old man,
  (viii) less than 2.7 mg/dL for a 41-50 year old woman,
  (ix) less than 3.3 mg/dL for a 51-60 year old man,
  (x) less than 2.4 mg/dL for a 51-60 year old woman,
  (xi) less than 3.0 mg/dL for a man over 60 years old, or
  (xii) less than 2.0 mg/dL for a woman over 60 years old
is disclosed In a forty fifth aspect, a method for selecting an individual for treatment with (R)-8-chloro-1-methyl-2,3,4,5-tetrahydro-1H-3-benzazepine or a pharmaceutically acceptable salt, solvate or hydrate thereof from a plurality of individuals in need of inducing satiety, comprising: a) determining the level of renal sufficiency of the individual; and b) selecting the individual for treatment with (R)-8-chloro-1-methyl-2,3,4,5-tetrahydro-1H-3-benzazepine or a pharmaceutically acceptable salt, solvate or hydrate thereof if the individual has a level of renal sufficiency selected from the group consisting of: no renal impairment, mild renal impairment, and moderate renal impairment is disclosed.

In a forty sixth aspect, a method for selecting an individual for treatment with (R)-8-chloro-1-methyl-2,3,4,5-tetrahydro-1H-3-benzazepine or a pharmaceutically acceptable salt, solvate or hydrate thereof from a plurality of individuals in need of inducing satiety, comprising: a) determining an approximate serum creatinine concentration for the individual, and b) selecting the individual for treatment with (R)-8-chloro-1 methyl-2,3,4,5-tetrahydro-1H-3-benzazepine or a pharmaceutically acceptable salt, solvate or hydrate thereof if the individual has an approximate serum creatinine concentration of:
  (i) less than 4.9 mg/dL for an 18-20 year old man,
  (ii) less than 3.5 mg/dL for an 18-20 year old woman,
  (iii) less than 4.5 mg/dL for a 21-30 year old man,
  (iv) less than 3.2 mg/dL for a 21-30 year old woman,
  (v) less than 4.1 mg/dL for a 31-40 year old man,
  (vi) less than 2.9 mg/dL for a 31-40 year old woman,
  (vii) less than 3.7 mg/dL for a 41-50 year old man,
  (viii) less than 2.7 mg/dL for a 41-50 year old woman, (ix) less than 3.3 mg/dL for a 51-60 year old man,
(x) less than 2.4 mg/dL for a 51-60 year old woman,
(xi) less than 3.0 mg/dL for a man over 60 years old, or
(xii) less than 2.0 mg/dL for a woman over 60 years old
is disclosed In a forty seventh aspect, a compound for use in a method of inducing satiety in an individual, said method comprising prescribing or administering said compound to said individual, wherein said individual has previously been determined to have a level of renal sufficiency selected from the group consisting of: no renal impairment, mild renal impairment, and moderate renal impairment; wherein said compound is (R)-8-chloro-1-methyl-2,3,4,5-tetrahydro-1H-3-benzazepine or a pharmaceutically acceptable salt, solvate or hydrate thereof is disclosed In a forty eighth aspect, a compound for use in a method of inducing satiety in an individual, said method comprising prescribing or administering said compound at a dosage level appropriate for the level of renal sufficiency of said individual, wherein said individual has previously been determined to have a level of renal sufficiency selected from the group consisting of: no renal impairment, mild renal impairment, moderate renal impairment, severe renal impairment and ESRD; wherein said compound is (R)-8-chloro-1-methyl-2,3,4,5-tetrahydro-1H-3-benzazepine or a pharmaceutically acceptable salt, solvate or hydrate thereof is disclosed.

In a forty ninth aspect, a compound for use in a method of inducing satiety in an individual, said method comprising determining the level of renal sufficiency of said individual and prescribing or administering said compound at a dosage level appropriate for the level of renal sufficiency of said individual, wherein said individual has a level of renal sufficiency selected from the group consisting of: no renal impairment, mild renal impairment, moderate renal impairment, severe renal impairment and ESRD; wherein said compound is (R)-8-chloro-1-methyl-2,3,4,5-tetrahydro-1H-3-benzazepine or a pharmaceutically acceptable salt, solvate or hydrate thereof is disclosed.

In a fiftieth aspect, a low dosage formulation of a compound for use in a method of inducing satiety in an individual, said method comprising prescribing or administering said low dosage formulation of the compound to said individual, wherein said individual has previously been determined to have renal impairment; wherein said compound is (R)-8-chloro-1-methyl-2,3,4,5-tetrahydro-1H-3-benzazepine or a pharmaceutically acceptable salt, solvate or hydrate thereof is disclosed.

In a fifty first aspect, a low dosage formulation of a compound for use in a method of inducing satiety in an individual, wherein said low dosage reduces or prevents a toxic event in said individual to said compound, wherein said individual has previously been determined to have renal impairment; and wherein said compound is (R)-8-chloro-1-methyl-2,3,4,5-tetrahydro-1H-3-benzazepine or a pharmaceutically acceptable salt, solvate or hydrate thereof is disclosed.

In the thirty fifth through fifty first aspects, the following embodiments, for example and without limitation, are envisioned. In some embodiments, said individual in need of inducing satiety is an individual with an initial body mass index $\geq 30$ kg/m$^2$. In some embodiments, said individual in need of inducing satiety is an individual with an initial body mass index $\geq 27$ kg/m$^2$ in the presence of at least one weight related comorbid condition. In some embodiments, said weight related comorbid condition is selected from the group consisting of: hypertension, dyslipidemia, cardiovascular disease, glucose intolerance and sleep apnea. In some embodiments, the methods of the thirty fifth through fifty first aspects further comprise prescribing or administering phentermine to said individual. In some embodiments, the Cockcroft-Gault equation is used to determine the level of renal sufficiency of the individual. In some embodiments, the individual's ideal body weight is used in the Cockcroft-Gault equation and in some embodiments the individual's actual body weight is used in the Cockcroft-Gault equation. In some embodiments, the individual's serum creatinine concentration is used to determine the level of renal sufficiency of the individual.

In a fifty second aspect, a method for treatment of obesity in an individual in need thereof, comprising a) determining the level of renal sufficiency of the individual, and b) prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a level of renal sufficiency selected from the group consisting of: no renal impairment, mild renal impairment, and moderate renal impairment is disclosed.

In a fifty third aspect, a method for treatment of obesity in an individual in need thereof, comprising: a) determining the level of renal sufficiency of the individual, and b) prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual does not have severe renal impairment or end stage renal disease (ESRD) is disclosed.

In a fifty fourth aspect, a method for treatment of obesity in an individual in need thereof, comprising: a) determining the level of renal sufficiency of the individual, and b) prescribing or administering a reduced dosage regimen of (R)-8-chloro-1-methyl-2,3,4,5-tetrahydro-1H-3-benzazepine or a pharmaceutically acceptable salt, solvate or hydrate thereof to the individual provided that the individual has renal impairment is disclosed.

In a fifty fifth aspect, a method for treatment of obesity in an individual in need thereof, comprising: a) determining an approximate serum creatinine concentration for the individual, and b) prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual provided that the individual has an approximate serum creatinine concentration of:
(i) less than 4.9 mg/dL for an 18-20 year old man,
(ii) less than 3.5 mg/dL for an 18-20 year old woman,
(iii) less than 4.5 mg/dL for a 21-30 year old man,
(iv) less than 3.2 mg/dL for a 21-30 year old woman,
(v) less than 4.1 mg/dL for a 31-40 year old man,
(vi) less than 2.9 mg/dL for a 31-40 year old woman,
(viii) less than 2.7 mg/dL for a 41-50 year old woman,
(ix) less than 3.3 mg/dL for a 51-60 year old man,
(x) less than 2.4 mg/dL for a 51-60 year old woman,
(xi) less than 3.0 mg/dL for a man over 60 years old, or
(xii) less than 2.0 mg/dL for a woman over 60 years old
is disclosed In a fifty sixth aspect, a method for treatment of obesity in an individual in need thereof, comprising: a) determining a creatinine clearance rate using the Cockcroft-Gault equation for the individual, and b) prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a creatinine clearance rate of greater than about 80 mL/minute using the Cockcroft-Gault equation is disclosed.

In a fifty seventh aspect, a method for treatment of obesity in an individual in need thereof, comprising: a) determining a creatinine clearance rate using the Cockcroft-Gault equation for the individual, and b) prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a creatinine clearance rate of greater than about 50 mL/minute using the Cockcroft-Gault equation is disclosed.

In a fifty eighth aspect, a method for treatment of obesity in an individual in need thereof, comprising: a) determining a creatinine clearance rate using the Cockcroft-Gault equation for the individual, and b) prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a creatinine clearance rate of greater than about 30 mL/minute using the Cockcroft-Gault equation is disclosed.

In an fifty ninth aspect, a method for reducing the risk of an adverse event in an individual in need of treatment of obesity, comprising: a) determining the level of renal sufficiency of the individual, and b) prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a level of renal sufficiency selected from the group consisting of: no renal impairment, mild renal impairment, and moderate renal impairment is disclosed.

In a sixtieth aspect, a method for reducing the risk of an adverse event in an individual in need of treatment of obesity, comprising: a) determining the level of renal sufficiency of the individual, and b) prescribing or administering a reduced dosage regimen of (R)-8-chloro-1-methyl-2,3,4,5-tetrahydro-1H-3-benzazepine or a pharmaceutically acceptable salt, solvate or hydrate thereof to the individual provided that the individual has renal impairment is disclosed.

In a sixty first aspect, a method for reducing the risk of an adverse event in an individual in need of treatment of obesity, comprising: a) determining an approximate serum creatinine concentration for the individual, and b) prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual provided that the individual has an approximate serum creatinine concentration of:
  (i) less than 4.9 mg/dL for an 18-20 year old man,
  (ii) less than 3.5 mg/dL for an 18-20 year old woman,
  (iii) less than 4.5 mg/dL for a 21-30 year old man,
  (iv) less than 3.2 mg/dL for a 21-30 year old woman,
  (v) less than 4.1 mg/dL for a 31-40 year old man,
  (vi) less than 2.9 mg/dL for a 31-40 year old woman,
  (vii) less than 3.7 mg/dL for a 41-50 year old man,
  (viii) less than 2.7 mg/dL for a 41-50 year old woman,
  (ix) less than 3.3 mg/dL for a 51-60 year old man,
  (x) less than 2.4 mg/dL for a 51-60 year old woman,
  (xi) less than 3.0 mg/dL for a man over 60 years old, or
  (xii) less than 2.0 mg/dL for a woman over 60 years old
is disclosed In an sixty second aspect, a method for selecting an individual for treatment with (R)-8-chloro-1-methyl-2,3,4,5-tetrahydro-1H-3-benzazepine or a pharmaceutically acceptable salt, solvate or hydrate thereof from a plurality of individuals in need of treatment of obesity, comprising: a) determining the level of renal sufficiency of the individual; and b) selecting the individual for treatment with (R)-8-chloro-1-methyl-2,3,4,5-tetrahydro-1H-3-benzazepine or a pharmaceutically acceptable salt, solvate or hydrate thereof if the individual has a level of renal sufficiency selected from the group consisting of: no renal impairment, mild renal impairment, and moderate renal impairment is disclosed.

In a sixty third aspect, a method for selecting an individual for treatment with (R)-8-chloro-1-methyl-2,3,4,5-tetrahydro-1H-3-benzazepine or a pharmaceutically acceptable salt, solvate or hydrate thereof from a plurality of individuals in need of treatment for obesity, comprising: a) determining an approximate serum creatinine concentration for the individual, and b) selecting the individual for treatment with (R)-8-chloro-1-methyl-2,3,4,5-tetrahydro-1H-3-benzazepine or a pharmaceutically acceptable salt, solvate or hydrate thereof if the individual has an approximate serum creatinine concentration of:
  (i) less than 4.9 mg/dL for an 18-20 year old man,
  (ii) less than 3.5 mg/dL for an 18-20 year old woman,
  (iii) less than 4.5 mg/dL for a 21-30 year old man,
  (iv) less than 3.2 mg/dL for a 21-30 year old woman,
  (v) less than 4.1 mg/dL for a 31-40 year old man,
  (vi) less than 2.9 mg/dL for a 31-40 year old woman,
  (vii) less than 3.7 mg/dL for a 41-50 year old man,
  (viii) less than 2.7 mg/dL for a 41-50 year old woman,
  (ix) less than 3.3 mg/dL for a 51-60 year old man,
  (x) less than 2.4 mg/dL for a 51-60 year old woman,
  (xi) less than 3.0 mg/dL for a man over 60 years old, or
  (xii) less than 2.0 mg/dL for a woman over 60 years old
is disclosed In a sixty fourth aspect, a compound for use in a method for treatment of obesity in an individual, said method comprising prescribing or administering said compound to said individual, wherein said individual has previously been determined to have a level of renal sufficiency selected from the group consisting of: no renal impairment, mild renal impairment, and moderate renal impairment; wherein said compound is (R)-8-chloro-1-methyl-2,3,4,5-tetrahydro-1H-3-benzazepine or a pharmaceutically acceptable salt, solvate or hydrate thereof is disclosed.

In a sixty fifth aspect, a compound for use in a method for treatment of obesity in an individual, said method comprising prescribing and administering said compound at a dosage level appropriate for the level of renal sufficiency of said individual, wherein said individual has previously been determined to have a level of renal sufficiency selected from the group consisting of: no renal impairment, mild renal impairment, moderate renal impairment, severe renal impairment and ESRD; wherein said compound is (R)-8-chloro-1-methyl-2,3,4,5-tetrahydro-1H-3-benzazepine or a pharmaceutically acceptable salt, solvate or hydrate thereof is disclosed.

In a sixty sixth aspect, a compound for use in a method for treatment of obesity in an individual, said method comprising determining the level of renal sufficiency of said individual and prescribing or administering said compound at a dosage level appropriate for the level of renal sufficiency of said individual, wherein said individual has a level of renal sufficiency selected from the group consisting of: no renal impairment, mild renal impairment, moderate renal impairment, severe renal impairment and ESRD; wherein said compound is (R)-8-chloro-1-methyl-2,3,4,5-tetrahydro-1H-

3-benzazepine or a pharmaceutically acceptable salt, solvate or hydrate thereof is disclosed.

In a sixty seventh aspect, a low dosage formulation of a compound for use in a method for treatment of obesity in an individual, said method comprising prescribing or administering said low dosage formulation of the compound to said individual, wherein said individual has previously been determined to have renal impairment; wherein said compound is (R)-8-chloro-1-methyl-2,3,4,5-tetrahydro-1H-3-benzazepine or a pharmaceutically acceptable salt, solvate or hydrate thereof is disclosed.

In a sixty eighth aspect, a low dosage formulation of a compound for use in a method for treatment of obesity in an individual, wherein said low dosage reduces or prevents a toxic event in said individual to said compound, wherein said individual has previously been determined to have renal impairment; and wherein said compound is (R)-8-chloro-1-methyl-2,3,4,5-tetrahydro-1H-3-benzazepine or a pharmaceutically acceptable salt, solvate or hydrate thereof is disclosed.

In the fifty second through sixty eighth aspects, the following embodiments, for example and without limitation, are envisioned. In some embodiments, said treatment of obesity comprises weight loss. In some embodiments, said treatment of obesity comprises maintenance of weight loss. In some embodiments, said treatment of obesity further comprises a reduced-calorie diet. In some embodiments, said treatment of obesity further comprises a program of regular exercise. In some embodiments, said treatment of obesity further comprises both a reduced-calorie diet and a program of regular exercise. In some embodiments, said individual in need of treatment of obesity is an individual with an initial body mass index ≥30 kg/m. In some embodiments, said individual in need of treatment of obesity is an individual with an initial body mass index ≥27 kg/m$^2$ in the presence of at least one weight related comorbid condition. In some embodiments, said weight related comorbid condition is selected from the group consisting of: hypertension, dyslipidemia, cardiovascular disease, glucose intolerance and sleep apnea. In some embodiments, the methods of the fifty second through sixty eighth aspects further comprise prescribing or administering phentermine to said individual. In some embodiments, the Cockcroft-Gault equation is used to determine the level of renal sufficiency of the individual. In some embodiments, the individual's ideal body weight is used in the Cockcroft-Gault equation and in some embodiments the individual's actual body weight is used in the Cockcroft-Gault equation. In some embodiments, the individual's serum creatinine concentration is used to determine the level of renal sufficiency of the individual.

In a sixty ninth aspect, a method for prevention of obesity in an individual in need thereof, comprising a) determining the level of renal sufficiency of the individual, and b) prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a level of renal sufficiency selected from the group consisting of: no renal impairment, mild renal impairment, and moderate renal impairment is disclosed.

In a seventieth aspect, a method for prevention of obesity in an individual in need thereof, comprising: a) determining the level of renal sufficiency of the individual, and b) prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual does not have severe renal impairment or end stage renal disease (ESRD) is disclosed.

In a seventy first aspect, a method for prevention of obesity in an individual in need thereof, comprising: a) determining the level of renal sufficiency of the individual, and b) prescribing or administering a reduced dosage regimen of (R)-8-chloro-1-methyl-2,3,4,5-tetrahydro-1H-3-benzazepine or a pharmaceutically acceptable salt, solvate or hydrate thereof to the individual provided that the individual has renal impairment is disclosed.

In a seventy second aspect, a method for prevention of obesity in an individual in need thereof, comprising: a) determining an approximate serum creatinine concentration for the individual, and b) prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual provided that the individual has an approximate serum creatinine concentration of:

(i) less than 4.9 mg/dL for an 18-20 year old man,
(ii) less than 3.5 mg/dL for an 18-20 year old woman,
(iii) less than 4.5 mg/dL for a 21-30 year old man,
(iv) less than 3.2 mg/dL for a 21-30 year old woman,
(v) less than 4.1 mg/dL for a 31-40 year old man,
(vi) less than 2.9 mg/dL for a 31-40 year old woman,
(viii) less than 2.7 mg/dL for a 41-50 year old woman,
(ix) less than 3.3 mg/dL for a 51-60 year old man,
(x) less than 2.4 mg/dL for a 51-60 year old woman,
(xi) less than 3.0 mg/dL for a man over 60 years old, or
(xii) less than 2.0 mg/dL for a woman over 60 years old
is disclosed In a seventy third aspect, a method for prevention of obesity in an individual in need thereof, comprising: a) determining a creatinine clearance rate using the Cockcroft-Gault equation for the individual, and b) prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a creatinine clearance rate of greater than about 80 mL/minute using the Cockcroft-Gault equation is disclosed.

In a seventy fourth aspect, a method for prevention of obesity in an individual in need thereof, comprising: a) determining a creatinine clearance rate using the Cockcroft-Gault equation for the individual, and b) prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a creatinine clearance rate of greater than about 50 mL/minute using the Cockcroft-Gault equation is disclosed.

In a seventy fifth aspect, a method for prevention of obesity in an individual in need thereof, comprising: a) determining a creatinine clearance rate using the Cockcroft-Gault equation for the individual, and b) prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a creatinine clearance rate of greater than about 30 mL/minute using the Cockcroft-Gault equation is disclosed.

In an seventy sixth aspect, a method for reducing the risk of an adverse event in an individual in need for prevention of obesity, comprising: a) determining the level of renal sufficiency of the individual, and b) prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a level of renal sufficiency selected from the group consisting of: no renal impairment, mild renal impairment, and moderate renal impairment is disclosed.

In a seventy seventh aspect, a method for reducing the risk of an adverse event in an individual in need for prevention of obesity, comprising: a) determining the level of renal sufficiency of the individual, and b) prescribing or administering a reduced dosage regimen of (R)-8-chloro-1-methyl-2,3,4,5-tetrahydro-1H-3-benzazepine or a pharmaceutically acceptable (salt, solvate or hydrate thereof to the individual provided that the individual has renal impairment is disclosed In a seventy eighth aspect, a method for reducing the risk of an adverse event in an individual in need for prevention of obesity, comprising: a) determining an approximate serum creatinine concentration for the individual, and b) prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual provided that the individual has an approximate serum creatinine concentration of:
  (i) less than 4.9 mg/dL for an 18-20 year old man,
  (ii) less than 3.5 mg/dL for an 18-20 year old woman,
  (iii) less than 4.5 mg/dL for a 21-30 year old man,
  (iv) less than 3.2 mg/dL for a 21-30 year old woman,
  (v) less than 4.1 mg/dL for a 31-40 year old man,
  (vi) less than 2.9 mg/dL for a 31-40 year old woman,
  (vii) less than 3.7 mg/dL for a 41-50 year old man,
  (viii) less than 2.7 mg/dL for a 41-50 year old woman,
  (ix) less than 3.3 mg/dL for a 51-60 year old man,
  (x) less than 2.4 mg/dL for a 51-60 year old woman,
  (xi) less than 3.0 mg/dL for a man over 60 years old, or
  (xii) less than 2.0 mg/dL for a woman over 60 years old
is disclosed In a seventy ninth aspect, a method for selecting an individual for treatment with (R)-8-chloro-1-methyl-2,3,4,5-tetrahydro-1H-3-benzazepine or a pharmaceutically acceptable salt, solvate or hydrate thereof from a plurality of individuals in need for prevention of obesity, comprising: a) determining the level of renal sufficiency of the individual; and b) selecting the individual for treatment with (R)-8-chloro-1-methyl-2,3,4,5-tetrahydro-1H-3-benzazepine or a pharmaceutically acceptable salt, solvate or hydrate thereof if the individual has a level of renal sufficiency selected from the group consisting of: no renal impairment, mild renal impairment, and moderate renal impairment is disclosed.

In an eightieth aspect, a method for selecting an individual for treatment with (R)-8-chloro-1-methyl-2,3,4,5-tetrahydro-1H-3-benzazepine or a pharmaceutically acceptable salt, solvate or hydrate thereof from a plurality of individuals in need for prevention of obesity, comprising: a) determining an approximate serum creatinine concentration for the individual, and b) selecting the individual for treatment with (R)-8-chloro-1-methyl-2,3,4,5-tetrahydro-1H-3-benzazepine or a pharmaceutically acceptable salt, solvate or hydrate thereof if the individual has an approximate serum creatinine concentration of:
  (i) less than 4.9 mg/dL for an 18-20 year old man,
  (ii) less than 3.5 mg/dL for an 18-20 year old woman,
  (iii) less than 4.5 mg/dL for a 21-30 year old man,
  (iv) less than 3.2 mg/dL for a 21-30 year old woman,
  (v) less than 4.1 mg/dL for a 31-40 year old man,
  (vi) less than 2.9 mg/dL for a 31-40 year old woman,
  (vii) less than 3.7 mg/dL for a 41-50 year old man,
  (viii) less than 2.7 mg/dL for a 41-50 year old woman,
  (ix) less than 3.3 mg/dL for a 51-60 year old man,
  (x) less than 2.4 mg/dL for a 51-60 year old woman,
  (xi) less than 3.0 mg/dL for a man over 60 years old, or
  (xii) less than 2.0 mg/dL for a woman over 60 years old
is disclosed In an eighty first aspect, a compound for use in a method for prevention of obesity in an individual, said method comprising prescribing or administering said compound to said individual, wherein said individual has previously been determined to have a level of renal sufficiency selected from the group consisting of: no renal impairment, mild renal impairment, and moderate renal impairment; wherein said compound is (R)-8-chloro-1-methyl-2,3,4,5-tetrahydro-1H-3-benzazepine or a pharmaceutically acceptable salt, solvate or hydrate thereof is disclosed.

In an eighty second aspect, a compound for use in a method for prevention of obesity in an individual, said method comprising prescribing or administering said compound at a dosage level appropriate for the level of renal sufficiency of said individual, wherein said individual has previously been determined to have a level of renal sufficiency selected from the group consisting of: no renal impairment, mild renal impairment, moderate renal impairment, severe renal impairment and ESRD; wherein said compound is (R)-8-chloro-1-methyl-2,3,4,5-tetrahydro-1H-3-benzazepine or a pharmaceutically acceptable salt, solvate or hydrate thereof is disclosed.

In an eighty third aspect, a compound for use in a method for prevention of obesity in an individual, said method comprising determining the level of renal sufficiency of said individual and prescribing or administering said compound at a dosage level appropriate for the level of renal sufficiency of said individual, wherein said individual has a level of renal sufficiency selected from the group consisting of: no renal impairment, mild renal impairment, moderate renal impairment, severe renal impairment and ESRD; wherein said compound is (R)-8-chloro-1-methyl-2,3,4,5-tetrahydro-1H-3-benzazepine or a pharmaceutically acceptable salt, solvate or hydrate thereof is disclosed.

In an eighty fourth aspect, a low dosage formulation of a compound for use in a method for prevention of obesity in an individual, said method comprising prescribing or administering said low dosage formulation of the compound to said individual, wherein said individual has previously been determined to have renal impairment; wherein said compound is (R)-8-chloro-1-methyl-2,3,4,5-tetrahydro-1H-3-benzazepine or a pharmaceutically acceptable salt, solvate or hydrate thereof is disclosed.

In an eighty fifth aspect, a low dosage formulation of a compound for use in a method for prevention of obesity in an individual, wherein said low dosage reduces or prevents a toxic event in said individual to said compound, wherein said individual has previously been determined to have renal impairment; and wherein said compound is (R)-8-chloro-1-methyl-2,3,4,5-tetrahydro-1H-3-benzazepine or a pharmaceutically acceptable salt, solvate or hydrate thereof is disclosed.

In the fifty second through eighty fi aspects, the following embodiments, for example and without limitation, are envisioned. In some embodiments, said prevention of obesity comprises weight loss. In some embodiments, said prevention of obesity comprises maintenance of weight loss. In some embodiments, said prevention of obesity further comprises a reduced-calorie diet. In some embodiments, said prevention of obesity further comprises a program of regular exercise. In some embodiments, said prevention of obesity further comprises both a reduced-calorie diet and a program of regular exercise. In some embodiments, said individual in need for prevention of obesity is an individual with an initial body mass index ≥27 kg/m² in the presence of at least one weight related comorbid condition. In some embodiments, said weight related comorbid condition is selected from the group consisting of: hypertension, dyslipidemia, cardiovascular disease, glucose intolerance and sleep apnea. In some embodiments, the methods of the fifty second through eighty fifth aspects further comprise prescribing or administering phentermine to said individual. In some embodiments, the Cockcroft-Gault equation is used to determine the level of renal sufficiency of the individual. In some embodiments, the individual's ideal body weight is used in the Cockcroft-Gault equation and in some embodiments the individual's actual body weight is used in the Cockcroft-Gault equation. In some embodiments, the individual's serum creatinine concentration is used to determine the level of renal sufficiency of the individual.

DETAILED DESCRIPTION

Figure 3:
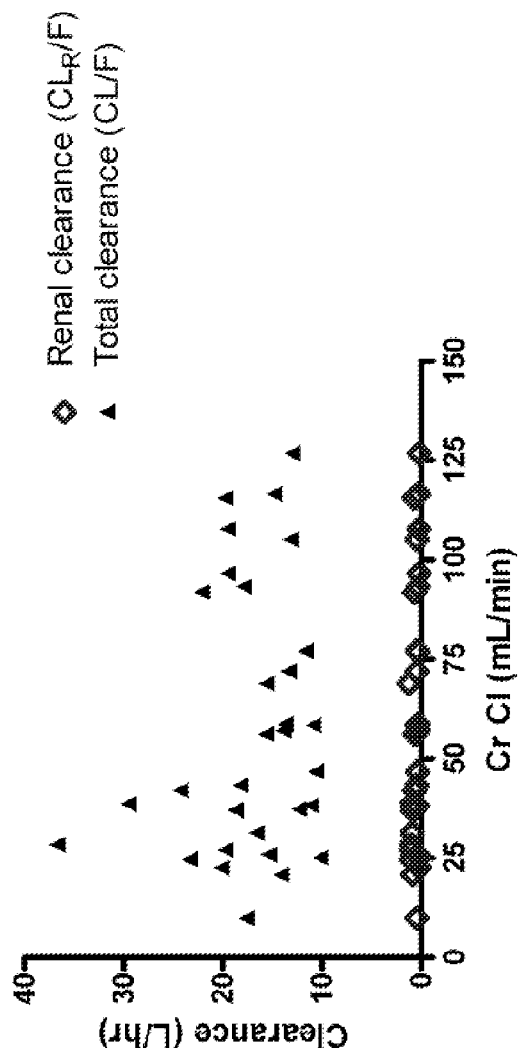
FIG. 3 shows comparison of renal clearance and total clearance of lorcaserin using ideal body weight calculation.

The interaction of renal sufficiency with the pharmacokinetics, tolerability and safety of lorcaserin has been assessed in a formal pharmacokinetic study in subjects with renal impairment and in the populations studied in phase 2 and phase 3 clinical studies. As shown in Example 2, lorcaserin exposure was not clearly affected by renal impairment (Example 2) and total lorcaserin clearance was not significantly correlated with creatinine clearance (FIG. 3).

Figure 1A:
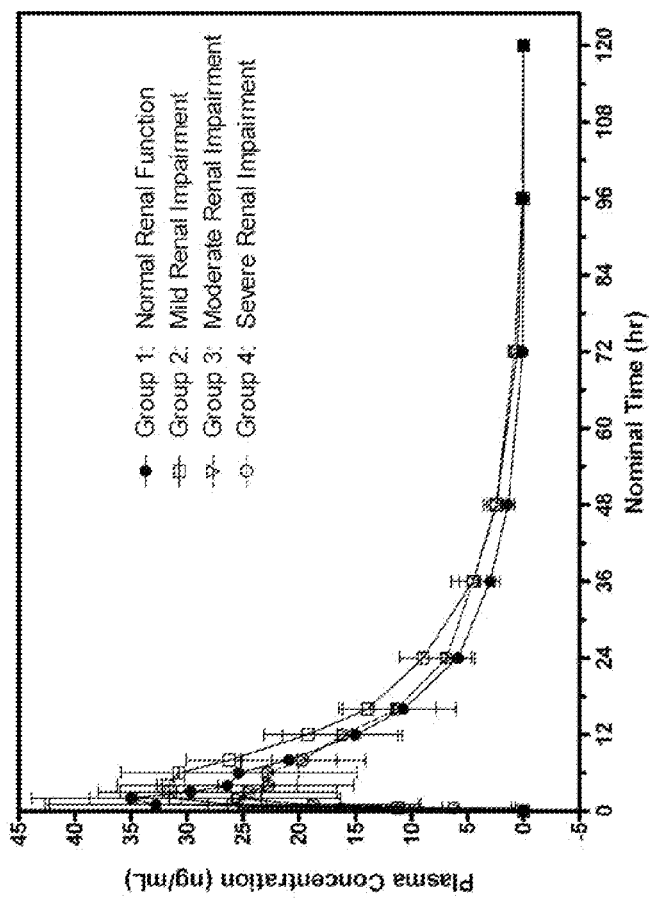
FIG. 1A shows mean plasma concentration versus time profiles of lorcaserin after a 10 mg dose for groups 1-4 (group 1: normal renal function, group 2: mild renal impairment, group 3: moderate renal impairment, group 4: severe renal impairment).
Figure 1B:
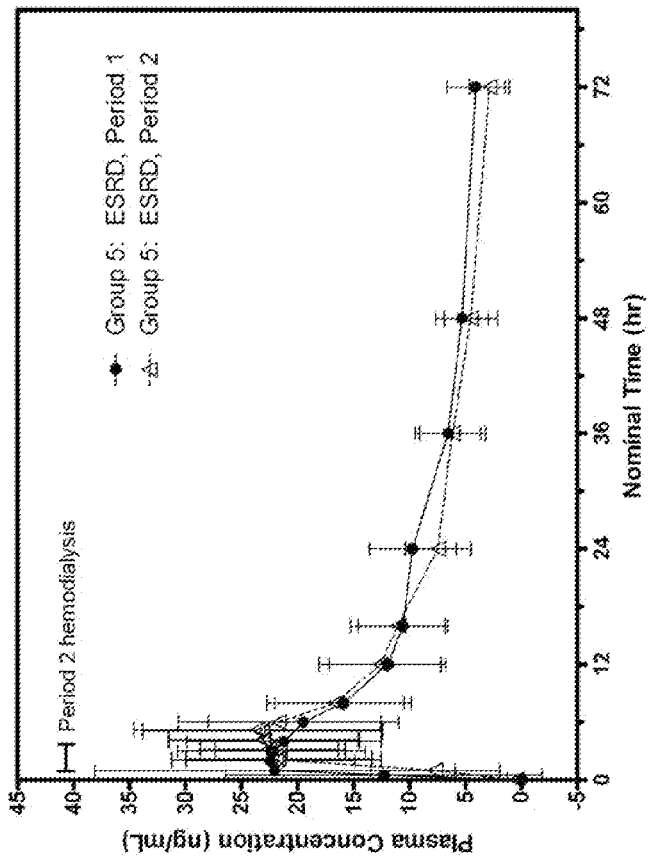
FIG. 1B shows mean plasma concentration versus time profiles of lorcaserin after a 10 mg dose for group 5 (group 5: end stage renal disease, period 1 and period 2).
Figure 1C:
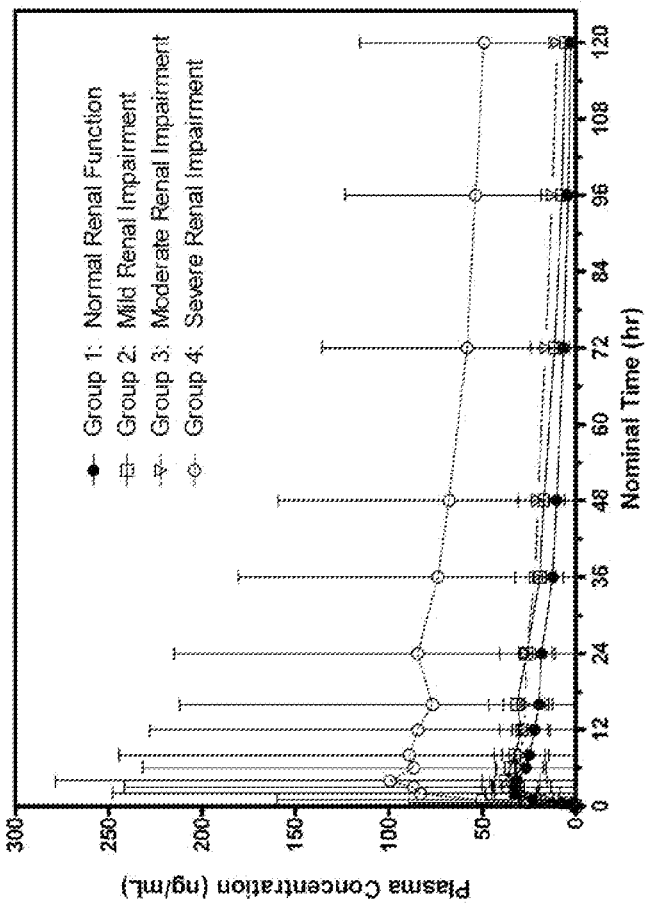
FIG. 1C shows mean plasma concentration versus time profiles of M1 after a 10 mg dose for groups 1-4.
Figure 1D:
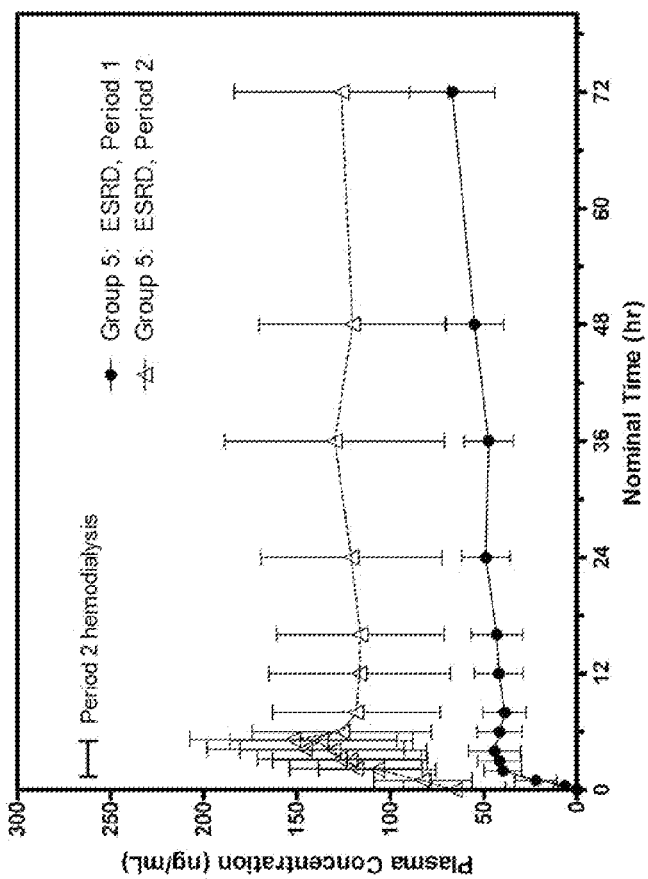
FIG. 1D shows mean plasma concentration versus time profiles of M1 after a 10 mg dose for group 5.
Figure 1E:
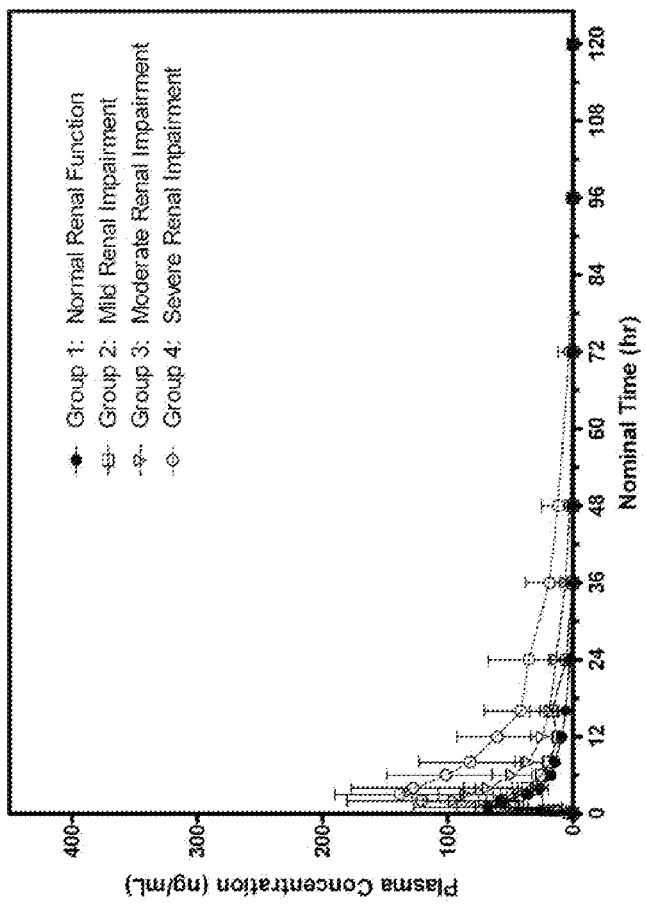
FIG. 1E shows mean plasma concentration versus time profiles of M5 after a 10 mg dose for groups 1-4.
Figure 1F:
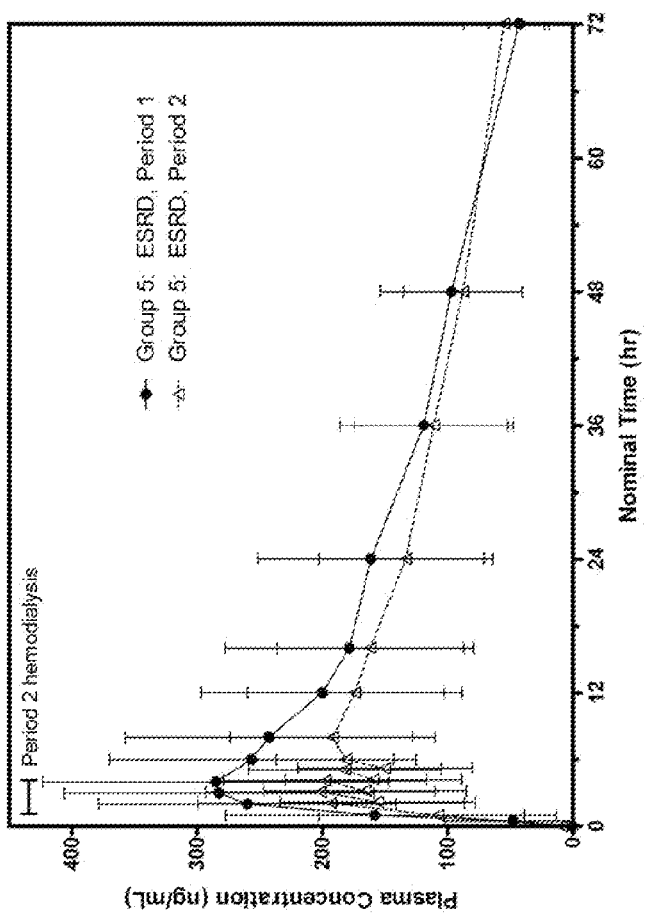
FIG. 1F shows mean plasma concentration versus time profiles of M5 after a 10 mg dose for group 5.
Figure 4:
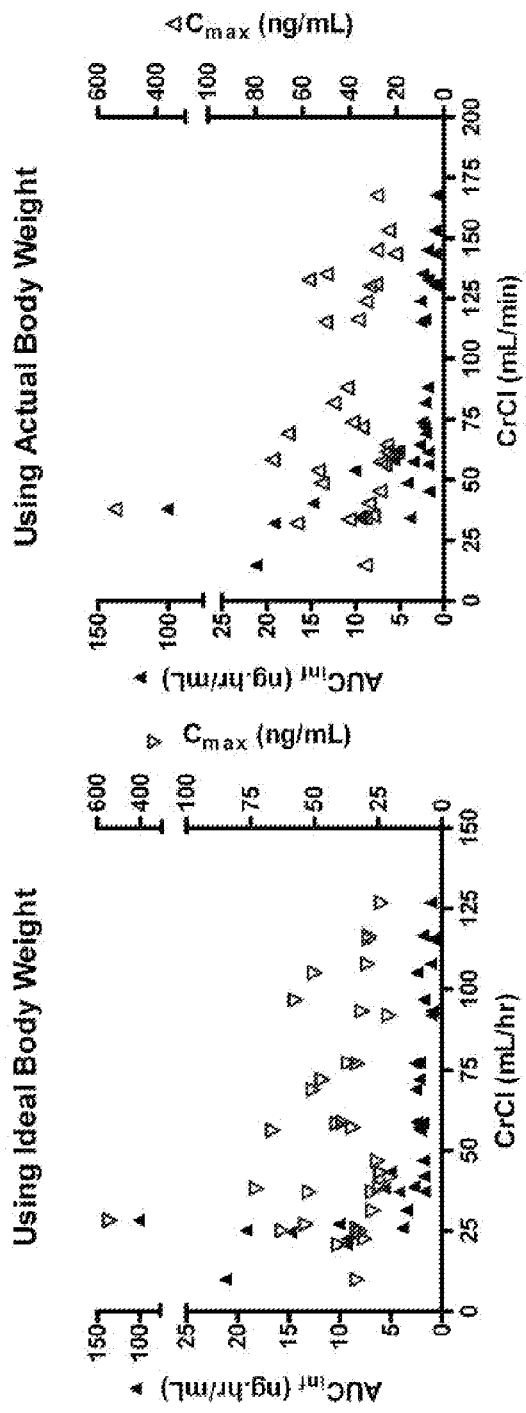
FIG. 4 shows correlation of M1 exposure with creatinine clearance. The left panel shows results using ideal body weight and the right panel shows results using actual body weight.

In contrast to the parent compound lorcaserin, the major circulating metabolite M1 (lorcaserin sulfamate) was significantly affected by renal impairment. Although M1 is a minor metabolite in urine, plasma exposure was increased in subjects with renal impairment (Example 3, Table 4 and FIGS. 1C, 1D). In addition, M1 exposure ($AUC_{0-inf}$) was significantly inversely correlated with creatinine clearance and $C_{max}$ was not correlated with creatinine clearance (Table 5, FIG. 4). Plasma exposure of M5 (N-carbamoyl glucuronide of lorcaserin), the major urinary metabolite, was increased with increasing renal impairment. (FIG. 5, Table 6) and that M5 $AUC_{0-inf}$, but not $C_{max}$ was significantly correlated with creatinine clearance (Table 7).

Modeling of steady state exposures following lorcaserin 10 mg BID was performed using simulations and noncompartmental analysis based upon data from pharmacokinetic studies with once daily (QD) dosing (Table 8). For example, based on the modeled values, subjects with severe renal impairment will reach M1 $C_{max}$ levels of 1090 ng/mL (Table 8). Actual M1 levels over time in individuals with severe renal impairment was also determined (Table 13). As shown in Table 13, the maximum individual $C_{max}$ was more than five times the mean $C_{max}$ for the subjects studied. Therefore some individuals could reach a level of five times the steady state mean level of 1090 ng/mL which is approximately the $C_{max}$ in monkeys given the NOAEL dose (Table 9), leaving no margin between exposure levels at the NOAEL dose and projected exposure levels in individuals with severe renal impairment.

In sum, based on clinical findings and the current guidance provided by the Federal Drug Agency, no lorcaserin dose adjustment should be needed in individuals with mild or moderate renal impairment, but given the predicted level of M1 and M5 in individuals with severe renal impairment, lorcaserin should be used with caution in individuals with moderate renal impairment and should not be used in individuals with severe renal impairment or end stage renal disease (Example 7).

Definitions

ADMINISTERING: As used herein, "administering" means to provide a compound or other therapy, remedy or treatment. For example, a health care practitioner can directly provide a compound to an individual in the form of a sample, or can indirectly provide a compound to an individual by providing an oral or written prescription for the compound. Also, for example, an individual can obtain a compound by themselves without the involvement of a health care practitioner. Administration of the compound may or may not involve the individual actually internalizing the compound. In the case where an individual internalizes the compound the body is transformed by the compound in some way.

ADVERSE EVENT OR TOXIC EVENT: As used herein, an "adverse event" or "toxic event" is any untoward medical occurrence that may present itself during treatment. Adverse events associated with treatment with Compound 1 or a pharmaceutically acceptable salt, solvate or hydrate thereof are disclosed herein, for example, in Example 6 and Table 11. Possible adverse events disclosed in Example 6 include, abdominal pain, diarrhea, dyspepsia, stomach discomfort, and worsening renal impairment, dizziness, headache. Other possible adverse events based on observations from studies in monkeys include emesis, decreased food intake, weight loss, decreased activity, spontaneous penile erection, tremors or seizures. Additional possible adverse events include, for example, nausea, blurred vision, paresthesias, dry mouth and fatigue. In the methods disclosed herein, the term adverse event can be replaced by other more general terms such as toxicity. The term "reducing the risk" of an adverse event means reducing the probability that an adverse event or toxic event could occur.

INDIVIDUAL: As used herein, an "individual" is a human. An individual can be an adult or prepubertal (a child) and can be of any gender. The individual can be a patient or other individual seeking treatment. The methods disclosed herein can also apply to non-human mammals such as livestock or pets.

LEVEL OF RENAL SUFFICIENCY: As used herein, the term "level of renal sufficiency" means the level of renal (kidney) function in an individual. As used herein, the levels of renal sufficiency in an individual include: no renal impairment, mild renal impairment, moderate renal impairment, severe renal impairment and end stage renal disease (ESRD). The term renal impairment includes mild renal impairment, moderate renal impairment, severe renal impairment and end stage renal disease (ESRD).

PLURALITY OF INDIVIDUALS: As used herein, a "plurality of individuals" means more than one individual.

PRESCRIBING: As used herein, "prescribing" means to order, authorize or recommend the use of a drug or other therapy, remedy or treatment. In some embodiments, a health care practitioner can orally advise, recommend or authorize the use of a compound, dosage regimen or other treatment to an individual. In this case the health care practitioner may or may not provide a prescription for the compound, dosage regimen or treatment. Further the health care practitioner may or may not provide the recommended compound or treatment. For example, the health care practitioner can advise the individual where to obtain the compound without providing the compound. In some embodiments, a health care practitioner can provide a prescription for the compound, dosage regimen or treatment to the individual. For example, a health care practitioner can give a written or oral prescription to an individual. A prescription can be written on paper or on electronic media such as a computer file, for example, on a hand held computer device. For example, a health care practitioner can transform a piece of paper or electronic media with a prescription for a compound, dosage regimen or treatment. In addition, a prescription can be called in (oral) or faxed in (written) to a pharmacy or a dispensary. In some embodiments, a sample of the compound or treatment can be given to the individual. As used herein, giving a sample of a compound constitutes an implicit prescription for the compound. Different health care systems around the world use different methods for prescribing and administering compounds or treatments and these methods are encompassed by the disclosure.

A prescription can include, for example, an individual's name and/or identifying information such as date of birth. In addition, for example, a prescription can include, the medication name, medication strength, dose, frequency of administration, route of administration, number or amount to be dispensed, number of refills, physician name, physician signature. Further, for example, a prescription can include a DEA number or state number.

PREVENTION: As used herein, the term "prevention" such as prevention of obesity means prevention of the occurrence or onset of one or more symptoms associated with a particular disorder and does not necessarily mean the complete prevention of a disorder. For example, the term "prevent," "preventing" and "prevention" refers to the administration of therapy on a prophylactic or preventative basis to an individual who may ultimately manifest at least one symptom of a disease or condition but who has not yet done so. Such individuals can be identified on the basis of risk factors that are known to correlate with the subsequent occurrence of the disease. Alternatively, prevention therapy can be administered without prior identification of a risk factor, as a prophylactic measure. Delaying the onset of the at least one symptom can also be considered prevention or prophylaxis.

As used herein, "prevention of obesity in an individual in need thereof" refers to a judgment made by a healthcare practitioner that an individual requires or will benefit from prevention of obesity. This judgment is made based on a variety of factors that are in the realm of a healthcare practitioner's expertise, but that includes the knowledge that the individual has a condition that is treatable by the methods disclosed herein.

REDUCED DOSAGE REGIMEN: A "reduced dosage regimen" as used herein means a reduction in the amount of a compound such as Compound 1 or a pharmaceutically acceptable salt, solvate or hydrate thereof that an individual is prescribed or administered in a fixed time period compared to the recommended dosage regimen. In some embodiments, the reduction in the amount of a compound that an individual is administered in a fixed time period compared to the recommended dosage is accomplished by reducing the amount of Compound 1 in each unit dose. For example, one recommended dosage regimen for Compound 1 or a pharmaceutically acceptable salt, solvate or hydrate thereof is a 10 mg capsule taken twice a day. A reduced dosage regimen can be a capsule (unit dose) with less than 10 mg taken twice a day, for example, a capsule with 9 mg, 8 mg, 7 mg, 6 mg, 5 mg, 4 mg, 3 mg, 2 mg, 1 mg or less than 1 mg taken twice a day. A capsule (unit dose) with less than 10 mg is an example of a low dosage formulation. In some embodiments, the reduction in the amount of a compound that an individual is administered in a fixed time period compared to the recommended dosage is accomplished by increasing the time interval between doses. For example, a 10 mg capsule can be administered once per day instead of twice per day to effectively reduce the dose. In addition, both a decrease in the amount of compound per unit dose and an increase the time interval between doses can be used. Since dosing can be dependent on body weight, it may be that a recommended dosage regimen is expressed in mg of compound per kg of body weight instead of a fixed amount of compound for all individuals. A reduction in the mg of compound per kg of body weight is an example of a reduced dosage regimen. Any embodiment that employs a reduced dosage regimen can equally employ a low dosage formulation.

RENAL IMPAIRMENT: As used herein, "no renal impairment" means the individual has normal renal function. Levels of renal function, renal sufficiency or renal impairment can be determined using any of the methods known in the art or described herein. Regarding terms such as "mild renal impairment", "moderate renal impairment", "severe renal impairment" and "end stage renal disease (ESRD)" cut-offs to define these levels of renal sufficiency are dependent on the test done to determine the level of renal sufficiency.

Different thresholds or cutoffs can be used to determine the level of renal sufficiency in an individual depending on the technique used and the interpretation of the health care practitioner. Several variables can be considered when determining the level of renal sufficiency in an individual including, for example, whether an individual is obese, the individual's race, the individual's gender, and the individual's age. Recommendations regarding classification of renal sufficiency are known in the art. These recommendations may change over time as newer techniques or better equations are used to more accurately determine renal function in an individual.

SATIETY: As used herein, "satiety" is the quality or state of being fed or gratified to or beyond capacity. Satiety is a feeling that an individual has and so it is often determined by asking the individual, orally or in writing, if they feel full, sated, or satisfied at timed intervals during a meal. For example, an individual who feels sated may report feeling full, feeling a decreased or absent hunger, feeling a decreased or absent desire to eat, or feeling a lack of drive to cat. While fullness is a physical sensation, satiety is a mental feeling. An individual who feels full, sated or satisfied is more likely to stop eating and therefore inducing satiety can result in a decrease in food intake in an individual.

As used herein, "inducing satiety in an individual in need thereof" refers to a judgment made by a healthcare practitioner that an individual requires or will benefit from inducing satiety. This judgment is made based on a variety of factors that are in the realm of a healthcare practitioner's expertise, but that includes the knowledge that the individual has a condition, for example, obesity, that is treatable by the methods of the disclosure.

THERAPEUTICALLY EFFECTIVE AMOUNT: The term "therapeutically effective amount" refers to the amount of active compound or pharmaceutical agent that elicits the biological or medicinal response in a tissue, system, animal, individual or human that is being sought by a researcher, veterinarian, medical doctor or other clinician or caregiver or by an individual, which includes one or more of the following:

(1) Preventing the disease, for example, preventing a disease, condition or disorder in an individual that may be predisposed to the disease, condition or disorder but does not yet experience or display the pathology or symptomatology of the disease;

(2) Inhibiting the disease, for example, inhibiting a disease, condition or disorder in an individual that is experiencing or displaying the pathology or symptomatology of the disease, condition or disorder (i.e., arresting further development of the pathology and/or symptomatology); and (3) Ameliorating the disease, for example, ameliorating a disease, condition or disorder in an individual that is experiencing or displaying the pathology or symptomatology of the disease, condition or disorder (i.e., reversing the pathology and/or symptomatology).

TREAT, TREATING, OR TREATMENT: As used herein the term "treat," "treating" or "treatment" refers to the administration of therapy to an individual who already manifests at least one symptom of a disease or condition or who has previously manifested at least one symptom of a disease or condition. For example, "treating" can include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylacticly and/or therapeutically. For example, the term "treating" in reference to a disorder means a reduction in severity of one or more symptoms associated with a particular disorder. Therefore, treating a disorder does not necessarily mean a reduction in severity of all symptoms associated with a disorder and does not necessarily mean a complete reduction in the severity of one or more symptoms associated with a disorder. For example, a method for treatment of obesity can result in weight loss; however, the weight loss does not need to be enough such that the individual is no longer obese. It has been shown that even modest decreases in weight or related parameters such as BMI, waist circumference and percent body fat, can result in improvement of health, for example, lower blood pressure, improved blood lipid profiles, or a reduction in sleep apnea.

As used herein, "treatment of obesity in an individual in need thereof" refers to a judgment made by a healthcare practitioner that an individual requires or will benefit from treatment of obesity. This judgment is made based on a variety of factors that are in the realm of a healthcare practitioner's expertise, but that includes the knowledge that the individual has a condition that is treatable by the methods of the disclosure.

WEIGHT MANAGEMENT: As used herein, the term "weight management" means controlling body weight and in the context of the present disclosure is directed toward weight loss and the maintenance of weight loss (also called weight maintenance herein). In addition to controlling body weight, weight management includes controlling parameters related to body weight, for example, BMI, percent body fat and waist circumference. For example, weight management for an individual who is overweight or obese can mean losing weight with the goal of keeping weight in a healthier range. Also, for example, weight management for an individual who is overweight or obese can include losing body fat or circumference around the waist with or without the loss of body weight.

Maintenance of weight loss (weight maintenance) includes preventing, reducing or controlling weight gain after weight loss. It is well known that weight gain often occurs after weight loss. Weight loss can occur, for example, from dieting, exercising, illness, drug treatment, surgery or any combination of these methods, but often an individual that has lost weight will regain some or all of the lost weight. Therefore, weight maintenance in an individual who has lost weight can include preventing weight gain after weight loss, reducing the amount of weight gained after weight loss, controlling weight gain after weight loss or slowing the rate of weight gain after weight loss.

As used herein, "weight management in an individual in need thereof" refers to a judgment made by a healthcare practitioner that an individual requires or will benefit from weight management treatment. This judgment is made based on a variety of factors that are in the realm of a healthcare practitioner's expertise, but that includes the knowledge that the individual has a condition that is treatable by the methods disclosed herein.

Throughout this specification, unless the context requires otherwise, the word "comprise", or variations such as "comprises" or "comprising" will be understood to imply the inclusion of a stated step or element or integer or group of steps or elements or integers but not the exclusion of any other step or element or integer or group of elements or integers.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

Each embodiment described herein is to be applied mutatis mutandis to each and every other embodiment unless specifically stated otherwise.

Those skilled in the art will appreciate that the invention(s) described herein is susceptible to variations and modifications other than those specifically described. It is to be understood that the invention(s) includes all such variations and modifications. The invention(s) also includes all of the steps, features, compositions and compounds referred to or indicated in this specification, individually or collectively, and any and all combinations or any two or more of said steps or features unless specifically stated otherwise.

The present invention(s) is not to be limited in scope by the specific embodiments described herein, which are intended for the purpose of exemplification only. Functionally-equivalent products, compositions and methods are clearly within the scope of the invention(s), as described herein.

It is appreciated that certain features of the invention(s), which are, for clarity, described in the context of separate embodiments, can also be provided in combination in a single embodiment. Conversely, various features of the invention(s), which are, for brevity, described in the context of a single embodiment, can also be provided separately or in any suitable subcombination. For example, a method that recites prescribing or administering (R)-8-chloro-1-methyl-2,3,4,5-tetrahydro-1H-3-benzazepine can be separated into two methods; one reciting prescribing (R)-8-chloro-1-methyl-2,3,4,5-tetrahydro-1H-3-benzazepine and the other reciting administering (R)-8-chloro-1-methyl-2,3,4,5-tetrahydro-1H-3-benzazepine. In addition, for example, a method that recites prescribing (R)-8-chloro-1-methyl-2,3,4,5-tetrahydro-1H-3-benzazepine and a separate method of the invention reciting administering (R)-8-chloro-1-methyl-2,3,4,5-tetrahydro-1H-3-benzazepine can be combined into a single method reciting prescribing and/or administering (R)-8-chloro-1-methyl-2,3,4,5-tetrahydro-1H-3-benzazepine.

The selective 5-HT$_{2C}$-receptor agonist (R)-8-chloro-1-methyl-2,3,4,5-tetrahydro-H-3-benzazepine (Compound 1), is useful for, inter alia, weight management, including weight loss and maintenance of weight loss (weight maintenance). Compound 1 is disclosed in PCT patent publication WO2003/086303, which is incorporated herein by reference in its entirety.

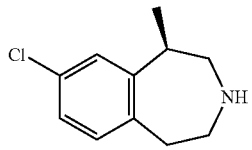

1

Various synthetic routes to (R)-8-chloro-1-methyl-2,3,4,5-tetrahydro-1H-3-benzazepine, its related salts, enantiomers, crystalline forms, and intermediates, have been reported in WO 2005/019179, WO2006/069363, WO2007/120517, WO2008/070111, and WO2009/111004 each of which is incorporated herein by reference in its entirety.

Combinations of (R)-8-Chloro-1-methyl-2,3,4,5-tetrahydro-H-3-benzazepine with other agents, including without limitation, phentermine, and uses of such combinations in therapy are described in WO2006/071740, which is incorporated herein by reference in its entirety.

(R)-8-Chloro-1-methyl-2,3,4,5-tetrahydro-1H-3-benzazepine hydrochloride (lorcaserin hydrochloride) is an agonist of the 5-HT$_{2C}$ receptor and shows effectiveness at reducing obesity in animal models and humans. In December 2009, Arena Pharmaceuticals submitted a New Drug Application, or NDA, for lorcaserin to the FDA. The NDA submission is based on an extensive data package from lorcaserin's clinical development program that includes 18 clinical trials totaling 8,576 patients. The pivotal phase 3 clinical trial program evaluated nearly 7,200 patients treated for up to two years, and showed that lorcaserin consistently produced significant weight loss with excellent tolerability. About two-thirds of patients achieved at least 5% weight loss and over one-third achieved at least 10% weight loss. On average, patients lost 17 to 18 pounds or about 8% of their weight. Secondary endpoints, including body composition, lipids, cardiovascular risk factors and glycemic parameters improved compared to placebo. Heart rate and blood pressure went down. Lorcaserin did not increase the risk of cardiac valvulopathy. Lorcaserin improved quality of life, and there was no signal for depression or suicidal ideation. The only adverse event that exceeded the placebo rate by 5% was generally mild or moderate, transient headache. Based on a normal BMI of 25, patients in the first phase 3 trial lost about one-third of their excess body weight. The average weight loss was 35 pounds or 16% of body weight for the top quartile of patients in the second phase 3 trial.

Throughout this application the compound (R)-8-chloro-1-methyl-2,3,4,5-tetrahydro-1H-3-benzazepine is also referred to as "Compound 1". Therefore, "Compound 1 or a pharmaceutically acceptable salt, solvate or hydrate thereof" is (R)-8-chloro-1-methyl-2,3,4,5-tetrahydro-1H-3-benzazepine or a pharmaceutically acceptable salt, solvate or hydrate thereof. Likewise, "Compound 1 hydrochloride and hydrates thereof" is (R)-8-chloro-1-methyl-2,3,4,5-tetrahydro-1H-3-benzazepine hydrochloride and hydrates thereof. Further, "Compound 1 hydrochloride hemihydrate" is (R)-8-chloro-1-methyl-2,3,4,5-tetrahydro-1H-3-benzazepine hydrochloride hemihydrate and "Compound 1 hydrochloride hemihydrate, Form III" is (R)-8-chloro-1-methyl-2,3,4,5-tetrahydro-H-3-benzazepine hydrochloride hemihydrate, Form III.

In some embodiments, the terms "(R)-8-chloro-1-methyl-2,3,4,5-tetrahydro-1H-3-benzazepine or a pharmaceutically acceptable salt, solvate, or hydrate thereof" and "(R)-8-chloro-1-methyl-2,3,4,5-tetrahydro-1H-3-benzazepine, and pharmaceutically acceptable salts, solvates, and hydrates thereof" as used herein encompass any one of the following salts, or a Markush group comprising any combination of the following salts:

(R)-8-chloro-1-methyl-2,3,4,5-tetrahydro-1H-3-benzazepine hydroiodide salt;
(R)-8-chloro-1-methyl-2,3,4,5-tetrahydro-1H-3-benzazepine maleate salt;
(R)-8-chloro-1-methyl-2,3,4,5-tetrahydro-1H-3-benzazepine fumarate salt; and
(R)-8-chloro-1-methyl-2,3,4,5-tetrahydro-1H-3-benzazepine hemifumarate salt;
(R)-8-chloro-1-methyl-2,3,4,5-tetrahydro-1H-3-benzazepine orotate salt;
(R)-8-chloro-1-methyl-2,3,4,5-tetrahydro-1H-3-benzazepine di-acetamidobenzoate salt-cocrystal;

(R)-8-chloro-1-methyl-2,3,4,5-tetrahydro-1H-3-benzazepine trans-cinnamate salt;
(R)-8-chloro-1-methyl-2,3,4,5-tetrahydro-1H-3-benzazepine heminapadisilate salt;
(R)-8-chloro-1-methyl-2,3,4,5-tetrahydro-1H-3-benzazepine (±)-mandelate salt;
(R)-8-chloro-1-methyl-2,3,4,5-tetrahydro-1H-3-benzazepine hemipamoate salt;
(R)-8-chloro-1-methyl-2,3,4,5-tetrahydro-1H-3-benzazepine (1S)-(+)-10-camsylate salt;
(R)-8-chloro-1-methyl-2,3,4,5-tetrahydro-1H-3-benzazepine hemi-L-malate salt;
(R)-8-chloro-1-methyl-2,3,4,5-tetrahydro-1H-3-benzazepine L-glutamate salt;
(R)-8-chloro-1-methyl-2,3,4,5-tetrahydro-1H-3-benzazepine L-aspartate salt;
(R)-8-chloro-1-methyl-2,3,4,5-tetrahydro-1H-3-benzazepine hemimucate salt;
(R)-8-chloro-1-methyl-2,3,4,5-tetrahydro-1H-3-benzazepine pyroglutamate salt;
(R)-8-chloro-1-methyl-2,3,4,5-tetrahydro-1H-3-benzazepine glucuronate salt; and
(R)-8-chloro-1-methyl-2,3,4,5-tetrahydro-1H-3-benzazepine di-camphorate salt;
(R)-8-chloro-1-methyl-2,3,4,5-tetrahydro-1H-3-benzazepine bisulfate salt;
(R)-8-chloro-1-methyl-2,3,4,5-tetrahydro-1H-3-benzazepine hemisulfate salt;
(R)-8-chloro-1-methyl-2,3,4,5-tetrahydro-1H-3-benzazepine mesylate salt;
(R)-8-chloro-1-methyl-2,3,4,5-tetrahydro-1H-3-benzazepine hydrobromide salt;
(R)-8-chloro-1-methyl-2,3,4,5-tetrahydro-1H-3-benzazepine nitrate salt;
(R)-8-chloro-1-methyl-2,3,4,5-tetrahydro-1H-3-benzazepine sesqui-oxalate salt-cocrystal;
(R)-8-chloro-1-methyl-2,3,4,5-tetrahydro-1H-3-benzazepine adipate salt;
(R)-8-chloro-1-methyl-2,3,4,5-tetrahydro-1H-3-benzazepine malonate salt;
(R)-8-chloro-1-methyl-2,3,4,5-tetrahydro-1H-3-benzazepine hemimalonate salt;
(R)-8-chloro-1-methyl-2,3,4,5-tetrahydro-1H-3-benzazepine glycolate salt;
(R)-8-chloro-1-methyl-2,3,4,5-tetrahydro-1H-3-benzazepine hemi-edisylate salt;
(R)-8-chloro-1-methyl-2,3,4,5-tetrahydro-1H-3-benzazepine phosphate salt;
(R)-8-chloro-1-methyl-2,3,4,5-tetrahydro-1H-3-benzazepine citrate salt;
(R)-8-chloro-1-methyl-2,3,4,5-tetrahydro-H-3-benzazepine hemi-oxalate salt;
(R)-8-chloro-1-methyl-2,3,4,5-tetrahydro-1H-3-benzazepine succinate salt; and
(R)-8-chloro-1-methyl-2,3,4,5-tetrahydro-1H-3-benzazepine oxoglutarate salt; and
pharmaceutically acceptable solvates and hydrates thereof.

In some embodiments, the terms "(R)-8-chloro-1-methyl-2,3,4,5-tetrahydro-1H-3-benzazepine or a pharmaceutically acceptable salt, solvate, or hydrate thereof" and "(R)-8-chloro-1-methyl-2,3,4,5-tetrahydro-1H-3-benzazepine, and pharmaceutically acceptable salts, solvates, and hydrates thereof" as used herein encompass any one of the following salts, or a Markush group comprising any combination of the following salts:
(R)-8-chloro-1-methyl-2,3,4,5-tetrahydro-1H-3-benzazepine hydroiodide salt;
(R)-8-chloro-1-methyl-2,3,4,5-tetrahydro-1H-3-benzazepine maleate salt;
(R)-8-chloro-1-methyl-2,3,4,5-tetrahydro-1H-3-benzazepine fumarate salt;
(R)-8-chloro-1-methyl-2,3,4,5-tetrahydro-1H-3-benzazepine hemifumarate salt;
(R)-8-chloro-1-methyl-2,3,4,5-tetrahydro-1H-3-benzazepine orotate salt;
(R)-8-chloro-1-methyl-2,3,4,5-tetrahydro-1H-3-benzazepine orotate salt hydrate;
(R)-8-chloro-1-methyl-2,3,4,5-tetrahydro-1H-3-benzazepine di-4-acetamidobenzoate salt-cocrystal methyl ethyl ketone solvate;
(R)-8-chloro-1-methyl-2,3,4,5-tetrahydro-1H-3-benzazepine trans-cinnamate salt;
(R)-8-chloro-1-methyl-2,3,4,5-tetrahydro-1H-3-benzazepine heminapadisilate salt;
(R)-8-chloro-1-methyl-2,3,4,5-tetrahydro-1H-3-benzazepine heminapadisilate salt solvate 1;
(R)-8-chloro-1-methyl-2,3,4,5-tetrahydro-1H-3-benzazepine heminapadisilate salt solvate 2;
(R)-8-chloro-1-methyl-2,3,4,5-tetrahydro-1H-3-benzazepine (t)-mandelate salt hydrate;
(R)-8-chloro-1-methyl-2,3,4,5-tetrahydro-1H-3-benzazepine hemipamoate salt hydrate;
(R)-8-chloro-1-methyl-2,3,4,5-tetrahydro-11H-3-benzazepine (1S)-(+)-10-camsylate salt;
(R)-8-chloro-1-methyl-2,3,4,5-tetrahydro-1H-3-benzazepine hemi-L-malate salt;
(R)-8-chloro-1-methyl-2,3,4,5-tetrahydro-1H-3-benzazepine L-glutamate salt;
(R)-8-chloro-1-methyl-2,3,4,5-tetrahydro-1H-3-benzazepine L-aspartate salt;
(R)-8-chloro-1-methyl-2,3,4,5-tetrahydro-1H-3-benzazepine hemimucate salt;
(R)-8-chloro-1-methyl-2,3,4,5-tetrahydro-1H-3-benzazepine pyroglutamate salt;
(R)-8-chloro-1-methyl-2,3,4,5-tetrahydro-1H-3-benzazepine glucuronate salt;
(R)-8-chloro-1-methyl-2,3,4,5-tetrahydro-1H-3-benzazepine di-camphorate salt solvate;
(R)-8-chloro-1-methyl-2,3,4,5-tetrahydro-1H-3-benzazepine bisulfate salt;
(R)-8-chloro-1-methyl-2,3,4,5-tetrahydro-1H-3-benzazepine hemisulfate salt hydrate;
(R)-8-chloro-1-methyl-2,3,4,5-tetrahydro-1H-3-benzazepine mesylate salt;
(R)-8-chloro-1-methyl-2,3,4,5-tetrahydro-1H-3-benzazepine hydrobromide salt hemihydrate;
(R)-8-chloro-1-methyl-2,3,4,5-tetrahydro-1H-3-benzazepine nitrate salt;
(R)-8-chloro-1-methyl-2,3,4,5-tetrahydro-1H-3-benzazepine sesqui-oxalate salt-cocrystal;
(R)-8-chloro-1-methyl-2,3,4,5-tetrahydro-1H-3-benzazepine adipate salt;
(R)-8-chloro-1-methyl-2,3,4,5-tetrahydro-1H-3-benzazepine malonate salt;
(R)-8-chloro-1-methyl-2,3,4,5-tetrahydro-1H-3-benzazepine hemimalonate salt;
(R)-8-chloro-1-methyl-2,3,4,5-tetrahydro-1H-3-benzazepine glycolate salt;
(R)-8-chloro-1-methyl-2,3,4,5-tetrahydro-H-3-benzazepine hemi-edisylate salt;
(R)-8-chloro-1-methyl-2,3,4,5-tetrahydro-1H-3-benzazepine phosphate salt;
(R)-8-chloro-1-methyl-2,3,4,5-tetrahydro-1H-3-benzazepine citrate salt hemihydrate;

(R)-8-chloro-1-methyl-2,3,4,5-tetrahydro-1H-3-benzazepine hemi-oxalate salt;
(R)-8-chloro-1-methyl-2,3,4,5-tetrahydro-1H-3-benzazepine succinate salt;
(R)-8-chloro-1-methyl-2,3,4,5-tetrahydro-1H-3-benzazepine oxoglutarate salt; and
(R)-8-chloro-1-methyl-2,3,4,5-tetrahydro-1H-3-benzazepine oxoglutarate salt solvate.

The preceding salts were prepared and characterized using the following experimental procedures and physicochemical data.

(R)-8-Chloro-1-methyl-2,3,4,5-tetrahydro-1H-3-benzazepine hydroiodide salt was prepared by the dropwise addition of one equivalent of aqueous HI (~57%) to a solution of (R)-8-chloro-1-methyl-2,3,4,5-tetrahydro-1H-3-benzazepine free base in isopropyl acetate. A precipitate formed after 7 days stirring with evaporation. The solid was slurried in ethyl acetate with ~3% water added for 5 h. The solid was recovered by centrifuge filtration (10,000 rpm for 1 minute, nylon filter). (R)-8-Chloro-1-methyl-2,3,4,5-tetrahydro-1H-3-benzazepine hydroiodide salt had an extrapolated melting onset temperature by DSC of 155-156° C.

(R)-8-Chloro-1-methyl-2,3,4,5-tetrahydro-1H-3-benzazepine maleate salt was prepared by dropwise addition of a solution of 1 or 2 equivalents of maleic acid in methanol to a solution of (R)-8-chloro-1-methyl-2,3,4,5-tetrahydro-1H-3-benzazepine free base in isopropyl acetate or acetonitrile with vigorous stirring. The resulting slurry was heated to 60° C. and held at that temperature for ~1 h before it was cooled to room temperature and stirred overnight. The title salt was recovered by filtration, washed with isopropyl acetate or acetonitrile and dried on the filter before characterization. (R)-8-Chloro-1-methyl-2,3,4,5-tetrahydro-1H-3-benzazepine maleate salt had an extrapolated melting onset temperature by DSC of about 166° C.

(R)-8-Chloro-1-methyl-2,3,4,5-tetrahydro-1H-3-benzazepine fumarate salt was prepared by dropwise addition of an equimolar amount of fumaric acid in 1:1 water:EtOH (~0.6 M) to a solution of (R)-8-chloro-1-methyl-2,3,4,5-tetrahydro-1H-3-benzazepine in isopropyl acetate with vigorous stirring. The resulting suspension was heated to 60° C., held at that temperature for 1 h, and then allowed to cool to ambient temperature while stirring overnight. The mixture was filtered and the solid was washed with isopropyl acetate and dried on the filter. Alternatively, (R)-8-chloro-1-methyl-2,3,4,5-tetrahydro-1H-3-benzazepine fumarate salt was prepared by adding either a half molar or an equimolar amount of dry solid fumaric acid to solution of (R)-8-chloro-1-methyl-2,3,4,5-tetrahydro-1H-3-benzazepine in isopropyl acetate. The mixture was slurried at ~60° C. and stirred for ~2 h. The heat source was removed and the mixture was left to stir for 3 days at ~26° C. The solid precipitate was recovered by filtration, and then re-slurried for ~24 h in water or ethanol. The solid was recovered by filtration and slurried for an additional 4 days in n-propanol, acetonitrile, or water. (R)-8-Chloro-1-methyl-2,3,4,5-tetrahydro-1H-3-benzazepine fumarate salt had an extrapolated melting onset temperature by DSC of 218-219° C.

(R)-8-Chloro-1-methyl-2,3,4,5-tetrahydro-1H-3-benzazepine hemifumarate salt was prepared by dropwise addition of a half-molar amount of fumaric acid in 1:1 water:EtOH (~0.6 M) to a solution of (R)-8-chloro-1-methyl-2,3,4,5-tetrahydro-1H-3-benzazepine in isopropyl acetate with vigorous stirring. A suspension resulted. It was heated to 60° C., held at that temperature for 1 h, and then the heat source was removed and the sample was allowed to cool to ambient temperature while stirring overnight. The suspension was filtered and the solid was washed with isopropyl acetate and dried on the filter. (R)-8-Chloro-1-methyl-2,3,4,5-tetrahydro-1H-3-benzazepine hemifumarate salt had an extrapolated melting onset temperature by DSC of 158° C.

(R)-8-Chloro-1-methyl-2,3,4,5-tetrahydro-H-3-benzazepine orotate salt was prepared by addition of one equivalent of orotic acid to a solution of (R)-8-chloro-1-methyl-2,3,4,5-tetrahydro-1H-3-benzazepine in isopropanol, ethyl acetate, or acetone at 60° C. Orotic acid, at 60° C., was added drop-wise, in the corresponding solvent, with vigorous stirring. Precipitation occurred immediately and the suspension was allowed to cool and stir overnight. The resulting solid was recovered by filtration and air-dried in a fume hood overnight. (R)-8-Chloro-1-methyl-2,3,4,5-tetrahydro-1H-3-benzazepine orotate salt had an extrapolated initial melting onset temperature by DSC of 236° C.

(R)-8-Chloro-1-methyl-2,3,4,5-tetrahydro-1H-3-benzazepine orotate salt hydrate was prepared by addition of one equivalent of orotic acid to a solution of (R)-8-chloro-1-methyl-2,3,4,5-tetrahydro-1H-3-benzazepine in acetonitrile or isopropanol at 60° C. Orotic acid, at 60° C., was added drop-wise, in the corresponding solvent, with vigorous stirring. Precipitation occurred immediately and the suspension was allowed to cool and stir overnight. Compound 1 orotate salt hydrate prepared in isopropanol consisted of a mixture of the anhydrous and hydrated forms which was converted to the hydrated form by slurring in isopropanol for two days. Alternatively, (R)-8-Chloro-1-methyl-2,3,4,5-tetrahydro-1H-3-benzazepine orotate salt hydrate was prepared by slurrying anhydrous (R)-8-chloro-1-methyl-2,3,4,5-tetrahydro-1H-3-benzazepine orotate salt in water. (R)-8-Chloro-1-methyl-2,3,4,5-tetrahydro-1H-3-benzazepine orotate salt hydrate had an extrapolated melt/recrystallization onset temperature by DSC of 173° C.

(R)-8-Chloro-1-methyl-2,3,4,5-tetrahydro-1H-3-benzazepine di-4-acetamidobenzoate salt-cocrystal methyl ethyl ketone solvate was prepared by combining one equivalent of 4-acetamidobenzoic acid with (R)-8-chloro-1-methyl-2,3,4,5-tetrahydro-1H-3-benzazepine in n-propanol or methanol at 50° C. then cooling slowly and stirring overnight. The resulting clear solution was evaporated to a mixture of oil and solids. Upon trituration with MEK a white solid formed and was filtered and dried. (R)-8-Chloro-1-methyl-2,3,4,5-tetrahydro-1H-3-benzazepine di-4-acetamidobenzoate salt-cocrystal methyl ethyl ketone solvate had an extrapolated melting/desolvation onset temperature by DSC of 113° C.

(R)-8-Chloro-1-methyl-2,3,4,5-tetrahydro-1H-3-benzazepine trans-cinnamate salt was prepared by combining one equivalent of trans-cinnamic acid with (R)-8-chloro-1-methyl-2,3,4,5-tetrahydro-1H-3-benzazepine in acetonitrile at 50° C. The sample was cooled slowly and stirred overnight. The resulting white solid was isolated by filtration and dried. Similar samples prepared in isopropanol, acetone or THF produced white solids only after removal of solvent and trituration with MTBE. (R)-8-Chloro-1-methyl-2,3,4,5-tetrahydro-1H-3-benzazepine trans-cinnamate salt had an extrapolated melting onset temperature by DSC of 106° C.

(R)-8-Chloro-1-methyl-2,3,4,5-tetrahydro-1H-3-benzazepine heminapadisilate salt was prepared by addition of a molar equivalent of naphthalene-1,5-disulfonic acid to a solution of (R)-8-chloro-1-methyl-2,3,4,5-tetrahydro-1H-3-benzazepine in isopropanol or acetonitrile at 60° C. Naphthalene-1,5-disulfonic acid, at 60° C., was added drop-wise, in the corresponding solvent, with vigorous stirring. Precipitation occurred immediately in acetonitrile and the suspension was allowed to cool and stir overnight. Addition of water precipitated the salt in isopropanol and the suspension was allowed to cool and stir overnight. The resulting solid was recovered by filtration and air-dried in a fume hood overnight. (R)-8-Chloro-1-methyl-2,3,4,5-tetrahydro-1H-3-benzazepine heminapadisilate salt had an extrapolated melting onset temperature by DSC of about 266° C.

(R)-8-Chloro-1-methyl-2,3,4,5-tetrahydro-1H-3-benzazepine heminapadisilate salt solvate 1 was prepared by addition of one equivalent of naphthalene-1,5-disulfonic acid to a solution of (R)-8-chloro-1-methyl-2,3,4,5-tetrahydro-1H-3-benzazepine in ethyl acetate at 60° C. Naphthalene-1,5-disulfonic acid in ethyl acetate, at 60° C., was added dropwise with vigorous stirring. Precipitation occurred immediately and the suspension was allowed to cool and stir overnight. The resulting solid was recovered by filtration and air-dried in a fume hood overnight. (R)-8-Chloro-1-methyl-2,3,4,5-tetrahydro-1H-3-benzazepine heminapadisilate salt solvate 1 had an extrapolated desolvation onset temperature by DSC of about 101° C.

(R)-8-Chloro-1-methyl-2,3,4,5-tetrahydro-1H-3-benzazepine heminapadisilate salt solvate 2 was prepared by the addition of one equivalent of naphthalene-1,5-disulfonic acid to a solution of (R)-8-chloro-1-methyl-2,3,4,5-tetrahydro-1H-3-benzazepine in acetone at 60° C. Naphthalene-1,5-disulfonic acid in acetone at 60° C. was added dropwise with vigorous stirring. A yellow oil precipitated and the suspension was allowed to cool and stir overnight. A white precipitate was observed after stirring overnight. The resulting solid was recovered by filtration and air-dried in a fume hood overnight. (R)-8-Chloro-1-methyl-2,3,4,5-tetrahydro-1H-3-benzazepine heminapadisilate salt solvate 2 had an extrapolated desolvation onset temperature by DSC of about 129° C.

(R)-8-Chloro-1-methyl-2,3,4,5-tetrahydro-1H-3-benzazepine (±)-mandelate salt hydrate was prepared by the addition of one equivalent of (±)-mandelic acid to a solution of (R)-8-chloro-1-methyl-2,3,4,5-tetrahydro-1H-3-benzazepine in acetonitrile, ethyl acetate, or acetone at 60° C. (±)-Mandelic acid, at 60° C., was added dropwise, in the corresponding solvent, with vigorous stirring. Addition of water to these three samples precipitated the salt and it was allowed to cool and stir overnight. The resulting solids were recovered by filtration and air-dried in a fume hood overnight. (R)-8-Chloro-1-methyl-2,3,4,5-tetrahydro-1H-3-benzazepine (±)-mandelate salt hydrate had an extrapolated desolvation onset temperature by DSC of about 74° C.

(R)-8-Chloro-1-methyl-2,3,4,5-tetrahydro-1H-3-benzazepine hemipamoate salt hydrate was prepared by the addition of 0.25 molar equivalents of pamoic acid to a solution of (R)-8-chloro-1-methyl-2,3,4,5-tetrahydro-1H-3-benzazepine in isopropanol, acetonitrile, ethyl acetate, or acetone at 60° C. Pamoic acid, at 60° C., was added dropwise, in the corresponding solvent, with vigorous stirring. Precipitation occurred immediately and the suspension was allowed to cool and stir overnight. The resulting solid was recovered by filtration and air-dried in a fume hood overnight. (R)-8-Chloro-1-methyl-2,3,4,5-tetrahydro-1H-3-benzazepine hemipamoate salt hydrate had an extrapolated melting onset temperature by DSC of about 244° C.

(R)-8-Chloro-1-methyl-2,3,4,5-tetrahydro-1H-3-benzazepine (1S)-(+)-10-camsylate salt was prepared by the dropwise addition of 1 mole equivalent of ~3.6 M aqueous (1S)-(+)-10-camphorsulfonic acid to a solution of (R)-8-chloro-1-methyl-2,3,4,5-tetrahydro-1H-3-benzazepine in acetonitrile with vigorous stirring. Immediate precipitation was observed and the solid was collected by filtration and washed with isopropyl alcohol. (R)-8-Chloro-1-methyl-2,3,4,5-tetrahydro-1H-3-benzazepine (1S)-(+)-10-camsylate salt had an extrapolated melting onset temperature by DSC of about 176° C.

(R)-8-Chloro-1-methyl-2,3,4,5-tetrahydro-1H-3-benzazepine hemi-L-malate salt was prepared by the dropwise addition of L-malic acid (0.5 eq.), either in solution in hot MeOH or as a solid, to a solution of (R)-8-chloro-1-methyl-2,3,4,5-tetrahydro-1H-3-benzazepine in isopropyl acetate. The mixture was heated to ~60° C. and held at that temperature for ~1 h. The mixture was then allowed to cool to room temperature and stirred for 1-3 days. The solid product was isolated by vacuum filtration and dried on the filter or in an oven at 40° C. (R)-8-Chloro-1-methyl-2,3,4,5-tetrahydro-1H-3-benzazepine hemi-L-malate salt had an extrapolated melting onset temperature by DSC of 155-156° C.

(R)-8-Chloro-1-methyl-2,3,4,5-tetrahydro-1H-3-benzazepine L-glutamate salt was prepared by addition of L-glutamic acid (0.5-1 eq.) in hot EtOH/H$_2$O (~2:1) to a solution of (R)-8-chloro-1-methyl-2,3,4,5-tetrahydro-1H-3-benzazepine in isopropyl acetate, followed by evaporation of the solvent overnight to produce a solid. The solid was slurried in isopropyl acetate and then isolated by filtration. Alternatively, (R)-8-Chloro-1-methyl-2,3,4,5-tetrahydro-1H-3-benzazepine L-glutamate salt was prepared by addition of a solution of L-glutamic acid (1 eq.) in hot H$_2$O to a solution of (R)-8-chloro-1-methyl-2,3,4,5-tetrahydro-1H-3-benzazepine. The product crystallized without the need for evaporation of the solvent. (R)-8-Chloro-1-methyl-2,3,4,5-tetrahydro-1H-3-benzazepine L-glutamate salt had an extrapolated melting onset temperature by DSC of about 187° C.

(R)-8-Chloro-1-methyl-2,3,4,5-tetrahydro-1H-3-benzazepine L-aspartate salt was prepared by addition of a solution of (R)-8-chloro-1-methyl-2,3,4,5-tetrahydro-1H-3-benzazepine in either acetone or acetonitrile to one equivalent of aspartic acid solid. The mixture was heated to 50° C. then slow-cooled and stirred overnight. (R)-8-Chloro-1-methyl-2,3,4,5-tetrahydro-1H-3-benzazepine L-aspartate salt had an extrapolated melting onset temperature by DSC of about 174° C.

(R)-8-Chloro-1-methyl-2,3,4,5-tetrahydro-1H-3-benzazepine hemimucate salt was synthesized from (R)-8-chloro-1-methyl-2,3,4,5-tetrahydro-H-3-benzazepine (2 equivalents) and mucic acid (I equivalent) in THF, acetone or IPA (~10 mg/mL) with 4% water. (R)-8-Chloro-1-methyl-2,3,4,5-tetrahydro-1H-3-benzazepine hemimucate salt had an extrapolated melting onset temperature by DSC of about 208° C.

(R)-8-Chloro-1-methyl-2,3,4,5-tetrahydro-1H-3-benzazepine glucuronate salt was prepared by addition of a molar equivalent of D-glucuronic acid to a solution of (R)-8-chloro-1-methyl-2,3,4,5-tetrahydro-1H-3-benzazepine in isopropanol, acetonitrile, ethyl acetate, or acetone at 60° C. D-glucuronic acid, dissolved in the corresponding solvent at 60° C., was added dropwise with vigorous stirring. Precipitation occurred immediately and the suspension was allowed to cool and stir overnight. The resulting solid was recovered by filtration and dried in a fume hood overnight. (R)-8-Chloro-1-methyl-2,3,4,5-tetrahydro-1H-3-benzazepine glucuronate salt had an extrapolated melting onset temperature by DSC of about 164° C.

(R)-8-Chloro-1-methyl-2,3,4,5-tetrahydro-1H-3-benzazepine pyroglutamate salt was prepared by combining one equivalent of pyroglutamic acid with (R)-8-chloro-1-methyl-2,3,4,5-tetrahydro-1H-3-benzazepine in ethyl acetate at 60° C. then cooling slowly and stirring overnight. The resulting white solid was isolated by filtration and dried. (R)-8-Chloro-1-methyl-2,3,4,5-tetrahydro-1H-3-benzazepine pyroglutamate salt had an extrapolated melting onset temperature by DSC of about 139° C.

(R)-8-Chloro-1-methyl-2,3,4,5-tetrahydro-1H-3-benzazepine di-camphorate salt solvate was prepared by combining equal molar amounts of (R)-8-chloro-1-methyl-2,3, 4,5-tetrahydro-1H-3-benzazepine and (1R,3S)-(+)-camphoric acid in ethyl acetate with 4% water. The solution was heated to 50° C. then slowly cooled. Upon cooling the sample was a clear solution and did not change after addition of MTBE. The sample was evaporated to a clear oil which formed a white solid after standing at room temperature. (R)-8-Chloro-1-methyl-2,3,4,5-tetrahydro-1H-3-benzazepine di-camphorate salt had an extrapolated melting onset temperature by DSC of about 90° C.

(R)-8-Chloro-1-methyl-2,3,4,5-tetrahydro-1H-3-benzazepine bisulfate salt was prepared by drop-wise addition of 1 mole equivalent of concentrated sulfuric acid to a solution of (R)-8-chloro-1-methyl-2,3,4,5-tetrahydro-1H-3-benzazepine free base in either isopropyl acetate or acetonitrile with vigorous stirring. Precipitation occurred immediately and the suspension was allowed to stir for 1 to 2 days. The resulting solid was recovered by filtration. (R)-8-Chloro-1-methyl-2,3,4,5-tetrahydro-H-3-benzazepine bisulfate salt had an extrapolated melting onset temperature by DSC of about 162° C.

(R)-8-Chloro-1-methyl-2,3,4,5-tetrahydro-1H-3-benzazepine hemisulfate salt was prepared by the drop-wise addition of 0.5 mole equivalent of concentrated sulfuric acid to a solution of (R)-8-chloro-1-methyl-2,3,4,5-tetrahydro-1H-3-benzazepine free base in either isopropyl acetate or acetonitrile with vigorous stirring. Precipitation occurred immediately and the suspension was allowed to stir for 1 to 2 days. The resulting yellow solid was recovered by filtration. Acetone was added to the solid followed by sufficient water to cause dispersal (<5%). This mixture was slurried for 4 h and the solid was collected by centrifuge filtration (10,000 rpm for 1 min). The filtrate contained an oil droplet and the filter cake had a small amount of color at the bottom. The white upper portion of the filter cake was removed and air-dried overnight to leave the title salt as a white solid. (R)-8-Chloro-1-methyl-2,3,4,5-tetrahydro-1H-3-benzazepine hemisulfate salt had an extrapolated melting onset temperature by DSC of about 79° C.

(R)-8-Chloro-1-methyl-2,3,4,5-tetrahydro-1H-3-benzazepine mesylate salt was prepared by the dropwise addition of one equivalent of methanesulfonic acid (99.5%) to a solution of (R)-8-chloro-1-methyl-2,3,4,5-tetrahydro-1H-3-benzazepine free base in acetonitrile, or isopropyl acetate with vigorous stirring. Crystallization occurred either immediately or within 24 hours after the solution was heated to ~60° C. and then allowed to cool to RT while stirring. (R)-8-Chloro-1-methyl-2,3,4,5-tetrahydro-1H-3-benzazepine mesylate salt had an extrapolated melting onset temperature by DSC of about 178° C.

(R)-8-Chloro-1-methyl-2,3,4,5-tetrahydro-H-3-benzazepine hydrobromide salt hemihydrate was prepared by the dropwise addition of one equivalent of aqueous HBr (~48%) to a solution of (R)-8-chloro-1-methyl-2,3,4,5-tetrahydro-1H-3-benzazepine free base in isopropyl acetate, acetonitrile, or ethyl acetate with vigorous stirring. The product readily precipitated from the reaction in isopropyl acetate. In acetonitrile the solvent was evaporated to near dryness to obtain a solid. In ethyl acetate, seeds were added and the reaction was allowed to stir unstoppered to initiate crystallization. The reaction was then closed and stirring was continued to afford a yellow suspension. The suspension was filtered and the solid was washed with cold ethyl acetate. The resulting white solid was under nitrogen at ~38° C., and held overnight at 25° C./75% RH. (R)-8-Chloro-1-methyl-2,3,4,5-tetrahydro-1H-3-benzazepine hydrobromide salt hemihydrate had an extrapolated dehydration onset temperature by TGA of about 72.5° C.

(R)-8-Chloro-1-methyl-2,3,4,5-tetrahydro-1H-3-benzazepine nitrate salt was prepared by dropwise addition of aqueous $HNO_3$ to a solution of (R)-8-chloro-1-methyl-2,3,4,5-tetrahydro-1H-3-benzazepine free base in isopropyl acetate or acetonitrile with vigorous stirring. (R)-8-Chloro-1-methyl-2,3,4,5-tetrahydro-1H-3-benzazepine nitrate salt had an extrapolated melting onset temperature by DSC of about 124° C.

(R)-8-Chloro-1-methyl-2,3,4,5-tetrahydro-1H-3-benzazepine sesqui-oxalate salt-cocrystal was prepared by addition of oxalic acid (0.5 eq.) to a solution of (R)-8-chloro-1-methyl-2,3,4,5-tetrahydro-H-3-benzazepine in isopropyl acetate. (R)-8-Chloro-1-methyl-2,3,4,5-tetrahydro-1H-3-benzazepine sesqui-oxalate salt-cocrystal had an initial endotherm with an extrapolated onset temperature by DSC of about 105° C. and a second endotherm with an extrapolated melting onset temperature by DSC of about 111° C.

(R)-8-Chloro-1-methyl-2,3,4,5-tetrahydro-1H-3-benzazepine adipate salt was prepared by addition of adipic acid (0.5-1 eq.) in acetone to a solution of (R)-8-chloro-1-methyl-2,3,4,5-tetrahydro-1H-3-benzazepine at ~62° C. Precipitation occurred within 5 min and the suspension was allowed to cool to ambient temperature with stirring. (R)-8-Chloro-1-methyl-2,3,4,5-tetrahydro-1H-3-benzazepine adipate salt had multiple endothermic events by DSC starting at onset temperatures between 104° C. and 107° C.

(R)-8-Chloro-1-methyl-2,3,4,5-tetrahydro-1H-3-benzazepine malonate salt was prepared by addition of malonic acid (1 eq.) to a solution of (R)-8-chloro-1-methyl-2,3,4,5-tetrahydro-1H-3-benzazepine in isopropyl acetate. (R)-8-Chloro-1-methyl-2,3,4,5-tetrahydro-1H-3-benzazepine malonate salt had an extrapolated melting onset temperature by DSC of about 143° C.

(R)-8-Chloro-1-methyl-2,3,4,5-tetrahydro-1H-3-benzazepine hemimalonate salt was prepared by addition of malonic acid (0.5 eq.) to a solution of (R)-8-chloro-1-methyl-2,3,4,5-tetrahydro-1H-3-benzazepine in isopropyl acetate. (R)-8-Chloro-1-methyl-2,3,4,5-tetrahydro-1H-3-benzazepine hemimalonate salt had an extrapolated melting onset temperature by DSC of 135-136° C.

(R)-8-Chloro-1-methyl-2,3,4,5-tetrahydro-1H-3-benzazepine glycolate salt was prepared by the addition of one equivalent of glycolic acid to a solution of (R)-8-chloro-1-methyl-2,3,4,5-tetrahydro-1H-3-benzazepine in ethyl acetate or acetone at 60° C. Glycolic acid, at 60° C., was added dropwise, in the corresponding solvent, with vigorous stirring. Precipitation occurred immediately and the suspension was allowed to cool and stir overnight. The resulting solid was recovered by filtration and air-dried in a fume hood overnight. (R)-8-Chloro-1-methyl-2,3,4,5-tetrahydro-1H-3-benzazepine glycolate salt had an extrapolated melting onset temperature by DSC of about 138° C.

(R)-8-Chloro-1-methyl-2,3,4,5-tetrahydro-1H-3-benzazepine hemi-edisylate salt was prepared by the dropwise addition of 0.5 equivalents of aqueous 1,2-ethanedisulfonic acid dihydrate (~3.7 M) to a solution of (R)-8-chloro-1-methyl-2,3,4,5-tetrahydro-1H-3-benzazepine free base in either acetonitrile or isopropyl acetate with vigorous stirring. Immediate precipitation was observed. The solid obtained was washed with isopropyl alcohol and allowed to dry on the filter. (R)-8-Chloro-1-methyl-2,3,4,5-tetrahydro-1H-3-benzazepine hemi-edisylate salt had an extrapolated melting onset temperature by DSC of about 298° C.

(R)-8-Chloro-1-methyl-2,3,4,5-tetrahydro-1H-3-benzazepine phosphate salt was prepared by dropwise addition of ortho-phosphoric acid (85%) (0.5-1 mole equivalent) to a solution of (R)-8-chloro-1-methyl-2,3,4,5-tetrahydro-1H-3-benzazepine free base in isopropyl acetate or acetonitrile with vigorous stirring. Immediate precipitation was observed in all experiments. Initially amorphous material was slurried in acetone; initially crystalline material was slurried/ripened in n-propanol for 3 days. (R)-8-Chloro-1-methyl-2,3,4,5-tetrahydro-1H-3-benzazepine phosphate salt had an extrapolated melting onset temperature by DSC of about 208° C.

(R)-8-Chloro-1-methyl-2,3,4,5-tetrahydro-1H-3-benzazepine citrate salt hemihydrate was prepared by dropwise addition of 1 mole equivalent of citric acid in hot MeOH to a solution of (R)-8-chloro-1-methyl-2,3,4,5-tetrahydro-1H-3-benzazepine in isopropyl acetate. Precipitation occurred spontaneously. (R)-8-Chloro-1-methyl-2,3,4,5-tetrahydro-1H-3-benzazepine citrate salt hemihydrate had a dehydration onset temperature by DSC of about 80° C.

(R)-8-Chloro-1-methyl-2,3,4,5-tetrahydro-1H-3-benzazepine hemi-oxalate salt was prepared by dropwise addition of 1 mole equivalent of oxalic acid as a solid or as a solution in MeOH (~2.5 M) to a solution of (R)-8-chloro-1-methyl-2,3,4,5-tetrahydro-1H-3-benzazepine in isopropyl acetate. (R)-8-Chloro-1-methyl-2,3,4,5-tetrahydro-1H-3-benzazepine hemi-oxalate salt had an extrapolated melting onset temperature by DSC of about 212° C.

(R)-8-Chloro-1-methyl-2,3,4,5-tetrahydro-1H-3-benzazepine succinate salt was prepared by the addition of succinic acid (0.5-1 eq.) in hot EtOH to a solution of (R)-8-chloro-1-methyl-2,3,4,5-tetrahydro-1H-3-benzazepine in isopropyl acetate. After overnight stirring, a solid was recovered by suction filtration and washed in isopropyl acetate. (R)-8-Chloro-1-methyl-2,3,4,5-tetrahydro-1H-3-benzazepine succinate salt had an extrapolated melting onset temperature by DSC of about 179.1° C.

(R)-8-Chloro-1-methyl-2,3,4,5-tetrahydro-1H-3-benzazepine oxoglutarate salt was prepared by addition of one equivalent of α-oxo-glutaric acid to a solution of (R)-8-chloro-1-methyl-2,3,4,5-tetrahydro-1H-3-benzazepine in ethyl acetate at 60° C. α-Oxo-glutaric acid in ethyl acetate at 60° C. was added dropwise with vigorous stirring. Precipitation occurred immediately and the suspension was allowed to cool and stir overnight. The resulting solid was recovered by filtration and air-dried in a fume hood overnight. (R)-8-Chloro-1-methyl-2,3,4,5-tetrahydro-1H-3-benzazepine oxoglutarate salt had an extrapolated melting onset temperature by DSC of about 115° C.

(R)-8-Chloro-1-methyl-2,3,4,5-tetrahydro-1H-3-benzazepine oxoglutarate salt solvate was prepared by addition of a molar equivalent of α-oxo-glutaric acid to a solution of (R)-8-chloro-1-methyl-2,3,4,5-tetrahydro-1H-3-benzazepine in acetonitrile at 60° C. α-Oxo-glutaric acid in acetonitrile at 60° C. was added dropwise with vigorous stirring. Precipitation occurred immediately and the suspension was allowed to cool and stir overnight. The resulting solid was recovered by filtration and air-dried in a fume hood overnight. (R)-8-Chloro-1-methyl-2,3,4,5-tetrahydro-1H-3-benzazepine oxoglutarate salt solvate had an extrapolated desolvation onset temperature by DSC of about 91° C., and a second endotherm with an extrapolated onset temperature by DSC of about 113° C.

It is understood that when the phrase "pharmaceutically acceptable salts, solvates and hydrates" or the phrase "pharmaceutically acceptable salt, solvate or hydrate" is used when referring to compounds described herein, it embraces pharmaceutically acceptable solvates and/or hydrates of the compounds, pharmaceutically acceptable salts of the compounds, as well as pharmaceutically acceptable solvates and/or hydrates of pharmaceutically acceptable salts of the compounds. It is also understood that when the phrase "pharmaceutically acceptable solvates and hydrates" or the phrase "pharmaceutically acceptable solvate or hydrate" is used when referring to compounds described herein that are salts, it embraces pharmaceutically acceptable solvates and/or hydrates of such salts.

It will be apparent to those skilled in the art that the dosage forms described herein may comprise, as the active component, either a compound described herein or a pharmaceutically acceptable salt or as a solvate or hydrate thereof. Moreover, various hydrates and solvates of the compounds described herein and their salts will find use as intermediates in the manufacture of pharmaceutical compositions. Typical procedures for making and identifying suitable hydrates and solvates, outside those mentioned herein, are well known to those in the art; see for example, pages 202-209 of K. J. Guillory, "Generation of Polymorphs, Hydrates, Solvates, and Amorphous Solids," in: Polymorphism in Pharmaceutical Solids, ed. Harry G. Britain, Vol. 95, Marcel Dekker, Inc., New York, 1999. Accordingly, one aspect of the present disclosure pertains to methods of administering hydrates and solvates of compounds described herein and/or their pharmaceutical acceptable salts, that can be isolated and characterized by methods known in the art, such as, thermogravimetric analysis (TGA), TGA-mass spectroscopy, TGA-Infrared spectroscopy, powder X-ray diffraction (XRPD), Karl Fisher titration, high resolution X-ray diffraction, and the like. There are several commercial entities that provide quick and efficient services for identifying solvates and hydrates on a routine basis. Example companies offering these services include Wilmington PharmaTech (Wilmington, Del.), Avantium Technologies (Amsterdam) and Aptuit (Greenwich, Conn.).

The present disclosure includes all isotopes of atoms occurring in the present compounds, salts and crystalline forms thereof. Isotopes include those atoms having the same atomic number but different mass numbers. By way of general example, and without limitation, isotopes of hydrogen include $^2H$ (deuterium) and $^3H$ (tritium). Isotopes of carbon include $^{13}C$ and $^{14}C$.

Generally, disclosed herein are methods for treating an indication, comprising determining the level of renal sufficiency of the individual and prescribing or administering a compound such as Compound 1 or a pharmaceutically acceptable salt, solvate or hydrate thereof to the individual. Several indications are encompassed as well as several different methods of determining the level of renal sufficiency of the individual, and different remedies are prescribed or administered to the individual. As disclosed above, certain features of the methods, which are, for clarity, described in the context of separate embodiments, can also be provided in combination in a single embodiment. Conversely, various features of the methods, which are, for brevity, described in the context of a single embodiment, can also be provided separately or in any suitable subcombination.

Regarding indications, the disclosure encompasses a method for weight management in an individual in need thereof, decreasing food intake in an individual, inducing satiety in an individual, for the treatment of obesity, and the prevention of obesity. In addition, the disclosure encompasses a method of weight loss in an individual or method for maintenance of weight loss in an individual. Further, the disclosure encompasses a method of treating an individual in need of treatment with Compound 1 or a pharmaceutically acceptable salt, solvate or hydrate thereof, and of treating a disorder related to 5-$HT_{2C}$ receptor activity. Any of these indications can be combined with any of the methods of determining the level of renal sufficiency in an individual, and any remedy prescribed or administered to the individual unless specifically stated otherwise or the context requires otherwise.

Regarding the methods of determining if the level of renal sufficiency in an individual, in some embodiments the level of renal sufficiency is determined by the Cockcroft-Gault equation which can be calculated using the individual's actual, ideal or otherwise adjusted body weight. In other embodiments the level of renal sufficiency is determined by calculating the glomerular filtration rate (GFR) of the individual by one of many methods known in the art such as using a radioactively labeled marker. The GFR can also be estimated using the Cockcroft-Gault equation or the modification of diet in renal disease (MDRD) formula, usually calculated with 4 or 6 variables. The serum creatinine concentration of the individual can also be used to determine the level of renal sufficiency of an individual. In some embodiments, the method of determining the level of renal sufficiency in the individual is not specified. In some embodiments the individual is asked about their level of renal sufficiency either orally or on a form.

The levels of renal sufficiency of an individual can include, for example, no renal impairment (i.e., normal renal function), mild renal impairment, moderate renal impairment, severe renal impairment and ESRD. In some embodiments, the level of renal sufficiency is not specified. The methods herein can comprise prescribing or administering different remedies such as Compound 1 or a pharmaceutically acceptable salt, solvate or hydrate thereof, Compound 1 hydrochloride and hydrates thereof, Compound 1 hydrochloride hemihydrate or Compound 1 hydrochloride hemihydrate, Form III. The method can also comprise prescribing or administering a reduced dosage regimen of Compound 1 or a pharmaceutically acceptable salt, solvate or hydrate thereof, or an anti-obesity drug other than Compound 1 or a pharmaceutically acceptable salt, solvate or hydrate thereof, or a reduced-calorie diet and/or regular exercise program.

Disclosed herein is a method for weight management in an individual in need thereof, comprising prescribing or administering a therapeutically effective amount of (R)-8-chloro-1-methyl-2,3,4,5-tetrahydro-H-3-benzazepine or a pharmaceutically acceptable salt, solvate or hydrate thereof to the individual, provided that the individual has a level of renal sufficiency selected from the group consisting of: no renal impairment, mild renal impairment, and moderate renal impairment.

Also disclosed is a method for weight management in an individual in need thereof, comprising: a) determining the level of renal sufficiency of the individual, and b) prescribing a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a level of renal sufficiency selected from the group consisting of: no renal impairment, mild renal impairment, and moderate renal impairment. In addition, disclosed herein is a method for weight management in an individual in need thereof, comprising: a) determining the level of renal sufficiency of the individual, and b) administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a level of renal sufficiency selected from the group consisting of: no renal impairment, mild renal impairment, and moderate renal impairment.

In addition, disclosed herein is a method for weight management in an individual in need thereof, comprising prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual does not have severe renal impairment or ESRD.

Also disclosed herein is a method for weight management in an individual in need thereof, comprising: a) determining the level of renal sufficiency of the individual, and b) prescribing therapeutically effective amount of (R)-8-chloro-1-methyl-2,3,4,5-tetrahydro-1H-3-benzazepine or a pharmaceutically acceptable salt, solvate or hydrate thereof to the individual, provided that the individual does not have severe renal impairment or ESRD. In addition, disclosed herein is a method for weight management in an individual in need thereof, comprising: a) determining the level of renal sufficiency of the individual, and b) administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual does not have severe renal impairment or ESRD.

If it is determined that (R)-8-chloro-1-methyl-2,3,4,5-tetrahydro-1H-3-benzazepine or a pharmaceutically acceptable salt, solvate or hydrate thereof can safely be given to an individual with severe renal impairment in any aspect or embodiment of the disclosure that includes prescribing or administering or otherwise using the compound for individuals with severe renal impairment or ESRD, the disclosure specifically embraces just prescribing or administering or otherwise using the compound for individuals with ESRD.

Therefore, for example, the disclosure provides a method for weight management in an individual in need thereof, comprising: a) determining the level of renal sufficiency of the individual, and b) prescribing therapeutically effective amount of (R)-8-chloro-1-methyl-2,3,4,5-tetrahydro-1H-3-benzazepine or a pharmaceutically acceptable salt, solvate or hydrate thereof to the individual, provided that the individual does not have ESRD. In addition, disclosed herein is a method for weight management in an individual in need thereof, comprising: a) determining the level of renal sufficiency of the individual, and b) administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual does not have ESRD.

Likewise any aspect or embodiment of the disclosure that includes prescribing or administering or otherwise using the compound for individuals with a level of renal sufficiency selected from the group consisting of: no renal impairment, mild renal impairment, and moderate renal impairment, the disclosure specifically embraces prescribing or administering or otherwise using the compound for individuals with a level of renal sufficiency selected from the group consisting of no renal impairment, mild renal impairment, moderate renal impairment and severe renal impairment.

Therefore, for example, the disclosure provides a method for weight management in an individual in need thereof, comprising: a) determining the level of renal sufficiency of the individual, and b) prescribing a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a level of renal sufficiency selected from the group consisting of: no renal impairment, mild renal impairment, moderate renal impairment, and severe renal impairment. In addition, the disclosure provides a method for weight management in an individual in need thereof, comprising: a) determining the level of renal sufficiency of the individual, and b) administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a level of renal sufficiency selected from the group consisting of: no renal impairment, mild renal impairment, moderate renal impairment and severe renal impairment.

Similarly, in some embodiments, the individual has ESRD.

In some embodiments (R)-8-chloro-1-methyl-2,3,4,5-tetrahydro-1H-3-benzazepine or a pharmaceutically acceptable salt, solvate or hydrate thereof is (R)-8-chloro-1-methyl-2,3,4,5-tetrahydro-1H-3-benzazepine hydrochloride and hydrates thereof.

In some embodiments (R)-8-chloro-1-methyl-2,3,4,5-tetrahydro-1H-3-benzazepine or a pharmaceutically acceptable salt, solvate or hydrate thereof is (R)-8-chloro-1-methyl-2,3,4,5-tetrahydro-1H-3-benzazepine hydrochloride hemihydrate.

In some embodiments (R)-8-chloro-1-methyl-2,3,4,5-tetrahydro-1H-3-benzazepine or a pharmaceutically acceptable salt, solvate or hydrate thereof is (R)-8-chloro-1-methyl-2,3,4,5-tetrahydro-1H-3-benzazepine hydrochloride hemihydrate, Form III (as described herein).

In some embodiments, the Cockcroft-Gault equation is used to determine the level of renal sufficiency of the individual.

In some embodiments, the individual's ideal body weight is used in the Cockcroft-Gault equation and in other embodiments the individual's actual body weight is used in the Cockcroft-Gault equation.

In some embodiments, the individual's serum creatinine concentration is used to determine the level of renal sufficiency of the individual.

As used herein, the term "weight management" means controlling body weight and in the context of the present disclosure is directed toward weight loss and the maintenance of weight loss (also called weight maintenance herein). In addition to controlling body weight, weight management includes controlling parameters related to body weight, for example, BMI, percent body fat and waist circumference. For example, weight management for an individual who is overweight or obese can mean losing weight with the goal of keeping weight in a healthier range. Also, for example, weight management for an individual who is overweight or obese can include losing body fat or circumference around the waist with or without the loss of body weight.

Maintenance of weight loss (weight maintenance) includes preventing, reducing or controlling weight gain after weight loss. It is well known that weight gain often occurs after weight loss. Weight loss can occur, for example, from dieting, exercising, illness, drug treatment, surgery or any combination of these methods, but often an individual that has lost weight will regain some or all of the lost weight Therefore, weight maintenance in an individual who has lost weight can include preventing weight gain after weight loss, reducing the amount of weigh gained after weight loss, controlling weight gain after weight loss or slowing the rate of weight gain after weight loss.

As used herein, an "individual" is a human. An individual can be an adult or prepubertal (a child) and can be of any gender. The individual can be a patient or other individual seeking treatment. The methods disclosed herein can also apply to non-human mammals such as livestock or pets.

As used herein, "weight management in an individual in need thereof" refers to a judgment made by a healthcare practitioner that an individual requires or will benefit from weight management treatment. This judgment is made based on a variety of factors that are in the realm of a healthcare practitioner's expertise, but that includes the knowledge that the individual has a condition that is treatable by the methods disclosed herein.

A healthcare practitioner can include, for example, a physician, nurse, nurse practitioner or other related health care professional who can prescribe or administer compounds (drugs) for weight management, decreasing food intake, inducing satiety, and treating or preventing obesity. In addition, a healthcare practitioner can include anyone who can recommend, prescribe, administer or prevent an individual from receiving a compound or drug including, for example, an insurance provider.

In some embodiments, an individual in need of weight management is an individual who is overweight. In some embodiments, an individual in need of weight management is an individual who has excess visceral adiposity. In some embodiments, an individual in need of weight management is an individual who is obese. To determine whether an individual is overweight or obese one can determine a body weight, a body mass index (BMI), a waist circumference or a body fat percentage of the individual to determine if the individual meets a body weight threshold, a BMI threshold, a waist circumference threshold or a body fat percentage threshold.

Determination of body weight can be through the use of a visual estimation of body weight, the use of a weight measuring device, such as an electronic weight scale or a mechanical beam scale. In some embodiments, an individual in need of weight management is an adult male with a body weight greater than about 90 kg, greater than about 100 kg, or greater than about 110 kg. In some embodiments, an individual in need of weight management is an adult female with a body weight greater than about 80 kg, greater than about 90 kg, or greater than about 100 kg. In some embodiments, the individual is prepubertal and has a body weight greater than about 30 kg, greater than about 40 kg, or greater than about 50 kg.

Whether an individual is overweight or obese can be determined on the basis of their body mass index (BMI) which is calculated by dividing body weight (kg) by height squared ($m^2$). Thus, the units of BMI are $kg/m^2$ and it is possible to calculate the BMI range associated with minimum mortality in each decade of life. According to the classification from the World Health Organization (W.H.O.), overweight is defined as a BMI in the range 25-30 $kg/m^2$, and obesity as a BMI greater than 30 $kg/m^2$ (see below for a detailed W.H.O. BMI classification).

| | BMI(kg/m2) | |
|---|---|---|
| Classification | Principal cut-off points | Additional cut-off points |
| Underweight | <18.50 | <18.50 |
| Severe thinness | <16.00 | <16.00 |
| Moderate thinness | 16.00-16.99 | 16.00-16.99 |
| Mild thinness | 17.00-18.49 | 17.00-18.49 |
| Normal range | 18.50-24.99 | 18.50-22.99 |
| | | 23.00-24.99 |
| Overweight | ≥25.00 | ≥25.00 |
| Pre-obese | 25.00-29.99 | 25.00-27.49 |
| | | 27.50-29.99 |
| Obese | ≥30.00 | ≥30.00 |
| Obese class I | 30.00-34.99 | 30.00-32.49 |
| | | 32.50-34.99 |
| Obese class II | 35.00-39.99 | 35.00-37.49 |
| | | 37.50-39.99 |
| Obese class III | ≥40.00 | ≥40.00 |

The International Classification of adult underweight, overweight and obesity according to BMI (World Health Organization)

Source: Adapted from WHO, 1995, WHO, 2000 and WHO 2004.

The healthy range of BMI, and other measures of whether one is overweight or obese, can also be dependent on genetic or racial differences. For example, since Asian populations develop negative health consequences at a lower BMI than Caucasians, some nations have redefined obesity for their populations. For example, in Japan any BMI greater than 25 is defined as obese and in China any BMI greater than 28 is defined as obese. Similarly, different threshold values for body weight, waist circumference or body fat percentage can be used for different populations of individuals. The additional cut-off points included in the table above (for example, 23, 27.5, 32.5 and 37.5) were added as points for public health action. The WHO recommends that countries should use all categories for reporting purposes with a view to facilitating international comparisons.

Determination of BMI can be through the use of a visual estimation of BMI, the use of a height measuring device such as a stadiometer or a height rod and the use of a weight measuring device, such as an electronic weight scale or a mechanical beam scale. In some embodiments, the individual in need of weight management is an adult with a BMI of greater than about 25 kg/m$^2$, greater than about 26 kg/m$^2$, greater than about 27 kg/m$^2$, greater than about 28 kg/m$^2$, greater than about 29 kg/m$^2$, greater than about 30 kg/m, greater than about 31 kg/m$^2$, greater than about 32 d kg/m$^2$, greater than about 33 kg/m$^2$, greater than about 34 kg/m$^2$, greater than about 35 kg/m$^2$, greater than about 36 kg/m$^2$, greater than about 37 kg/m$^2$, greater than about 38 kg/m$^2$, greater than about 39 kg/m$^2$, or greater than about 40 kg/m$^2$. In some embodiments, the individual is prepubertal with a BMI of greater than about 20 kg/m$^2$, greater than about 21 kg/m$^2$, greater than about 22 kg/m$^2$, greater than about 23 kg/m$^2$, greater than about 24 kg/m$^2$, greater than about 25 kg/m$^2$, greater than about 26 kg/m$^2$, greater than about 27 kg/m$^2$, greater than about 28 kg/m$^2$, greater than about 29 kg/m$^2$, greater than about 30 kg/m$^2$, greater than about 31 kg/m$^2$, greater than about 32 kg/m$^2$, greater than about 33 kg/m$^2$, greater than about 34 kg/m$^2$, or greater than about 35 kg/m$^2$.

Determination of waist circumference can be through the use of a visual estimation of waist circumference or the use of a waist circumference measuring device such as a tape measure.

Determinations of the healthy range of waist circumference and percentage body fat in an individual are dependent on gender. For example, women typically have smaller waist circumferences than men and so the waist circumference threshold for being overweight or obese is lower for a woman. In addition, women typically have a greater percentage of body fat than men and so the percentage body fat threshold for being overweight or obese for a woman is higher than for a man. Further, the healthy range of BMI and other measures of whether one is overweight or obese can be dependent on age. For example, the body weight threshold for considering whether one is overweight or obese is lower for a child (prepubertal individual) than an adult.

In some embodiments, the individual in need of weight management is an adult male with a waist circumference of greater than about 100 cm, greater than about 110 cm, greater than about 120 cm, greater than about 110 cm or an adult female with a waist circumference of greater than about 80 cm, greater than about 90 cm, or greater than about 100 cm. In some embodiments, the individual is prepubertal with a waist circumference of about of greater than about 60 cm, greater than about 70 cm, or greater than about 80 cm.

Determination of body fat percentage can be through the use of a visual estimation of body fat percentage or the use of a body fat percentage measuring device such as bioelectric impedance, computed tomography, magnetic resonance imaging, near infrared interactance, dual energy X ray absorptiometry, use of ultrasonic waves, use of body average density measurement, use of skinfold methods, or use of height and circumference methods. In some embodiments, the individual in need of weight management is an adult male with a body fat percentage of greater than about 25%, greater than about 30%, or greater than about 35% or an adult female with a body fat percentage of greater than about 30%, greater than about 35%, or greater than about 40%. In some embodiments, the individual is prepubertal with a body fat percentage of greater than about 30%, greater than about 35%, or greater than about 40%.

As used herein, the term "level of renal sufficiency" means the level of renal (kidney) function in an individual. As used herein, the levels of renal sufficiency in an individual include: no renal impairment, mild renal impairment, moderate renal impairment, severe renal impairment and end stage renal disease (ESRD). The term renal impairment includes mild renal impairment, moderate renal impairment, severe renal impairment and end stage renal disease (ESRD).

As disclosed herein, and known to one skilled in the art, there are several methods for determining the level of renal sufficiency in an individual. For example, the level of renal sufficiency in an individual can be determined by review of past testing done on the individual (i.e. the individual's renal sufficiency has previously been determined). In some embodiments, a health care practitioner determines the level of renal sufficiency of the individual by reading a report. A report can be, for example, a form or questionnaire that the individual or their representative fills out, a medical chart for the individual, a medical record for the individual or a laboratory report for the individual. Several tests to determine the level of renal sufficiency in an individual are known in the art and described herein. In some embodiments, a health care practitioner asks the individual their level of renal sufficiency (i.e. the individual self-reports their level of renal sufficiency).

The level of renal sufficiency in an individual can also be determined for the first time when the individual visits the health care practitioner. In some embodiments, an individual is asked orally or in writing a series of questions to determine the individual's level of renal sufficiency. Questions can include asking about risk factors that are related to renal sufficiency. Risk factors relevant to an individual's level of renal sufficiency include, for example, does the individual have diabetes, high blood pressure, gout, coronary artery disease, congestive heart failure, severe liver disease or a history of kidney surgery. Other risk factors associated with renal impairment that can be included are, for example, advanced age (for example, 60 years old or older), being male, use of a nephrotoxic drug such as furosemide, chemotherapy or HIV infection, protein in the urine, or a solitary kidney.

In some embodiments, an individual is given a test to determine the level of renal sufficiency of the individual. For example, a health care practitioner can order urinalysis or a blood panel for the individual. Urinalysis can include, for example, timed urine collection or a 24 hour urine collection. Urine can be analyzed for the level of protein, glucose, ketones or abnormal debris called casts or the level of specific markers such as creatinine can be determined. A blood panel can be analyzed for markers such as creatinine, blood urea nitrogen (BUN), and electrolytes, for example.

In some embodiments a glomerular filtration rate (GFR) or estimated GFR is determined for the individual to determine the level of renal sufficiency for the individual. GFR is currently considered to be an excellent overall index of renal function (see Lameire et al., Am J. of Cardiology 98:21K-26K (2006) and references therein). GFR can be defined as the volume of plasma cleared of an ideal substance per unit of time (usually expressed as mL/min). The GFR can be determined by measuring the renal excretion of a suitable marker such as inulin that is freely filtered at the glomerulus and not reabsorbed or secreted in the tubule. Standard inulin clearance requires an intravenous priming dose of inulin, followed by a constant infusion to establish a steady-state inulin plasma concentration. After an equilibration for about 45 minutes, serial urine samples are collected every 10-20 minutes through an indwelling bladder catheter or urine is obtained voluntarily every 20-30 minutes from an individual who is not catheterized. In practice, determination of GFR using inulin can be difficult since the collection of timed urine in individuals is inexact and there are often technical difficulties encountered in performing inulin infusion and reaching a steady state of inulin distribution (see Schwartz and Furth, Pediatr Nephrol 22:1839-1848 (2007) and references therein).

Because of difficulties with administering and measuring inulin, standard endogenous creatinine clearances have been used to estimate GFR. Creatinine results from the enzymatic degradation of creatine synthesized in skeletal muscle. Urinary excretion of creatinine is therefore a product of muscle catabolism and hence an index of muscle mass. Creatinine is eliminated exclusively by the kidneys via glomerular filtration and, to a lesser extent, by tubular secretion. Endogenous creatinine clearance can provide an acceptable measurement for GFR for clinical purposes. Creatinine clearance is often normalized to body surface area (BSA) by being multiplied by the factor 1.73/BSA in square meters. Creatinine clearance protocols require simplified urine collections; however, difficulties with collecting urine have led to protocols for estimating GFR from serum creatinine. Several formulas are used to estimate GFR including, for example, the Cockcroft-Gault equation and the Modification of Diet in Renal Disease (MDRD) formulas. In some embodiments, GFR is estimated using serum creatinine levels.

The Cockcroft-Gault equation estimates creatinine clearance on the basis of serum creatinine level, age, sex and weight (see Traynor et al. BMJ 33:733-737 (2006) and references therein). It is based on creatinine excretion in men with normal renal function with a correction for women. It tends to overestimate renal function at lower levels, particularly when obesity or fluid overload is present as the resultant increase in weight does not reflect an increase in muscle mass. As disclosed herein, an individual's ideal or otherwise adjusted body weight can be used in the Cockcroft-Gault equation or an individual's actual body weight can be used.

A Cockcroft-Gault equation is:

$$\text{Estimated creatinine clearance } (Cl_{Cr}) = \frac{(140 - \text{age}) \times \text{weight} \times 1.2}{SCr} \times (0.85 \text{ if female})$$

where age is expressed in years, SCr in micromole/L and weight in kg (see Traynor, ibid).

A Cockcroft-Gault equation using ideal body weight (IBW) is:

Female:
$$GFR \text{ (mL/min)} = 0.85 \times \frac{(140 - \text{age}) \times \text{ideal body weight (kg)}}{72 \times \text{serum creatinine (mg/dL)}}$$

Male:
$$GFR \text{ (mL/min)} = \frac{(140 - \text{age}) \times \text{ideal body weight (kg)}}{72 \times \text{serum creatinine (mg/dL)}}$$

Estimate Ideal Body Weight (IBW) in kg
Females: IBW=45.5 kg+2.3 kg for each inch over 5 feet
Males: IBW=50 kg+2.3 kg for each inch over 5 feet A formula derived from data on individuals with advanced renal failure in the Modification of Diet in Renal Disease Study is referred to as the 6-variable MDRD. This formula gives an estimate of glomerular filtration rate in mL/min adjusted for body surface area of 1.73 m² and is based on an individual's age, sex, race and levels of serum urea, serum creatinine and serum albumin. For example, different numbers are used if an individual is black or part of the African American race. A simplified version of the formula using only an individual's age, sex, race, and serum creatinine level is referred to as the 4-variable MDRD.

A 6-variable MDRD is:
$170 \times (S_{Cr}/88.4)^{-0.999} \times \text{age}^{-0.176} \times (SU/0.357)^{-0.170} \times (SAlb \times 10)^{+0.318} \times (0.762 \text{ if female}) \times (1.80 \text{ if black})$ where $S_{Cr}$=serum creatinine in micromole/L, sU=serum urea in millimol/L, SAlb=serum albumin in g/L, and age is expressed in years (sec Traynor, ibid)

A 4-variable MDRD is:
$186.3 \times (S_{Cr}/88.4)^{-1.154} \times \text{age}^{-0.203} \times (0.742 \text{ if female}) \times (1.21 \text{ if black})$ where $S_{Cr}$=serum creatinine in micromole/L and age is expressed in years (see Traynor, ibid)

A modified 4-variable MDRD (traceable by isotope dilution mass spectrometry) is:
$F \times 175 \times (S_{Cr}/88.4)^{-1.154} \times \text{age}^{-0.203} \times (0.742 \text{ if female}) \times (1.21 \text{ if black})$
where F=correction factor, $S_{Cr}$=serum creatinine in micromole/L and age is expressed in years (see Traynor, ibid)

In addition to measurement of creatinine, protocols exist for estimating GFR using cystatin C. Because cystatin C is metabolized and not excreted it cannot be used to measure GFR by standard urinary clearance techniques, but is measured instead from the blood.

Another method for determining GFR is to use a single injection clearance technique. The renal clearance of a substance that is not metabolically produced or degraded, and that is excreted from the body completely or almost completely in the urine, can be calculated from compartmental analysis by monitoring its rate of disappearance from the plasma following a single intravenous injection. Radioactive markers used for single injection clearance techniques include, for example, $^{125}$I-iothalamate, chromium ethylenediamine tetracetic acid ($^{51}$Cr-EDTA), or diethylenetriamine pentacetic acid ($^{99m}$Tc-DTPA). An alternative to the use of radioactivity is the use of a radiocontrast agent such as iohexol. Iohexol is a non-ionic, low osmolar, X-ray contract medium (Omnipaque; Amersham Health, NJ) that is eliminated from plasma exclusively by glomerular filtration. Both urinary clearance of iohexol and plasma disappearance of iohexol methods can be used to determine GFR.

As understood by one skilled in the art, other methods of determining the level of renal sufficiency of the individual are possible. For example, other formulas for estimating GFR are known in the art such as the Salazar-Corcoran equation. Also, for example, an absolute, non-corrected GFR can be used (Delanaye et al., Nephrol. Dial. Transplant (2005) 20:2024-2028). In addition, clearance of other compounds such as urea, urate, low molecular weight proteins such as beta 2 microglobulin, alpha 1 microglobulin and retinol binding protein are known in the art.

In some embodiments, GFR is determined using inulin clearance. In some embodiments, GFR is determined using creatinine clearance. In some embodiments, GFR is estimated using serum creatinine levels. In some embodiments, GFR is estimated using the Cockcroft-Gault equation. In some embodiments, the individual's actual body weight is used in the Cockcroft-Gault equation. In some embodiments, an adjusted body weight for the individual is used in the Cockcroft-Gault equation. In some embodiments, the individual's ideal body weight is used in the Cockcroft-Gault equation. In some embodiments, GFR is estimated using the Modification of Diet in Renal Disease (MDRD) formula. In some embodiments, GFR is estimated using the 6-variable Modification of Diet in Renal Disease (MDRD) formula. In some embodiments, GFR is estimated using the 4-variable Modification of Diet in Renal Disease (MDRD) formula. In some embodiments, GFR is estimated using cystatin C. In some embodiments GFR is determined using a single injection clearance technique. In some embodiments, GFR is determined using a radioactive marker. In some embodiments, GFR is determined using $^{125}$I-iothalamate, chromium ethylenediamine tetracetic acid ($^{51}$Cr-EDTA), or diethylenetriamine pentacetic acid ($^{99m}$Tc-DTPA). In some embodiments, GFR is determined using a radiocontrast agent. In some embodiments, GFR is determined using iohexol.

Accordingly, in some embodiments, the level of renal sufficiency in an individual is determined using inulin clearance. In some embodiments, the level of renal sufficiency in an individual is determined using creatinine clearance. In some embodiments, the level of renal sufficiency in an individual is estimated using serum creatinine levels. In some embodiments, the level of renal sufficiency in an individual is estimated using the Cockcroft-Gault equation. In some embodiments, the individual's actual body weight is used in the Cockcroft-Gault equation. In some embodiments, an adjusted body weight for the individual is used in the Cockcroft-Gault equation. In some embodiments, the individual's ideal body weight is used in the Cockcroft-Gault equation. In some embodiments, the level of renal sufficiency in an individual is estimated using the Modification of Diet in Renal Disease (MDRD) formula. In some embodiments, the level of renal sufficiency in an individual is estimated using the 6-variable Modification of Diet in Renal Disease (MDRD) formula. In some embodiments, the level of renal sufficiency in an individual is estimated using the 4-variable Modification of Diet in Renal Disease (MDRD) formula. In some embodiments, the level of renal sufficiency in an individual is estimated using cystatin C. In some embodiments the level of renal sufficiency in an individual is determined using a single injection clearance technique. In some embodiments, the level of renal sufficiency in an individual is determined using a radioactive marker. In some embodiments, the level of renal sufficiency in an individual is determined using $^{125}$I-iothalamate, chromium ethylenediamine tetracetic acid ($^{51}$Cr-EDTA), or diethylenetriamine pentacetic acid ($^{99m}$Tc-DTPA). In some embodiments, the level of renal sufficiency in an individual is determined using a radiocontrast agent. In some embodiments, the level of renal sufficiency in an individual is determined using iohexol.

As used herein, "no renal impairment" means the individual has normal renal function. Levels of renal function, renal sufficiency or renal impairment can be determined using any of the methods known in the art or described herein. Regarding terms such as "mild renal impairment", "moderate renal impairment", "severe renal impairment" and "end stage renal disease (ESRD)" cut-offs to define these levels of renal sufficiency are dependent on the test done to determine the level of renal sufficiency.

Different thresholds or cut-offs can be used to determine the level of renal sufficiency in an individual depending on the technique used and the interpretation of the health care practitioner. Several variables can be considered when determining the level of renal sufficiency in an individual including, for example, whether an individual is obese, the individual's race, the individual's gender, and the individual's age. Recommendations regarding classification of renal sufficiency are known in the art. These recommendations may change over time as newer techniques or better equations are used to more accurately determine renal function in an individual.

Currently, one common method for determining the level of renal sufficiency in an individual is determining creatinine clearance ($Cl_{Cr}$) in the individual using of the Cockcroft-Gault equation. As disclosed herein, the individual's actual body weight, ideal body weight, or otherwise adjusted body weight can be used in the equation. In some embodiments, the following are criteria for determining the level of renal sufficiency using creatinine clearance ($Cl_{Cr}$) and the Cockcroft-Gault equation:

Normal>80 mL/min

Mild renal impairment=51-80 mL/min
Moderate renal impairment=31-50 mL/min
Severe renal impairment=5-30 mL/min or ≤30 mL/min
End stage renal disease (ESRD) are those requiring dialysis Another method for determining the level of renal sufficiency in an individual is to determine an approximate serum creatinine (mg/dL) concentration for the individual. In some embodiments, a way to identify individuals with severe renal impairment (or ESRD) is to determine approximate serum creatinine (mg/dL) and use the following criteria to identify the individual as having severe renal impairment (or ESRD):

| | Approximate Serum Creatinine (mg/dL) | |
|---|---|---|
| Age Range | Men | Women |
| 18-20 | >4.9 | >3.5 |
| 21-30 | >4.5 | >3.2 |
| 31-40 | >4.1 | >2.9 |
| 41-50 | >3.7 | >2.7 |
| 51-60 | >3.3 | >2.4 |
| >60 | >3.0 | >2.0 |

As used herein, "prescribing" means to order, authorize or recommend the use of a drug or other therapy, remedy or treatment. In some embodiments, a health care practitioner can orally advise, recommend or authorize the use of a compound, dosage regimen or other treatment to an individual. In this case the health care practitioner may or may not provide a prescription for the compound, dosage regimen or treatment. Further the health care practitioner may or may not provide the recommended compound or treatment. For example, the health care practitioner can advise the individual where to obtain the compound without providing the compound. In some embodiments, a health care practitioner can provide a prescription for the compound, dosage regimen or treatment to the individual. For example, a health care practitioner can give a written or oral prescription to an individual. A prescription can be written on paper or on electronic media such as a computer file, for example, on a hand held computer device. For example, a health care practitioner can transform a piece of paper or electronic media with a prescription for a compound, dosage regimen or treatment. In addition, a prescription can be called in (oral) or faxed in (written) to a pharmacy or a dispensary. In some embodiments, a sample of the compound or treatment can be given to the individual. As used herein, giving a sample of a compound constitutes an implicit prescription for the compound. Different health care systems around the world use different methods for prescribing and administering compounds or treatments and these methods are encompassed by the disclosure.

A prescription can include, for example, an individual's name and/or identifying information such as date of birth. In addition, for example, a prescription can include, the medication name, medication strength, dose, frequency of administration, route of administration, number or amount to be dispensed, number of refills, physician name, physician signature. Further, for example, a prescription can include a DEA number or state number.

As used herein, "administering" means to provide a compound or other therapy, remedy or treatment. For example, a health care practitioner can directly provide a compound to an individual in the form of a sample, or can indirectly provide a compound to an individual by providing an oral or written prescription for the compound. Also, for example, an individual can obtain a compound by themselves without the involvement of a health care practitioner. Administration of the compound may or may not involve the individual actually internalizing the compound. In the case where an individual internalizes the compound the body is transformed by the compound in some way.

In some embodiments, a health care provider administers Compound 1 or a pharmaceutically acceptable salt, solvate or hydrate thereof to an individual in the form of a sample.

The disclosure provides a method for weight management in an individual in need thereof, comprising prescribing or administering a reduced dosage regimen of (R)-8-chloro-1-methyl-2,3,4,5-tetrahydro-1H-3-benzazepine or a pharmaceutically acceptable salt, solvate or hydrate thereof to the individual provided that the individual has renal impairment.

The disclosure also provides a method for weight management in an individual in need thereof, comprising: a) determining the level of renal sufficiency of the individual, and b) prescribing a reduced dosage regimen of (R)-8-chloro-1-methyl-2,3,4,5-tetrahydro-1H-3-benzazepine or a pharmaceutically acceptable salt, solvate or hydrate thereof to the individual provided that the individual has renal impairment. In addition, disclosed herein is a method for weight management in an individual in need thereof, comprising: a) determining the level of renal sufficiency of the individual, and b) administering a reduced dosage regimen of (R)-8-chloro-1-methyl-2,3,4,5-tetrahydro-H-3-benzazepine or a pharmaceutically acceptable salt, solvate or hydrate thereof to the individual provided that the individual has renal impairment. In some embodiments, the individual has mild renal impairment, moderate renal impairment, severe renal impairment or ESRD. In some embodiments, the individual has moderate renal impairment, severe renal impairment or ESRD. In some embodiments, the individual has severe renal impairment or ESRD. In some embodiments, the individual has ESRD.

A "reduced dosage regimen" as used herein means a reduction in the amount of a compound such as Compound 1 or a pharmaceutically acceptable salt, solvate or hydrate thereof that an individual is prescribed or administered in a fixed time period compared to the recommended dosage regimen. In some embodiments, the reduction in the amount of a compound that an individual is administered in a fixed time period compared to the recommended dosage is accomplished by reducing the amount of Compound 1 in each unit dose. For example, one recommended dosage regimen for Compound 1 or a pharmaceutically acceptable salt, solvate or hydrate thereof is a 10 mg capsule taken twice a day. A reduced dosage regimen can be a capsule (unit dose) with less than 10 mg taken twice a day, for example, a capsule with 9 mg, 8 mg, 7 mg, 6 mg, 5 mg, 4 mg, 3 mg, 2 mg, 1 mg or less than 1 mg taken twice a day. A capsule (unit dose) with less than 10 mg is an example of a low dosage formulation. In some embodiments, the reduction in the amount of a compound that an individual is administered in a fixed time period compared to the recommended dosage is accomplished by increasing the time interval between doses. For example, a 10 mg capsule can be administered once per day instead of twice per day to effectively reduce the dose. In addition, both a decrease in the amount of compound per unit dose and an increase the time interval between doses can be used. Since dosing can be dependent on body weight, it may be that a recommended dosage regimen is expressed in mg of compound per kg of body weight instead of a fixed amount of compound for all individuals. A reduction in the mg of compound per kg of body weight is an example of a reduced dosage regimen. Any embodiment that employs a reduced dosage regimen can equally employ a low dosage formulation.

Formulations, such as a low dosage formulation, can be prepared by any suitable method, typically by uniformly mixing the active compound(s) with liquids or finely divided solid carriers, or both, in the required proportions and then, if necessary, forming the resulting mixture into a desired shape.

Conventional excipients, such as binding agents, fillers, acceptable wetting agents, tabletting lubricants and disintegrants can be used in tablets and capsules for oral administration. Liquid preparations for oral administration can be in the form of solutions, emulsions, aqueous or oily suspensions and syrups. Alternatively, the oral preparations can be in the form of dry powder that can be reconstituted with water or another suitable liquid vehicle before use. Additional additives such as suspending or emulsifying agents, non-aqueous vehicles (including edible oils), preservatives and flavorings and colorants can be added to the liquid preparations. Parenteral dosage forms can be prepared by dissolving the compound in a suitable liquid vehicle and filter sterilizing the solution before filling and sealing an appropriate vial or ampule. These are just a few examples of the many appropriate methods well known in the art for preparing dosage forms. Suitable pharmaceutically-acceptable carriers, outside those mentioned herein, are known in the art; for example, see Remington, *The Science and Practice of Pharmacy,* 20$^{th}$ Edition, 2000, Lippincott Williams & Wilkins, (Editors: Gennaro et al.)

While it is possible that, for use in the prophylaxis or treatment, a compound can, in an alternative use, be administered as a raw or pure chemical, it is preferable however to present the compound or active ingredient as a pharmaceutical formulation or composition further comprising a pharmaceutically acceptable carrier.

Pharmaceutical formulations include those suitable for oral, rectal, nasal, topical (including buccal and sub-lingual), vaginal or parenteral (including intramuscular, subcutaneous and intravenous) administration or in a form suitable for administration by inhalation, insufflation or by a transdermal patch. Transdermal patches dispense a drug at a controlled rate by presenting the drug for absorption in an efficient manner with minimal degradation of the drug. Typically, transdermal patches comprise an impermeable backing layer, a single pressure sensitive adhesive and a removable protective layer with a release liner. One of ordinary skill in the art will understand and appreciate the techniques appropriate for manufacturing a desired efficacious transdermal patch based upon the needs of the artisan.

The compounds provided herein, together with a conventional adjuvant, carrier, or diluent, can thus be placed into the form of pharmaceutical formulations and unit dosages thereof and in such form may be employed as solids, such as tablets or filled capsules, or liquids such as solutions, suspensions, emulsions, elixirs, gels or capsules filled with the same, all for oral use, in the form of suppositories for rectal administration; or in the form of sterile injectable solutions for parenteral (including subcutaneous) use. Such pharmaceutical compositions and unit dosage forms thereof can comprise conventional ingredients in conventional proportions, with or without additional active compounds or principles and such unit dosage forms may contain any suitable effective amount of the active ingredient commensurate with the intended daily dosage range to be employed.

For oral administration, the pharmaceutical composition can be in the form of, for example, a tablet, capsule, suspension or liquid. The pharmaceutical composition is preferably made in the form of a dosage unit containing a particular amount of the active ingredient. Examples of such dosage units are capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate. The active ingredient may also be administered by injection as a composition wherein, for example, saline, dextrose or water may be used as a suitable pharmaceutically acceptable carrier.

The dose when using the compounds provided herein can vary within wide limits and as is customary and is known to the physician, it is to be tailored to the individual conditions in each individual case. It depends, for example, on the nature and severity of the illness to be treated, on the condition of the patient, on the compound employed or on whether an acute or chronic disease state is treated or prophylaxis conducted or on whether further active compounds are administered in addition to the compounds provided herein. Representative doses include, but are not limited to, about 0.001 mg to about 5000 mg, about 0.001 mg to about 2500 mg, about 0.001 mg to about 1000 mg, 0.001 mg to about 500 mg, 0.001 mg to about 250 mg, about 0.001 mg to 100 mg, about 0.001 mg to about 50 mg and about 0.001 mg to about 25 mg. Multiple doses may be administered during the day, especially when relatively large amounts are deemed to be needed, for example 2, 3 or 4 doses. Depending on the individual and as deemed appropriate from the patient's physician or caregiver it may be necessary to deviate upward or downward from the doses described herein.

The amount of active ingredient, or an active salt or derivative thereof, required for use in treatment will vary not only with the particular salt selected but also with the route of administration, the nature of the condition being treated and the age and condition of the patient and will ultimately be at the discretion of the attendant physician or clinician. In general, one skilled in the art understands how to extrapolate in vivo data obtained in a model system, typically an animal model, to another, such as a human. In some circumstances, these extrapolations may merely be based on the weight of the animal model in comparison to another, such as a mammal, preferably a human, however, more often, these extrapolations are not simply based on weights, but rather incorporate a variety of factors. Representative factors include the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized, on whether an acute or chronic disease state is being treated or prophylaxis conducted or on whether further active compounds are administered in addition to the compounds provided herein and as part of a drug combination. The dosage regimen for treating a disease condition with the compounds and/or compositions provided herein is selected in accordance with a variety factors as cited above. Thus, the actual dosage regimen employed may vary widely and therefore may deviate from a preferred dosage regimen and one skilled in the art will recognize that dosage and dosage regimen outside these typical ranges can be tested and, where appropriate, may be used in the methods disclosed herein.

The desired dose may conveniently be presented in a single dose or as divided doses administered at appropriate intervals, for example, as two, three, four or more sub-doses per day.

The sub-dose itself may be further divided, e.g., into a number of discrete loosely spaced administrations. The daily dose can be divided, especially when relatively large amounts are administered as deemed appropriate, into several, for example 2, 3 or 4 part administrations. If appropriate, depending on individual behavior, it may be necessary to deviate upward or downward from the daily dose indicated.

The compounds provided herein can be administered in a wide variety of oral and parenteral dosage forms. It will be obvious to those skilled in the art that the following dosage forms may comprise, as the active component, either a compound provided herein or a pharmaceutically acceptable salt, solvate or hydrate of a compound provided herein.

Some embodiments include a method of producing a pharmaceutical composition for "combination-therapy" comprising admixing at least one compound according to any of the compound embodiments disclosed herein, together with at least one known pharmaceutical agent as described herein and a pharmaceutically acceptable carrier.

Disclosed herein is a method for weight management in an individual in need thereof, comprising prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual provided that the individual has an approximate serum creatinine concentration of:
  (i) less than 4.9 mg/dL for an 18-20 year old man,
  (ii) less than 3.5 mg/dL for an 18-20 year old woman,
  (iii) less than 4.5 mg/dL for a 21-30 year old man,
  (iv) less than 3.2 mg/dL for a 21-30 year old woman,
  (v) less than 4.1 mg/dL for a 31-40 year old man,
  (vi) less than 2.9 mg/dL for a 31-40 year old woman,
  (viii) less than 2.7 mg/dL for a 41-50 year old woman,
  (ix) less than 3.3 mg/dL for a 51-60 year old man,
  (x) less than 2.4 mg/dL for a 51-60 year old woman,
  (xi) less than 3.0 mg/dL for a man over 60 years old, or
  (xii) less than 2.0 mg/dL for a woman over 60 years old.

In any aspect or embodiment where the following language is used "an approximate serum creatinine concentration of:
  (i) less than 4.9 ms/dL for an 18-20 year old man,
  (ii) less than 3.5 mg/dL for an 18-20 year old woman,
  (iii) less than 4.5 mg/dL for a 21-30 year old man,
  (iv) less than 3.2 mg/dL for a 21-30 year old woman,
  (v) less than 4.1 mg/dL for a 31-40 year old man,
  (vi) less than 2.9 mg/dL for a 31-40 year old woman,
  (viii) less than 2.7 mg/dL for a 41-50 year old woman,
  (ix) less than 3.3 mg/dL for a 51-60 year old man,
  (x) less than 2.4 mg/dL for a 51-60 year old woman,
  (xi) less than 3.0 mg/dL for a man over 60 years old, or
  (xii) less than 2.0 mg/dL for a woman over 60 years old"
    this is interpreted as being identical to: "a serum creatinine concentration of:
  (i) less than about 4.9 mg/dL for an 18-20 year old man,
  (ii) less than about 3.5 mg/dL for an 18-20 year old woman,
  (iii) less than about 4.5 mg/dL for a 21-30 year old man,
  (iv) less than about 3.2 mg/dL for a 21-30 year old woman,
  (v) less than about 4.1 mg/dL for a 31-40 year old man,
  (vi) less than about 2.9 mg/dL for a 31-40 year old woman,
  (viii) less than about 2.7 mg/dL for a 41-50 year old woman,
  (ix) less than about 3.3 mg/dL for a 51-60 year old man,
  (x) less than about 2.4 mg/dL for a 51-60 year old woman,
  (xi) less than about 3.0 mg/dL for a man over 60 years old, or
  (xii) less than about 2.0 mg/dL for a woman over 60 years old.

Similarly, in any aspect or embodiment where the following language is used "an approximate serum creatinine concentration of:
  (i) more than 4.9 mg/dL for an 18-20 year old man,
  (ii) more than 3.5 mg/dL for an 18-20 year old woman,
  (iii) more than 4.5 mg/dL for a 21-30 year old man,
  (iv) more than 3.2 mg/dL for a 21-30 year old woman,
  (v) more than 4.1 mg/dL for a 31-40 year old man,
  (vi) more than 2.9 mg/dL for a 31-40 year old woman,
  (viii) more than 2.7 mg/dL for a 41-50 year old woman,
  (ix) more than 3.3 mg/dL for a 51-60 year old man,
  (x) more than 2.4 mg/dL for a 51-60 year old woman,
  (xi) more than 3.0 mg/dL for a man over 60 years old, or
  (xii) more than 2.0 mg/dL for a woman over 60 years old
    this is interpreted as being identical to: "a serum creatinine concentration of:
  (i) more than about 4.9 mg/dL for an 18-20 year old man,
  (ii) more than about 3.5 mg/dL for an 18-20 year old woman,
  (iii) more than about 4.5 mg/dL for a 21-30 year old man,
  (iv) more than about 3.2 mg/dL for a 21-30 year old woman,
  (v) more than about 4.1 mg/dL for a 31-40 year old man,
  (vi) more than about 2.9 mg/dL for a 31-40 year old woman,
  (viii) more than about 2.7 mg/dL for a 41-50 year old woman,
  (ix) more than about 3.3 mg/dL for a 51-60 year old man,
  (x) more than about 2.4 mg/dL for a 51-60 year old woman,
  (xi) more than about 3.0 mg/dL for a man over 60 years old, or
  (xii) more than about 2.0 mg/dL for a woman over 60 years old."

Also disclosed herein is a method for weight management in an individual in need thereof, comprising a) determining an approximate serum creatinine concentration for the individual, and b) prescribing a therapeutically effective amount of (R)-8-chloro-1-methyl-2,3,4,5-tetrahydro-1H-3-benzazepine or a pharmaceutically acceptable salt, solvate or hydrate thereof to the individual provided that the individual has an approximate serum creatinine concentration of:
  (i) less than 4.9 mg/dL for an 18-20 year old man,
  (ii) less than 3.5 mg/dL for an 18-20 year old woman,
  (iii) less than 4.5 mg/dL for a 21-30 year old man,
  (iv) less than 3.2 mg/dL for a 21-30 year old woman,
  (v) less than 4.1 mg/dL for a 31-40 year old man,
  (vi) less than 2.9 mg/dL for a 31-40 year old woman,
  (viii) less than 2.7 mg/dL for a 41-50 year old woman,
  (ix) less than 3.3 mg/dL for a 51-60 year old man,
  (x) less than 2.4 mg/dL for a 51-60 year old woman,
  (xi) less than 3.0 mg/dL for a man over 60 years old, or
  (xii) less than 2.0 mg/dL for a woman over 60 years old.

In addition, disclosed herein is a method for weight management in an individual in need thereof, comprising: a) determining an approximate serum creatinine concentration for the individual, and b) administering a therapeutically effective amount of (R)-8-chloro-1-methyl-2,3,4,5-tetrahydro-1H-3-benzazepine or a pharmaceutically acceptable salt, solvate or hydrate thereof to the individual provided that the individual has an approximate serum creatinine concentration of:
  (i) less than 4.9 mg/dL for an 18-20 year old man,
  (ii) less than 3.5 mg/dL for an 18-20 year old woman,
  (iii) less than 4.5 mg/dL for a 21-30 year old man,
  (iv) less than 3.2 mg/dL for a 21-30 year old woman,
  (v) less than 4.1 mg/dL for a 31-40 year old man, (vi) less than 2.9 mg/dL for a 31-40 year old woman,
(vii) less than 3.7 mg/dL for a 41-50 year old man,
(viii) less than 2.7 mg/dL for a 41-50 year old woman,
(ix) less than 3.3 mg/dL for a 51-60 year old man,
(x) less than 2.4 mg/dL for a 51-60 year old woman,
(xi) less than 3.0 mg/dL for a man over 60 years old, or
(xii) less than 2.0 mg/dL for a woman over 60 years old.

Disclosed herein is a method for weight management in an individual in need thereof, comprising prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a creatinine clearance rate of greater than about 80 mL/minute, greater than about 50 mL/minute or greater than about 30 mL/minute using the Cockcroft-Gault equation.

Also disclosed is a method for weight management in an individual in need thereof, comprising: a) determining a creatinine clearance rate using the Cockcroft-Gault equation for the individual, and b) prescribing a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a creatinine clearance rate of greater than about 80 mL/minute using the Cockcroft-Gault equation. In addition, disclosed herein is a method for weight management in an individual in need thereof, comprising: a) determining a creatinine clearance rate using the Cockcroft-Gault equation for the individual, and b) administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a creatinine clearance rate of greater than about 80 mL/minute using the Cockcroft-Gault equation.

As used herein, the term "greater than" is used interchangeable with the symbol > and the term less than is used interchangeable with the symbol <. Likewise the term less than or equal to is interchangeable with the symbol ≤.

When an integer is used in a method disclosed herein, the term "about" can be inserted before the integer. For example, the term "greater than 80 mL/minute" can be substituted with "greater than about 80 mL/minute".

Disclosed herein is a method for weight management in an individual in need thereof, comprising: a) determining a creatinine clearance rate using the Cockcroft-Gault equation for the individual, and b) prescribing a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a creatinine clearance rate of greater than about 50 mL/minute using the Cockcroft-Gault equation. In addition, disclosed herein is a method for weight management in an individual in need thereof, comprising: a) determining a creatinine clearance rate using the Cockcroft-Gault equation for the individual, and b) administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a creatinine clearance rate of greater than about 50 mL/minute using the Cockcroft-Gault equation.

Disclosed herein is a method for weight management in an individual in need thereof, comprising: a) determining a creatinine clearance rate using the Cockcroft-Gault equation for the individual, and b) prescribing a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a creatinine clearance rate of greater than about 30 mL/minute using the Cockcroft-Gault equation. In addition, disclosed herein is a method for weight management in an individual in need thereof, comprising: a) determining a creatinine clearance rate using the Cockcroft-Gault equation for the individual, and b) administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a creatinine clearance rate of greater than about 30 mL/minute using the Cockcroft-Gault equation.

Generally, disclosed herein are methods for reducing the risk of an adverse event in an individual in need of treatment for an indication, comprising determining the level of renal sufficiency of the individual and prescribing or administering a compound such as Compound 1 or a pharmaceutically acceptable salt, solvate or hydrate thereof to the individual. Several indications are encompassed as well as several different methods of determining the level of renal sufficiency of the individual, and different remedies are prescribed or administered to the individual. As disclosed above, certain features of the methods, which are, for clarity, described in the context of separate embodiments, can also be provided in combination in a single embodiment. Conversely, various features of the methods, which are, for brevity, described in the context of a single embodiment, can also be provided separately or in any suitable subcombination.

Regarding indications, the disclosure encompasses a method for weight management in an individual in need thereof, decreasing food intake in an individual, inducing satiety in an individual, for the treatment of obesity, and the prevention of obesity. In addition, the disclosure encompasses a method of weight loss in an individual or method for maintenance of weight loss in an individual. Further, the disclosure encompasses a method of treating an individual in need of treatment with Compound 1 or a pharmaceutically acceptable salt, solvate or hydrate thereof, and of treating a disorder related to 5-HT$_{2C}$ receptor activity. Any of these indications can be combined with any of the methods of determining the level of renal sufficiency in an individual, and any remedy prescribed or administered to the individual unless specifically stated otherwise or the context requires otherwise.

Regarding the methods of determining the level of renal sufficiency in an individual, in some embodiments the level of renal sufficiency is determined by the Cockcroft-Gault equation which can be calculated using the individual's actual, ideal or otherwise adjusted body weight. In other embodiments the level of renal sufficiency is determined by calculating the glomerular filtration rate (GFR) of the individual by one of many methods known in the art such as using a radioactively labeled marker. The GFR can also be estimated using the Cockcroft-Gault equation or the modification of diet in renal disease (MDRD) formula, usually calculated with 4 or 6 variables. The serum creatinine concentration of the individual can also be used to determine the level of renal sufficiency of an individual. In some embodiments, the method of determining the level of renal sufficiency in the individual is not specified. In some embodiments the individual is asked about their level of renal sufficiency either orally or on a form.

The levels of renal sufficiency of an individual can include, for example, no renal impairment (i.e., normal renal function), mild renal impairment, moderate renal impairment, severe renal impairment and ESRD. In some embodiments, the level of renal sufficiency is not specified. The methods disclosed herein can comprise prescribing or administering different remedies such as Compound 1 or a pharmaceutically acceptable salt, solvate or hydrate thereof, Compound 1 hydrochloride and hydrates thereof, Compound 1 hydrochloride hemihydrate or Compound 1 hydrochloride hemihydrate, Form III. The method can also comprise prescribing or administering a reduced dosage regimen of Compound 1 or a pharmaceutically acceptable salt, solvate or hydrate thereof, or an anti-obesity drug other than Compound 1 or a pharmaceutically acceptable salt, solvate or hydrate thereof, or a reduced-calorie diet and/or regular exercise program.

Disclosed herein is a method for reducing the risk of an adverse event in an individual in need of weight management, comprising prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a level of renal sufficiency selected from the group consisting of: no renal impairment, mild renal impairment, and moderate renal impairment.

Disclosed herein is a method for reducing the risk of an adverse event in an individual in need of weight management, comprising: a) determining the level of renal sufficiency of the individual, and b) prescribing a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a level of renal sufficiency selected from the group consisting of: no renal impairment, mild renal impairment, and moderate renal impairment. Also disclosed herein is a method for reducing the risk of an adverse event in an individual in need of weight management, comprising: a) determining the level of renal sufficiency of the individual, and b) administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a level of renal sufficiency selected from the group consisting of: no renal impairment, mild renal impairment, and moderate renal impairment.

As used herein, an "adverse event" or "toxic event" is any untoward medical occurrence that may present itself during treatment. Adverse events associated with treatment with Compound 1 or a pharmaceutically acceptable salt, solvate or hydrate thereof are disclosed herein, for example, in Example 6 and Table 11. Possible adverse events disclosed in Example 6 include, abdominal pain, diarrhea, dyspepsia, stomach discomfort, and worsening renal impairment, dizziness, headache. Other possible adverse events based on observations from studies in monkeys include emesis, decreased food intake, weight loss, decreased activity, spontaneous penile erection, tremors or seizures. Additional possible adverse events include, for example, nausea, blurred vision, paresthesias, dry mouth and fatigue. In the methods disclosed herein, the term adverse event can be replaced by other more general terms such as toxicity. The term "reducing the risk" of an adverse event means reducing the probability that an adverse event or toxic event could occur.

Disclosed herein is a method for reducing the risk of an adverse event in an individual in need of weight management, comprising prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual does not have severe renal impairment or ESRD.

Also disclosed herein is a method for reducing the risk of an adverse event in an individual in need of weight management, comprising prescribing or administering a reduced dosage regimen of (R)-8-chloro-1-methyl-2,3,4,5-tetrahydro-1H-3-benzazepine or a pharmaceutically acceptable salt, solvate or hydrate thereof to the individual provided that the individual has renal impairment.

Disclosed herein is a method for reducing the risk of an adverse event in an individual in need of weight management, comprising: a) determining the level of renal sufficiency of the individual, and b) prescribing a reduced dosage regimen of (R)-8-chloro-1-methyl-2,3,4,5-tetrahydro-1H-3-benzazepine or a pharmaceutically acceptable salt, solvate or hydrate thereof to the individual provided that the individual has renal impairment. Also disclosed herein is a method for reducing the risk of an adverse event in an individual in need of weight management, comprising: a) determining the level of renal sufficiency of the individual, and b) administering a reduced dosage regimen of (R)-8-chloro-1-methyl-2,3,4,5-tetrahydro-1H-3-benzazepine or a pharmaceutically acceptable salt, solvate or hydrate thereof to the individual provided that the individual has renal impairment.

Further disclosed herein is a method for reducing the risk of an adverse event in an individual in need of weight management, comprising prescribing or administering a therapeutically effective amount of (R)-8-chloro-1-methyl-2,3,4,5-tetrahydro-H-3-benzazepine or a pharmaceutically acceptable salt, solvate or hydrate thereof to the individual provided that the individual has an approximate serum creatinine concentration of:
  (i) less than 4.9 mg/dL for an 18-20 year old man,
  (ii) less than 3.5 mg/dL for an 18-20 year old woman,
  (iii) less than 4.5 mg/dL for a 21-30 year old man,
  (iv) less than 3.2 mg/dL for a 21-30 year old woman,
  (v) less than 4.1 mg/dL for a 31-40 year old man,
  (vi) less than 2.9 mg/dL for a 31-40 year old woman,
  (vii) less than 3.7 mg/dL for a 41-50 year old man,
  (viii) less than 2.7 mg/dL for a 41-50 year old woman,
  (ix) less than 3.3 mg/dL for a 51-60 year old man,
  (x) less than 2.4 mg/dL for a 51-60 year old woman,
  (xi) less than 3.0 mg/dL for a man over 60 years old, or
  (xii) less than 2.0 mg/dL for a woman over 60 years old.

Disclosed herein is a method for reducing the risk of an adverse event in an individual in need of weight management, comprising: a) determining an approximate serum creatinine concentration for the individual, and b) prescribing a therapeutically effective amount of (R)-8-chloro-1-methyl-2,3,4,5-tetrahydro-1H-3-benzazepine or a pharmaceutically acceptable salt, solvate or hydrate thereof to the individual provided that the individual has an approximate serum creatinine concentration of:
  (i) less than 4.9 mg/dL for an 18-20 year old man,
  (ii) less than 3.5 mg/dL for an 18-20 year old woman,
  (iii) less than 4.5 mg/dL for a 21-30 year old man,
  (iv) less than 3.2 mg/dL for a 21-30 year old woman,
  (v) less than 4.1 mg/dL for a 31-40 year old man,
  (vi) less than 2.9 mg/dL for a 31-40 year old woman,
  (vii) less than 3.7 mg/dL for a 41-50 year old man,
  (viii) less than 2.7 mg/dL for a 41-50 year old woman,
  (ix) less than 3.3 mg/dL for a 51-60 year old man,
  (x) less than 2.4 mg/dL for a 51-60 year old woman,
  (xi) less than 3.0 mg/dL for a man over 60 years old, or (xii) less than 2.0 mg/dL for a woman over 60 years old.

Also disclosed herein is a method for reducing the risk of an adverse event in an individual in need of weight management, comprising: a) determining an approximate serum creatinine concentration for the individual, and b) administering a therapeutically effective amount of (R)-8-chloro-1-methyl-2,3,4,5-tetrahydro-1H-3-benzazepine or a pharmaceutically acceptable salt, solvate or hydrate thereof to the individual provided that the individual has an approximate serum creatinine concentration of:

(i) less than 4.9 mg/dL for an 18-20 year old man,
(ii) less than 3.5 mg/dL for an 18-20 year old woman,
(iii) less than 4.5 mg/dL for a 21-30 year old man,
(iv) less than 3.2 mg/dL for a 21-30 year old woman,
(v) less than 4.1 mg/dL for a 31-40 year old man,
(vi) less than 2.9 mg/dL for a 31-40 year old woman,
(vii) less than 3.7 mg/dL for a 41-50 year old man,
(viii) less than 2.7 mg/dL for a 41-50 year old woman,
(ix) less than 3.3 mg/dL for a 51-60 year old man,
(x) less than 2.4 mg/dL for a 51-60 year old woman,
(xi) less than 3.0 mg/dL for a man over 60 years old, or
(xii) less than 2.0 mg/dL for a woman over 60 years old.

Disclosed herein is a method for reducing the risk of an adverse event in an individual in need of weight management comprising prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a creatinine clearance rate of greater than about 80 mL/minute, greater than about 50 mL/minute or greater than about 30 mL/minute using the Cockcroft-Gault equation.

Generally, disclosed herein are methods for selecting an individual for treatment with (R)-8-chloro-1-methyl-2,3,4,5-tetrahydro-H-3-benzazepine or a pharmaceutically acceptable salt, solvate or hydrate thereof, comprising determining the level of renal sufficiency of the individual and selecting the individual for treatment with (R)-8-chloro-1-methyl-2,3,4,5-tetrahydro-1H-3-benzazepine or a pharmaceutically acceptable salt, solvate or hydrate thereof based on the individual's renal sufficiency.

Regarding the methods of determining the level of renal sufficiency in an individual, in some embodiments the level of renal sufficiency is determined by the Cockcroft-Gault equation which can be calculated using the individual's actual, ideal or otherwise adjusted body weight. In other embodiments the level of renal sufficiency is determined by calculating the glomerular filtration rate (GFR) of the individual by one of many methods known in the art such as using a radioactively labeled marker. The GFR can also be estimated using the Cockcroft-Gault equation or the modification of diet in renal disease (MDRD) formula, usually calculated with 4 or 6 variables. The serum creatinine concentration of the individual can also be used to determine the level of renal sufficiency of an individual. In some embodiments, the method of determining the level of renal sufficiency in the individual is not specified. In some embodiments the individual is asked about their level of renal sufficiency either orally or on a form.

The levels of renal sufficiency of an individual can include, for example, no renal impairment (i.e., normal renal function), mild renal impairment, moderate renal impairment, severe renal impairment and ESRD. In some embodiments, the level of renal sufficiency is not specified. The methods disclosed herein can comprise selecting the individual for treatment with different remedies such as Compound 1 or a pharmaceutically acceptable salt, solvate or hydrate thereof, Compound 1 hydrochloride and hydrates thereof, Compound 1 hydrochloride hemihydrate or Compound 1 hydrochloride hemihydrate, Form III. The method can also comprise selecting an individual for treatment with a reduced dosage regimen of Compound 1 or a pharmaceutically acceptable salt, solvate or hydrate thereof, or an anti-obesity drug other than Compound 1 or a pharmaceutically acceptable salt, solvate or hydrate thereof.

Disclosed herein is a method for selecting an individual for treatment with (R)-8-chloro-1-methyl-2,3,4,5-tetrahydro-1H-3-benzazepine or a pharmaceutically acceptable salt, solvate or hydrate thereof from a plurality of individuals in need of weight management, comprising selecting the individual for treatment with (R)-8-chloro-1-methyl-2,3,4,5-tetrahydro-1H-3-benzazepine or a pharmaceutically acceptable salt, solvate or hydrate thereof if the individual has a level of renal sufficiency selected from the group consisting of: no renal impairment, mild renal impairment, and moderate renal impairment.

As used herein, a "plurality of individuals" means more than one individual. For example, a plurality of individuals can be a small or large population of individuals. According to the methods disclosed herein, these individuals are screened for treatment with Compound 1 or a pharmaceutically acceptable salt, solvate or hydrate thereof based on their level of renal sufficiency.

Also disclosed herein is a method for selecting an individual for treatment with (R)-8-chloro-1-methyl-2,3,4,5-tetrahydro-1H-3-benzazepine or a pharmaceutically acceptable salt, solvate or hydrate thereof from a plurality of individuals in need of weight management, comprising: a) determining the level of renal sufficiency of the individual; and b) selecting the individual for treatment with (R)-8-chloro-1-methyl-2,3,4,5-tetrahydro-1H-3-benzazepine or a pharmaceutically acceptable salt, solvate or hydrate thereof if the individual has a level of renal sufficiency selected from the group consisting of: no renal impairment, mild renal impairment, and moderate renal impairment.

Disclosed herein is a method for selecting an individual for treatment with (R)-8-chloro-1-methyl-2,3,4,5-tetrahydro-1H-3-benzazepine or a pharmaceutically acceptable salt, solvate or hydrate thereof from a plurality of individuals in need of weight management, comprising selecting the individual for treatment with (R)-8-chloro-1-methyl-2,3,4,5-tetrahydro-1H-3-benzazepine or a pharmaceutically acceptable salt, solvate or hydrate thereof if the individual does not have severe renal impairment or ESRD.

Also disclosed herein is a method for selecting an individual for treatment with (R)-8-chloro-1-methyl-2,3,4,5-tetrahydro-1H-3-benzazepine or a pharmaceutically acceptable salt, solvate or hydrate thereof from a plurality of individuals in need of weight management, comprising selecting the individual for treatment with a reduced dosage regimen of (R)-8-chloro-1-methyl-2,3,4,5-tetrahydro-1H-3-benzazepine or a pharmaceutically acceptable salt, solvate or hydrate thereof if the individual has renal impairment.

Further disclosed herein is a method for selecting an individual for treatment with (R)-8-chloro-1-methyl-2,3,4, 5-tetrahydro-1H-3-benzazepine or a pharmaceutically acceptable salt, solvate or hydrate thereof from a plurality of individuals in need of weight management, comprising selecting the individual for treatment with (R)-8-chloro-1-methyl-2,3,4,5-tetrahydro-1H-3-benzazepine or a pharmaceutically acceptable salt, solvate or hydrate thereof if the individual has an approximate serum creatinine concentration of:

(i) less than 4.9 mg/dL for an 18-20 year old man,
(ii) less than 3.5 mg/dL for an 18-20 year old woman,
(iii) less than 4.5 mg/dL for a 21-30 year old man,
(iv) less than 3.2 mg/dL for a 21-30 year old woman,
(v) less than 4.1 mg/dL for a 31-40 year old man,
(vi) less than 2.9 mg/dL for a 31-40 year old woman,
(vii) less than 3.7 mg/dL for a 41-50 year old man,
(viii) less than 2.7 mg/dL for a 41-50 year old woman,
(ix) less than 3.3 mg/dL for a 51-60 year old man,
(x) less than 2.4 mg/dL for a 51-60 year old woman,
(xi) less than 3.0 mg/dL for a man over 60 years old, or
(xii) less than 2.0 mg/dL for a woman over 60 years old.

In addition, disclosed herein is a method for selecting an individual for treatment with (R)-8-chloro-1-methyl-2,3,4,5-tetrahydro-1H-3-benzazepine or a pharmaceutically acceptable salt, solvate or hydrate thereof from a plurality of individuals in need of weight management, comprising: a) determining an approximate serum creatinine concentration for the individual, and b) selecting the individual for treatment with (R)-8-chloro-1-methyl-2,3,4,5-tetrahydro-1H-3-benzazepine or a pharmaceutically acceptable salt, solvate or hydrate thereof if the individual has an approximate serum creatinine concentration of:
(i) less than 4.9 mg/dL for an 18-20 year old man,
(ii) less than 3.5 mg/dL for an 18-20 year old woman,
(iii) less than 4.5 mg/dL for a 21-30 year old man,
(iv) less than 3.2 mg/dL for a 21-30 year old woman,
(v) less than 4.1 mg/dL for a 31-40 year old man,
(vi) less than 2.9 mg/dL for a 31-40 year old woman,
(vii) less than 3.7 mg/dL for a 41-50 year old man,
(viii) less than 2.7 mg/dL for a 41-50 year old woman,
(ix) less than 3.3 mg/dL for a 51-60 year old man,
(x) less than 2.4 mg/dL for a 51-60 year old woman,
(xi) less than 3.0 mg/dL for a man over 60 years old, or
(xii) less than 2.0 mg/dL for a woman over 60 years old.

Further disclosed herein is a method for selecting an individual for treatment with (R)-8-chloro-1-methyl-2,3,4,5-tetrahydro-11H-3-benzazepine or a pharmaceutically acceptable salt, solvate or hydrate thereof from a plurality of individuals in need of weight management, comprising selecting the individual for treatment with (R)-8-chloro-1-methyl-2,3,4,5-tetrahydro-1H-3-benzazepine or a pharmaceutically acceptable salt, solvate or hydrate thereof provided that the individual has a creatinine clearance rate of greater than about 80 mL/minute, greater than about 50 mL/minute or greater than about 30 mL/minute using the Cockcroft-Gault equation.

Disclosed herein is a compound for use in a method of weight management in an individual, said method comprising prescribing said compound to said individual, wherein said individual has previously been determined to have a level of renal sufficiency selected from the group consisting of: no renal impairment, mild renal impairment, and moderate renal impairment; wherein said compound is (R)-8-chloro-1-methyl-2,3,4,5-tetrahydro-1H-3-benzazepine or a pharmaceutically acceptable salt, solvate or hydrate thereof. In addition, disclosed herein is a compound for use in a method of weight management in an individual, said method comprising administering said compound to said individual, wherein said individual has previously been determined to have a level of renal sufficiency selected from the group consisting of: no renal impairment, mild renal impairment, and moderate renal impairment; wherein said compound is (R)-8-chloro-1-methyl-2,3,4,5-tetrahydro-1H-3-benzazepine or a pharmaceutically acceptable salt, solvate or hydrate thereof.

For example, disclosed herein is a compound for use in a method of weight management in an individual, said method comprising prescribing a therapeutically effective amount of said compound to said individual, wherein said individual has previously been determined to have a level of renal sufficiency selected from the group consisting of: no renal impairment, mild renal impairment, and moderate renal impairment; wherein said compound is (R)-8-chloro-1-methyl-2,3,4,5-tetrahydro-1H-3-benzazepine or a pharmaceutically acceptable salt, solvate or hydrate thereof. In addition, disclosed herein is a compound for use in a method of weight management in an individual, said method comprising administering a therapeutically effective amount of said compound to said individual, wherein said individual has previously been determined to have a level of renal sufficiency selected from the group consisting of: no renal impairment, mild renal impairment, and moderate renal impairment; wherein said compound is (R)-8-chloro-1-methyl-2,3,4,5-tetrahydro-1H-3-benzazepine or a pharmaceutically acceptable salt, solvate or hydrate thereof.

Further disclosed herein is a compound for use in a method of weight management in an individual, said method comprising prescribing said compound at a dosage level appropriate for the level of renal sufficiency of said individual, wherein said individual has previously been determined to have a level of renal sufficiency selected from the group consisting of: no renal impairment, mild renal impairment, moderate renal impairment, severe renal impairment and ESRD; wherein said compound is (R)-8-chloro-1-methyl-2,3,4,5-tetrahydro-1H-3-benzazepine or a pharmaceutically acceptable salt, solvate or hydrate thereof. In addition, disclosed herein is a compound for use in a method of weight management in an individual, said method comprising administering said compound at a dosage level appropriate for the level of renal sufficiency of said individual, wherein said individual has previously been determined to have a level of renal sufficiency selected from the group consisting of: no renal impairment, mild renal impairment, moderate renal impairment, severe renal impairment and ESRD; wherein said compound is (R)-8-chloro-1-methyl-2,3,4,5-tetrahydro-1H-3-benzazepine or a pharmaceutically acceptable salt, solvate or hydrate thereof.

Also disclosed herein is a compound for use in a method of weight management in an individual, said method comprising determining the level of renal sufficiency of said individual and prescribing said compound at a dosage level appropriate for the level of renal sufficiency of said individual, wherein said individual has a level of renal sufficiency selected from the group consisting of: no renal impairment, mild renal impairment, moderate renal impairment, severe renal impairment and ESRD; wherein said compound is (R)-8-chloro-1-methyl-2,3,4,5-tetrahydro-1H-3-benzazepine or a pharmaceutically acceptable salt, solvate or hydrate thereof.

In addition, disclosed herein is a compound for use in a method of weight management in an individual, said method comprising determining the level of renal sufficiency of said individual and administering said compound at a dosage level appropriate for the level of renal sufficiency of said individual, wherein said individual has a level of renal sufficiency selected from the group consisting of: no renal impairment, mild renal impairment, moderate renal impairment, severe renal impairment and ESRD; wherein said compound is (R)-8-chloro-1-methyl-2,3,4,5-tetrahydro-1H-3-benzazepine or a pharmaceutically acceptable salt, solvate or hydrate thereof.

A dosage level appropriate for the level of renal sufficiency of an individual can be, for example, a dosage level as disclosed throughout this application. In some embodiments, a dosage level appropriate for the level of renal sufficiency is a full dosage regimen. In some embodiments, a dosage level appropriate for the level of renal sufficiency is 10 mg (R)-8-chloro-1-methyl-2,3,4,5-tetrahydro-1H-3-benzazepine or a pharmaceutically acceptable salt, solvate or hydrate thereof, twice a day. In some embodiments, a dosage level appropriate for the level of renal sufficiency is a reduced dosage regimen. In some embodiments, a low dosage formulation is a dosage level appropriate for a level of renal sufficiency. For example, a low dosage formulation of (R)-8-chloro-1-methyl-2,3,4,5-tetrahydro-1H-3-benzazepine or a pharmaceutically acceptable salt, solvate or hydrate thereof can be an appropriate dosage for an individual with renal impairment. In some embodiments, a dosage level appropriate for the level of renal sufficiency is no dose (i.e. the compound is not prescribed or administered). For example, the compound would not be prescribed or administered to an individual with severe renal impairment or ESRD For example, disclosed herein is a compound for use in a method of weight management in an individual, said method comprising prescribing or administering a reduced dosage regimen of said compound; wherein said compound is (R)-8-chloro-1-methyl-2,3,4,5-tetrahydro-1H-3-benzazepine or a pharmaceutically acceptable salt, solvate or hydrate thereof.

Disclosed herein is a compound for use in a method of weight management in an individual having moderate, mild or no renal impairment, said method comprising prescribing said compound to said individual, wherein said individual has previously been determined to have a level of renal sufficiency selected from the group consisting of: no renal impairment, mild renal impairment, and moderate renal impairment; wherein said compound is (R)-8-chloro-1-methyl-2,3,4,5-tetrahydro-1H-3-benzazepine or a pharmaceutically acceptable salt, solvate or hydrate thereof. In addition, disclosed herein is a compound for use in a method of weight management in an individual having moderate, mild or no renal impairment, said method comprising administering said compound to said individual, wherein said individual has previously been determined to have a level of renal sufficiency selected from the group consisting of: no renal impairment, mild renal impairment, and moderate renal impairment; wherein said compound is (R)-8-chloro-1-methyl-2,3,4,5-tetrahydro-1H-3-benzazepine or a pharmaceutically acceptable salt, solvate or hydrate thereof.

Also disclosed herein is a low dosage formulation of a compound for use in a method of weight management in an individual, said method comprising prescribing said low dosage formulation of the compound to said individual, wherein said individual has previously been determined to have renal impairment; wherein said compound is (R)-8-chloro-1-methyl-2,3,4,5-tetrahydro-1H-3-benzazepine or a pharmaceutically acceptable salt, solvate or hydrate thereof. In addition, disclosed herein is a low dosage formulation of a compound for use in a method of weight management in an individual, said method comprising administering said low dosage formulation of the compound to said individual, wherein said individual has previously been determined to have renal impairment; wherein said compound is (R)-8-chloro-1-methyl-2,3,4,5-tetrahydro-1H-3-benzazepine or a pharmaceutically acceptable salt, solvate or hydrate thereof.

Disclosed herein is a low dosage formulation of a compound for use in a method of weight management in an individual, wherein said low dosage reduces a toxic event in said individual to said compound, wherein said individual has previously been determined to have renal impairment; and wherein said compound is (R)-8-chloro-1-methyl-2,3,4,5-tetrahydro-1H-3-benzazepine or a pharmaceutically acceptable salt, solvate or hydrate thereof. In addition, disclosed herein is a low dosage formulation of a compound for use in a method of weight management in an individual, wherein said low dosage prevents a toxic event in said individual to said compound, wherein said individual has previously been determined to have renal impairment; and wherein said compound is (R)-8-chloro-1-methyl-2,3,4,5-tetrahydro-1H-3-benzazepine or a pharmaceutically acceptable salt, solvate or hydrate thereof.

One aspect of the present disclosure pertains to methods for weight management, comprising administering to an individual in need thereof, a therapeutically effective amount of a compound, a crystalline form, a pharmaceutical composition, or a dosage form of Compound 1. Compound 1 can be prescribed or administered as an adjunct to diet and exercise for weight management in an individual.

In some embodiments, the weight management comprises weight loss.

In some embodiments, the weight management comprises maintenance of weight loss.

In some embodiments, the weight management further comprises prescribing or administering a reduced-calorie diet.

In some embodiments, the weight management further comprises prescribing or administering a program of regular exercise.

In some embodiments, the weight management further comprises prescribing or administering both a reduced-calorie diet and a program of regular exercise.

In some embodiments, the individual is a patient with an initial body mass index $\geq 30$ kg/m$^2$.

In some embodiments, the individual is a patient with an initial body mass index $\geq 27$ kg/m$^2$ in the presence of at least one weight related comorbid condition.

In some embodiments, the individual is a patient with an initial body mass index $\geq 27$ kg/m$^2$ in the presence of at least one weight related comorbid condition selected from: hypertension, dyslipidemia, cardiovascular disease, glucose intolerance and sleep apnea.

In some embodiments, the individual has an initial body mass index $\geq 30$ kg/m$^2$.

In some embodiments, the individual has an initial body mass index $\geq 27$ kg/m$^2$.

In some embodiments, the individual has an initial body mass index $\geq 27$ kg/m$^2$ in the presence of at least one weight related comorbid condition.

In some embodiments, the individual has an initial body mass index $\geq 27$ kg/m$^2$ in the presence of at least one weight related comorbid condition selected from: hypertension, dyslipidemia, cardiovascular disease, glucose intolerance and sleep apnea.

In some embodiments, the individual has an initial body mass index $\geq 25$ kg/m$^2$.

In some embodiments, the individual has an initial body mass index $\geq 25$ kg/m$^2$ in the presence of at least one weight related comorbid condition.

In some embodiments, the individual has an initial body mass index $\geq 25$ kg/m$^2$ in the presence of at least one weight related comorbid condition selected from: hypertension, dyslipidemia, cardiovascular disease, glucose intolerance and sleep apnea.

In some embodiments, the method for weight management further comprises prescribing or administering a weight loss compound or procedure in addition to prescribing or administering (R)-8-chloro-1-methyl-2,3,4,5-tetrahydro-1H-3-benzazepine or a pharmaceutically acceptable salt, solvate or hydrate thereof. In some embodiments, the method for weight management further comprises prescribing or administering phentermine to the individual. In some embodiments, (R)-8-chloro-1-methyl-2,3,4,5-tetrahydro-H-3-benzazepine or a pharmaceutically acceptable salt, solvate or hydrate thereof is prescribed or administered before or after a surgical weight loss procedure, for example, a lap band or gastric bypass surgery.

Disclosed herein is a method for reducing the risk of an adverse event in an individual in need of weight management, comprising administering a therapeutically effective amount of (R)-8-chloro-1-methyl-2,3,4,5-tetrahydro-1H-3-benzazepine or a pharmaceutically acceptable salt, solvate or hydrate thereof to the individual, wherein the level of renal sufficiency of the individual has been determined, and provided that the individual has a level of renal sufficiency selected from the group consisting of: no renal impairment, mild renal impairment, and moderate renal impairment. Further disclosed herein is a method for reducing the risk of an adverse event in an individual in need of weight management, comprising administering a reduced dosage regimen of (R)-8-chloro-1-methyl-2,3,4,5-tetrahydro-1H-3-benzazepine or a pharmaceutically acceptable salt, solvate or hydrate thereof to the individual, wherein the level of renal sufficiency of the individual has been determined, and provided that the individual has renal impairment. Also disclosed herein is a method for reducing the risk of an adverse event in an individual in need of weight management, comprising administering a therapeutically effective amount of (R)-8-chloro-1-methyl-2,3,4,5-tetrahydro-1H-3-benzazepine or a pharmaceutically acceptable salt, solvate or hydrate thereof to the individual, wherein an approximate serum creatinine concentration has been determined for the individual, and provided that the individual has an approximate serum creatinine concentration of:

(i) less than 4.9 mg/dL for an 18-20 year old man,
(ii) less than 3.5 mg/dL for an 18-20 year old woman,
(iii) less than 4.5 mg/dL for a 21-30 year old man,
(iv) less than 3.2 mg/dL for a 21-30 year old woman,
(v) less than 4.1 mg/dL for a 31-40 year old man,
(vi) less than 2.9 mg/dL for a 31-40 year old woman,
(vii) less than 3.7 mg/dL for a 41-50 year old man,
(viii) less than 2.7 mg/dL for a 41-50 year old woman,
(ix) less than 3.3 mg/dL for a 51-60 year old man,
(x) less than 2.4 mg/dL for a 51-60 year old woman,
(xi) less than 3.0 mg/dL for a man over 60 years old, or
(xii) less than 2.0 mg/dL for a woman over 60 years old.

Disclosed herein is a method for selecting an individual for treatment with (R)-8-chloro-1-methyl-2,3,4,5-tetrahydro-1H-3-benzazepine or a pharmaceutically acceptable salt, solvate or hydrate thereof from a plurality of individuals in need of weight management, comprising selecting the individual for treatment with (R)-8-chloro-1-methyl-2,3,4,5-tetrahydro-H-3-benzazepine or a pharmaceutically acceptable salt, solvate or hydrate thereof if it is determined that the individual has a level of renal sufficiency selected from the group consisting of: no renal impairment, mild renal impairment, and moderate renal impairment. Further disclosed herein is a method for selecting an individual for treatment with (R)-8-chloro-1-methyl-2,3,4,5-tetrahydro-1H-3-benzazepine or a pharmaceutically acceptable salt, solvate or hydrate thereof from a plurality of individuals in need of weight management, comprising selecting the individual for treatment with (R)-8-chloro-1-methyl-2,3,4,5-tetrahydro-1H-3-benzazepine or a pharmaceutically acceptable salt, solvate or hydrate thereof if it is determined that the individual has an approximate serum creatinine concentration of:

(i) less than 4.9 mg/dL for an 18-20 year old man,
(ii) less than 3.5 mg/dL for an 18-20 year old woman,
(iii) less than 4.5 mg/dL for a 21-30 year old man,
(iv) less than 3.2 mg/dL for a 21-30 year old woman,
(v) less than 4.1 mg/dL for a 31-40 year old man,
(vi) less than 2.9 mg/dL for a 31-40 year old woman,
(vii) less than 3.7 mg/dL for a 41-50 year old man,
(viii) less than 2.7 mg/dL for a 41-50 year old woman,
(ix) less than 3.3 mg/dL for a 51-60 year old man,
(x) less than 2.4 mg/dL for a 51-60 year old woman,
(xi) less than 3.0 mg/dL for a man over 60 years old, or
(xii) less than 2.0 mg/dL for a woman over 60 years old.

Disclosed herein is a method for decreasing food intake in an individual in need thereof, comprising prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a level of renal sufficiency selected from the group consisting of: no renal impairment, mild renal impairment, and moderate renal impairment.

Also disclosed herein is a method for decreasing food intake in an individual in need thereof, comprising: a) determining the level of renal sufficiency of the individual, and b) prescribing a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a level of renal sufficiency selected from the group consisting of: no renal impairment, mild renal impairment, and moderate renal impairment. In addition, disclosed herein is a method for decreasing food intake in an individual in need thereof, comprising: a) determining the level of renal sufficiency of the individual, and b) administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a level of renal sufficiency selected from the group consisting of: no renal impairment, mild renal impairment, and moderate renal impairment.

In addition, disclosed herein is a method for decreasing food intake in an individual in need thereof, comprising prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual does not have severe renal impairment or end stage renal disease (ESRD).

Also disclosed herein is a method for decreasing food intake in an individual in need thereof, comprising: a) determining the level of renal sufficiency of the individual, and b) prescribing therapeutically effective amount of (R)-8-chloro-1-methyl-2,3,4,5-tetrahydro-1H-3-benzazepine or a pharmaceutically acceptable salt, solvate or hydrate thereof to the individual, provided that the individual does not have severe renal impairment or end stage renal disease (ESRD). In addition, disclosed herein is a method for decreasing food intake in an individual in need thereof, comprising: a) determining the level of renal sufficiency of the individual, and b) administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual does not have severe renal impairment or ESRD.

In some embodiments (R)-8-chloro-1-methyl-2,3,4,5-tetrahydro-1H-3-benzazepine or a pharmaceutically acceptable salt, solvate or hydrate thereof is (R)-8-chloro-1-methyl-2,3,4,5-tetrahydro-1H-3-benzazepine hydrochloride and hydrates thereof.

In some embodiments (R)-8-chloro-1-methyl-2,3,4,5-tetrahydro-1H-3-benzazepine or a pharmaceutically acceptable salt, solvate or hydrate thereof is (R)-8-chloro-1-methyl-2,3,4,5-tetrahydro-1H-3-benzazepine hydrochloride hemihydrate.

In some embodiments (R)-8-chloro-1-methyl-2,3,4,5-tetrahydro-1H-3-benzazepine or a pharmaceutically acceptable salt, solvate or hydrate thereof is (R)-8-chloro-1-methyl-2,3,4,5-tetrahydro-1H-3-benzazepine hydrochloride hemihydrate, Form III.

In some embodiments, the Cockcroft-Gault equation is used to determine the level of renal sufficiency of the individual.

In some embodiments, the individual's ideal body weight is used in the Cockcroft-Gault equation and in other embodiments the individual's actual body weight is used in the Cockcroft-Gault equation.

In some embodiments, the individual's serum creatinine concentration is used to determine the level of renal sufficiency of the individual.

As used herein, "decreasing food intake in an individual in need thereof" refers to a judgment made by a healthcare practitioner that an individual requires or will benefit from decreasing food intake. This judgment is made based on a variety of factors that are in the realm of a healthcare practitioner's expertise, but that includes the knowledge that the individual has a condition, for example, obesity, that is treatable by the methods disclosed herein.

In some embodiments, an individual in need of decreasing food intake is an individual who is overweight. In some embodiments, an individual in need of decreasing food intake is an individual who is obese.

Disclosed herein is a method for decreasing food intake in an individual in need thereof, comprising prescribing or administering a reduced dosage regimen of (R)-8-chloro-1-methyl-2,3,4,5-tetrahydro-1H-3-benzazepine or a pharmaceutically acceptable salt, solvate or hydrate thereof to the individual provided that the individual has renal impairment.

Also disclosed herein is a method for decreasing food intake in an individual in need thereof, comprising: a) determining the level of renal sufficiency of the individual, and b) prescribing a reduced dosage regimen of (R)-8-chloro-1-methyl-2,3,4,5-tetrahydro-1H-3-benzazepine or a pharmaceutically acceptable salt, solvate or hydrate thereof to the individual provided that the individual has renal impairment. In addition, disclosed herein is a method for decreasing food intake in an individual in need thereof, comprising: a) determining the level of renal sufficiency of the individual, and b) administering a reduced dosage regimen of (R)-8-chloro-1-methyl-2,3,4,5-tetrahydro-1H-3-benzazepine or a pharmaceutically acceptable salt, solvate or hydrate thereof to the individual provided that the individual has renal impairment. In some embodiments, the individual has mild renal impairment, moderate renal impairment, severe renal impairment or ESRD. In some embodiments, the individual has moderate renal impairment, severe renal impairment or ESRD. In some embodiments, the individual has severe renal impairment or ESRD. In some embodiments, the individual has ESRD.

Disclosed herein is a method for decreasing food intake in an individual in need thereof, comprising prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual provided that the individual has an approximate serum creatinine concentration of:
(i) less than 4.9 mg/dL for an 18-20 year old man,
(ii) less than 3.5 mg/dL for an 18-20 year old woman,
(iii) less than 4.5 mg/dL for a 21-30 year old man,
(iv) less than 3.2 mg/dL for a 21-30 year old woman,
(v) less than 4.1 mg/dL for a 31-40 year old man,
(vi) less than 2.9 mg/dL for a 31-40 year old woman,
(viii) less than 2.7 mg/dL for a 41-50 year old woman,
(ix) less than 3.3 mg/dL for a 51-60 year old man,
(x) less than 2.4 mg/dL for a 51-60 year old woman,
(xi) less than 3.0 mg/dL for a man over 60 years old, or
(xii) less than 2.0 mg/dL for a woman over 60 years old.

Also disclosed herein is a method for decreasing food intake in an individual in need thereof, comprising a) determining an approximate serum creatinine concentration for the individual, and b) prescribing a therapeutically effective amount of (R)-8-chloro-1-methyl-2,3,4,5-tetrahydro-1H-3-benzazepine or a pharmaceutically acceptable salt, solvate or hydrate thereof to the individual provided that the individual has an approximate serum creatinine concentration of:
(i) less than 4.9 mg/dL for an 18-20 year old man,
(ii) less than 3.5 mg/dL for an 18-20 year old woman,
(iii) less than 4.5 mg/dL for a 21-30 year old man,
(iv) less than 3.2 mg/dL for a 21-30 year old woman,
(v) less than 4.1 mg/dL for a 31-40 year old man,
(vi) less than 2.9 mg/dL for a 31-40 year old woman,
(viii) less than 2.7 mg/dL for a 41-50 year old woman,
(ix) less than 3.3 mg/dL for a 51-60 year old man,
(x) less than 2.4 mg/dL for a 51-60 year old woman,
(xi) less than 3.0 mg/dL for a man over 60 years old, or
(xii) less than 2.0 mg/dL for a woman over 60 years old.

In addition, disclosed herein is a method for decreasing food intake in an individual in need thereof, comprising: a) determining an approximate serum creatinine concentration for the individual, and b) administering a therapeutically effective amount of (R)-8-chloro-1-methyl-2,3,4,5-tetrahydro-1H-3-benzazepine or a pharmaceutically acceptable salt, solvate or hydrate thereof to the individual provided that the individual has an approximate serum creatinine concentration of:
(i) less than 4.9 mg/dL for an 18-20 year old man,
(ii) less than 3.5 mg/dL for an 18-20 year old woman,
(iii) less than 4.5 mg/dL for a 21-30 year old man,
(iv) less than 3.2 mg/dL for a 21-30 year old woman,
(v) less than 4.1 mg/dL for a 31-40 year old man,
(vi) less than 2.9 mg/dL for a 31-40 year old woman,
(vii) less than 3.7 mg/dL for a 41-50 year old man,
(viii) less than 2.7 mg/dL for a 41-50 year old woman,
(ix) less than 3.3 mg/dL for a 51-60 year old man,
(x) less than 2.4 mg/dL for a 51-60 year old woman,
(xi) less than 3.0 mg/dL for a man over 60 years old, or
(xii) less than 2.0 mg/dL for a woman over 60 years old.

Disclosed herein is a method for decreasing food intake in an individual in need thereof, comprising prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a creatinine clearance rate of greater than about 80 mL/minute, greater than about 50 mL/minute or greater than about 30 mL/minute using the Cockcroft-Gault equation.

Also disclosed herein is a method for decreasing food intake in an individual in need thereof, comprising: a) determining a creatinine clearance rate using the Cockcroft-Gault equation for the individual, and b) prescribing a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a creatinine clearance rate of greater than about 80 mL/minute using the Cockcroft-Gault equation. In addition, disclosed herein is a method for decreasing food intake in an individual in need thereof, comprising: a) determining a creatinine clearance rate using the Cockcroft-Gault equation for the individual, and b) administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a creatinine clearance rate of greater than about 80 mL/minute using the Cockcroft-Gault equation.

Disclosed herein is a method for decreasing food intake in an individual in need thereof, comprising: a) determining a creatinine clearance rate using the Cockcroft-Gault equation for the individual, and b) prescribing a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a creatinine clearance rate of greater than about 50 mL/minute using the Cockcroft-Gault equation. In addition, disclosed herein is a method for decreasing food intake in an individual in need thereof, comprising: a) determining a creatinine clearance rate using the Cockcroft-Gault equation for the individual, and b) administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a creatinine clearance rate of greater than about 50 mL/minute using the Cockcroft-Gault equation.

Disclosed herein is a method for decreasing food intake in an individual in need thereof, comprising: a) determining a creatinine clearance rate using the Cockcroft-Gault equation for the individual, and b) prescribing a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a creatinine clearance rate of greater than about 30 mL/minute using the Cockcroft-Gault equation. In addition, disclosed herein is a method for decreasing food intake in an individual in need thereof, comprising: a) determining a creatinine clearance rate using the Cockcroft-Gault equation for the individual, and b) administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a creatinine clearance rate of greater than about 30 mL/minute using the Cockcroft-Gault equation.

Disclosed herein is a method for reducing the risk of an adverse event in an individual in need of decreasing food intake, comprising prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a level of renal sufficiency selected from the group consisting of: no renal impairment, mild renal impairment, and moderate renal impairment.

Disclosed herein is a method for reducing the risk of an adverse event in an individual in need of decreasing food intake, comprising: a) determining the level of renal sufficiency of the individual, and b) prescribing a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a level of renal sufficiency selected from the group consisting of: no renal impairment, mild renal impairment, and moderate renal impairment. Also disclosed herein is a method for reducing the risk of an adverse event in an individual in need of decreasing food intake, comprising: a) determining the level of renal sufficiency of the individual, and b) administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a level of renal sufficiency selected from the group consisting of: no renal impairment, mild renal impairment, and moderate renal impairment.

Disclosed herein is a method for reducing the risk of an adverse event in an individual in need of decreasing food intake, comprising prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual does not have severe renal impairment or ESRD.

Also disclosed herein is a method for reducing the risk of an adverse event in an individual in need of decreasing food intake, comprising prescribing or administering a reduced dosage regimen of (R)-8-chloro-1-methyl-2,3,4,5-tetrahydro-1H-3-benzazepine or a pharmaceutically acceptable salt, solvate or hydrate thereof to the individual provided that the individual has renal impairment.

Disclosed herein is a method for reducing the risk of an adverse event in an individual in need of decreasing food intake, comprising: a) determining the level of renal sufficiency of the individual, and b) prescribing a reduced dosage regimen of (R)-8-chloro-1-methyl-2,3,4,5-tetrahydro-1H-3-benzazepine or a pharmaceutically acceptable salt, solvate or hydrate thereof to the individual provided that the individual has renal impairment. Also disclosed herein is a method for reducing the risk of an adverse event in an individual in need of decreasing food intake, comprising: a) determining the level of renal sufficiency of the individual, and b) administering a reduced dosage regimen of (R)-8-chloro-1-methyl-2,3,4,5-tetrahydro-1H-3-benzazepine or a pharmaceutically acceptable salt, solvate or hydrate thereof to the individual provided that the individual has renal impairment.

Further disclosed herein is a method for reducing the risk of an adverse event in an individual in need of decreasing food intake, comprising prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual provided that the individual has an approximate serum creatinine concentration of:
   (i) less than 4.9 mg/dL for an 18-20 year old man,
   (ii) less than 3.5 mg/dL for an 18-20 year old woman,
   (iii) less than 4.5 mg/dL for a 21-30 year old man,
   (iv) less than 3.2 mg/dL for a 21-30 year old woman,
   (v) less than 4.1 mg/dL for a 31-40 year old man,
   (vi) less than 2.9 mg/dL for a 31-40 year old woman, (vii) less than 3.7 mg/dL for a 41-50 year old man,
(viii) less than 2.7 mg/dL for a 41-50 year old woman,
(ix) less than 3.3 mg/dL for a 51-60 year old man,
(x) less than 2.4 mg/dL for a 51-60 year old woman,
(xi) less than 3.0 mg/dL for a man over 60 years old, or
(xii) less than 2.0 mg/dL for a woman over 60 years old.

Disclosed herein is a method for reducing the risk of an adverse event in an individual in need of decreasing food intake, comprising: a) determining an approximate serum creatinine concentration for the individual, and b) prescribing a therapeutically effective amount of (R)-8-chloro-1-methyl-2,3,4,5-tetrahydro-1H-3-benzazepine or a pharmaceutically acceptable salt, solvate or hydrate thereof to the individual provided that the individual has an approximate serum creatinine concentration of:
(i) less than 4.9 mg/dL for an 18-20 year old man,
(ii) less than 3.5 mg/dL for an 18-20 year old woman,
(iii) less than 4.5 mg/dL for a 21-30 year old man,
(iv) less than 3.2 mg/dL for a 21-30 year old woman,
(v) less than 4.1 mg/dL for a 31-40 year old man,
(vi) less than 2.9 mg/dL for a 31-40 year old woman,
(vii) less than 3.7 mg/dL for a 41-50 year old man,
(viii) less than 2.7 mg/dL for a 41-50 year old woman,
(ix) less than 3.3 mg/dL for a 51-60 year old man,
(x) less than 2.4 mg/dL for a 51-60 year old woman,
(xi) less than 3.0 mg/dL for a man over 60 years old, or
(xii) less than 2.0 mg/dL for a woman over 60 years old.

Also disclosed herein is a method for reducing the risk of an adverse event in an individual in need of decreasing food intake, comprising: a) determining an approximate serum creatinine concentration for the individual, and b) administering a therapeutically effective amount of (R)-8-chloro-1-methyl-2,3,4,5-tetrahydro-H-3-benzazepine or a pharmaceutically acceptable salt, solvate or hydrate thereof to the individual provided that the individual has an approximate serum creatinine concentration of:
(i) less than 4.9 mg/dL for an 18-20 year old man,
(ii) less than 3.5 mg/dL for an 18-20 year old woman,
(iii) less than 4.5 mg/dL for a 21-30 year old man,
(iv) less than 3.2 mg/dL for a 21-30 year old woman,
(v) less than 4.1 mg/dL for a 31-40 year old man,
(vi) less than 2.9 mg/dL for a 31-40 year old woman,
(vii) less than 3.7 mg/dL for a 41-50 year old man,
(viii) less than 2.7 mg/dL for a 41-50 year old woman,
(ix) less than 3.3 mg/dL for a 51-60 year old man,
(x) less than 2.4 mg/dL for a 51-60 year old woman,
(xi) less than 3.0 mg/dL for a man over 60 years old, or
(xii) less than 2.0 mg/dL for a woman over 60 years old.

Disclosed herein is a method for reducing the risk of an adverse event in an individual in need of decreasing food intake comprising prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a creatinine clearance rate of greater than about 80 mL/minute, greater than about 50 mL/minute or greater than about 30 mL/minute using the Cockcroft-Gault equation.

Disclosed herein is a method for selecting an individual for treatment with (R)-8-chloro-1-methyl-2,3,4,5-tetrahydro-1H-3-benzazepine or a pharmaceutically acceptable salt, solvate or hydrate thereof from a plurality of individuals in need of decreasing food intake, comprising selecting the individual for treatment with (R)-8-chloro-1-methyl-2,3,4,5-tetrahydro-1H-3-benzazepine or a pharmaceutically acceptable salt, solvate or hydrate thereof if the individual has a level of renal sufficiency selected from the group consisting of: no renal impairment, mild renal impairment, and moderate renal impairment.

Also disclosed herein is a method for selecting an individual for treatment with (R)-8-chloro-1-methyl-2,3,4,5-tetrahydro-1H-3-benzazepine or a pharmaceutically acceptable salt, solvate or hydrate thereof from a plurality of individuals in need of decreasing food intake, comprising: a) determining the level of renal sufficiency of the individual; and b) selecting the individual for treatment with (R)-8-chloro-1-methyl-2,3,4,5-tetrahydro-1H-3-benzazepine or a pharmaceutically acceptable salt, solvate or hydrate thereof if the individual has a level of renal sufficiency selected from the group consisting of: no renal impairment, mild renal impairment, and moderate renal impairment.

Disclosed herein is a method for selecting an individual for treatment with (R)-8-chloro-1-methyl-2,3,4,5-tetrahydro-1H-3-benzazepine or a pharmaceutically acceptable salt, solvate or hydrate thereof from a plurality of individuals in need of decreasing food intake, comprising selecting the individual for treatment with (R)-8-chloro-1-methyl-2,3,4,5-tetrahydro-1H-3-benzazepine or a pharmaceutically acceptable salt, solvate or hydrate thereof provided that the individual does not have severe renal impairment or ESRD.

Also disclosed herein is a method for selecting an individual for treatment with (R)-8-chloro-1-methyl-2,3,4,5-tetrahydro-1H-3-benzazepine or a pharmaceutically acceptable salt, solvate or hydrate thereof from a plurality of individuals in need of decreasing food intake, comprising selecting the individual for treatment with a reduced dosage regimen of (R)-8-chloro-1-methyl-2,3,4,5-tetrahydro-1H-3-benzazepine or a pharmaceutically acceptable salt, solvate or hydrate thereof if the individual has renal impairment.

Further disclosed herein is a method for selecting an individual for treatment with (R)-8-chloro-1-methyl-2,3,4,5-tetrahydro-1H-3-benzazepine or a pharmaceutically acceptable salt, solvate or hydrate thereof from a plurality of individuals in need of decreasing food intake, comprising selecting the individual for treatment with (R)-8-chloro-1-methyl-2,3,4,5-tetrahydro-1H-3-benzazepine or a pharmaceutically acceptable salt, solvate or hydrate thereof if the individual has an approximate serum creatinine concentration of:
(i) less than 4.9 mg/dL for an 18-20 year old man,
(ii) less than 3.5 mg/dL for an 18-20 year old woman,
(iii) less than 4.5 mg/dL for a 21-30 year old man,
(iv) less than 3.2 mg/dL for a 21-30 year old woman,
(v) less than 4.1 mg/dL for a 31-40 year old man,
(vi) less than 2.9 mg/dL for a 31-40 year old woman,
(vii) less than 3.7 mg/dL for a 41-50 year old man,
(viii) less than 2.7 mg/dL for a 41-50 year old woman,
(ix) less than 3.3 mg/dL for a 51-60 year old man,
(x) less than 2.4 mg/dL for a 51-60 year old woman,
(xi) less than 3.0 mg/dL for a man over 60 years old, or
(xii) less than 2.0 mg/dL for a woman over 60 years old.

In addition, disclosed herein is a method for selecting an individual for treatment with (R)-8-chloro-1-methyl-2,3,4,5-tetrahydro-1H-3-benzazepine or a pharmaceutically acceptable salt, solvate or hydrate thereof from a plurality of individuals in need of decreasing food intake, comprising: a) determining an approximate serum creatinine concentration for the individual, and b) selecting the individual for treatment with (R)-8-chloro-1-methyl-2,3,4,5-tetrahydro-1H-3-benzazepine or a pharmaceutically acceptable salt, solvate or hydrate thereof if the individual has an approximate serum creatinine concentration of:
(i) less than 4.9 mg/dL for an 18-20 year old man,
(ii) less than 3.5 mg/dL for an 18-20 year old woman, (iii) less than 4.5 mg/dL for a 21-30 year old man,
(iv) less than 3.2 mg/dL for a 21-30 year old woman,
(v) less than 4.1 mg/dL for a 31-40 year old man,
(vi) less than 2.9 mg/dL for a 31-40 year old woman,
(vii) less than 3.7 mg/dL for a 41-50 year old man,
(viii) less than 2.7 mg/dL for a 41-50 year old woman,
(ix) less than 3.3 mg/dL for a 51-60 year old man,
(x) less than 2.4 mg/dL for a 51-60 year old woman,
(xi) less than 3.0 mg/dL for a man over 60 years old, or
(xii) less than 2.0 mg/dL for a woman over 60 years old.

Further disclosed herein is a method for selecting an individual for treatment with (R)-8-chloro-1-methyl-2,3,4,5-tetrahydro-1H-3-benzazepine or a pharmaceutically acceptable salt, solvate or hydrate thereof from a plurality of individuals in need of decreasing food intake, comprising selecting the individual for treatment with (R)-8-chloro-1-methyl-2,3,4,5-tetrahydro-1H-3-benzazepine or a pharmaceutically acceptable salt, solvate or hydrate thereof provided that the individual has a creatinine clearance rate of greater than about 80 mL/minute, greater than about 50 mL/minute or greater than about 30 mL/minute using the Cockcroft-Gault equation.

Also disclosed herein is a compound for use in a method of decreasing food intake in an individual, said method comprising prescribing said compound to said individual, wherein said individual has previously been determined to have a level of renal sufficiency selected from the group consisting of: no renal impairment, mild renal impairment, and moderate renal impairment; wherein said compound is (R)-8-chloro-1-methyl-2,3,4,5-tetrahydro-1H-3-benzazepine or a pharmaceutically acceptable salt, solvate or hydrate thereof. In addition, disclosed herein is a compound for use in a method of decreasing food intake in an individual, said method comprising administering said compound to said individual, wherein said individual has previously been determined to have a level of renal sufficiency selected from the group consisting of: no renal impairment, mild renal impairment, and moderate renal impairment; wherein said compound is (R)-8-chloro-1-methyl-2,3,4,5-tetrahydro-1H-3-benzazepine or a pharmaceutically acceptable salt, solvate or hydrate thereof.

For example, disclosed herein is a compound for use in a method of decreasing food intake in an individual, said method comprising prescribing a therapeutically effective amount of said compound to said individual, wherein said individual has previously been determined to have a level of renal sufficiency selected from the group consisting of: no renal impairment, mild renal impairment, and moderate renal impairment; wherein said compound is (R)-8-chloro-1-methyl-2,3,4,5-tetrahydro-1H-3-benzazepine or a pharmaceutically acceptable salt, solvate or hydrate thereof. In addition, disclosed herein is a compound for use in a method of decreasing food intake in an individual, said method comprising administering a therapeutically effective amount of said compound to said individual, wherein said individual has previously been determined to have a level of renal sufficiency selected from the group consisting of: no renal impairment, mild renal impairment, and moderate renal impairment; wherein said compound is (R)-8-chloro-1-methyl-2,3,4,5-tetrahydro-1H-3-benzazepine or a pharmaceutically acceptable salt, solvate or hydrate thereof.

Disclosed herein is a compound for use in a method of decreasing food intake in an individual, said method comprising prescribing said compound at a dosage level appropriate for the level of renal sufficiency of said individual, wherein said individual has previously been determined to have a level of renal sufficiency selected from the group consisting of: no renal impairment, mild renal impairment, moderate renal impairment, severe renal impairment and ESRD; wherein said compound is (R)-8-chloro-1-methyl-2,3,4,5-tetrahydro-1H-3-benzazepine or a pharmaceutically acceptable salt, solvate or hydrate thereof. Also disclosed herein is a compound for use in a method of decreasing food intake in an individual, said method comprising administering said compound at a dosage level appropriate for the level of renal sufficiency of said individual, wherein said individual has previously been determined to have a level of renal sufficiency selected from the group consisting of: no renal impairment, mild renal impairment, moderate renal impairment, severe renal impairment and ESRD; wherein said compound is (R)-8-chloro-1-methyl-2,3,4,5-tetrahydro-1H-3-benzazepine or a pharmaceutically acceptable salt, solvate or hydrate thereof.

In addition, disclosed herein is a compound for use in a method of decreasing food intake in an individual, said method comprising determining the level of renal sufficiency of said individual and prescribing said compound at a dosage level appropriate for the level of renal sufficiency of said individual, wherein said individual has a level of renal sufficiency selected from the group consisting of: no renal impairment, mild renal impairment, moderate renal impairment, severe renal impairment and ESRD; wherein said compound is (R)-8-chloro-1-methyl-2,3,4,5-tetrahydro-1H-3-benzazepine or a pharmaceutically acceptable salt, solvate or hydrate thereof. Further, disclosed herein is a compound for use in a method of decreasing food intake in an individual, said method comprising determining the level of renal sufficiency of said individual and administering said compound at a dosage level appropriate for the level of renal sufficiency of said individual, wherein said individual has a level of renal sufficiency selected from the group consisting of: no renal impairment, mild renal impairment, moderate renal impairment, severe renal impairment and ESRD; wherein said compound is (R)-8-chloro-1-methyl-2,3,4,5-tetrahydro-1H-3-benzazepine or a pharmaceutically acceptable salt, solvate or hydrate thereof. For example, disclosed herein is a compound for use decreasing food intake in an individual, said method comprising prescribing or administering a reduced dosage regimen of said compound; wherein said compound is (R)-8-chloro-1-methyl-2,3,4,5-tetrahydro-1H-3-benzazepine or a pharmaceutically acceptable salt, solvate or hydrate thereof.

Disclosed herein is a compound for use in a method of decreasing food intake in an individual having moderate, mild or no renal impairment, said method comprising prescribing said compound to said individual, wherein said individual has previously been determined to have a level of renal sufficiency selected from the group consisting of: no renal impairment, mild renal impairment, and moderate renal impairment; wherein said compound is (R)-8-chloro-1-methyl-2,3,4,5-tetrahydro-1H-3-benzazepine or a pharmaceutically acceptable salt, solvate or hydrate thereof. In addition, disclosed herein is a compound for use in a method of decreasing food intake in an individual having moderate, mild or no renal impairment, said method comprising administering said compound to said individual, wherein said individual has previously been determined to have a level of renal sufficiency selected from the group consisting of: no renal impairment, mild renal impairment, and moderate renal impairment; wherein said compound is (R)-8-chloro-1-methyl-2,3,4,5-tetrahydro-1H-3-benzazepine or a pharmaceutically acceptable salt, solvate or hydrate thereof.

Disclosed herein is a low dosage formulation of a compound for use in a method of decreasing food intake in an individual, said method comprising prescribing said low dosage formulation of the compound to said individual, wherein said individual has previously been determined to have renal impairment; wherein said compound is (R)-8-chloro-1-methyl-2,3,4,5-tetrahydro-1H-3-benzazepine or a pharmaceutically acceptable salt, solvate or hydrate thereof. In addition, disclosed herein is a low dosage formulation of a compound for use in a method of decreasing food intake in an individual, said method comprising administering said low dosage formulation of the compound to said individual, wherein said individual has previously been determined to have renal impairment; wherein said compound is (R)-8-chloro-1-methyl-2,3,4,5-tetrahydro-1H-3-benzazepine or a pharmaceutically acceptable salt, solvate or hydrate thereof.

Disclosed herein is a low dosage formulation of a compound for use in a method of decreasing food intake in an individual, wherein said low dosage reduces a toxic event in said individual to said compound, wherein said individual has previously been determined to have renal impairment; and wherein said compound is (R)-8-chloro-1-methyl-2,3,4,5-tetrahydro-1H-3-benzazepine or a pharmaceutically acceptable salt, solvate or hydrate thereof. Disclosed herein is a low dosage formulation of a compound for use in a method of decreasing food intake in an individual, wherein said low dosage prevents a toxic event in said individual to said compound, wherein said individual has previously been determined to have renal impairment; and wherein said compound is (R)-8-chloro-1-methyl-2,3,4,5-tetrahydro-1H-3-benzazepine or a pharmaceutically acceptable salt, solvate or hydrate thereof.

One aspect of the present disclosure pertains to methods for decreasing food intake, comprising administering to an individual in need thereof, a therapeutically effective amount of a compound, a crystalline form, a pharmaceutical composition, or a dosage form of the present disclosure.

In some embodiments, the individual in need of decreasing food intake is a patient with an initial body mass index ≥30 kg/m$^2$.

In some embodiments, the individual in need of decreasing food intake is a patient with an initial body mass index ≥27 kg/m$^2$ in the presence of at least one weight related comorbid condition.

In some embodiments, the individual in need of decreasing food, intake is a patient with an initial body mass index ≥27 kg/m$^2$ in the presence of at least one weight related comorbid condition selected from: hypertension, dyslipidemia, cardiovascular disease, glucose intolerance and sleep apnea.

In some embodiments, the individual in need of decreasing food intake has an initial body mass index ≥30 kg/m$^2$.

In some embodiments, the individual in need of decreasing food intake has an initial body mass index ≥27 kg/m$^2$.

In some embodiments, the individual in need of decreasing food intake has an initial body mass index ≥27 kg/m$^2$ in the presence of at least one weight related comorbid condition.

In some embodiments, the individual in need of decreasing food intake has an initial body mass index ≥27 kg/m$^2$ in the presence of at least one weight related comorbid condition selected from: hypertension, dyslipidemia, cardiovascular disease, glucose intolerance and sleep apnea.

In some embodiments, the individual in need of decreasing food intake has an initial body mass index ≥25 kg/m$^2$.

In some embodiments, the individual in need of decreasing food intake has an initial body mass index ≥25 kg/m$^2$ in the presence of at least one weight related comorbid condition.

In some embodiments, the individual in need of decreasing food intake has an initial body mass index ≥25 kg/m$^2$ in the presence of at least one weight related comorbid condition selected from: hypertension, dyslipidemia, cardiovascular disease, glucose intolerance and sleep apnea.

In some embodiments, decreasing food intake comprises weight loss. In some embodiments, decreasing food intake comprises maintenance of weight loss. In some embodiments, decreasing food intake further comprises a reduced-calorie diet. In some embodiments, decreasing food intake further comprises a program of regular exercise. In some embodiments, decreasing food intake further comprises both a reduced-calorie diet and a program of regular exercise.

In some embodiments, the method for decreasing food intake further comprises prescribing or administering a weight loss compound or procedure in addition to prescribing or administering (R)-8-chloro-1-methyl-2,3,4,5-tetrahydro-1H-3-benzazepine or a pharmaceutically acceptable salt, solvate or hydrate thereof. In some embodiments, the method for decreasing food intake further comprises prescribing or administering phentermine to the individual. In some embodiments, (R)-8-chloro-1-methyl-2,3,4,5-tetrahydro-1H-3-benzazepine or a pharmaceutically acceptable salt, solvate or hydrate thereof is prescribed or administered before or after a surgical weight loss procedure, for example, a lap band or gastric bypass surgery.

Disclosed herein is a method for reducing the risk of an adverse event in an individual in need of decreasing food intake, comprising administering a therapeutically effective amount of (R)-8-chloro-1-methyl-2,3,4,5-tetrahydro-1H-3-benzazepine or a pharmaceutically acceptable salt, solvate or hydrate thereof to the individual, wherein the level of renal sufficiency of the individual has been determined, and provided that the individual has a level of renal sufficiency selected from the group consisting of: no renal impairment, mild renal impairment, and moderate renal impairment. Further disclosed herein is a method for reducing the risk of an adverse event in an individual in need of decreasing food intake, comprising administering a reduced dosage regimen of (R)-8-chloro-1-methyl-2,3,4,5-tetrahydro-1H-3-benzazepine or a pharmaceutically acceptable salt, solvate or hydrate thereof to the individual, wherein the level of renal sufficiency of the individual has been determined, and provided that the individual has renal impairment. Also disclosed herein is a method for reducing the risk of an adverse event in an individual in need of decreasing food intake, comprising administering a therapeutically effective amount of (R)-8-chloro-1-methyl-2,3,4,5-tetrahydro-1H-3-benzazepine or a pharmaceutically acceptable salt, solvate or hydrate thereof to the individual, wherein an approximate serum creatinine concentration has been determined for the individual, and provided that the individual has an approximate serum creatinine concentration of:

(i) less than 4.9 mg/dL for an 18-20 year old man,
(ii) less than 3.5 mg/dL for an 18-20 year old woman,
(iii) less than 4.5 mg/dL for a 21-30 year old man,
(iv) less than 3.2 mg/dL for a 21-30 year old woman,
(v) less than 4.1 mg/dL for a 31-40 year old man,
(vi) less than 2.9 mg/dL for a 31-40 year old woman,
(vii) less than 3.7 mg/dL for a 41-50 year old man,
(viii) less than 2.7 mg/dL for a 41-50 year old woman,
(ix) less than 3.3 mg/dL for a 51-60 year old man,
(x) less than 2.4 mg/dL for a 51-60 year old woman,
(xi) less than 3.0 mg/dL for a man over 60 years old, or
(xii) less than 2.0 mg/dL for a woman over 60 years old.

Disclosed herein is a method for selecting an individual for treatment with (R)-8-chloro-1-methyl-2,3,4,5-tetrahydro-1H-3-benzazepine or a pharmaceutically acceptable salt, solvate or hydrate thereof from a plurality of individuals in need of decreasing food intake, comprising selecting the individual for treatment with (R)-8-chloro-1-methyl-2,3,4,5-tetrahydro-1H-3-benzazepine or a pharmaceutically acceptable salt, solvate or hydrate thereof if it is determined that the individual has a level of renal sufficiency selected from the group consisting of: no renal impairment, mild renal impairment, and moderate renal impairment. Further disclosed herein is a method for selecting an individual for treatment with (R)-8-chloro-1-methyl-2,3,4,5-tetrahydro-H-3-benzazepine or a pharmaceutically acceptable salt, solvate or hydrate thereof from a plurality of individuals in need of decreasing food intake, comprising selecting the individual for treatment with (R)-8-chloro-1-methyl-2,3,4,5-tetrahydro-1H-3-benzazepine or a pharmaceutically acceptable salt, solvate or hydrate thereof if it is determined that the individual has an approximate serum creatinine concentration of:
 (i) less than 4.9 mg/dL for an 18-20 year old man,
 (ii) less than 3.5 mg/dL for an 18-20-year old woman,
 (iii) less than 4.5 mg/dL for a 21-30 year old man,
 (iv) less than 3.2 mg/dL for a 21-30 year old woman,
 (v) less than 4.1 mg/dL for a 31-40 year old man,
 (vi) less than 2.9 mg/dL for a 31-40 year old woman,
 (vii) less than 3.7 mg/dL for a 41-50 year old man,
 (viii) less than 2.7 mg/dL for a 41-50 year old woman,
 (ix) less than 3.3 mg/dL for a 51-60 year old man,
 (x) less than 2.4 mg/dL for a 51-60 year old woman,
 (xi) less than 3.0 mg/dL for a man over 60 years old, or
 (xii) less than 2.0 mg/dL for a woman over 60 years old.

Disclosed herein is a method for inducing satiety in an individual in need thereof, comprising prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a level of renal sufficiency selected from the group consisting of: no renal impairment, mild renal impairment, and moderate renal impairment.

Also disclosed herein is a method for inducing satiety in an individual in need thereof, comprising: a) determining the level of renal sufficiency of the individual, and b) prescribing a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a level of renal sufficiency selected from the group consisting of: no renal impairment, mild renal impairment, and moderate renal impairment. In addition, disclosed herein is a method for inducing satiety in an individual in need thereof, comprising: a) determining the level of renal sufficiency of the individual, and b) administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a level of renal sufficiency selected from the group consisting of: no renal impairment, mild renal impairment, and moderate renal impairment.

In addition, disclosed herein is a method for inducing satiety in an individual in need thereof, comprising prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual does not have severe renal impairment or end stage renal disease (ESRD).

Also disclosed herein is a method for inducing satiety in an individual in need thereof, comprising: a) determining the level of renal sufficiency of the individual, and b) prescribing therapeutically effective amount of (R)-8-chloro-1-methyl-2,3,4,5-tetrahydro-1H-3-benzazepine or a pharmaceutically acceptable salt, solvate or hydrate thereof to the individual, provided that the individual does not have severe renal impairment or end stage renal disease (ESRD). In addition, disclosed herein is a method for inducing satiety in an individual in need thereof, comprising: a) determining the level of renal sufficiency of the individual, and b) administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual does not have severe renal impairment or ESRD.

In some embodiments (R)-8-chloro-1-methyl-2,3,4,5-tetrahydro-H-3-benzazepine or a pharmaceutically acceptable salt, solvate or hydrate thereof is (R)-8-chloro-1-methyl-2,3,4,5-tetrahydro-1H-3-benzazepine hydrochloride and hydrates thereof.

In some embodiments (R)-8-chloro-1-methyl-2,3,4,5-tetrahydro-H-3-benzazepine or a pharmaceutically acceptable salt, solvate or hydrate thereof is (R)-8-chloro-1-methyl-2,3,4,5-tetrahydro-1H-3-benzazepine hydrochloride hemihydrate.

In some embodiments (R)-8-chloro-1-methyl-2,3,4,5-tetrahydro-1H-3-benzazepine or a pharmaceutically acceptable salt, solvate or hydrate thereof is (R)-8-chloro-1-methyl-2,3,4,5-tetrahydro-1H-3-benzazepine hydrochloride hemihydrate, Form III.

In some embodiments, the Cockcroft-Gault equation is used to determine the level of renal sufficiency of the individual.

In some embodiments, the individual's ideal body weight is used in the Cockcroft-Gault equation and in other embodiments the individual's actual body weight is used in the Cockcroft-Gault equation.

In some embodiments, the individual's serum creatinine concentration is used to determine the level of renal sufficiency of the individual.

As used herein, "satiety" is the quality or state of being fed or gratified to or beyond capacity. Satiety is a feeling that an individual has and so it is often determined by asking the individual, orally or in writing, if they feel full, sated, or satisfied at timed intervals during a meal. For example, an individual who feels sated may report feeling full, feeling a decreased or absent hunger, feeling a decreased or absent desire to eat, or feeling a lack of drive to eat. While fullness is a physical sensation, satiety is a mental feeling. An individual who feels full, sated or satisfied is more likely to stop eating and therefore inducing satiety can result in a decrease in food intake in an individual.

As used herein, "inducing satiety in an individual in need thereof" refers to a judgment made by a healthcare practitioner that an individual requires or will benefit from inducing satiety.

This judgment is made based on a variety of factors that are in the realm of a healthcare practitioner's expertise, but that includes the knowledge that the individual has a condition, for example, obesity, that is treatable by the methods of the disclosure.

In some embodiments, an individual in need of inducing satiety is an individual who is overweight. In some embodiments, an individual in need of inducing satiety is an individual who is obese.

Disclosed herein is a method for inducing satiety in an individual in need thereof, comprising prescribing or administering a reduced dosage regimen of (R)-8-chloro-1-methyl-2,3,4,5-tetrahydro-1H-3-benzazepine or a pharmaceutically acceptable salt, solvate or hydrate thereof to the individual provided that the individual has renal impairment.

Also disclosed herein is a method for inducing satiety in an individual in need thereof, comprising: a) determining the level of renal sufficiency of the individual, and b) prescribing a reduced dosage regimen of (R)-8-chloro-1-methyl-2,3,4,5-tetrahydro-1H-3-benzazepine or a pharmaceutically acceptable salt, solvate or hydrate thereof to the individual provided that the individual has renal impairment. In addition, disclosed herein is a method for inducing satiety in an individual in need thereof, comprising: a) determining the level of renal sufficiency of the individual, and b) administering a reduced dosage regimen of (R)-8-chloro-1-methyl-2,3,4,5-tetrahydro-1H-3-benzazepine or a pharmaceutically acceptable salt, solvate or hydrate thereof to the individual provided that the individual has renal impairment. In some embodiments, the individual has mild renal impairment, moderate renal impairment, severe renal impairment or ESRD. In some embodiments, the individual has moderate renal impairment, severe renal impairment or ESRD. In some embodiments, the individual has severe renal impairment or ESRD. In some embodiments, the individual has ESRD.

Disclosed herein is a method for inducing satiety in an individual in need thereof, comprising prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual provided that the individual has an approximate serum creatinine concentration of:
  (i) less than 4.9 mg/dL for an 18-20 year old man,
  (ii) less than 3.5 mg/dL for an 18-20 year old woman,
  (iii) less than 4.5 mg/dL for a 21-30 year old man,
  (iv) less than 3.2 mg/dL for a 21-30 year old woman,
  (v) less than 4.1 mg/dL for a 31-40 year old man,
  (vi) less than 2.9 mg/dL for a 31-40 year old woman,
  (viii) less than 2.7 mg/dL for a 41-50 year old woman,
  (ix) less than 3.3 mg/dL for a 51-60 year old man,
  (x) less than 2.4 mg/dL for a 51-60 year old woman,
  (xi) less than 3.0 mg/dL for a man over 60 years old, or
  (xii) less than 2.0 mg/dL for a woman over 60 years old.

Disclosed herein is a method for inducing satiety in an individual in need thereof, comprising a) determining an approximate serum creatinine concentration for the individual, and b) prescribing a therapeutically effective amount of (R)-8-chloro-1-methyl-2,3,4,5-tetrahydro-1H-3-benzazepine or a pharmaceutically acceptable salt, solvate or hydrate thereof to the individual provided that the individual has an approximate serum creatinine concentration of:
  (i) less than 4.9 mg/dL for an 18-20 year old man,
  (ii) less than 3.5 mg/dL for an 18-20 year old woman,
  (iii) less than 4.5 mg/dL for a 21-30 year old man,
  (iv) less than 3.2 mg/dL for a 21-30 year old woman,
  (v) less than 4.1 mg/dL for a 31-40 year old man,
  (vi) less than 2.9 mg/dL for a 31-40 year old woman,
  (viii) less than 2.7 mg/dL for a 41-50 year old woman,
  (ix) less than 3.3 mg/dL for a 51-60 year old man,
  (x) less than 2.4 mg/dL for a 51-60 year old woman,
  (xi) less than 3.0 mg/dL for a man over 60 years old, or
  (xii) less than 2.0 mg/dL for a woman over 60 years old.

In addition, disclosed herein is a method for inducing satiety in an individual in need thereof, comprising: a) determining an approximate serum creatinine concentration for the individual, and b) administering a therapeutically effective amount of (R)-8-chloro-1-methyl-2,3,4,5-tetrahydro-1H-3-benzazepine or a pharmaceutically acceptable salt, solvate or hydrate thereof to the individual provided that the individual has an approximate serum creatinine concentration of:
  (i) less than 4.9 ms/dL for an 18-20 year old man,
  (ii) less than 3.5 mg/dL for an 18-20 year old woman,
  (iii) less than 4.5 mg/dL for a 21-30 year old man,
  (iv) less than 3.2 mg/dL for a 21-30 year old woman,
  (v) less than 4.1 mg/dL for a 31-40 year old man,
  (vi) less than 2.9 mg/dL for a 31-40 year old woman,
  (vii) less than 3.7 mg/dL for a 41-50 year old man,
  (viii) less than 2.7 mg/dL for a 41-50 year old woman,
  (ix) less than 3.3 mg/dL for a 51-60 year old man,
  (x) less than 2.4 mg/dL for a 51-60 year old woman,
  (xi) less than 3.0 mg/dL for a man over 60 years old, or
  (xii) less than 2.0 mg/dL for a woman over 60 years old.

Disclosed herein is a method for inducing satiety in an individual in need thereof, comprising prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a creatinine clearance rate of greater than about 80 mL/minute, greater than about 50 mL/minute or greater than about 30 mL/minute using the Cockcroft-Gault equation.

Disclosed herein is a method for inducing satiety in an individual in need thereof, comprising: a) determining a creatinine clearance rate using the Cockcroft-Gault equation for the individual, and b) prescribing a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a creatinine clearance rate of greater than about 80 mL/minute using the Cockcroft-Gault equation. In addition, disclosed herein is a method for inducing satiety in an individual in need thereof, comprising: a) determining a creatinine clearance rate using the Cockcroft-Gault equation for the individual, and b) administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a creatinine clearance rate of greater than about 80 mL/minute using the Cockcroft-Gault equation.

Disclosed herein is a method for inducing satiety in an individual in need thereof, comprising: a) determining a creatinine clearance rate using the Cockcroft-Gault equation for the individual, and b) prescribing a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a creatinine clearance rate of greater than about 50 mL/minute using the Cockcroft-Gault equation. In addition, disclosed herein is a method for inducing satiety in an individual in need thereof, comprising: a) determining a creatinine clearance rate using the Cockcroft-Gault equation for the individual, and b) administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a creatinine clearance rate of greater than about 50 mL/minute using the Cockcroft-Gault equation.

Disclosed herein is a method for inducing satiety in an individual in need thereof, comprising: a) determining a creatinine clearance rate using the Cockcroft-Gault equation for the individual, and b) prescribing a therapeutically effective amount of (R)-8-chloro-1-methyl-2,3,4,5-tetrahydro-H-3-benzazepine or a pharmaceutically acceptable salt, solvate or hydrate thereof to the individual, provided that the individual has a creatinine clearance rate of greater than about 30 mL/minute using the Cockcroft-Gault equation. In addition, disclosed herein is a method for inducing satiety in an individual in need thereof, comprising: a) determining a creatinine clearance rate using the Cockcroft-Gault equation for the individual, and b) administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a creatinine clearance rate of greater than about 30 mL/minute using the Cockcroft-Gault equation.

Disclosed herein is a method for reducing the risk of an adverse event in an individual in need of inducing satiety, comprising prescribing or administering a therapeutically effective amount of (R)-8-chloro-1-methyl-2,3,4,5-tetrahydro-H-3-benzazepine or a pharmaceutically acceptable salt, solvate or hydrate thereof to the individual, provided that the individual has a level of renal sufficiency selected from the group consisting of: no renal impairment, mild renal impairment, and moderate renal impairment.

Disclosed herein is a method for reducing the risk of an adverse event in an individual in need of inducing satiety, comprising: a) determining the level of renal sufficiency of the individual, and b) prescribing a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a level of renal sufficiency selected from the group consisting of: no renal impairment, mild renal impairment, and moderate renal impairment. Disclosed herein is a method for reducing the risk of an adverse event in an individual in need of inducing satiety, comprising: a) determining the level of renal sufficiency of the individual, and b) administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a level of renal sufficiency selected from the group consisting of: no renal impairment, mild renal impairment, and moderate renal impairment.

Disclosed herein is a method for reducing the risk of an adverse event in an individual in need of inducing satiety, comprising prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual does not have severe renal impairment or ESRD.

Also disclosed herein is a method for reducing the risk of an adverse event in an individual in need of inducing satiety, comprising prescribing or administering a reduced dosage regimen of (R)-8-chloro-1-methyl-2,3,4,5-tetrahydro-1H-3-benzazepine or a pharmaceutically acceptable salt, solvate or hydrate thereof to the individual provided that the individual has renal impairment.

Disclosed herein is a method for reducing the risk of an adverse event in an individual in need of inducing satiety, comprising: a) determining the level of renal sufficiency of the individual, and b) prescribing a reduced dosage regimen of (R)-8-chloro-1-methyl-2,3,4,5-tetrahydro-1H-3-benzazepine or a pharmaceutically acceptable salt, solvate or hydrate thereof to the individual provided that the individual has renal impairment. Also disclosed herein is a method for reducing the risk of an adverse event in an individual in need of inducing satiety, comprising: a) determining the level of renal sufficiency of the individual, and b) administering a reduced dosage regimen of (R)-8-chloro-1-methyl-2,3,4,5-tetrahydro-1H-3-benzazepine or a pharmaceutically acceptable salt, solvate or hydrate thereof to the individual provided that the individual has renal impairment.

Further disclosed herein is a method for reducing the risk of an adverse event in an individual in need of inducing satiety, comprising prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual provided that the individual has an approximate serum creatinine concentration of:
(i) less than 4.9 mg/dL for an 18-20 year old man,
(ii) less than 3.5 mg/dL for an 18-20 year old woman,
(iii) less than 4.5 mg/dL for a 21-30 year old man,
(iv) less than 3.2 mg/dL for a 21-30 year old woman,
(v) less than 4.1 mg/dL for a 31-40 year old man,
(vi) less than 2.9 mg/dL for a 31-40 year old woman,
(vii) less than 3.7 mg/dL for a 41-50 year old man,
(viii) less than 2.7 mg/dL for a 41-50 year old woman,
(ix) less than 3.3 mg/dL for a 51-60 year old man,
(x) less than 2.4 mg/dL for a 51-60 year old woman,
(xi) less than 3.0 mg/dL for a man over 60 years old, or
(xii) less than 2.0 mg/dL for a woman over 60 years old.

Disclosed herein is a method for reducing the risk of an adverse event in an individual in need of inducing satiety, comprising: a) determining an approximate serum creatinine concentration for the individual, and b) prescribing a therapeutically effective amount of (R)-8-chloro-1-methyl-2,3,4,5-tetrahydro-1H-3-benzazepine or a pharmaceutically acceptable salt, solvate or hydrate thereof to the individual provided that the individual has an approximate serum creatinine concentration of:
(i) less than 4.9 mg/dL for an 18-20 year old man,
(ii) less than 3.5 mg/dL for an 18-20 year old woman,
(iii) less than 4.5 mg/dL for a 21-30 year old man,
(iv) less than 3.2 mg/dL for a 21-30 year old woman,
(v) less than 4.1 mg/dL for a 31-40 year old man,
(vi) less than 2.9 mg/dL for a 31-40 year old woman,
(vii) less than 3.7 mg/dL for a 41-50 year old man,
(viii) less than 2.7 mg/dL for a 41-50 year old woman,
(ix) less than 3.3 mg/dL for a 51-60 year old man,
(x) less than 2.4 mg/dL for a 51-60 year old woman,
(xi) less than 3.0 mg/dL for a man over 60 years old, or
(xii) less than 2.0 mg/dL for a woman over 60 years old.

Also disclosed herein is a method for reducing the risk of an adverse event in an individual in need of inducing satiety, comprising: a) determining an approximate serum creatinine concentration for the individual, and b) administering a therapeutically effective amount of (R)-8-chloro-1-methyl-2,3,4,5-tetrahydro-1H-3-benzazepine or a pharmaceutically acceptable salt, solvate or hydrate thereof to the individual provided that the individual has an approximate serum creatinine concentration of:
(i) less than 4.9 mg/dL for an 18-20 year old man,
(ii) less than 3.5 mg/dL for an 18-20 year old woman,
(iii) less than 4.5 mg/dL for a 21-30 year old man,
(iv) less than 3.2 mg/dL for a 21-30 year old woman,
(v) less than 4.1 mg/dL for a 31-40 year old man,
(vi) less than 2.9 mg/dL for a 31-40 year old woman,
(vii) less than 3.7 mg/dL for a 41-50 year old man,
(viii) less than 2.7 mg/dL for a 41-50 year old woman, (ix) less than 3.3 mg/dL for a 51-60 year old man,
(x) less than 2.4 mg/dL for a 51-60 year old woman,
(xi) less than 3.0 mg/dL for a man over 60 years old, or
(xii) less than 2.0 mg/dL for a woman over 60 years old.

Disclosed herein is a method for reducing the risk of an adverse event in an individual in need of inducing satiety comprising prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a creatinine clearance rate of greater than about 80 mL/minute, greater than about 50 mL/minute or greater than about 30 mL/minute using the Cockcroft-Gault equation.

Disclosed herein is a method for selecting an individual for treatment with (R)-8-chloro-1-methyl-2,3,4,5-tetrahydro-1H-3-benzazepine or a pharmaceutically acceptable salt, solvate or hydrate thereof from a plurality of individuals in need of inducing satiety, comprising selecting the individual for treatment with (R)-8-chloro-1-methyl-2,3,4,5-tetrahydro-1H-3-benzazepine or a pharmaceutically acceptable salt, solvate or hydrate thereof if the individual has a level of renal sufficiency selected from the group consisting of: no renal impairment, mild renal impairment, and moderate renal impairment.

Also disclosed herein is a method for selecting an individual for treatment with (R)-8-chloro-1-methyl-2,3,4,5-tetrahydro-1H-3-benzazepine or a pharmaceutically acceptable salt, solvate or hydrate thereof from a plurality of individuals in need of inducing satiety, comprising: a) determining the level of renal sufficiency of the individual; and b) selecting the individual for treatment with (R)-8-chloro-1-methyl-2,3,4,5-tetrahydro-1H-3-benzazepine or a pharmaceutically acceptable salt, solvate or hydrate thereof if the individual has a level of renal sufficiency selected from the group consisting of: no renal impairment, mild renal impairment, and moderate renal impairment.

Disclosed herein is a method for selecting an individual for treatment with (R)-8-chloro-1-methyl-2,3,4,5-tetrahydro-1H-3-benzazepine or a pharmaceutically acceptable salt, solvate or hydrate thereof from a plurality of individuals in need of inducing satiety, comprising selecting the individual for treatment with (R)-8-chloro-1-methyl-2,3,4,5-tetrahydro-1H-3-benzazepine or a pharmaceutically acceptable salt, solvate or hydrate thereof provided that the individual does not have severe renal impairment or ESRD.

Also disclosed herein is a method for selecting an individual for treatment with (R)-8-chloro-1-methyl-2,3,4,5-tetrahydro-1H-3-benzazepine or a pharmaceutically acceptable salt, solvate or hydrate thereof from a plurality of individuals in need of inducing satiety, comprising selecting the individual for treatment with a reduced dosage regimen of (R)-8-chloro-1-methyl-2,3,4,5-tetrahydro-1H-3-benzazepine or a pharmaceutically acceptable salt, solvate or hydrate thereof if the individual has renal impairment.

Further disclosed herein a method for selecting an individual for treatment with (R)-8-chloro-1-methyl-2,3,4,5-tetrahydro-1H-3-benzazepine or a pharmaceutically acceptable salt, solvate or hydrate thereof from a plurality of individuals in need of inducing satiety, comprising selecting the individual for treatment with (R)-8-chloro-1-methyl-2,3,4,5-tetrahydro-1H-3-benzazepine or a pharmaceutically acceptable salt, solvate or hydrate thereof if the individual has an approximate serum creatinine concentration of:
(i) less than 4.9 mg/dL for an 18-20 year old man,
(ii) less than 3.5 mg/dL for an 18-20 year old woman,
(iii) less than 4.5 mg/dL for a 21-30 year old man,
(iv) less than 3.2 mg/dL for a 21-30 year old woman,
(v) less than 4.1 mg/dL for a 31-40 year old man,
(vi) less than 2.9 mg/dL for a 31-40 year old woman,
(vii) less than 3.7 mg/dL for a 41-50 year old man,
(viii) less than 2.7 mg/dL for a 41-50 year old woman,
(ix) less than 3.3 mg/dL for a 51-60 year old man,
(x) less than 2.4 mg/dL for a 51-60 year old woman,
(xi) less than 3.0 mg/dL for a man over 60 years old, or
(xii) less than 2.0 mg/dL for a woman over 60 years old.

In addition, disclosed herein is a method for selecting an individual for treatment with (R)-8-chloro-1-methyl-2,3,4,5-tetrahydro-1H-3-benzazepine or a pharmaceutically acceptable salt, solvate or hydrate thereof from a plurality of individuals in need of inducing satiety, comprising: a) determining an approximate serum creatinine concentration for the individual, and b) selecting the individual for treatment with (R)-8-chloro-1-methyl-2,3,4,5-tetrahydro-1H-3-benzazepine or a pharmaceutically acceptable salt, solvate or hydrate thereof if the individual has an approximate serum creatinine concentration of:
(i) less than 4.9 mg/dL for an 18-20 year old man,
(ii) less than 3.5 mg/dL for an 18-20 year old woman,
(iii) less than 4.5 mg/dL for a 21-30 year old man,
(iv) less than 3.2 mg/dL for a 21-30 year old woman,
(v) less than 4.1 mg/dL for a 31-40 year old man,
(vi) less than 2.9 mg/dL for a 31-40 year old woman,
(vii) less than 3.7 mg/dL for a 41-50 year old man,
(viii) less than 2.7 mg/dL for a 41-50 year old woman,
(ix) less than 3.3 mg/dL for a 51-60 year old man,
(x) less than 2.4 mg/dL for a 51-60 year old woman,
(xi) less than 3.0 mg/dL for a man over 60 years old, or
(xii) less than 2.0 mg/dL for a woman over 60 years old.

Further disclosed herein a method for selecting an individual for treatment with (R)-8-chloro-1-methyl-2,3,4,5-tetrahydro-1H-3-benzazepine or a pharmaceutically acceptable salt, solvate or hydrate thereof from a plurality of individuals in need of inducing satiety, comprising selecting the individual for treatment with (R)-8-chloro-1-methyl-2,3,4,5-tetrahydro-1H-3-benzazepine or a pharmaceutically acceptable salt, solvate or hydrate thereof provided that the individual has a creatinine clearance rate of greater than about 80 mL/minute, greater than about 50 mL/minute or greater than about 30 mL/minute using the Cockcroft-Gault equation.

Also disclosed herein is a compound for use in a method of inducing satiety in an individual, said method comprising prescribing said compound to said individual, wherein said individual has previously been determined to hive a level of renal sufficiency selected from the group consisting of: no renal impairment, mild renal impairment, and moderate renal impairment; wherein said compound is (R)-8-chloro-1-methyl-2,3,4,5-tetrahydro-1H-3-benzazepine or a pharmaceutically acceptable salt, solvate or hydrate thereof. In addition, disclosed herein is a compound for use in a method of inducing satiety in an individual, said method comprising administering said compound to said individual, wherein said individual has previously been determined to have a level of renal sufficiency selected from the group consisting of: no renal impairment, mild renal impairment, and moderate renal impairment; wherein said compound is (R)-8-chloro-1-methyl-2,3,4,5-tetrahydro-1H-3-benzazepine or a pharmaceutically acceptable salt, solvate or hydrate thereof.

For example, disclosed herein is a compound for use in a method of inducing satiety in an individual, said method comprising prescribing a therapeutically effective amount of said compound to said individual, wherein said individual has previously been determined to have a level of renal sufficiency selected from the group consisting of: no renal impairment, mild renal impairment, and moderate renal impairment; wherein said compound is (R)-8-chloro-1-methyl-2,3,4,5-tetrahydro-1H-3-benzazepine or a pharmaceutically acceptable salt, solvate or hydrate thereof. In addition, disclosed herein is a compound for use in a method of inducing satiety in an individual, said method comprising administering a therapeutically effective amount of said compound to said individual, wherein said individual has previously been determined to have a level of renal sufficiency selected from the group consisting of: no renal impairment, mild renal impairment, and moderate renal impairment; wherein said compound is (R)-8-chloro-1-methyl-2,3,4,5-tetrahydro-1H-3-benzazepine or a pharmaceutically acceptable salt, solvate or hydrate thereof.

Disclosed herein is a compound for use in a method of inducing satiety in an individual, said method comprising prescribing said compound at a dosage level appropriate for the level of renal sufficiency of said individual, wherein said individual has previously been determined to have a level of renal sufficiency selected from the group consisting of: no renal impairment, mild renal impairment, moderate renal impairment, severe renal impairment and ESRD; wherein said compound is (R)-8-chloro-1-methyl-2,3,4,5-tetrahydro-1H-3-benzazepine or a pharmaceutically acceptable salt, solvate or hydrate thereof. In addition, disclosed herein is a compound for use in a method of inducing satiety in an individual, said method comprising administering said compound at a dosage level appropriate for the level of renal sufficiency of said individual, wherein said individual has previously been determined to have a level of renal sufficiency selected from the group consisting of: no renal impairment, mild renal impairment, moderate renal impairment, severe renal impairment and ESRD; wherein said compound is (R)-8-chloro-1-methyl-2,3,4,5-tetrahydro-1H-3-benzazepine or a pharmaceutically acceptable salt, solvate or hydrate thereof.

Also disclosed herein is a compound for use in a method of inducing satiety in an individual, said method comprising determining the level of renal sufficiency of said individual and prescribing said compound at a dosage level appropriate for the level of renal sufficiency of said individual, wherein said individual has a level of renal sufficiency selected from the group consisting of: no renal impairment, mild renal impairment, moderate renal impairment, severe renal impairment and ESRD; wherein said compound is (R)-8-chloro-1-methyl-2,3,4,5-tetrahydro-1H-3-benzazepine or a pharmaceutically acceptable salt, solvate or hydrate thereof. Further, disclosed herein is a compound for use in a method of inducing satiety in an individual, said method comprising determining the level of renal sufficiency of said individual and administering said compound at a dosage level appropriate for the level of renal sufficiency of said individual, wherein said individual has a level of renal sufficiency selected from the group consisting of: no renal impairment, mild renal impairment, moderate renal impairment, severe renal impairment and ESRD; wherein said compound is (R)-8-chloro-1-methyl-2,3,4,5-tetrahydro-1H-3-benzazepine or a pharmaceutically acceptable salt, solvate or hydrate thereof.

For example, disclosed herein is a compound for use in a method of inducing satiety in an individual, said method comprising prescribing or administering a reduced dosage regimen of said compound; wherein said compound is (R)-8-chloro-1-methyl-2,3,4,5-tetrahydro-1H-3-benzazepine or a pharmaceutically acceptable salt, solvate or hydrate thereof.

Disclosed herein is a compound for use in a method of inducing satiety in an individual having moderate, mild or no renal impairment, said method comprising prescribing said compound to said individual, wherein said individual has previously been determined to have a level of renal sufficiency selected from the group consisting of: no renal impairment, mild renal impairment, and moderate renal impairment; wherein said compound is (R)-8-chloro-1-methyl-2,3,4,5-tetrahydro-1H-3-benzazepine or a pharmaceutically acceptable salt, solvate or hydrate thereof. In addition, disclosed herein is a compound for use in a method of inducing satiety in an individual having moderate, mild or no renal impairment, said method comprising administering said compound to said individual, wherein said individual has previously been determined to have a level of renal sufficiency selected from the group consisting of: no renal impairment, mild renal impairment, and moderate renal impairment; wherein said compound is (R)-8-chloro-1-methyl-2,3,4,5-tetrahydro-1H-3-benzazepine or a pharmaceutically acceptable salt, solvate or hydrate thereof.

Also disclosed herein is a low dosage formulation of a compound for use in a method of inducing satiety in an individual, said method comprising prescribing said low dosage formulation of the compound to said individual, wherein said individual has previously been determined to have renal impairment; wherein said compound is (R)-8-chloro-1-methyl-2,3,4,5-tetrahydro-1H-3-benzazepine or a pharmaceutically acceptable salt, solvate or hydrate thereof. In addition, disclosed herein is a low dosage formulation of a compound for use in a method of inducing satiety in an individual, said method comprising administering said low dosage formulation of the compound to said individual, wherein said individual has previously been determined to have renal impairment; wherein said compound is (R)-8-chloro-1-methyl-2,3,4,5-tetrahydro-1H-3-benzazepine or a pharmaceutically acceptable salt, solvate or hydrate thereof.

Disclosed herein is a low dosage formulation of a compound for use in a method of inducing satiety in an individual, wherein said low dosage reduces a toxic event in said individual to said compound, wherein said individual has previously been determined to have renal impairment; and wherein said compound is (R)-8-chloro-1-methyl-2,3,4,5-tetrahydro-1H-3-benzazepine or a pharmaceutically acceptable salt, solvate or hydrate thereof. Also disclosed herein is a low dosage formulation of a compound for use in a method of inducing satiety in an individual, wherein said low dosage prevents a toxic event in said individual to said compound, wherein said individual has previously been determined to have renal impairment; and wherein said compound is (R)-8-chloro-1-methyl-2,3,4,5-tetrahydro-1H-3-benzazepine or a pharmaceutically acceptable salt, solvate or hydrate thereof.

One aspect of the present disclosure pertains to methods for inducing satiety, comprising administering to an individual in need thereof, a therapeutically effective amount of a compound, a crystalline form, a pharmaceutical composition, or a dosage form of the present disclosure.

In some embodiments, the individual in need of inducing satiety is a patient with an initial body mass index $\geq 30$ kg/m$^2$.

In some embodiments, the individual in need of inducing satiety is a patient with an initial body mass index $\geq 27$ kg/m$^2$ in the presence of at least one weight related comorbid condition.

In some embodiments, the individual in need of inducing satiety is a patient with an initial body mass index $\geq 27$ kg/m$^2$ in the presence of at least one weight related comorbid condition selected from: hypertension, dyslipidemia, cardiovascular disease, glucose intolerance and sleep apnea.

In some embodiments, the individual in need of inducing satiety has an initial body mass index ≥30 kg/m².

In some embodiments, the individual in need of inducing satiety has an initial body mass index ≥27 kg/m².

In some embodiments, the individual in need of inducing satiety has an initial body mass index ≥27 kg/m² in the presence of at least one weight related comorbid condition.

In some embodiments, the individual in need of inducing satiety has an initial body mass index ≥27 kg/m² in the presence of at least one weight related comorbid condition selected from: hypertension, dyslipidemia, cardiovascular disease, glucose intolerance and sleep apnea.

In some embodiments, the individual in need of inducing satiety has an initial body mass index ≥25 kg/m².

In some embodiments, the individual in need of inducing satiety has an initial body mass index ≥25 kg/m² in the presence of at least one weight related comorbid condition.

In some embodiments, the individual in need of inducing satiety has an initial body mass index ≥25 kg/m² in the presence of at least one weight related comorbid condition selected from: hypertension, dyslipidemia, cardiovascular disease, glucose intolerance and sleep apnea.

In some embodiments, inducing satiety comprises weight loss. In some embodiments, inducing satiety comprises maintenance of weight loss. In some embodiments, inducing satiety further comprises a reduced-calorie diet. In some embodiments, inducing satiety further comprises a program of regular exercise. In some embodiments, inducing satiety further comprises both a reduced-calorie diet and a program of regular exercise.

In some embodiments, the method for inducing satiety further comprises prescribing or administering a weight loss compound or procedure in addition to prescribing or administering (R)-8-chloro-1-methyl-2,3,4,5-tetrahydro-1H-3-benzazepine or a pharmaceutically acceptable salt, solvate or hydrate thereof. In some embodiments, the method for inducing satiety further comprises prescribing or administering phentermine to the individual. In some embodiments, (R)-8-chloro-1-methyl-2,3,4,5-tetrahydro-1H-3-benzazepine or a pharmaceutically acceptable salt, solvate or hydrate thereof is prescribed or administered before or after a surgical weight loss procedure, for example, a lap band or gastric bypass surgery.

Disclosed herein is a method for reducing the risk of an adverse event in an individual in need of inducing satiety, comprising administering a therapeutically effective amount of (R)-8-chloro-1-methyl-2,3,4,5-tetrahydro-1H-3-benzazepine or a pharmaceutically acceptable salt, solvate or hydrate thereof to the individual, wherein the level of renal sufficiency of the individual has been determined, and provided that the individual has a level of renal sufficiency selected from the group consisting of: no renal impairment, mild renal impairment, and moderate renal impairment. Further disclosed herein is a method for reducing the risk of an adverse event in an individual in need of inducing satiety, comprising administering a reduced dosage regimen of (R)-8-chloro-1-methyl-2,3,4,5-tetrahydro-1H-3-benzazepine or a pharmaceutically acceptable salt, solvate or hydrate thereof to the individual, wherein the level of renal sufficiency of the individual has been determined, and provided that the individual has renal impairment. Also disclosed herein is a method for reducing the risk of an adverse event in an individual in need of inducing satiety, comprising administering a therapeutically effective amount of (R)-8-chloro-1-methyl-2,3,4,5-tetrahydro-1H-3-benzazepine or a pharmaceutically acceptable salt, solvate or hydrate thereof to the individual, wherein an approximate serum creatinine concentration has been determined for the individual, and provided that the individual has an approximate serum creatinine concentration of:

(i) less than 4.9 mg/dL for an 18-20 year old man,
(ii) less than 3.5 mg/dL for an 18-20 year old woman,
(iii) less than 4.5 mg/dL for a 21-30 year old man,
(iv) less than 3.2 mg/dL for a 21-30 year old woman,
(v) less than 4.1 mg/dL for a 31-40 year old man,
(vi) less than 2.9 mg/dL for a 31-40 year old woman,
(vii) less than 3.7 mg/dL for a 41-50 year old man,
(viii) less than 2.7 mg/dL for a 41-50 year old woman,
(ix) less than 3.3 mg/dL for a 51-60 year old man,
(x) less than 2.4 mg/dL for a 51-60 year old woman,
(xi) less than 3.0 mg/dL for a man over 60 years old, or
(xii) less than 2.0 mg/dL for a woman over 60 years old.

Disclosed herein is a method for selecting an individual for treatment with (R)-8-chloro-1-methyl-2,3,4,5-tetrahydro-1H-3-benzazepine or a pharmaceutically acceptable salt, solvate or hydrate thereof from a plurality of individuals in need of inducing satiety, comprising selecting the individual for treatment with (R)-8-chloro-1-methyl-2,3,4,5-tetrahydro-1H-3-benzazepine or a pharmaceutically acceptable salt, solvate or hydrate thereof if it is determined that the individual has a level of renal sufficiency selected from the group consisting of: no renal impairment, mild renal impairment, and moderate renal impairment. Further disclosed herein is a method for selecting an individual for treatment with (R)-8-chloro-1-methyl-2,3,4,5-tetrahydro-1H-3-benzazepine or a pharmaceutically acceptable salt, solvate or hydrate thereof from a plurality of individuals in need of inducing satiety, comprising selecting the individual for treatment with (R)-8-chloro-1-methyl-2,3,4,5-tetrahydro-1H-3-benzazepine or a pharmaceutically acceptable salt, solvate or hydrate thereof if it is determined that the individual has an approximate serum creatinine concentration of:

(i) less than 4.9 mg/dL for an 18-20 year old man,
(ii) less than 3.5 mg/dL for an 18-20 year old woman,
(iii) less than 4.5 mg/dL for a 21-30 year old man,
(iv) less than 3.2 mg/dL for a 21-30 year old woman,
(v) less than 4.1 mg/dL for a 31-40 year old man,
(vi) less than 2.9 mg/dL for a 31-40 year old woman,
(vii) less than 3.7 mg/dL for a 41-50 year old man,
(viii) less than 2.7 mg/dL for a 41-50 year old woman,
(ix) less than 3.3 mg/dL for a 51-60 year old man,
(x) less than 2.4 mg/dL for a 51-60 year old woman,
(xi) less than 3.0 mg/dL for a man over 60 years old, or
(xii) less than 2.0 mg/dL for a woman over 60 years old.

Disclosed herein is a method for treatment of obesity in an individual in need thereof, comprising prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a level of renal sufficiency selected from the group consisting of: no renal impairment, mild renal impairment, and moderate renal impairment.

Also disclosed herein is a method for treatment of obesity in an individual in need thereof, comprising: a) determining the level of renal sufficiency of the individual, and b) prescribing a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a level of renal sufficiency selected from the group consisting of: no renal impairment, mild renal impairment, and moderate renal impairment. In addition, disclosed herein is a method for treatment of obesity in an individual in need thereof, comprising: a) determining the level of renal sufficiency of the individual, and b) administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a level of renal sufficiency selected from the group consisting of: no renal impairment, mild renal impairment, and moderate renal impairment.

In addition, disclosed herein is a method for treatment of obesity in an individual in need thereof, comprising prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual does not have severe renal impairment or end stage renal disease (ESRD).

Also disclosed herein is a method for treatment of obesity in an individual in need thereof, comprising: a) determining the level of renal sufficiency of the individual, and b) prescribing therapeutically effective amount of (R)-8-chloro-1-methyl-2,3,4,5-tetrahydro-1H-3-benzazepine or a pharmaceutically acceptable salt, solvate or hydrate thereof to the individual, provided that the individual does not have severe renal impairment or end stage renal disease (ESRD). In addition, disclosed herein is a method for treatment of obesity in an individual in need thereof, comprising: a) determining the level of renal sufficiency of the individual, and b) administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual does not have severe renal impairment or ESRD.

In some embodiments (R)-8-chloro-1-methyl-2,3,4,5-tetrahydro-1H-3-benzazepine or a pharmaceutically acceptable salt, solvate or hydrate thereof is (R)-8-chloro-1-methyl-2,3,4,5-tetrahydro-1H-3-benzazepine hydrochloride and hydrates thereof.

In some embodiments (R)-8-chloro-1-methyl-2,3,4,5-tetrahydro-1H-3-benzazepine or a pharmaceutically acceptable salt, solvate or hydrate thereof is (R)-8-chloro-1-methyl-2,3,4,5-tetrahydro-1H-3-benzazepine hydrochloride hemihydrate.

In some embodiments (R)-8-chloro-1-methyl-2,3,4,5-tetrahydro-1H-3-benzazepine or a pharmaceutically acceptable salt, solvate or hydrate thereof is (R)-8-chloro-1-methyl-2,3,4,5-tetrahydro-1H-3-benzazepine hydrochloride hemihydrate, Form III.

In some embodiments, the Cockcroft-Gault equation is used to determine the level of renal sufficiency of the individual.

In some embodiments, the individual's ideal body weight is used in the Cockcroft-Gault equation and in other embodiments the individual's actual body weight is used in the Cockcroft-Gault equation.

In some embodiments, the individual's serum creatinine concentration is used to determine the level of renal sufficiency of the individual.

As used herein the term "treat," "treating" or "treatment" refers to the administration of therapy to an individual who already manifests at least one symptom of a disease or condition or who has previously manifested at least one symptom of a disease or condition. For example, "treating" can include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylacticly and/or therapeutically. For example, the term "treating" in reference to a disorder means a reduction in severity of one or more symptoms associated with a particular disorder. Therefore, treating a disorder does not necessarily mean a reduction in severity of all symptoms associated with a disorder and does not necessarily mean a complete reduction in the severity of one or more symptoms associated with a disorder. For example, a method for treatment of obesity can result in weight loss; however, the weight loss does not need to be enough such that the individual is no longer obese. It has been shown that even modest decreases in weight or related parameters such as BMI, waist circumference and percent body fat, can result in improvement of health, for example, lower blood pressure, improved blood lipid profiles, or a reduction in sleep apnea.

As used herein, "treatment of obesity in an individual in need thereof" refers to a judgment made by a healthcare practitioner that an individual requires or will benefit from treatment of obesity. This judgment is made based on a variety of factors that are in the realm of a healthcare practitioner's expertise, but that includes the knowledge that the individual has a condition that is treatable by the methods of the disclosure.

To determine whether an individual is obese one can determine a body weight, a body mass index (BMI), a waist circumference or a body fat percentage of the individual to determine if the individual meets a body weight threshold, a BMI threshold, a waist circumference threshold or a body fat percentage threshold.

Disclosed herein is a method for treatment of obesity in an individual in need thereof, comprising prescribing or administering a reduced dosage regimen of (R)-8-chloro-1-methyl-2,3,4,5-tetrahydro-1H-3-benzazepine or a pharmaceutically acceptable salt, solvate or hydrate thereof to the individual provided that the individual has renal impairment.

Also disclosed herein is a method for treatment of obesity in an individual in need thereof, comprising: a) determining the level of renal sufficiency of the individual, and b) prescribing a reduced dosage regimen of (R)-8-chloro-1-methyl-2,3,4,5-tetrahydro-1H-3-benzazepine or a pharmaceutically acceptable salt, solvate or hydrate thereof to the individual provided that the individual has renal impairment. In addition, disclosed herein is a method for treatment of obesity in an individual in need thereof, comprising: a) determining the level of renal sufficiency of the individual, and b) administering a reduced dosage regimen of (R)-8-chloro-1-methyl-2,3,4,5-tetrahydro-1H-3-benzazepine or a pharmaceutically acceptable salt, solvate or hydrate thereof to the individual provided that the individual has renal impairment. In some embodiments, the individual has mild renal impairment, moderate renal impairment, severe renal impairment or ESRD. In some embodiments, the individual has moderate renal impairment, severe renal impairment or ESRD. In some embodiments, the individual has severe renal impairment or ESRD. In some embodiments, the individual has ESRD.

Disclosed herein is a method for treatment of obesity in an individual in need thereof, comprising prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual provided that the individual has an approximate serum creatinine concentration of:
  (i) less than 4.9 mg/dL for an 18-20 year old man,
  (ii) less than 3.5 mg/dL for an 18-20 year old woman,
  (iii) less than 4.5 mg/dL for a 21-30 year old man,
  (iv) less than 3.2 mg/dL for a 21-30 year old woman,
  (v) less than 4.1 mg/dL for a 31-40 year old man,
  (vi) less than 2.9 mg/dL for a 31-40 year old woman,
  (viii) less than 2.7 mg/dL for a 41-50 year old woman,
  (ix) less than 3.3 mg/dL for a 51-60 year old man,
  (x) less than 2.4 mg/dL for a 51-60 year old woman,
  (xi) less than 3.0 mg/dL for a man over 60 years old, or
  (xii) less than 2.0 mg/dL for a woman over 60 years old.

Also disclosed herein is a method for treatment of obesity in an individual in need thereof, comprising a) determining an approximate serum creatinine concentration for the individual, and b) prescribing a therapeutically effective amount of (R)-8-chloro-1-methyl-2,3,4,5-tetrahydro-1H-3-benzazepine or a pharmaceutically acceptable salt, solvate or hydrate thereof to the individual provided that the individual has an approximate serum creatinine concentration of:
  (i) less than 4.9 mg/dL for an 18-20 year old man,
  (ii) less than 3.5 mg/dL for an 18-20 year old woman,
  (iii) less than 4.5 mg/dL for a 21-30 year old man,
  (iv) less than 3.2 mg/dL for a 21-30 year old woman,
  (v) less than 4.1 mg/dL for a 31-40 year old man,
  (vi) less than 2.9 mg/dL for a 31-40 year old woman,
  (viii) less than 2.7 mg/dL for a 41-50 year old woman,
  (ix) less than 3.3 mg/dL for a 51-60 year old man,
  (x) less than 2.4 mg/dL for a 51-60 year old woman,
  (xi) less than 3.0 mg/dL for a man over 60 years old, or
  (xii) less than 2.0 mg/dL for a woman over 60 years old.

In addition, disclosed herein is a method for treatment of obesity in an individual in need thereof, comprising: a) determining an approximate serum creatinine concentration for the individual, and b) administering a therapeutically effective amount of (R)-8-chloro-1-methyl-2,3,4,5-tetrahydro-1H-3-benzazepine or a pharmaceutically acceptable salt, solvate or hydrate thereof to the individual provided that the individual has an approximate serum creatinine concentration of:
  (i) less than 4.9 mg/dL for an 18-20 year old man,
  (ii) less than 3.5 mg/dL for an 18-20 year old woman,
  (iii) less than 4.5 mg/dL for a 21-30 year old man,
  (iv) less than 3.2 mg/dL for a 21-30 year old woman,
  (v) less than 4.1 mg/dL for a 31-40 year old man,
  (vi) less than 2.9 mg/dL for a 31-40 year old woman,
  (vii) less than 3.7 mg/dL for a 41-50 year old man,
  (viii) less than 2.7 mg/dL for a 41-50 year old woman,
  (ix) less than 3.3 mg/dL for a 51-60 year old man,
  (x) less than 2.4 mg/dL for a 51-60 year old woman,
  (xi) less than 3.0 mg/dL for a man over 60 years old, or
  (xii) less than 2.0 mg/dL for a woman over 60 years old.

Disclosed herein is a method for treatment of obesity in an individual in need thereof, comprising prescribing or administering a therapeutically effective amount of (R)-8-chloro-1-methyl-1-methyl-2,3,4,5-tetrahydro-1H-3-benzazepine or a pharmaceutically acceptable salt, solvate or hydrate thereof to the individual, provided that the individual has a creatinine clearance rate of greater than about 80 mL/minute, greater than about 50 mL/minute or greater than about 30 mL/minute using the Cockcroft-Gault equation.

Also disclosed herein is a method for treatment of obesity in an individual in need thereof, comprising: a) determining a creatinine clearance rate using the Cockcroft-Gault equation for the individual, and b) prescribing a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a creatinine clearance rate of greater than about 80 mL/minute using the Cockcroft-Gault equation. In addition, disclosed herein is a method for treatment of obesity in an individual in need thereof, comprising: a) determining a creatinine clearance rate using the Cockcroft-Gault equation for the individual, and b) administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a creatinine clearance rate of greater than about 80 mL/minute using the Cockcroft-Gault equation.

Disclosed herein is a method for treatment of obesity in an individual in need thereof, comprising: a) determining a creatinine clearance rate using the Cockcroft-Gault equation for the individual, and b) prescribing a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a creatinine clearance rate of greater than about 50 mL/minute using the Cockcroft-Gault equation. In addition, disclosed herein is a method for treatment of obesity in an individual in need thereof, comprising: a) determining a creatinine clearance rate using the Cockcroft-Gault equation for the individual, and b) administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a creatinine clearance rate of greater than about 50 mL/minute using the Cockcroft-Gault equation.

Disclosed herein is a method for treatment of obesity in an individual in need thereof, comprising: a) determining a creatinine clearance rate using the Cockcroft-Gault equation for the individual, and b) prescribing a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a creatinine clearance rate of greater than about 30 mL/minute using the Cockcroft-Gault equation. In addition, disclosed herein is a method for treatment of obesity in an individual in need thereof, comprising: a) determining a creatinine clearance rate using the Cockcroft-Gault equation for the individual, and b) administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a creatinine clearance rate of greater than about 30 mL/minute using the Cockcroft-Gault equation.

Disclosed herein is a method for reducing the risk of an adverse event in an individual in need of treatment of obesity, comprising prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a level of renal sufficiency selected from the group consisting of: no renal impairment, mild renal impairment, and moderate renal impairment.

Disclosed herein is a method for reducing the risk of an adverse event in an individual in need of treatment of obesity, comprising: a) determining the level of renal sufficiency of the individual, and b) prescribing a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a level of renal sufficiency selected from the group consisting of: no renal impairment, mild renal impairment, and moderate renal impairment. Also disclosed herein is a method for reducing the risk of an adverse event in an individual in need of treatment of obesity, comprising: a) determining the level of renal sufficiency of the individual, and b) administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a level of renal sufficiency selected from the group consisting of: no renal impairment, mild renal impairment, and moderate renal impairment.

Disclosed herein is a method for reducing the risk of an adverse event in an individual in need of treatment of obesity, comprising prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual does not have severe renal impairment or ESRD.

Also disclosed herein is a method for reducing the risk of an adverse event in an individual in need of treatment of obesity, comprising prescribing or administering a reduced dosage regimen of (R)-8-chloro-1-methyl-2,3,4,5-tetrahydro-1H-3-benzazepine or a pharmaceutically acceptable salt, solvate or hydrate thereof to the individual provided that the individual has renal impairment.

Disclosed herein is a method for reducing the risk of an adverse event in an individual in need of treatment of obesity, comprising: a) determining the level of renal sufficiency of the individual, and b) prescribing a reduced dosage regimen of (R)-8-chloro-1-methyl-2,3,4,5-tetrahydro-1H-3-benzazepine or a pharmaceutically acceptable salt, solvate or hydrate thereof to the individual provided that the individual has renal impairment. Also disclosed herein is a method for reducing the risk of an adverse event in an individual in need of treatment of obesity, comprising: a) determining the level of renal sufficiency of the individual, and b) administering a reduced dosage regimen of (R)-8-chloro-1-methyl-2,3,4,5-tetrahydro-1H-3-benzazepine or a pharmaceutically acceptable salt, solvate or hydrate thereof to the individual provided that the individual has renal impairment.

Further disclosed herein a method for reducing the risk of an adverse event in an individual in need of treatment of obesity, comprising prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual provided that the individual has an approximate serum creatinine concentration of:

(i) less than 4.9 mg/dL for an 18-20 year old man,
(ii) less than 3.5 mg/dL for an 18-20 year old woman,
(iii) less than 4.5 mg/dL for a 21-30 year old man,
(iv) less than 3.2 mg/dL for a 21-30 year old woman,
(v) less than 4.1 mg/dL for a 31-40 year old man,
(vi) less than 2.9 mg/dL for a 31-40 year old woman,
(vii) less than 3.7 mg/dL for a 41-50 year old man,
(viii) less than 2.7 mg/dL for a 41-50 year old woman,
(ix) less than 3.3 mg/dL for a 51-60 year old man,
(x) less than 2.4 mg/dL for a 51-60 year old woman,
(xi) less than 3.0 mg/dL for a man over 60 years old, or
(xii) less than 2.0 mg/dL for a woman over 60 years old.

Disclosed herein is a method for reducing the risk of an adverse event in an individual in need of treatment of obesity, comprising: a) determining an approximate serum creatinine concentration for the individual, and b) prescribing a therapeutically effective amount of (R)-8-chloro-1-methyl-2,3,4,5-tetrahydro-1H-3-benzazepine or a pharmaceutically acceptable salt, solvate or hydrate thereof to the individual provided that the individual has an approximate serum creatinine concentration of:

(i) less than 4.9 mg/dL for an 18-20 year old man,
(ii) less than 3.5 mg/dL for an 18-20 year old woman,
(iii) less than 4.5 mg/dL for a 21-30 year old man,
(iv) less than 3.2 mg/dL for a 21-30 year old woman,
(v) less than 4.1 mg/dL for a 31-40 year old man,
(vi) less than 2.9 mg/dL for a 31-40 year old woman,
(vii) less than 3.7 mg/dL for a 41-50 year old man,
(viii) less than 2.7 mg/dL for a 41-50 year old woman,
(ix) less than 3.3 mg/dL for a 51-60 year old man,
(x) less than 2.4 mg/dL for a 51-60 year old woman,
(xi) less than 3.0 mg/dL for a man over 60 years old, or
(xii) less than 2.0 mg/dL for a woman over 60 years old.

Also disclosed herein is a method for reducing the risk of an adverse event in an individual in need of treatment of obesity, comprising: a) determining an approximate serum creatinine concentration for the individual, and b) administering a therapeutically effective amount of (R)-8-chloro-1-methyl-2,3,4,5-tetrahydro-1H-3-benzazepine or a pharmaceutically acceptable salt, solvate or hydrate thereof to the individual provided that the individual has an approximate serum creatinine concentration of:

(i) less than 4.9 mg/dL for an 18-20 year old man,
(ii) less than 3.5 mg/dL for an 18-20 year old woman,
(iii) less than 4.5 mg/dL for a 21-30 year old man,
(iv) less than 3.2 mg/dL for a 21-30 year old woman,
(v) less than 4.1 mg/dL for a 31-40 year old man,
(vi) less than 2.9 mg/dL for a 31-40 year old woman,
(vii) less than 3.7 mg/dL for a 41-50 year old man,
(viii) less than 2.7 mg/dL for a 41-50 year old woman,
(ix) less than 3.3 mg/dL for a 51-60 year old man,
(x) less than 2.4 mg/dL for a 51-60 year old woman,
(xi) less than 3.0 mg/dL for a man over 60 years old, or
(xii) less than 2.0 mg/dL for a woman over 60 years old.

Disclosed herein is a method for reducing the risk of an adverse event in an individual in need of treatment of obesity comprising prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a creatinine clearance rate of greater than about 80 mL/minute, greater than about 50 mL/minute or greater than about 30 mL/minute using the Cockcroft-Gault equation.

Disclosed herein is a method for selecting an individual for treatment with (R)-8-chloro-1-methyl-2,3,4,5-tetrahydro-1H-3-benzazepine or a pharmaceutically acceptable salt, solvate or hydrate thereof from a plurality of individuals in need of treatment of obesity, comprising selecting the individual for treatment with (R)-8-chloro-1-methyl-2,3,4,5-tetrahydro-1H-3-benzazepine or a pharmaceutically acceptable salt, solvate or hydrate thereof if the individual has a level of renal sufficiency selected from the group consisting of: no renal impairment, mild renal impairment, and moderate renal impairment.

Also disclosed herein is a method for selecting an individual for treatment with (R)-8-chloro-1-methyl-2,3,4,5-tetrahydro-1H-3-benzazepine or a pharmaceutically acceptable salt, solvate or hydrate thereof from a plurality of individuals in need of treatment of obesity, comprising: a) determining the level of renal sufficiency of the individual; and b) selecting the individual for treatment with (R)-8-chloro-1-methyl-2,3,4,5-tetrahydro-1H-3-benzazepine or a pharmaceutically acceptable salt, solvate or hydrate thereof if the individual has a level of renal sufficiency selected from the group consisting of: no renal impairment, mild renal impairment, and moderate renal impairment.

Disclosed herein is a method for selecting an individual for treatment with (R)-8-chloro-1-methyl-2,3,4,5-tetrahydro-1H-3-benzazepine or a pharmaceutically acceptable salt, solvate or hydrate thereof from a plurality of individuals in need of treatment of obesity, comprising selecting the individual for treatment with (R)-8-chloro-1-methyl-2,3,4,5-tetrahydro-1H-3-benzazepine or a pharmaceutically acceptable salt, solvate or hydrate thereof provided that the individual does not have severe renal impairment or ESRD.

Also disclosed herein is a method for selecting an individual for treatment with (R)-8-chloro-1-methyl-2,3,4,5-tetrahydro-1H-3-benzazepine or a pharmaceutically acceptable salt, solvate or hydrate thereof from a plurality of individuals in need of treatment of obesity, comprising selecting the individual for treatment with a reduced dosage regimen of (R)-8-chloro-1-methyl-2,3,4,5-tetrahydro-1H-3-benzazepine or a pharmaceutically acceptable salt, solvate or hydrate thereof if the individual has renal impairment.

Further disclosed herein a method for selecting an individual for treatment with (R)-8-chloro-1-methyl-2,3,4,5-tetrahydro-1H-3-benzazepine or a pharmaceutically acceptable salt, solvate or hydrate thereof from a plurality of individuals in need of treatment of obesity, comprising selecting the individual for treatment with (R)-8-chloro-1-methyl-2,3,4,5-tetrahydro-1H-3-benzazepine or a pharmaceutically acceptable salt, solvate or hydrate thereof if the individual has an approximate serum creatinine concentration of:
  (i) less than 4.9 mg/dL for an 18-20 year old man,
  (ii) less than 3.5 mg/dL for an 18-20 year old woman,
  (iii) less than 4.5 mg/dL for a 21-30 year old man,
  (iv) less than 3.2 mg/dL for a 21-30 year old woman,
  (v) less than 4.1 mg/dL for a 31-40 year old man,
  (vi) less than 2.9 mg/dL for a 31-40 year old woman,
  (vii) less than 3.7 mg/dL for a 41-50 year old man,
  (viii) less than 2.7 mg/dL for a 41-50 year old woman,
  (ix) less than 3.3 mg/dL for a 51-60 year old man,
  (x) less than 2.4 mg/dL for a 51-60 year old woman,
  (xi) less than 3.0 mg/dL for a man over 60 years old, or
  (xii) less than 2.0 mg/dL for a woman over 60 years old.

In addition, disclosed herein is a method for selecting an individual for treatment with (R)-8-chloro-1-methyl-2,3,4,5-tetrahydro-1H-3-benzazepine or a pharmaceutically acceptable salt, solvate or hydrate thereof from a plurality of individuals in need of treatment of obesity, comprising: a) determining an approximate serum creatinine concentration for the individual, and b) selecting the individual for treatment with (R)-8-chloro-1-methyl-2,3,4,5-tetrahydro-1H-3-benzazepine or a pharmaceutically acceptable salt, solvate or hydrate thereof if the individual has an approximate serum creatinine concentration of:
  (i) less than 4.9 mg/dL for an 18-20 year old man,
  (ii) less than 3.5 mg/dL for an 18-20 year old woman,
  (iii) less than 4.5 mg/dL for a 21-30 year old man,
  (iv) less than 3.2 mg/dL for a 21-30 year old woman,
  (v) less than 4.1 mg/dL for a 31-40 year old man,
  (vi) less than 2.9 mg/dL for a 31-40 year old woman,
  (vii) less than 3.7 mg/dL for a 41-50 year old man,
  (viii) less than 2.7 mg/dL for a 41-50 year old woman,
  (ix) less than 3.3 mg/dL for a 51-60 year old man,
  (x) less than 2.4 mg/dL for a 51-60 year old woman,
  (xi) less than 3.0 mg/dL for a man over 60 years old, or
  (xii) less than 2.0 mg/dL for a woman over 60 years old.

Further disclosed herein a method for selecting an individual for treatment with (R)-8-chloro-1-methyl-2,3,4,5-tetrahydro-1H-3-benzazepine or a pharmaceutically acceptable salt, solvate or hydrate thereof from a plurality of individuals in need of treatment of obesity, comprising selecting the individual for treatment with (R)-8-chloro-1-methyl-2,3,4,5-tetrahydro-1H-3-benzazepine or a pharmaceutically acceptable salt, solvate or hydrate thereof provided that the individual has a creatinine clearance rate of greater than about 80 mL/minute, greater than about 50 mL/minute or greater than about 30 mL/minute using the Cockcroft-Gault equation.

Also disclosed herein is a compound for use in a method of treatment of obesity in an individual, said method comprising prescribing said compound to said individual, wherein said individual has previously been determined to have a level of renal sufficiency selected from the group consisting of: no renal impairment, mild renal impairment, and moderate renal impairment; wherein said compound is (R)-8-chloro-1-methyl-2,3,4,5-tetrahydro-1H-3-benzazepine or a pharmaceutically acceptable salt, solvate or hydrate thereof. In addition, disclosed herein is a compound for use in a method of treatment of obesity in an individual, said method comprising administering said compound to said individual, wherein said individual has previously been determined to have a level of renal sufficiency selected from the group consisting of: no renal impairment, mild renal impairment, and moderate renal impairment; wherein said compound is (R)-8-chloro-1-methyl-2,3,4,5-tetrahydro-1H-3-benzazepine or a pharmaceutically acceptable salt, solvate or hydrate thereof.

For example, also disclosed herein is a compound for use in a method of treatment of obesity in an individual, said method comprising prescribing a therapeutically effective amount of said compound to said individual, wherein said individual has previously been determined to have a level of renal sufficiency selected from the group consisting of: no renal impairment, mild renal impairment, and moderate renal impairment; wherein said compound is (R)-8-chloro-1-methyl-2,3,4,5-tetrahydro-1H-3-benzazepine or a pharmaceutically acceptable salt, solvate or hydrate thereof. In addition, disclosed herein is a compound for use in a method of treatment of obesity in an individual, said method comprising administering a therapeutically effective amount of said compound to said individual, wherein said individual has previously been determined to have a level of renal sufficiency selected from the group consisting of: no renal impairment, mild renal impairment, and moderate renal impairment; wherein said compound is (R)-8-chloro-1-methyl-2,3,4,5-tetrahydro-1H-3-benzazepine or a pharmaceutically acceptable salt, solvate or hydrate thereof.

Disclosed herein is a compound for use in a method for treatment of obesity in an individual, said method comprising prescribing said compound at a dosage level appropriate for the level of renal sufficiency of said individual, wherein said individual has previously been determined to have a level of renal sufficiency selected from the group consisting of: no renal impairment, mild renal impairment, moderate renal impairment, severe renal impairment and ESRD; wherein said compound is (R)-8-chloro-1-methyl-2,3,4,5-tetrahydro-1H-3-benzazepine or a pharmaceutically acceptable salt, solvate or hydrate thereof. In addition, disclosed herein is a compound for use in a method for treatment of obesity in an individual, said method comprising administering said compound at a dosage level appropriate for the level of renal sufficiency of said individual, wherein said individual has previously been determined to have a level of renal sufficiency selected from the group consisting of: no renal impairment, mild renal impairment, moderate renal impairment, severe renal impairment and ESRD; wherein said compound is (R)-8-chloro-1-methyl-2,3,4,5-tetrahydro-H-3-benzazepine or a pharmaceutically acceptable salt, solvate or hydrate thereof.

Also disclosed herein is a compound for use in a method for treatment of obesity in an individual, said method comprising determining the level of renal sufficiency of said individual and prescribing said compound at a dosage level appropriate for the level of renal sufficiency of said individual, wherein said individual has a level of renal sufficiency selected from the group consisting of: no renal impairment, mild renal impairment, moderate renal impairment, severe renal impairment and ESRD; wherein said compound is (R)-8-chloro-1-methyl-2,3,4,5-tetrahydro-1H-3-benzazepine or a pharmaceutically acceptable salt, solvate or hydrate thereof. Also disclosed herein is a compound for use in a method for treatment of obesity in an individual, said method comprising determining the level of renal sufficiency of said individual and administering said compound at a dosage level appropriate for the level of renal sufficiency of said individual, wherein said individual has a level of renal sufficiency selected from the group consisting of: no renal impairment, mild renal impairment, moderate renal impairment, severe renal impairment and ESRD; wherein said compound is (R)-8-chloro-1-methyl-2,3,4,5-tetrahydro-1H-3-benzazepine or a pharmaceutically acceptable salt, solvate or hydrate thereof.

Disclosed herein is a compound for use in a method for treatment of obesity in an individual, said method comprising prescribing or administering a reduced dosage regimen of said compound, wherein said compound is (R)-8-chloro-1-methyl-2,3,4,5-tetrahydro-1H-3-benzazepine or a pharmaceutically acceptable salt, solvate or hydrate thereof.

Disclosed herein is a compound for use in a method of treatment of obesity in an individual having moderate, mild or no renal impairment, said method comprising prescribing said compound to said individual, wherein said individual has previously been determined to have a level of renal sufficiency selected from the group consisting of: no renal impairment, mild renal impairment, and moderate renal impairment; wherein said compound is (R)-8-chloro-1-methyl-2,3,4,5-tetrahydro-1H-3-benzazepine or a pharmaceutically acceptable salt, solvate or hydrate thereof. In addition, disclosed herein is a compound for use in a method of treatment of obesity in an individual having moderate, mild or no renal impairment, said method comprising administering said compound to said individual, wherein said individual has previously been determined to have a level of renal sufficiency selected from the group consisting of: no renal impairment, mild renal impairment, and moderate renal impairment; wherein said compound is (R)-8-chloro-1-methyl-2,3,4,5-tetrahydro-1H-3-benzazepine or a pharmaceutically acceptable salt, solvate or hydrate thereof.

Also disclosed herein is a low dosage formulation of a compound for use in a method of treatment of obesity in an individual, said method comprising prescribing said low dosage formulation of the compound to said individual, wherein said individual has previously been determined to have renal impairment; wherein said compound is (R)-8-chloro-1-methyl-2,3,4,5-tetrahydro-1H-3-benzazepine or a pharmaceutically acceptable salt, solvate or hydrate thereof. In addition, disclosed herein is a low dosage formulation of a compound for use in a method of treatment of obesity in an individual, said method comprising administering said low dosage formulation of the compound to said individual, wherein said individual has previously been determined to have renal impairment; wherein said compound is (R)-8-chloro-1-methyl-2,3,4,5-tetrahydro-1H-3-benzazepine or a pharmaceutically acceptable salt, solvate or hydrate thereof.

Disclosed herein is a low dosage formulation of a compound for use in a method of treatment of obesity in an individual, wherein said low dosage reduces a toxic event in said individual to said compound, wherein said individual has previously been determined to have renal impairment; and wherein said compound is (R)-8-chloro-1-methyl-2,3,4,5-tetrahydro-1H-3-benzazepine or a pharmaceutically acceptable salt, solvate or hydrate thereof. Also disclosed herein is a low dosage formulation of a compound for use in a method of treatment of obesity in an individual, wherein said low dosage prevents a toxic event in said individual to said compound, wherein said individual has previously been determined to have renal impairment; and wherein said compound is (R)-8-chloro-1-methyl-2,3,4,5-tetrahydro-1H-3-benzazepine or a pharmaceutically acceptable salt, solvate or hydrate thereof.

One aspect of the present disclosure pertains to methods for treatment of obesity, comprising administering to an individual in need thereof, a therapeutically effective amount of a compound, a crystalline form, a pharmaceutical composition, or a dosage form of the present disclosure.

In some embodiments, the treatment of obesity comprises weight loss.

In some embodiments, the treatment of obesity comprises maintenance of weight loss.

In some embodiments, the treatment of obesity further comprises a reduced-calorie diet.

In some embodiments, the treatment of obesity further comprises a program of regular exercise.

In some embodiments, the treatment of obesity further comprises both a reduced-calorie diet and a program of regular exercise.

In some embodiments, the individual in need of treatment of obesity is a patient with an initial body mass index $\geq 30$ kg/m$^2$.

In some embodiments, the individual in need of treatment of obesity is an individual with an initial body mass index $\geq 27$ kg/m$^2$ in the presence of at least one weight related comorbid condition. For example, the individual can belong to an ethnic group where an initial BMI of $\geq 27$ kg/m$^2$ is considered obese.

In some embodiments, the individual in need of treatment of obesity is an individual with an initial body mass index $\geq 27$ kg/m$^2$ in the presence of at least one weight related comorbid condition selected from: hypertension, dyslipidemia, cardiovascular disease, glucose intolerance and sleep apnea.

In some embodiments, the individual in need of treatment of obesity has an initial body mass index $\geq 30$ kg/m$^2$.

In some embodiments, the individual in need of treatment of obesity has an initial body mass index $\geq 27$ kg/m$^2$.

In some embodiments, the individual in need of treatment of obesity has an initial body mass index $\geq 27$ kg/m$^2$ in the presence of at least one weight related comorbid condition.

In some embodiments, the individual in need of treatment of obesity has an initial body mass index $\geq 27$ kg/m$^2$ in the presence of at least one weight related comorbid condition selected from: hypertension, dyslipidemia, cardiovascular disease, glucose intolerance and sleep apnea.

In some embodiments, the method for treatment of obesity further comprises prescribing or administering a weight loss compound or procedure in addition to prescribing or administering (R)-8-chloro-1-methyl-2,3,4,5-tetrahydro-1H-3-benzazepine or a pharmaceutically acceptable salt, solvate or hydrate thereof. In some embodiments, the method for treatment of obesity further comprises prescribing or administering phentermine to the individual. In some embodiments, (R)-8-chloro-1-methyl-2,3,4,5-tetrahydro-1H-3-benzazepine or a pharmaceutically acceptable salt, solvate or hydrate thereof is prescribed or administered before or after a surgical weight loss procedure, for example, a lap band or gastric bypass surgery. In some embodiments, the method for the treatment of obesity further comprises gastric electrical stimulation.

Disclosed herein is a method for reducing the risk of an adverse event in an individual in need of treatment of obesity, comprising administering a therapeutically effective amount of (R)-8-chloro-1-methyl-2,3,4,5-tetrahydro-1H-3-benzazepine or a pharmaceutically acceptable salt, solvate or hydrate thereof to the individual, wherein the level of renal sufficiency of the individual has been determined, and provided that the individual has a level of renal sufficiency selected from the group consisting of: no renal impairment, mild renal impairment, and moderate renal impairment. Further disclosed herein is a method for reducing the risk of an adverse event in an individual in need of treatment of obesity, comprising administering a reduced dosage regimen of (R)-8-chloro-1-methyl-2,3,4,5-tetrahydro-1H-3-benzazepine or a pharmaceutically acceptable salt, solvate or hydrate thereof to the individual, wherein the level of renal sufficiency of the individual has been determined, and provided that the individual has renal impairment. Also disclosed herein is a method for reducing the risk of an adverse event in an individual in need of treatment of obesity, comprising administering a therapeutically effective amount of (R)-8-chloro-1-methyl-2,3,4,5-tetrahydro-1H-3-benzazepine or a pharmaceutically acceptable salt, solvate or hydrate thereof to the individual, wherein an approximate serum creatinine concentration has been determined for the individual, and provided that the individual has an approximate serum creatinine concentration of:

(i) less than 4.9 mg/dL for an 18-20 year old man,
(ii) less than 3.5 mg/dL for an 18-20 year old woman,
(iii) less than 4.5 mg/dL for a 21-30 year old man,
(iv) less than 3.2 mg/dL for a 21-30 year old woman,
(v) less than 4.1 mg/dL for a 31-40 year old man,
(vi) less than 2.9 mg/dL for a 31-40 year old woman,
(vii) less than 3.7 mg/dL for a 41-50 year old man,
(viii) less than 2.7 mg/dL for a 41-50 year old woman,
(ix) less than 3.3 mg/dL for a 51-60 year old man,
(x) less than 2.4 mg/dL for a 51-60 year old woman,
(xi) less than 3.0 mg/dL for a man over 60 years old, or
(xii) less than 2.0 mg/dL for a woman over 60 years old.

Disclosed herein is a method for selecting an individual for treatment with (R)-8-chloro-1-methyl-2,3,4,5-tetrahydro-1H-3-benzazepine or a pharmaceutically acceptable salt, solvate or hydrate thereof from a plurality of individuals in need of treatment of obesity, comprising selecting the individual for treatment with (R)-8-chloro-1-methyl-2,3,4,5-tetrahydro-1H-3-benzazepine or a pharmaceutically acceptable salt, solvate or hydrate thereof if it is determined that the individual has a level of renal sufficiency selected from the group consisting of: no renal impairment, mild renal impairment, and moderate renal impairment. Further disclosed herein is a method for selecting an individual for treatment with (R)-8-chloro-1-methyl-2,3,4,5-tetrahydro-1H-3-benzazepine or a pharmaceutically acceptable salt, solvate or hydrate thereof from a plurality of individuals in need of treatment of obesity, comprising selecting the individual for treatment with (R)-8-chloro-1-methyl-2,3,4,5-tetrahydro-1H-3-benzazepine or a pharmaceutically acceptable salt, solvate or hydrate thereof if it is determined that the individual has an approximate serum creatinine concentration of:

(i) less than 4.9 mg/dL for an 18-20 year old man,
(ii) less than 3.5 mg/dL for an 18-20 year old woman,
(iii) less than 4.5 mg/dL for a 21-30 year old man,
(iv) less than 3.2 mg/dL for a 21-30 year old woman,
(v) less than 4.1 mg/dL for a 31-40 year old man,
(vi) less than 2.9 mg/dL for a 31-40 year old woman,
(vii) less than 3.7 mg/dL for a 41-50 year old man,
(viii) less than 2.7 mg/dL for a 41-50 year old woman,
(ix) less than 3.3 mg/dL for a 51-60 year old man,
(x) less than 2.4 mg/dL for a 51-60 year old woman,
(xi) less than 3.0 mg/dL for a man over 60 years old, or
(xii) less than 2.0 mg/dL for a woman over 60 years old.

Disclosed herein is a method for prevention of obesity in an individual in need thereof, comprising prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a level of renal sufficiency selected from the group consisting of: no renal impairment, mild renal impairment, and moderate renal impairment.

Also disclosed herein is a method for prevention of obesity in an individual in need thereof, comprising: a) determining the level of renal sufficiency of the individual, and b) prescribing a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a level of renal sufficiency selected from the group consisting of: no renal impairment, mild renal impairment, and moderate renal impairment. In addition, disclosed herein is a method for prevention of obesity in an individual in need thereof, comprising: a) determining the level of renal sufficiency of the individual, and b) administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a level of renal sufficiency selected from the group consisting of: no renal impairment, mild renal impairment, and moderate renal impairment.

In addition, disclosed herein is a method for prevention of obesity in an individual in need thereof, comprising prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual does not have severe renal impairment or end stage renal disease (ESRD).

Also disclosed herein is a method for prevention of obesity in an individual in need thereof, comprising: a) determining the level of renal sufficiency of the individual, and b) prescribing therapeutically effective amount of (R)-8-chloro-1-methyl-2,3,4,5-tetrahydro-H-3-benzazepine or a pharmaceutically acceptable salt, solvate or hydrate thereof to the individual, provided that the individual does not have severe renal impairment or end stage renal disease (ESRD). In addition, disclosed herein is a method for prevention of obesity in an individual in need thereof, comprising: a) determining the level of renal sufficiency of the individual, and b) administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual does not have severe renal impairment or ESRD.

In some embodiments (R)-8-chloro-1-methyl-2,3,4,5-tetrahydro-1H-3-benzazepine or a pharmaceutically acceptable salt, solvate or hydrate thereof is (R)-8-chloro-1-methyl-2,3,4,5-tetrahydro-1H-3-benzazepine hydrochloride and hydrates thereof.

In some embodiments (R)-8-chloro-1-methyl-2,3,4,5-tetrahydro-1H-3-benzazepine or a pharmaceutically acceptable salt, solvate or hydrate thereof is (R)-8-chloro-1-methyl-2,3,4,5-tetrahydro-1H-3-benzazepine hydrochloride hemihydrate.

In some embodiments (R)-8-chloro-1-methyl-2,3,4,5-tetrahydro-1H-3-benzazepine or a pharmaceutically acceptable salt, solvate or hydrate thereof is (R)-8-chloro-1-methyl-2,3,4,5-tetrahydro-1H-3-benzazepine hydrochloride hemihydrate, Form III.

In some embodiments, the Cockcroft-Gault equation is used to determine the level of renal sufficiency of the individual.

In some embodiments, the individual's ideal body weight is used in the Cockcroft-Gault equation and in other embodiments the individual's actual body weight is used in the Cockcroft-Gault equation.

In some embodiments, the individual's serum creatinine concentration is used to determine the level of renal sufficiency of the individual.

As used herein, the term "prevention" such as prevention of obesity means prevention of the occurrence or onset of one or more symptoms associated with a particular disorder and does not necessarily mean the complete prevention of a disorder. For example, the term "prevent," "preventing" and "prevention" refers to the administration of therapy on a prophylactic or preventative basis to an individual who may ultimately manifest at least one symptom of a disease or condition but who has not yet done so. Such individuals can be identified on the basis of risk factors that are known to correlate with the subsequent occurrence of the disease. Alternatively, prevention therapy can be administered without prior identification of a risk factor, as a prophylactic measure. Delaying the onset of the at least one symptom can also be considered prevention or prophylaxis.

As used herein, "prevention of obesity in an individual in need thereof" refers to a judgment made by a healthcare practitioner that an individual requires or will benefit from prevention of obesity. This judgment is made based on a variety of factors that are in the realm of a healthcare practitioner's expertise, but that includes the knowledge that the individual has a condition that is treatable by the methods disclosed herein.

In some embodiments, an individual in need of prevention of obesity is an individual who is overweight (also called pre-obese). In some embodiments, an individual in need of prevention of obesity is an individual who has a family history of obesity. To determine whether an individual is overweight one can determine a body weight, a body mass index (BMI), a waist circumference or a body fat percentage of the individual to determine if the individual meets a body weight threshold, a BMI threshold, a waist circumference threshold or a body fat percentage threshold.

Disclosed herein is a method for prevention of obesity in an individual in need thereof, comprising prescribing or administering a reduced dosage regimen of (R)-8-chloro-1-methyl-2,3,4,5-tetrahydro-1H-3-benzazepine or a pharmaceutically acceptable salt, solvate or hydrate thereof to the individual provided that the individual has renal impairment.

Also disclosed herein is a method for prevention of obesity in an individual in need thereof, comprising: a) determining the level of renal sufficiency of the individual, and b) prescribing a reduced dosage regimen of (R)-8-chloro-1-methyl-2,3,4,5-tetrahydro-1H-3-benzazepine or a pharmaceutically acceptable salt, solvate or hydrate thereof to the individual provided that the individual has renal impairment. In addition, disclosed herein is a method for prevention of obesity in an individual in need thereof, comprising: a) determining the level of renal sufficiency of the individual, and b) administering a reduced dosage regimen of (R)-8-chloro-1-methyl-2,3,4,5-tetrahydro-1H-3-benzazepine or a pharmaceutically acceptable salt, solvate or hydrate thereof to the individual provided that the individual has renal impairment. In some embodiments, the individual has mild renal impairment, moderate renal impairment, severe renal impairment or ESRD. In some embodiments, the individual has moderate renal impairment, severe renal impairment or ESRD. In some embodiments, the individual has severe renal impairment or ESRD. In some embodiments, the individual has ESRD.

Disclosed herein is a method for prevention of obesity in an individual in need thereof, comprising prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual provided that the individual has an approximate serum creatinine concentration of:
(i) less than 4.9 mg/dL for an 18-20 year old man,
(ii) less than 3.5 mg/dL for an 18-20 year old woman,
(iii) less than 4.5 mg/dL for a 21-30 year old man,
(iv) less than 3.2 mg/dL for a 21-30 year old woman,
(v) less than 4.1 mg/dL for a 31-40 year old man,
(vi) less than 2.9 mg/dL for a 31-40 year old woman,
(viii) less than 2.7 mg/dL for a 41-50 year old woman,
(ix) less than 3.3 mg/dL for a 51-60 year old man,
(x) less than 2.4 mg/dL for a 51-60 year old woman,
(xi) less than 3.0 mg/dL for a man over 60 years old, or
(xii) less than 2.0 mg/dL for a woman over 60 years old.

Also disclosed herein is a method for prevention of obesity in an individual in need thereof, comprising a) determining an approximate serum creatinine concentration for the individual, and b) prescribing a therapeutically effective amount of (R)-8-chloro-1-methyl-2,3,4,5-tetrahydro-1H-3-benzazepine or a pharmaceutically acceptable salt, solvate or hydrate thereof to the individual provided that the individual has an approximate serum creatinine concentration of:
(i) less than 4.9 mg/dL for an 18-20 year old man,
(ii) less than 3.5 mg/dL for an 18-20 year old woman,
(iii) less than 4.5 mg/dL for a 21-30 year old man,
(iv) less than 3.2 mg/dL for a 21-30 year old woman,
(v) less than 4.1 mg/dL for a 31-40 year old man,
(vi) less than 2.9 mg/dL for a 31-40 year old woman,
(viii) less than 2.7 mg/dL for a 41-50 year old woman,
(ix) less than 3.3 mg/dL for a 51-60 year old man,
(x) less than 2.4 mg/dL for a 51-60 year old woman,
(xi) less than 3.0 mg/dL for a man over 60 years old, or
(xii) less than 2.0 mg/dL for a woman over 60 years old.

In addition, disclosed herein is a method for prevention of obesity in an individual in need thereof, comprising: a) determining an approximate serum creatinine concentration for the individual, and b) administering a therapeutically effective amount of (R)-8-chloro-1-methyl-2,3,4,5-tetrahydro-1H-3-benzazepine or a pharmaceutically acceptable salt, solvate or hydrate thereof to the individual provided that the individual has an approximate serum creatinine concentration of:
  (i) less than 4.9 mg/dL for an 18-20 year old man,
  (ii) less than 3.5 mg/dL for an 18-20 year old woman,
  (iii) less than 4.5 mg/dL for a 21-30 year old man,
  (iv) less than 3.2 mg/dL for a 21-30 year old woman,
  (v) less than 4.1 mg/dL for a 31-40 year old man,
  (vi) less than 2.9 mg/dL for a 31-40 year old woman,
  (vii) less than 3.7 mg/dL for a 41-50 year old man,
  (viii) less than 2.7 mg/dL for a 41-50 year old woman,
  (ix) less than 3.3 mg/dL for a 51-60 year old man,
  (x) less than 2.4 mg/dL for a 51-60 year old woman,
  (xi) less than 3.0 mg/dL for a man over 60 years old, or
  (xii) less than 2.0 mg/dL for a woman over 60 years old.

Disclosed herein is a method for prevention of obesity in an individual in need thereof, comprising prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a creatinine clearance rate of greater than about 80 mL/minute, greater than about 50 mL/minute or greater than about 30 mL/minute using the Cockcroft-Gault equation.

Also disclosed herein is a method for prevention of obesity in an individual in need thereof, comprising: a) determining a creatinine clearance rate using the Cockcroft-Gault equation for the individual, and b) prescribing a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a creatinine clearance rate of greater than about 80 mL/minute using the Cockcroft-Gault equation. In addition, disclosed herein is a method for prevention of obesity in an individual in need thereof, comprising: a) determining a creatinine clearance rate using the Cockcroft-Gault equation for the individual, and b) administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a creatinine clearance rate of greater than about 80 mL/minute using the Cockcroft-Gault equation.

Disclosed herein is a method for prevention of obesity in an individual in need thereof, comprising: a) determining a creatinine clearance rate using the Cockcroft-Gault equation for the individual, and b) prescribing a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a creatinine clearance rate of greater than about 50 mL/minute using the Cockcroft-Gault equation. In addition, disclosed herein is a method for prevention of obesity in an individual in need thereof, comprising: a) determining a creatinine clearance rate using the Cockcroft-Gault equation for the individual, and b) administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a creatinine clearance rate of greater than about 50 ml/minute using the Cockcroft-Gault equation.

Disclosed herein is a method for prevention of obesity in an individual in need thereof, comprising: a) determining a creatinine clearance rate using the Cockcroft-Gault equation for the individual, and b) prescribing a therapeutically effective amount of (R)-8-chloro-1-methyl-2,3,4,5-tetrahydro-H-3-benzazepine or a pharmaceutically acceptable salt, solvate or hydrate thereof to the individual, provided that the individual has a creatinine clearance rate of greater than about 30 mL/minute using the Cockcroft-Gault equation. In addition, disclosed herein is a method for prevention of obesity in an individual in need thereof, comprising: a) determining a creatinine clearance rate using the Cockcroft-Gault equation for the individual, and b) administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a creatinine clearance rate of greater than about 30 mL/minute using the Cockcroft-Gault equation.

Disclosed herein is a method for reducing the risk of an adverse event in an individual in need of prevention of obesity, comprising prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a level of renal sufficiency selected from the group consisting of: no renal impairment, mild renal impairment, and moderate renal impairment.

Disclosed herein is a method for reducing the risk of an adverse event in an individual in need of prevention of obesity, comprising: a) determining the level of renal sufficiency of the individual, and b) prescribing a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a level of renal sufficiency selected from the group consisting of: no renal impairment, mild renal impairment, and moderate renal impairment. Also disclosed herein is a method for reducing the risk of an adverse event in an individual in need of prevention of obesity, comprising: a) determining the level of renal sufficiency of the individual, and b) administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a level of renal sufficiency selected from the group consisting of: no renal impairment, mild renal impairment, and moderate renal impairment.

Disclosed herein is a method for reducing the risk of an adverse event in an individual in need of prevention of obesity, comprising prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual does not have severe renal impairment or ESRD.

Also disclosed herein is a method for reducing the risk of an adverse event in an individual in need of prevention of obesity, comprising prescribing or administering a reduced dosage regimen of (R)-8-chloro-1-methyl-2,3,4,5-tetrahydro-1H-3-benzazepine or a pharmaceutically acceptable salt, solvate or hydrate thereof to the individual provided that the individual has renal impairment.

Disclosed herein is a method for reducing the risk of an adverse event in an individual in need of prevention of obesity, comprising: a) determining the level of renal sufficiency of the individual, and b) prescribing a reduced dosage regimen of (R)-8-chloro-1-methyl-2,3,4,5-tetrahydro-1H-3-benzazepine or a pharmaceutically acceptable salt, solvate or hydrate thereof to the individual provided that the individual has renal impairment. Also disclosed herein is a method for reducing the risk of an adverse event in an individual in need of prevention of obesity, comprising: a) determining the level of renal sufficiency of the individual, and b) administering a reduced dosage regimen of (R)-8-chloro-1-methyl-2,3,4,5-tetrahydro-1H-3-benzazepine or a pharmaceutically acceptable salt, solvate or hydrate thereof to the individual provided that the individual has renal impairment.

Further disclosed herein a method for reducing the risk of an adverse event in an individual in need of prevention of obesity, comprising prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual provided that the individual has an approximate serum creatinine concentration of:
(i) less than 4.9 mg/dL for an 18-20 year old man,
(ii) less than 3.5 mg/dL for an 18-20 year old woman,
(iii) less than 4.5 mg/dL for a 21-30 year old man,
(iv) less than 3.2 mg/dL for a 21-30 year old woman,
(v) less than 4.1 mg/dL for a 31-40 year old man,
(vi) less than 2.9 mg/dL for a 31-40 year old woman,
(vii) less than 3.7 mg/dL for a 41-50 year old man,
(viii) less than 2.7 mg/dL for a 41-50 year old woman,
(ix) less than 3.3 mg/dL for a 51-60 year old man,
(x) less than 2.4 mg/dL for a 51-60 year old woman,
(xi) less than 3.0 mg/dL for a man over 60 years old, or
(xii) less than 2.0 mg/dL for a woman over 60 years old.

Disclosed herein is a method for reducing the risk of an adverse event in an individual in need of prevention of obesity, comprising: a) determining an approximate serum creatinine concentration for the individual, and b) prescribing a therapeutically effective amount of (R)-8-chloro-1-methyl-2,3,4,5-tetrahydro-1H-3-benzazepine or a pharmaceutically acceptable salt, solvate or hydrate thereof to the individual provided that the individual has an approximate serum creatinine concentration of:
(i) less than 4.9 mg/dL for an 18-20 year old man,
(ii) less than 3.5 mg/dL for an 18-20 year old woman,
(iii) less than 4.5 mg/dL for a 21-30 year old man,
(iv) less than 3.2 mg/dL for a 21-30 year old woman,
(v) less than 4.1 mg/dL for a 31-40 year old man,
(vi) less than 2.9 mg/dL for a 31-40 year old woman,
(vii) less than 3.7 mg/dL for a 41-50 year old man,
(viii) less than 2.7 mg/dL for a 41-50 year old woman,
(ix) less than 3.3 mg/dL for a 51-60 year old man,
(x) less than 2.4 mg/dL for a 51-60 year old woman,
(xi) less than 3.0 mg/dL for a man over 60 years old, or
(xii) less than 2.0 mg/dL for a woman over 60 years old.

Also disclosed herein is a method for reducing the risk of an adverse event in an individual in need of prevention of obesity, comprising: a) determining an approximate serum creatinine concentration for the individual, and b) administering a therapeutically effective amount of (R)-8-chloro-1-methyl-2,3,4,5-tetrahydro-1H-3-benzazepin or a pharmaceutically acceptable salt, solvate or hydrate thereof to the individual provided that the individual has an approximate serum creatinine concentration of:
(i) less than 4.9 mg/dL for an 18-20 year old man,
(ii) less than 3.5 mg/dL for an 18-20 year old woman,
(iii) less than 4.5 mg/dL for a 21-30 year old man,
(iv) less than 3.2 mg/dL for a 21-30 year old woman,
(v) less than 4.1 mg/dL for a 31-40 year old man,
(vi) less than 2.9 mg/dL for a 31-40 year old woman,
(vii) less than 3.7 mg/dL for a 41-50 year old man,
(viii) less than 2.7 mg/dL for a 41-50 year old woman,
(ix) less than 3.3 mg/dL for a 51-60 year old man,
(x) less than 2.4 mg/dL for a 51-60 year old woman,
(xi) less than 3.0 mg/dL for a man over 60 years old, or
(xii) less than 2.0 mg/dL for a woman over 60 years old.

Disclosed herein is a method for reducing the risk of an adverse event in an individual in need of prevention of obesity comprising prescribing or administering a therapeutically effective amount of (R)-8-chloro-1-methyl-2,3,4,5-tetrahydro-H-3-benzazepine or a pharmaceutically acceptable salt, solvate or hydrate thereof to the individual, provided that the individual has a creatinine clearance rate of greater than about 80 mL/minute, greater than about 50 mL/minute or greater than about 30 mL/minute using the Cockcroft-Gault equation.

Disclosed herein is a method for selecting an individual for treatment with (R)-8-chloro-1-methyl-2,3,4,5-tetrahydro-1H-3-benzazepine or a pharmaceutically acceptable salt, solvate or hydrate thereof from a plurality of individuals in need of prevention of obesity, comprising selecting the individual for treatment with (R)-8-chloro-1-methyl-2,3,4,5-tetrahydro-1H-3-benzazepine or a pharmaceutically acceptable salt, solvate or hydrate thereof if the individual has a level of renal sufficiency selected from the group consisting of: no renal impairment, mild renal impairment, and moderate renal impairment.

Also disclosed herein is a method for selecting an individual for treatment with (R)-8-chloro-1-methyl-2,3,4,5-tetrahydro-1H-3-benzazepine or a pharmaceutically acceptable salt, solvate or hydrate thereof from a plurality of individuals in need of prevention of obesity, comprising: a) determining the level of renal sufficiency of the individual; and b) selecting the individual for treatment with (R)-8-chloro-1-methyl-2,3,4,5-tetrahydro-1H-3-benzazepine or a pharmaceutically acceptable salt, solvate or hydrate thereof if the individual has a level of renal sufficiency selected from the group consisting of: no renal impairment, mild renal impairment, and moderate renal impairment.

Disclosed herein is a method for selecting an individual for treatment with (R)-8-chloro-1-methyl-2,3,4,5-tetrahydro-1H-3-benzazepin or a pharmaceutically acceptable salt, solvate or hydrate thereof from a plurality of individuals in need of prevention of obesity, comprising selecting the individual for treatment with (R)-8-chloro-1-methyl-2,3,4,5-tetrahydro-1H-3-benzazepine or a pharmaceutically acceptable salt, solvate or hydrate thereof provided that the individual does not have severe renal impairment or ESRD.

Also disclosed herein is a method for selecting an individual for treatment with (R)-8-chloro-1-methyl-2,3,4,5-tetrahydro-1H-3-benzazepine or a pharmaceutically acceptable salt, solvate or hydrate thereof from a plurality of individuals in need of prevention of obesity, comprising selecting the individual for treatment with a reduced dosage regimen of (R)-8-chloro-1-methyl-2,3,4,5-tetrahydro-1H-3-benzazepine or a pharmaceutically acceptable salt, solvate or hydrate thereof if the individual has renal impairment.

Further disclosed herein a method for selecting an individual for treatment with (R)-8-chloro-1-methyl-2,3,4,5-tetrahydro-1H-3-benzazepine or a pharmaceutically acceptable salt, solvate or hydrate thereof from a plurality of individuals in need of prevention of obesity, comprising selecting the individual for treatment with (R)-8-chloro-1-methyl-2,3,4,5-tetrahydro-1H-3-benzazepine or a pharmaceutically acceptable salt, solvate or hydrate thereof if the individual has an approximate serum creatinine concentration of:
(i) less than 4.9 mg/dL for an 18-20 year old man,
(ii) less than 3.5 mg/dL for an 18-20 year old woman,
(iii) less than 4.5 mg/dL for a 21-30 year old man,
(iv) less than 3.2 mg/dL for a 21-30 year old woman, (v) less than 4.1 mg/dL for a 31-40 year old man,
(vi) less than 2.9 mg/dL for a 31-40 year old woman,
(vii) less than 3.7 mg/dL for a 41-50 year old man,
(viii) less than 2.7 mg/dL for a 41-50 year old woman,
(ix) less than 3.3 mg/dL for a 51-60 year old man,
(x) less than 2.4 mg/dL for a 51-60 year old woman,
(xi) less than 3.0 mg/dL for a man over 60 years old, or
(xii) less than 2.0 mg/dL for a woman over 60 years old.

In addition, disclosed herein is a method for selecting an individual for treatment with (R)-8-chloro-1-methyl-2,3,4,5-tetrahydro-1H-3-benzazepine or a pharmaceutically acceptable salt, solvate or hydrate thereof from a plurality of individuals in need of prevention of obesity, comprising: a) determining an approximate serum creatinine concentration for the individual, and b) selecting the individual for treatment with (R)-8-chloro-1-methyl-2,3,4,5-tetrahydro-1H-3-benzazepine or a pharmaceutically acceptable salt, solvate or hydrate thereof if the individual has an approximate serum creatinine concentration of:
(i) less than 4.9 mg/dL for an 18-20 year old man,
(ii) less than 3.5 mg/dL for an 18-20 year old woman,
(iii) less than 4.5 mg/dL for a 21-30 year old man,
(iv) less than 3.2 mg/dL for a 21-30 year old woman,
(v) less than 4.1 mg/dL for a 31-40 year old man,
(vi) less than 2.9 mg/dL for a 31-40 year old woman,
(vii) less than 3.7 mg/dL for a 41-50 year old man,
(viii) less than 2.7 mg/dL for a 41-50 year old woman,
(ix) less than 3.3 mg/dL for a 51-60 year old man,
(x) less than 2.4 mg/dL for a 51-60 year old woman,
(xi) less than 3.0 mg/dL for a man over 60 years old, or
(xii) less than 2.0 mg/dL for a woman over 60 years old.

Further disclosed herein a method for selecting an individual for treatment with (R)-8-chloro-1-methyl-2,3,4,5-tetrahydro-1H-3-benzazepine or a pharmaceutically acceptable salt, solvate or hydrate thereof from a plurality of individuals in need of prevention of obesity, comprising selecting the individual for treatment with (R)-8-chloro-1-methyl-2,3,4,5-tetrahydro-1H-3-benzazepine or a pharmaceutically acceptable salt, solvate or hydrate thereof provided that the individual has a creatinine clearance rate of greater than about 80 mL/minute, greater than about 50 ml/minute or greater than about 30 mL/minute using the Cockcroft-Gault equation.

Also disclosed herein is a compound for use in a method of prevention of obesity in an individual, said method comprising prescribing said compound to said individual, wherein said individual has previously been determined to have a level of renal sufficiency selected from the group consisting of: no renal impairment, mild renal impairment, and moderate renal impairment; wherein said compound is (R)-8-chloro-1-methyl-2,3,4,5-tetrahydro-1H-3-benzazepine or a pharmaceutically acceptable salt, solvate or hydrate thereof. In addition, disclosed herein is a compound for use in a method of prevention of obesity in an individual, said method comprising administering said compound to said individual, wherein said individual has previously been determined to have a level of renal sufficiency selected from the group consisting of: no renal impairment, mild renal impairment, and moderate renal impairment; wherein said compound is (R)-8-chloro-1-methyl-2,3,4,5-tetrahydro-1H-3-benzazepine or a pharmaceutically acceptable salt, solvate or hydrate thereof.

For example, disclosed herein is a compound for use in a method of prevention of obesity in an individual, said method comprising prescribing a therapeutically effective amount of said compound to said individual, wherein said individual has previously been determined to have a level of renal sufficiency selected from the group consisting of: no renal impairment, mild renal impairment, and moderate renal impairment; wherein said compound is (R)-8-chloro-1-methyl-2,3,4,5-tetrahydro-1H-3-benzazepine or a pharmaceutically acceptable salt, solvate or hydrate thereof. In addition, disclosed herein is a compound for use in a method of prevention of obesity in an individual, said method comprising administering a therapeutically effective amount of said compound to said individual, wherein said individual has previously been determined to have a level of renal sufficiency selected from the group consisting of: no renal impairment, mild renal impairment, and moderate renal impairment; wherein said compound is (R)-8-chloro-1-methyl-2,3,4,5-tetrahydro-1H-3-benzazepine or a pharmaceutically acceptable salt, solvate or hydrate thereof.

Disclosed herein is a compound for use in a method of prevention of obesity in an individual, said method comprising prescribing said compound at a dosage level appropriate for the level of renal sufficiency of said individual, wherein said individual has previously been determined to have a level of renal sufficiency selected from the group consisting of: no renal impairment, mild renal impairment, moderate renal impairment, severe renal impairment and ESRD; wherein said compound is (R)-8-chloro-1-methyl-2,3,4,5-tetrahydro-1H-3-benzazepine or a pharmaceutically acceptable salt, solvate or hydrate thereof. In addition, disclosed herein is a compound for use in a method of prevention of obesity in an individual, said method comprising administering said compound at a dosage level appropriate for the level of renal sufficiency of said individual, wherein said individual has previously been determined to have a level of renal sufficiency selected from the group consisting of: no renal impairment, mild renal impairment, moderate renal impairment, severe renal impairment and ESRD; wherein said compound is (R)-8-chloro-1-methyl-2,3,4,5-tetrahydro-1H-3-benzazepine or a pharmaceutically acceptable salt, solvate or hydrate thereof.

Also disclosed herein is a compound for use in a method of prevention of obesity in an individual, said method comprising determining the level of renal sufficiency of said individual and prescribing said compound at a dosage level appropriate for the level of renal sufficiency of said individual, wherein said individual has a level of renal sufficiency selected from the group consisting of: no renal impairment, mild renal impairment, moderate renal impairment, severe renal impairment and ESRD; wherein said compound is (R)-8-chloro-1-methyl-2,3,4,5-tetrahydro-1H-3-benzazepine or a pharmaceutically acceptable salt, solvate or hydrate thereof. Also disclosed herein is a compound for use in a method of prevention of obesity in an individual, said method comprising determining the level of renal sufficiency of said individual and administering said compound at a dosage level appropriate for the level of renal sufficiency of said individual, wherein said individual has a level of renal sufficiency selected from the group consisting of: no renal impairment, mild renal impairment, moderate renal impairment, severe renal impairment and ESRD; wherein said compound is (R)-8-chloro-1-methyl-2,3,4,5-tetrahydro-1H-3-benzazepine or a pharmaceutically acceptable salt, solvate or hydrate thereof.

Disclosed herein is a compound for use in a method of prevention of obesity in an individual, said method comprising prescribing or administering a reduced dosage regimen of said compound, wherein said compound is (R)-8-chloro-1-methyl-2,3,4,5-tetrahydro-1H-3-benzazepine or a pharmaceutically acceptable salt, solvate or hydrate thereof.

Disclosed herein is a compound for use in a method of prevention of obesity in an individual having moderate, mild or no renal impairment, said method comprising prescribing said compound to said individual, wherein said individual has previously been determined to have a level of renal sufficiency selected from the group consisting of: no renal impairment, mild renal impairment, and moderate renal impairment; wherein said compound is (R)-8-chloro-1-methyl-2,3,4,5-tetrahydro-1H-3-benzazepine or a pharmaceutically acceptable salt, solvate or hydrate thereof. In addition, disclosed herein is a compound for use in a method of prevention of obesity in an individual having moderate, mild or no renal impairment, said method comprising administering said compound to said individual, wherein said individual has previously been determined to have a level of renal sufficiency selected from the group consisting of: no renal impairment, mild renal impairment, and moderate renal impairment; wherein said compound is (R)-8-chloro-1-methyl-2,3,4,5-tetrahydro-1H-3-benzazepine or a pharmaceutically acceptable salt, solvate or hydrate thereof.

Also disclosed herein is a low dosage formulation of a compound for use in a method of prevention of obesity in an individual, said method comprising prescribing said low dosage formulation of the compound to said individual, wherein said individual has previously been determined to have renal impairment; wherein said compound is (R)-8-chloro-1-methyl-2,3,4,5-tetrahydro-1H-3-benzazepine or a pharmaceutically acceptable salt, solvate or hydrate thereof. In addition, disclosed herein is a low dosage formulation of a compound for use in a method of prevention of obesity in an individual, said method comprising administering said low dosage formulation of the compound to said individual, wherein said individual has previously been determined to have renal impairment; wherein said compound is (R)-8-chloro-1-methyl-2,3,4,5-tetrahydro-1H-3-benzazepine or a pharmaceutically acceptable salt, solvate or hydrate thereof.

Disclosed herein is a low dosage formulation of a compound for use in a method of prevention of obesity in an individual, wherein said low dosage reduces a toxic event in said individual to said compound, wherein said individual has previously been determined to have renal impairment; and wherein said compound is (R)-8-chloro-1-methyl-2,3,4,5-tetrahydro-1H-3-benzazepine or a pharmaceutically acceptable salt, solvate or hydrate thereof. A low dosage formulation of a compound for use in a method of prevention of obesity in an individual, wherein said low dosage prevents a toxic event in said individual to said compound, wherein said individual has previously been determined to have renal impairment; and wherein said compound is (R)-8-chloro-1-methyl-2,3,4,5-tetrahydro-1H-3-benzazepine or a pharmaceutically acceptable salt, solvate or hydrate thereof.

One aspect of the present disclosure pertains to methods for prevention of obesity, comprising administering to an individual in need thereof, a therapeutically effective amount of a compound, a crystalline form, a pharmaceutical composition, or a dosage form of the present disclosure.

In some embodiments, the prevention of obesity comprises weight loss.

In some embodiments, the prevention of obesity comprises maintenance of weight loss.

In some embodiments, the prevention of obesity further comprises a reduced-calorie diet.

In some embodiments, the prevention of obesity further comprises a program of regular exercise.

In some embodiments, the prevention of obesity further comprises both a reduced-calorie diet and a program of regular exercise.

In some embodiments, the individual in need of prevention of obesity is a patient with an initial body mass index ≥27 kg/m² in the presence of at least one weight related comorbid condition.

In some embodiments, the individual in need of prevention of obesity is a patient with an initial body mass index ≥27 kg/m² in the presence of at least one weight related comorbid condition selected from: hypertension, dyslipidemia, cardiovascular disease, glucose intolerance and sleep apnea.

In some embodiments, the individual in need of prevention of obesity has an initial body mass index ≥27 kg/m².

In some embodiments, the individual in need of prevention of obesity has an initial body mass index ≥27 kg/m² in the presence of at least one weight related comorbid condition.

In some embodiments, the individual in need of prevention of obesity has an initial body mass index ≥27 kg/m² in the presence of at least one weight related comorbid condition selected from: hypertension, dyslipidemia, cardiovascular disease, glucose intolerance and sleep apnea.

In some embodiments, the individual in need of prevention of obesity has an initial body mass index ≥25 kg/m².

In some embodiments, the individual in need of prevention of obesity has an initial body mass index ≥25 kg/m² in the presence of at least one weight related comorbid condition.

In some embodiments, the individual in need of prevention of obesity has an initial body mass index ≥25 kg/m² in the presence of at least one weight related comorbid condition selected from: hypertension, dyslipidemia, cardiovascular disease, glucose intolerance and sleep apnea.

In some embodiments, the method for prevention of obesity further comprises prescribing or administering a weight loss compound or procedure in addition to prescribing or administering (R)-8-chloro-1-methyl-2,3,4,5-tetrahydro-1H-3-benzazepine or a pharmaceutically acceptable salt, solvate or hydrate thereof. In some embodiments, the method for prevention of obesity further comprises prescribing or administering phentermine to the individual. In some embodiments, (R)-8-chloro-1-methyl-2,3,4,5-tetrahydro-1H-3-benzazepine or a pharmaceutically acceptable salt, solvate or hydrate thereof is prescribed or administered before or after a surgical weight loss (bariatric) procedure, for example, a lap band or gastric bypass surgery.

One aspect of the present disclosure pertains to a method for weight management in an individual in need thereof, comprising: a) determining an approximate serum creatinine concentration for the individual, and b) not prescribing or administering (R)-8-chloro-1-methyl-2,3,4,5-tetrahydro-1H-3-benzazepine or a pharmaceutically acceptable salt, solvate or hydrate thereof to the individual provided that the individual has an approximate serum creatinine concentration of:

(i) more than 4.9 mg/dL for an 18-20 year old man,
(ii) more than 3.5 mg/dL for an 18-20 year old woman,
(iii) more than 4.5 mg/dL for a 21-30 year old man,
(iv) more than 3.2 mg/dL for a 21-30 year old woman,
(v) more than 4.1 mg/dL for a 31-40 year old man,
(vi) more than 2.9 mg/dL for a 31-40 year old woman,
(vii) more than 3.7 mg/dL for a 41-50 year old man,
(viii) more than 2.7 mg/dL for a 41-50 year old woman,
(ix) more than 3.3 mg/dL for a 51-60 year old man,
(x) more than 2.4 mg/dL for a 51-60 year old woman, (xi) more than 3.0 mg/dL for a man over 60 years old, or
(xii) more than 2.0 mg/dL for a woman over 60 years old.

The disclosure also pertains to the above method for decreasing food intake in an individual, inducing satiety in an individual, treatment of obesity and prevention of obesity.

One aspect of the present disclosure pertains to a method for reducing the risk of an adverse event in an individual in an individual in need of weight management, comprising: a) determining an approximate serum creatinine concentration for the individual, and b) not prescribing or administering (R)-8-chloro-1-methyl-2,3,4,5-tetrahydro-1H-3-benzazepine or a pharmaceutically acceptable salt, solvate or hydrate thereof to the individual provided that the individual has an approximate serum creatinine concentration of:
(i) more than 4.9 mg/dL for an 18-20 year old man,
(ii) more than 3.5 mg/dL for an 18-20 year old woman,
(iii) more than 4.5 mg/dL for a 21-30 year old man,
(iv) more than 3.2 mg/dL for a 21-30 year old woman,
(v) more than 4.1 mg/dL for a 31-40 year old man,
(vi) more than 2.9 mg/dL for a 31-40 year old woman,
(vii) more than 3.7 mg/dL for a 41-50 year old man,
(viii) more than 2.7 mg/dL for a 41-50 year old woman,
(ix) more than 3.3 mg/dL for a 51-60 year old man,
(x) more than 2.4 mg/dL for a 51-60 year old woman,
(xi) more than 3.0 mg/dL for a man over 60 years old, or
(xii) more than 2.0 mg/dL for a woman over 60 years old.

One aspect of the present disclosure pertains to a method for selecting an individual for treatment with (R)-8-chloro-1-methyl-2,3,4,5-tetrahydro-1H-3-benzazepine or a pharmaceutically acceptable salt, solvate or hydrate thereof from a plurality of individuals in need of weight management comprising a) determining an approximate serum creatinine concentration for the individual, and b) not selecting the individual for treatment with (R)-8-chloro-1-methyl-2,3,4,5-tetrahydro-1H-3-benzazepine or a pharmaceutically acceptable salt, solvate or hydrate thereof to the individual provided that the individual has an approximate serum creatinine concentration of:
(i) more than 4.9 mg/dL for an 18-20 year old man,
(ii) more than 3.5 mg/dL for an 18-20 year old woman,
(iii) more than 4.5 mg/dL for a 21-30 year old man,
(iv) more than 3.2 mg/dL for a 21-30 year old woman,
(v) more than 4.1 mg/dL for a 31-40 year old man,
(vi) more than 2.9 mg/dL for a 31-40 year old woman,
(vii) more than 3.7 mg/dL for a 41-50 year old man,
(viii) more than 2.7 mg/dL for a 41-50 year old woman,
(ix) more than 3.3 mg/dL for a 51-60 year old man,
(x) more than 2.4 mg/dL for a 51-60 year old woman,
(xi) more than 3.0 mg/dL for a man over 60 years old, or
(xii) more than 2.0 mg/dL for a woman over 60 years old.

One aspect of the present disclosure pertains to a method for treatment of a disorder related to 5-HT$_{2c}$ receptor activity in an individual, comprising a) determining the level of renal sufficiency of the individual, and b) prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a level of renal sufficiency selected from the group consisting of: no renal impairment, mild renal impairment, and moderate renal impairment.

One aspect of the present disclosure pertains to a method for reducing the risk of an adverse event in an individual in need of treatment of a disorder related to 5-HT$_{2c}$ receptor activity, comprising a) determining the level of renal sufficiency of the individual, and b) prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a level of renal sufficiency selected from the group consisting of: no renal impairment, mild renal impairment, and moderate renal impairment.

One aspect of the present disclosure pertains to a method for selecting an individual for treatment with (R)-8-chloro-1-methyl-2,3,4,5-tetrahydro-1H-3-benzazepine or a pharmaceutically acceptable salt, solvate or hydrate thereof from a plurality of individuals in need of treatment of a disorder related to 5-HT$_{2c}$ receptor activity, comprising a) determining the level of renal sufficiency of the individual, and b) selecting the individual for treatment with (R)-8-chloro-1-methyl-2,3,4,5-tetrahydro-1H-3-benzazepine or a pharmaceutically acceptable salt, solvate or hydrate thereof to the individual, provided that the individual has a level of renal sufficiency selected from the group consisting of: no renal impairment, mild renal impairment, and moderate renal impairment.

One aspect of the present disclosure pertains to a method for weight maintenance in an individual, comprising a) determining the level of renal sufficiency of the individual, and b) prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a level of renal sufficiency selected from the group consisting of: no renal impairment, mild renal impairment, and moderate renal impairment.

One aspect of the present disclosure pertains to a method for reducing the risk of an adverse event in an individual in need of weight maintenance, comprising a) determining the level of renal sufficiency of the individual, and b) prescribing or administering a therapeutically effective amount of (R)-8-chloro-1-methyl-2,3,4,5-tetrahydro-1H-3-benzazepine or a pharmaceutically acceptable salt, solvate or hydrate thereof to the individual, provided that the individual has a level of renal sufficiency selected from the group consisting of: no renal impairment, mild renal impairment, and moderate renal impairment.

One aspect of the present disclosure pertains to a method for selecting an individual for treatment with (R)-8-chloro-1-methyl-2,3,4,5-tetrahydro-1H-3-benzazepine or a pharmaceutically acceptable salt, solvate or hydrate thereof from a plurality of individuals in need of weight maintenance, comprising a) determining the level of renal sufficiency of the individual, and b) selecting the individual for treatment with (R)-8-chloro-1-methyl-2,3,4,5-tetrahydro-1H-3-benzazepine or a pharmaceutically acceptable salt, solvate or hydrate thereof to the individual, provided that the individual has a level of renal sufficiency selected from the group consisting of: no renal impairment, mild renal impairment, and moderate renal impairment.

One aspect of the present disclosure pertains to methods for the treatment of a disorder related to 5-HT$_{2C}$ receptor activity in an individual, comprising prescribing or administering to an individual in need thereof, a therapeutically effective amount of a compound, a crystalline form, a pharmaceutical composition, or a dosage form of the present disclosure. In some embodiments, the compound is (R)-8-chloro-1-methyl-2,3,4,5-tetrahydro-1H-3-benzazepine or a pharmaceutically acceptable salt, solvate or hydrate thereof.

One aspect of the present disclosure pertains to methods for inducing weight loss, BMI loss, waist circumference loss or body fat percentage loss, comprising administering to an individual in need thereof, a therapeutically effective amount of a compound, a crystalline form, a pharmaceutical composition, or a dosage form of the present disclosure.

One aspect of the present disclosure pertains to methods for inducing weight loss, BMI loss, waist circumference loss or body fat percentage loss in an individual in preparation of the individual for bariatric surgery, comprising administering to an individual in need thereof, a therapeutically effective amount of a compound, a crystalline form, a pharmaceutical composition, or a dosage form of the present disclosure.

One aspect of the present disclosure pertains to methods for maintaining weight loss, BMI loss, waist circumference loss or body fat percentage loss in an individual, comprising administering to an individual in need thereof, a therapeutically effective amount of a compound, a crystalline form, a pharmaceutical composition, or a dosage form of the present disclosure.

One aspect of the present disclosure pertains to methods for maintaining weight loss, BMI loss, waist circumference loss or body fat percentage loss in an individual following bariatric surgery, comprising administering to an individual in need thereof, a therapeutically effective amount of a compound, a crystalline form, a pharmaceutical composition, or a dosage form of the present disclosure.

One aspect of the present disclosure pertains to methods for decreasing hunger in an individual, comprising administering to an individual in need thereof, a therapeutically effective amount of a compound, a crystalline form, a pharmaceutical composition, or a dosage form of the present disclosure.

One aspect of the present disclosure pertains to methods for decreasing food cravings in an individual, comprising administering to an individual in need thereof, a therapeutically effective amount of a compound, a crystalline form, a pharmaceutical composition, or a dosage form of the present disclosure.

One aspect of the present disclosure pertains to methods for increasing intermeal interval in an individual, comprising administering to an individual in need thereof, a therapeutically effective amount of a compound, a crystalline form, a pharmaceutical composition, or a dosage form of the present disclosure.

One aspect of the present disclosure pertains to methods for the treatment of a disorder selected from: schizophrenia, anxiety, depression, psychoses and alcohol addiction, comprising administering to an individual in need thereof, a therapeutically effective amount of a compound, a crystalline form, a pharmaceutical composition, or a dosage form of the present disclosure.

In some embodiments, the disorder is schizophrenia.
In some embodiments, the disorder is anxiety.
In some embodiments, the disorder is depression.
In some embodiments, the disorder is psychoses.
In some embodiments, the disorder is alcohol addiction.

One aspect of the present disclosure pertains to methods for treating an individual in need of treatment with (R)-8-chloro-1-methyl-2,3,4,5-tetrahydro-1H-3-benzazepine or a pharmaceutically acceptable salt, solvate or hydrate thereof comprising prescribing or administering with (R)-8-chloro-1-methyl-2,3,4,5-tetrahydro-1H-3-benzazepine or a pharmaceutically acceptable salt, solvate or hydrate thereof to the individual provided that the individual does not have severe renal impairment or ESRD. An individual in need of treatment with (R)-8-chloro-1-methyl-2,3,4,5-tetrahydro-1H-3-benzazepine or a pharmaceutically acceptable salt, solvate or hydrate thereof includes any individual who would benefit from use of (R)-8-chloro-1-methyl-2,3,4,5-tetrahydro-1H-3-benzazepine (Compound 1) or a pharmaceutically acceptable salt, solvate or hydrate thereof. Since Compound 1 is a selective 5-HT$_{2C}$ receptor agonist, any individual who would benefit from use of a selective 5-HT$_{2C}$ receptor agonist is encompassed. For example, the 5-HT$_{2C}$ receptor has been shown to have a role in the regulation of feeding behavior as well as a role in obsessive compulsive disorder, eating disorders, some forms of depression and epilepsy. The 5-HT$_{2C}$ receptor has also been shown to play a role in Alzheimer disease, erectile dysfunction, and sexual dysfunction. Accordingly, 5-HT$_{2C}$ agonists can be useful for the treatment or prophylaxis of 5-HT$_{2C}$ mediated diseases or disorders such as obesity, eating disorders, psychiatric disorders, Alzheimer disease, sexual dysfunction and disorders related thereto.

In some embodiments, an individual in need of treatment with (R)-8-chloro-1-methyl-2,3,4,5-tetrahydro-1H-3-benzazepine or a pharmaceutically acceptable salt, solvate or hydrate thereof is an individual who wants to lose weight. In some embodiments, an individual in need of treatment with (R)-8-chloro-1-methyl-2,3,4,5-tetrahydro-1H-3-benzazepine or a pharmaceutically acceptable salt, solvate or hydrate thereof is an individual who wants to maintain weight loss (weight maintenance). For example, such an individual in need of treatment with (R)-8-chloro-1-methyl-2,3,4,5-tetrahydro-1H-3-benzazepine or a pharmaceutically acceptable salt, solvate or hydrate thereof can be an individual who has lost weight and wants to maintain weight loss or prevent, reduce or control weight gain after weight loss.

Once aspect of the disclosure pertains to a compound for use in a method of preventing or treating obesity or weight gain associated conditions in a patient, said method comprising determining the level of renal impairment in said patient and administering said compound at a dosage level appropriate for the level of renal impairment to said patient, wherein said patient has previously been determined to have moderate, mild or no renal impairment; wherein said compound 1 is (R)-8-chloro-1-methyl-2,3,4,5-tetrahydro-1H-3-benzazepine or a pharmaceutical salt, solvate or hydrate thereof.

For example, Compound 1 or a pharmaceutically acceptable salt, solvate or hydrate thereof should not be prescribed or administered to an individual with severe renal impairment or ESRD. In addition, for example, a lower dosage of Compound 1 or a pharmaceutically acceptable salt, solvate or hydrate thereof can be prescribed or administered to an individual with mild or moderate renal impairment.

Once aspect of the disclosure pertains to a compound for use in a method of preventing or treating obesity or weight gain associated conditions in a patient, said method comprising prescribing said compound to said patient, wherein said patient has previously been determined to have moderate, mild or no renal impairment; wherein said compound is (R)-8-chloro-1-methyl-2,3,4,5-tetrahydro-1H-3-benzazepine or a pharmaceutical salt, solvate or hydrate thereof.

Once aspect of the disclosure pertains to a compound for use in a method of preventing or treating obesity or weight gain associated conditions in a patient, said method comprising determining the level of renal impairment in said patient and prescribing said compound at a dosage level appropriate for the level of renal impairment; wherein said compound is (R)-8-chloro-1-methyl-2,3,4,5-tetrahydro-1H-3-benzazepine or a pharmaceutical salt, solvate or hydrate thereof.

Once aspect of the disclosure pertains to a compound for use in a method of preventing or treating obesity or weight gain associated conditions in a patient having [a] moderate, mild or no renal impairment, said method comprising administering said compound to said patient, wherein said patient has previously been determined to have moderate, mild or no renal impairment; wherein said compound is (R)-8-chloro-1-methyl-2,3,4,5-tetrahydro-H-3-benzazepine or a pharmaceutical salt, solvate or hydrate thereof.

Once aspect of the disclosure pertains to a compound for use in a method of preventing or treating obesity or weight gain associated conditions in a patient having [a] moderate, mild or no renal impairment, said method comprising prescribing said compound to said patient, wherein said patient has previously been determined to have moderate, mild or no renal impairment; wherein said compound is (R)-8-chloro-1-methyl-2,3,4,5-tetrahydro-1H-3-benzazepine or a pharmaceutical salt, solvate or hydrate thereof.

Once aspect of the disclosure pertains to a low dosage formulation of a compound for use in a method of preventing or treating obesity or weight gain associated conditions in a patient, said method comprising administering said low dosage formulation of the compound to said patient, wherein said patient has previously been determined to have renal impairment; wherein said compound is (R)-8-chloro-1-methyl-2,3,4,5-tetrahydro-1H-3-benzazepine or a pharmaceutical salt, solvate or hydrate thereof.

Once aspect of the disclosure pertains to a low dosage formulation of a compound for use in a method of preventing or treating obesity or weight gain associated conditions in a patient, said method comprising prescribing said low dosage formulation of the compound to said patient, wherein said patient has previously been determined to have renal impairment; wherein said compound is (R)-8-chloro-1-methyl-2,3,4,5-tetrahydro-1H-3-benzazepine or a pharmaceutical salt, solvate or hydrate thereof.

Once aspect of the disclosure pertains to a low dosage formulation of a compound for use in a method of preventing a toxic event in a patient being treated for obesity or weight gain associated conditions, said method comprising administering said low dosage formulation of the compound to said patient, wherein said patient has previously been determined to have renal impairment; wherein said compound is (R)-8-chloro-1-methyl-2,3,4,5-tetrahydro-1H-3-benzazepine or a pharmaceutical salt, solvate or hydrate thereof.

Once aspect of the disclosure pertains to a low dosage formulation of a compound for use in a method of preventing a toxic event in a patient being treated for obesity or weight gain associated conditions, said method comprising prescribing said low dosage formulation of the compound to said patient, wherein said patient has previously been determined to have renal impairment; wherein said compound is (R)-8-chloro-1-methyl-2,3,4,5-tetrahydro-1H-3-benzazepine or a pharmaceutical salt, solvate or hydrate thereof.

In one aspect of the disclosure, a test dose or doses of Compound 1 or a pharmaceutically acceptable salt, solvate or hydrate thereof can be given to an individual and the level of a metabolite or metabolites of Compound 1 or a pharmaceutically acceptable salt, solvate or hydrate thereof can be measured for the individual. For example, the level of metabolite M1 and/or M5 can be measured. The level of metabolite(s) can be measured, for example, over different time intervals. Measurement of metabolite(s) of Compound 1 or a pharmaceutically acceptable salt, solvate or hydrate thereof have been reported herein, for example, in Example 3 Table 4, Example 4 Table 6, and Example 8 Table 13. If the level of metabolite(s) in the individual is below a threshold level then Compound 1 or a pharmaceutically acceptable salt, solvate or hydrate thereof can be prescribed or administered to the individual. However, if the level of metabolite(s) in the individual is above a threshold level then Compound 1 or a pharmaceutically acceptable salt, solvate or hydrate thereof would be contraindicated for the individual. Threshold levels for metabolites M1 and M5 can be determined, for example, by testing metabolite levels in human clinical trials or estimated, for example, based on the level of these metabolites in monkeys at the NOAEL dose (see for example, Table 9 for M1).

Therefore, one aspect of the disclosure pertains to a method for weight management, decreasing food intake, inducing satiety, preventing or treating obesity in an individual comprising determining the level of a metabolite of (R)-8-chloro-1-methyl-2,3,4,5-tetrahydro-1H-3-benzazepine or a pharmaceutically acceptable salt, solvate or hydrate thereof in an individual, and prescribing or administering (R)-8-chloro-1-methyl-2,3,4,5-tetrahydro-1H-3-benzazepine or a pharmaceutically acceptable salt, solvate or hydrate thereof to the individual provided that the individual has a level of metabolite that is below a threshold level for the metabolite.

Further disclosed herein is a method for assisting weight management in an individual in need thereof, comprising measuring the level of renal sufficiency of the individual, wherein a measurement of a level of renal sufficiency selected from the group consisting of: no renal impairment, mild renal impairment, and moderate renal impairment indicates that the individual is suitable for prescription of a therapeutically effective amount of (R)-8-chloro-1-methyl-2,3,4,5-tetrahydro-1H-3-benzazepine or a pharmaceutically acceptable salt, solvate or hydrate thereof. In addition, disclosed herein is a method for assisting weight management in an individual in need thereof, comprising measuring the level of renal sufficiency of the individual, wherein a measurement of a level of renal sufficiency selected from the group consisting of: no renal impairment, mild renal impairment, and moderate renal impairment indicates that the individual is suitable to receive administration of a therapeutically effective amount of (R)-8-chloro-1-methyl-2,3,4,5-tetrahydro-1H-3-benzazepine or a pharmaceutically acceptable salt, solvate or hydrate thereof.

Further disclosed herein is a method for assisting weight management in an individual in need thereof, comprising measuring the level of renal sufficiency of the individual, wherein a measurement of a level of renal sufficiency of severe renal impairment or ESRD indicates that the individual is suitable for prescription of a therapeutically effective amount of (R)-8-chloro-1-methyl-2,3,4,5-tetrahydro-1H-3-benzazepine or a pharmaceutically acceptable salt, solvate or hydrate thereof. In addition, disclosed herein is a method for assisting weight management in an individual in need thereof, comprising measuring the level of renal sufficiency of the individual, wherein a measurement of a level of renal sufficiency of severe renal impairment or ESRD indicates that the individual is suitable to receive administration of a therapeutically effective amount of (R)-8-chloro-1-methyl-2,3,4,5-tetrahydro-1H-3-benzazepine or a pharmaceutically acceptable salt, solvate or hydrate thereof.

Further disclosed herein is a method for assisting weight management in an individual in need thereof, comprising measuring the level of renal sufficiency of the individual, wherein a measurement of a level of renal sufficiency indicating renal impairment indicates that the individual is suitable for prescription of a reduced dosage regiment of (R)-8-chloro-1-methyl-2,3,4,5-tetrahydro-1H-3-benzazepine or a pharmaceutically acceptable salt, solvate or hydrate thereof. In addition, disclosed herein is a method for assisting weight management in an individual in need thereof, comprising measuring the level of renal sufficiency of the individual, wherein a measurement of a level of renal sufficiency indicating renal impairment indicates that the individual is suitable to receive administration of a reduced dosage regiment of (R)-8-chloro-1-methyl-2,3,4,5-tetrahydro-1H-3-benzazepine or a pharmaceutically acceptable salt, solvate or hydrate thereof.

Further disclosed herein is a method for assisting weight management in an individual in need thereof, comprising measuring an approximate serum creatinine concentration for the individual, wherein a measurement of an approximate serum creatinine concentration of:
   (i) less than 4.9 mg/dL for an 18-20 year old man,
   (ii) less than 3.5 mg/dL for an 18-20 year old woman,
   (iii) less than 4.5 mg/dL for a 21-30 year old man,
   (iv) less than 3.2 mg/dL for a 21-30 year old woman,
   (v) less than 4.1 mg/dL for a 31-40 year old man,
   (vi) less than 2.9 mg/dL for a 31-40 year old woman,
   (viii) less than 2.7 mg/dL for a 41-50 year old woman,
   (ix) less than 3.3 mg/dL for a 51-60 year old man,
   (x) less than 2.4 mg/dL for a 51-60 year old woman,
   (xi) less than 3.0 mg/dL for a man over 60 years old, or
   (xii) less than 2.0 mg/dL for a woman over 60 years old
indicates that the individual is suitable for prescription of a therapeutically effective amount of (R)-8-chloro-1-methyl-2,3,4,5-tetrahydro-1H-3-benzazepine or a pharmaceutically acceptable salt, solvate or hydrate thereof. Also disclosed herein is a method for assisting weight management in an individual in need thereof, comprising measuring an approximate serum creatinine concentration for the individual, wherein a measurement of an approximate serum creatinine concentration of:
   (i) less than 4.9 mg/dL for an 18-20 year old man,
   (ii) less than 3.5 mg/dL for an 18-20 year old woman,
   (iii) less than 4.5 mg/dL for a 21-30 year old man,
   (iv) less than 3.2 mg/dL for a 21-30 year old woman,
   (v) less than 4.1 mg/dL for a 31-40 year old man,
   (vi) less than 2.9 mg/dL for a 31-40 year old woman,
   (viii) less than 2.7 mg/dL for a 41-50 year old woman,
   (ix) less than 3.3 mg/dL for a 51-60 year old man,
   (x) less than 2.4 mg/dL for a 51-60 year old woman,
   (xi) less than 3.0 mg/dL for a man over 60 years old, or
   (xii) less than 2.0 mg/dL for a woman over 60 years old
indicates that the individual is suitable to receive administration of a therapeutically effective amount of (R)-8-chloro-1-methyl-2,3,4,5-tetrahydro-1H-3-benzazepine or a pharmaceutically acceptable salt, solvate or hydrate thereof.

Further disclosed herein is a method for assisting weight management in an individual in need thereof, comprising measuring a creatinine clearance rate using the Cockcroft-Gault equation for the individual wherein a measurement of a creatinine clearance rate of greater than about 80 mL/minute using the Cockcroft-Gault equation indicates that the individual is suitable for prescription of a therapeutically effective amount of (R)-8-chloro-1-methyl-2,3,4,5-tetrahydro-1H-3-benzazepine or a pharmaceutically acceptable salt, solvate or hydrate thereof. In addition, disclosed herein is a method for assisting weight management in an individual in need thereof, comprising measuring a creatinine clearance rate using the Cockcroft-Gault equation for the individual wherein a measurement of a creatinine clearance rate of greater than about 80 ml/minute using the Cockcroft-Gault equation indicates that the individual is suitable to receive administration of a therapeutically effective amount of (R)-8-chloro-1-methyl-2,3,4,5-tetrahydro-1H-3-benzazepine or a pharmaceutically acceptable salt, solvate or hydrate thereof.

Further disclosed herein is a method for assisting weight management in an individual in need thereof, comprising measuring a creatinine clearance rate using the Cockcroft-Gault equation for the individual wherein a measurement of a creatinine clearance rate of greater than about 50 mL/minute using the Cockcroft-Gault equation indicates that the individual is suitable for prescription of a therapeutically effective amount of (R)-8-chloro-1-methyl-2,3,4,5-tetrahydro-1H-3-benzazepine or a pharmaceutically acceptable salt, solvate or hydrate thereof. In addition, disclosed herein is a method for assisting weight management in an individual in need thereof, comprising measuring a creatinine clearance rate using the Cockcroft-Gault equation for the individual wherein a measurement of a creatinine clearance rate of greater than about 50 mL/minute using the Cockcroft-Gault equation indicates that the individual is suitable to receive administration of a therapeutically effective amount of (R)-8-chloro-1-methyl-2,3,4,5-tetrahydro-1H-3-benzazepine or a pharmaceutically acceptable salt, solvate or hydrate thereof.

Further disclosed herein is a method for assisting weight management in an individual in need thereof, comprising measuring a creatinine clearance rate using the Cockcroft-Gault equation for the individual wherein a measurement of a creatinine clearance rate of greater than about 30 mL/minute using the Cockcroft-Gault equation indicates that the individual is suitable for prescription of a therapeutically effective amount of (R)-8-chloro-1-methyl-2,3,4,5-tetrahydro-1H-3-benzazepine or a pharmaceutically acceptable salt, solvate or hydrate thereof. In addition, disclosed herein is a method for assisting weight management in an individual in need thereof, comprising measuring a creatinine clearance rate using the Cockcroft-Gault equation for the individual wherein a measurement of a creatinine clearance rate of greater than about 30 mL/minute using the Cockcroft-Gault equation indicates that the individual is suitable to receive administration of a therapeutically effective amount of (R)-8-chloro-1-methyl-2,3,4,5-tetrahydro-1H-3-benzazepine or a pharmaceutically acceptable salt, solvate or hydrate thereof.

Further disclosed herein is a method for assisting reducing the risk of an adverse event in an individual in need of weight management, comprising measuring the level of renal sufficiency of the individual, wherein a measurement of a level of renal sufficiency selected from the group consisting of: no renal impairment, mild renal impairment, and moderate renal impairment indicates that the individual is suitable for prescription of a therapeutically effective amount of (R)-8-chloro-1-methyl-2,3,4,5-tetrahydro-1H-3-benzazepine or a pharmaceutically acceptable salt, solvate or hydrate thereof. Also disclosed herein is a method for assisting reducing the risk of an adverse event in an individual in need of weight management, comprising measuring the level of renal sufficiency of the individual, wherein a measurement of a level of renal sufficiency selected from the group consisting of: no renal impairment, mild renal impairment, and moderate renal impairment indicates that the individual is suitable to receive administration of a therapeutically effective amount of (R)-8-chloro-1-methyl-2,3,4,5-tetrahydro-1H-3-benzazepine or a pharmaceutically acceptable salt, solvate or hydrate thereof.

Further disclosed herein is a method for assisting reducing the risk of an adverse event in an individual in need of weight management, comprising measuring the level of renal sufficiency of the individual, wherein a measurement of a level of renal sufficiency indicating renal impairment indicates that the individual is suitable for prescription of a reduced dosage regimen of (R)-8-chloro-1-methyl-2,3,4,5-tetrahydro-1H-3-benzazepine or a pharmaceutically acceptable salt, solvate or hydrate thereof. Also disclosed herein is a method for assisting reducing the risk of an adverse event in an individual in need of weight management, comprising measuring the level of renal sufficiency of the individual, wherein a measurement of a level of renal sufficiency indicating renal impairment indicates that the individual is suitable to receive administration of a reduced dosage regimen of (R)-8-chloro-1-methyl-2,3,4,5-tetrahydro-1H-3-benzazepine or a pharmaceutically acceptable salt, solvate or hydrate thereof.

Further disclosed herein is a method for assisting reducing the risk of an adverse event in an individual in need of weight management, comprising measuring an approximate serum creatinine concentration for the individual, wherein a measurement of an approximate serum creatinine concentration of:
 (i) less than 4.9 mg/dL for an 18-20 year old man,
 (ii) less than 3.5 mg/dL for an 18-20 year old woman,
 (iii) less than 4.5 mg/dL for a 21-30 year old man,
 (iv) less than 3.2 mg/dL for a 21-30 year old woman,
 (v) less than 4.1 mg/dL for a 31-40 year old man,
 (vi) less than 2.9 mg/dL for a 31-40 year old woman,
 (vii) less than 3.7 mg/dL for a 41-50 year old man,
 (viii) less than 2.7 mg/dL for a 41-50 year old woman,
 (ix) less than 3.3 mg/dL for a 51-60 year old man,
 (x) less than 2.4 mg/dL for a 51-60 year old woman,
 (xi) less than 3.0 mg/dL for a man over 60 years old, or
 (xii) less than 2.0 mg/dL for a woman over 60 years old
indicates that the individual is suitable for prescription of a therapeutically effective amount of (R)-8-chloro-1-methyl-2,3,4,5-tetrahydro-H-3-benzazepine or a pharmaceutically acceptable salt, solvate or hydrate thereof. Also disclosed herein is a method for assisting reducing the risk of an adverse event in an individual in need of weight management, comprising measuring an approximate serum creatinine concentration for the individual, wherein a measurement of an approximate serum creatinine concentration of:
 (i) less than 4.9 mg/dL for an 18-20 year old man,
 (ii) less than 3.5 mg/dL for an 18-20 year old woman,
 (iii) less than 4.5 mg/dL for a 21-30 year old man,
 (iv) less than 3.2 mg/dL for a 21-30 year old woman,
 (v) less than 4.1 mg/dL for a 31-40 year old man,
 (vi) less than 2.9 mg/dL for a 31-40 year old woman,
 (vii) less than 3.7 mg/dL for a 41-50 year old man,
 (viii) less than 2.7 mg/dL for a 41-50 year old woman,
 (ix) less than 3.3 mg/dL for a 51-60 year old man,
 (x) less than 2.4 mg/dL for a 51-60 year old woman,
 (xi) less than 3.0 mg/dL for a man over 60 years old, or
 (xii) less than 2.0 mg/dL for a woman over 60 years old
indicates that the individual is suitable to receive administration of a therapeutically effective amount of (R)-8-chloro-1-methyl-2,3,4,5-tetrahydro-1H-3-benzazepine or a pharmaceutically acceptable salt, solvate or hydrate thereof.

Further disclosed herein is a method for assisting selecting an individual for treatment with (R)-8-chloro-1-methyl-2,3,4,5-tetrahydro-1H-3-benzazepine or a pharmaceutically acceptable salt, solvate or hydrate thereof from a plurality of individuals in need of weight management, comprising measuring the level of renal sufficiency of the individual, wherein a measurement of a level of renal sufficiency selected from the group consisting of: no renal impairment, mild renal impairment, and moderate renal impairment indicates the individual is selected for treatment with (R)-8-chloro-1-methyl-2,3,4,5-tetrahydro-1H-3-benzazepine or a pharmaceutically acceptable salt, solvate or hydrate thereof. Also disclosed herein is a method for assisting selecting an individual for treatment with (R)-8-chloro-1-methyl-2,3,4,5-tetrahydro-1H-3-benzazepine or a pharmaceutically acceptable salt, solvate or hydrate thereof from a plurality of individuals in need of weight management, comprising measuring the level of renal sufficiency of the individual, wherein a measurement of an approximate serum creatinine concentration of
 (i) less than 4.9 mg/dL for an 18-20 year old man,
 (ii) less than 3.5 mg/dL for an 18-20 year old woman,
 (iii) less than 4.5 mg/dL for a 21-30 year old man,
 (iv) less than 3.2 mg/dL for a 21-30 year old woman,
 (v) less than 4.1 mg/dL for a 31-40 year old man,
 (vi) less than 2.9 mg/dL for a 31-40 year old woman,
 (vii) less than 3.7 mg/dL for a 41-50 year old man,
 (viii) less than 2.7 mg/dL for a 41-50 year old woman,
 (ix) less than 3.3 mg/dL for a 51-60 year old man,
 (x) less than 2.4 mg/dL for a 51-60 year old woman,
 (xi) less than 3.0 mg/dL for a man over 60 years old, or
 (xii) less than 2.0 mg/dL for a woman over 60 years old
indicates that the individual is selected for treatment with (R)-8-chloro-1-methyl-2,3,4,5-tetrahydro-1H-3-benzazepine or a pharmaceutically acceptable salt, solvate or hydrate thereof.

Further disclosed herein is a composition for use in a method of weight management in an individual, said composition comprising (R)-8-chloro-1-methyl-2,3,4,5-tetrahydro-1H-3-benzazepine or a pharmaceutically acceptable salt, solvate or hydrate thereof, wherein said individual has previously been determined to have a level of renal sufficiency selected from the group consisting of: no renal impairment, mild renal impairment, and moderate renal impairment.

Further disclosed herein is a low dosage formulation of a compound for use in a method of weight management in an individual, wherein said individual has previously been determined to have renal impairment; wherein said compound is (R)-8-chloro-1-methyl-2,3,4,5-tetrahydro-1H-3-benzazepine or a pharmaceutically acceptable salt, solvate or hydrate thereof. Also disclosed is a low dosage formulation of a compound for use in a method of weight management in an individual, wherein said low dosage reduces a toxic event in said individual to said compound, wherein said individual has previously been determined to have renal impairment; and wherein said compound is (R)-8-chloro-1-methyl-2,3,4,5-tetrahydro-1H-3-benzazepine or a pharmaceutically acceptable salt, solvate or hydrate thereof. In addition, disclosed is a low dosage formulation of a compound for use in a method of weight management in an individual, wherein said low dosage prevents a toxic event in said individual to said compound, wherein said individual has previously been determined to have renal impairment; and wherein said compound is R)-8-chloro-1-methyl-2,3,4,5-tetrahydro-1H-3-benzazepine or a pharmaceutically acceptable salt, solvate or hydrate thereof.

Further disclosed herein is a composition for use in a method of weight management in an individual in need thereof, comprising a therapeutically effective amount of R)-8-chloro-1-methyl-2,3,4,5-tetrahydro-1H-3-benzazepine or a pharmaceutically acceptable salt, solvate or hydrate thereof, wherein the individual has an approximate serum creatinine concentration of:
 (i) less than 4.9 mg/dL for an 18-20 year old man,
 (ii) less than 3.5 mg/dL for an 18-20 year old woman, (iii) less than 4.5 mg/dL for a 21-30 year old man,
(iv) less than 3.2 mg/dL for a 21-30 year old woman,
(v) less than 4.1 mg/dL for a 31-40 year old man,
(vi) less than 2.9 mg/dL for a 31-40 year old woman,
(vii) less than 3.7 mg/dL for a 41-50 year old man,
(viii) less than 2.7 mg/dL for a 41-50 year old woman,
(ix) less than 3.3 mg/dL for a 51-60 year old man,
(x) less than 2.4 mg/dL for a 51-60 year old woman,
(xi) less than 3.0 mg/dL for a man over 60 years old, or
(xii) less than 2.0 mg/dL for a woman over 60 years old.

In addition, disclosed herein is a composition for use in a method of reducing the risk of an adverse event in an individual in need of weight management, comprising a therapeutically effective amount of R)-8-chloro-1-methyl-2,3,4,5-tetrahydro-1H-3-benzazepine or a pharmaceutically acceptable salt, solvate or hydrate thereof, wherein the individual has an approximate serum creatinine concentration of:
(i) less than 4.9 mg/dL for an 18-20 year old man;
(ii) less than 3.5 mg/dL for an 18-20 year old woman,
(iii) less than 4.5 mg/dL for a 21-30 year old man,
(iv) less than 3.2 mg/dL for a 21-30 year old woman,
(v) less than 4.1 mg/dL for a 31-40 year old man,
(vi) less than 2.9 mg/dL for a 31-40 year old woman,
(vii) less than 3.7 mg/dL for a 41-50 year old man,
(viii) less than 2.7 mg/dL for a 41-50 year old woman,
(ix) less than 3.3 mg/dL for a 51-60 year old man,
(x) less than 2.4 mg/dL for a 51-60 year old woman,
(xi) less than 3.0 mg/dL for a man over 60 years old, or
(xii) less than 2.0 mg/dL for a woman over 60 years old.

Further disclosed herein is a kit for use in a method of weight management in an individual in need thereof, comprising: a) a therapeutically effective amount of R)-8-chloro-1-methyl-2,3,4,5-tetrahydro-1H-3-benzazepine or a pharmaceutically acceptable salt, solvate or hydrate thereof, and b) instructions indicating that the compound is to be administered to an individual having an approximate serum creatinine concentration of:
(i) less than 4.9 mg/dL for an 18-20 year old man,
(ii) less than 3.5 mg/dL for an 18-20 year old woman,
(iii) less than 4.5 mg/dL for a 21-30 year old man,
(iv) less than 3.2 mg/dL for a 21-30 year old woman,
(v) less than 4.1 mg/dL for a 31-40 year old man,
(vi) less than 2.9 mg/dL for a 31-40 year old woman,
(vii) less than 3.7 mg/dL for a 41-50 year old man,
(viii) less than 2.7 mg/dL for a 41-50 year old woman,
(ix) less than 3.3 mg/dL for a 51-60 year old man,
(x) less than 2.4 mg/dL for a 51-60 year old woman,
(xi) less than 3.0 mg/dL for a man over 60 years old, or
(xii) less than 2.0 mg/dL for a woman over 60 years old.

Also disclosed herein is a kit for reducing the risk of an adverse event in an individual in need of weight management, comprising: a) a therapeutically effective amount of R)-8-chloro-1-methyl-2,3,4,5-tetrahydro-1H-3-benzazepine or a pharmaceutically acceptable salt, solvate or hydrate thereof, and b) instructions indicating that the compound is to be administered to an individual having an approximate serum creatinine concentration of:
(i) less than 4.9 mg/dL for an 18-20 year old man,
(ii) less than 3.5 mg/dL for an 18-20 year old woman,
(iii) less than 4.5 mg/dL for a 21-30 year old man,
(iv) less than 3.2 mg/dL for a 21-30 year old woman,
(v) less than 4.1 mg/dL for a 31-40 year old man,
(vi) less than 2.9 mg/dL for a 31-40 year old woman,
(vii) less than 3.7 mg/dL for a 41-50 year old man,
(viii) less than 2.7 mg/dL for a 41-50 year old woman,
(ix) less than 3.3 mg/dL for a 51-60 year old man,
(x) less than 2.4 mg/dL for a 51-60 year old woman,
(xi) less than 3.0 mg/dL for a man over 60 years old, or
(xii) less than 2.0 mg/dL for a woman over 60 years old.

As throughout the application, in some embodiments, weight management comprises weight loss. In some embodiments, weight management comprises maintenance of weight loss. In some embodiments, weight management further comprises prescribing or administering a reduced-calorie diet. In some embodiments, weight management further comprises prescribing or administering a program of regular exercise. In some embodiments, weight management further comprises prescribing or administering both a reduced-calorie diet and a program of regular exercise.

In some embodiments, the individual is a patient with an initial body mass index $\geq 30$ kg/m$^2$. In some embodiments, the individual is a patient with an initial body mass index $\geq 27$ kg/m$^2$ in the presence of at least one weight related comorbid condition. In some embodiments, the individual is a patient with an initial body mass index $\geq 27$ kg/m$^2$ in the presence of at least one weight related comorbid condition selected from: hypertension, dyslipidemia, cardiovascular disease, glucose intolerance and sleep apnea. In some embodiments, the individual has an initial body mass index $\geq 30$ kg/m$^2$. In some embodiments, the individual has an initial body mass index $\geq 27$ kg/m$^2$. In some embodiments, the individual has an initial body mass index $\geq 27$ kg/m$^2$ in the presence of at least one weight related comorbid condition. In some embodiments, the individual has an initial body mass index $\geq 27$ kg/m$^2$ in the presence of at least one weight related comorbid condition selected from: hypertension, dyslipidemia, cardiovascular disease, glucose intolerance and sleep apnea. In some embodiments, the individual has an initial body mass index $\geq 25$ kg/m$^2$. In some embodiments, the individual has an initial body mass index $\geq 25$ kg/m$^2$ in the presence of at least one weight related comorbid condition. In some embodiments, the individual has an initial body mass index $\geq 25$ kg/m$^2$ in the presence of at least one weight related comorbid condition selected from: hypertension, dyslipidemia, cardiovascular disease, glucose intolerance and sleep apnea.

In some embodiments, the compositions or low dosage formulations characterized in the composition or formulation is administered in conjunction with phentermine to the individual. In some embodiments, a kit disclosed herein further comprises phentermine.

In some embodiments, the Cockcroft-Gault equation is used to determine the level of renal sufficiency of the individual. In some embodiments, the individual's ideal body weight is used in the equation and in other embodiments, the individual's actual body weight is used in the equation. In some embodiments, the individual's serum creatinine concentration is used to determine the level of renal sufficiency of the individual.

Further disclosed herein is a method for assisting decreasing food intake in an individual in need thereof, comprising measuring the level of renal sufficiency of the individual, wherein a measurement of a level of renal sufficiency selected from the group consisting of: no renal impairment, mild renal impairment, and moderate renal impairment indicates that the individual is suitable for prescription of a therapeutically effective amount of (R)-8-chloro-1-methyl-2,3,4,5-tetrahydro-1H-3-benzazepine or a pharmaceutically acceptable salt, solvate or hydrate thereof. In addition, disclosed herein is a method for assisting decreasing food intake in an individual in need thereof, comprising measuring the level of renal sufficiency of the individual, wherein a measurement of a level of renal sufficiency selected from the group consisting of: no renal impairment, mild renal impairment, and moderate renal impairment indicates that the individual is suitable to receive administration of a therapeutically effective amount of (R)-8-chloro-1-methyl-2,3,4,5-tetrahydro-1H-3-benzazepine or a pharmaceutically acceptable salt, solvate or hydrate thereof.

Further disclosed herein is a method for assisting decreasing food intake in an individual in need thereof, comprising measuring the level of renal sufficiency of the individual, wherein a measurement of a level of renal sufficiency of severe renal impairment or ESRD indicates that the individual is suitable for prescription of a therapeutically effective amount of (R)-8-chloro-1-methyl-2,3,4,5-tetrahydro-1H-3-benzazepine or a pharmaceutically acceptable salt, solvate or hydrate thereof. In addition, disclosed herein is a method for assisting decreasing food intake in an individual in need thereof, comprising measuring the level of renal sufficiency of the individual, wherein a measurement of a level of renal sufficiency of severe renal impairment or ESRD indicates that the individual is suitable to receive administration of a therapeutically effective amount of (R)-8-chloro-1-methyl-2,3,4,5-tetrahydro-1H-3-benzazepine or a pharmaceutically acceptable salt, solvate or hydrate thereof.

Further disclosed herein is a method for assisting decreasing food intake in an individual in need thereof, comprising measuring the level of renal sufficiency of the individual, wherein a measurement of a level of renal sufficiency indicating renal impairment indicates that the individual is suitable for prescription of a reduced dosage regiment of (R)-8-chloro-1-methyl-2,3,4,5-tetrahydro-1H-3-benzazepine or a pharmaceutically acceptable salt, solvate or hydrate thereof. In addition, disclosed herein is a method for assisting decreasing food intake in an individual in need thereof, comprising measuring the level of renal sufficiency of the individual, wherein a measurement of a level of renal sufficiency indicating renal impairment indicates that the individual is suitable to receive administration of a reduced dosage regiment of (R)-8-chloro-1-methyl-2,3,4,5-tetrahydro-1H-3-benzazepine or a pharmaceutically acceptable salt, solvate or hydrate thereof.

Further disclosed herein is a method for assisting decreasing food intake in an individual in need thereof, comprising measuring an approximate serum creatinine concentration for the individual, wherein a measurement of an approximate serum creatinine concentration of:
(i) less than 4.9 mg/dL for an 18-20 year old man,
(ii) less than 3.5 mg/dL for an 18-20 year old woman,
(iii) less than 4.5 mg/dL for a 21-30 year old man,
(iv) less than 3.2 mg/dL for a 21-30 year old woman,
(v) less than 4.1 mg/dL for a 31-40 year old man,
(vi) less than 2.9 mg/dL for a 31-40 year old woman,
(viii) less than 2.7 mg/dL for a 41-50 year old woman,
(ix) less than 3.3 mg/dL for a 51-60 year old man,
(x) less than 2.4 mg/dL for a 51-60 year old woman,
(xi) less than 3.0 mg/dL for a man over 60 years old, or
(xii) less than 2.0 mg/dL for a woman over 60 years old
indicates that the individual is suitable for prescription of a therapeutically effective amount of (R)-8-chloro-1-methyl-2,3,4,5-tetrahydro-1H-3-benzazepine or a pharmaceutically acceptable salt, solvate or hydrate thereof. Also disclosed herein is a method for assisting decreasing food intake in an individual in need thereof, comprising measuring an approximate serum creatinine concentration for the individual, wherein a measurement of an approximate serum creatinine concentration of:
(i) less than 4.9 mg/dL for an 18-20 year old man,
(ii) less than 3.5 mg/dL for an 18-20 year old woman,
(iii) less than 4.5 mg/dL for a 21-30 year old man,
(iv) less than 3.2 mg/dL for a 21-30 year old woman,
(v) less than 4.1 mg/dL for a 31-40 year old man,
(vi) less than 2.9 mg/dL for a 31-40 year old woman,
(viii) less than 2.7 mg/dL for a 41-50 year old woman,
(ix) less than 3.3 mg/dL for a 51-60 year old man,
(x) less than 2.4 mg/dL for a 51-60 year old woman,
(xi) less than 3.0 mg/dL for a man over 60 years old, or
(xii) less than 2.0 mg/dL for a woman over 60 years old
indicates that the individual is suitable to receive administration of a therapeutically effective amount of (R)-8-chloro-1-methyl-2,3,4,5-tetrahydro-H-3-benzazepine or a pharmaceutically acceptable salt, solvate or hydrate thereof.

Further disclosed herein is a method for assisting decreasing food intake in an individual in need thereof, comprising measuring a creatinine clearance rate using the Cockcroft-Gault equation for the individual wherein a measurement of a creatinine clearance rate of greater than about 80 mL/minute using the Cockcroft-Gault equation indicates that the individual is suitable for prescription of a therapeutically effective amount of (R)-8-chloro-1-methyl-2,3,4,5-tetrahydro-1H-3-benzazepine or a pharmaceutically acceptable salt, solvate or hydrate thereof. In addition, disclosed herein is a method for assisting decreasing food intake in an individual in need thereof, comprising measuring a creatinine clearance rate using the Cockcroft-Gault equation for the individual wherein a measurement of a creatinine clearance rate of greater than about 80 mL/minute using the Cockcroft-Gault equation indicates that the individual is suitable to receive administration of a therapeutically effective amount of (R)-8-chloro-1-methyl-2,3,4,5-tetrahydro-1H-3-benzazepine or a pharmaceutically acceptable salt, solvate or hydrate thereof.

Further disclosed herein is a method for assisting decreasing food intake in an individual in need thereof, comprising measuring a creatinine clearance rate using the Cockcroft-Gault equation for the individual wherein a measurement of a creatinine clearance rate of greater than about 50 mL/minute using the Cockcroft-Gault equation indicates that the individual is suitable for prescription of a therapeutically effective amount of (R)-8-chloro-1-methyl-2,3,4,5-tetrahydro-1H-3-benzazepine or a pharmaceutically acceptable salt, solvate or hydrate thereof. In addition, disclosed herein is a method for assisting decreasing food intake in an individual in need thereof, comprising measuring a creatinine clearance rate using the Cockcroft-Gault equation for the individual wherein a measurement of a creatinine clearance rate of greater than about 50 mL/minute using the Cockcroft-Gault equation indicates that the individual is suitable to receive administration of a therapeutically effective amount of (R)-8-chloro-1-methyl-2,3,4,5-tetrahydro-1H-3-benzazepine or a pharmaceutically acceptable salt, solvate or hydrate thereof.

Further disclosed herein is a method for assisting decreasing food intake in an individual in need thereof, comprising measuring a creatinine clearance rate using the Cockcroft-Gault equation for the individual wherein a measurement of a creatinine clearance rate of greater than about 30 mL/minute using the Cockcroft-Gault equation indicates that the individual is suitable for prescription of a therapeutically effective amount of (R)-8-chloro-1-methyl-2,3,4,5-tetrahydro-1H-3-benzazepine or a pharmaceutically acceptable salt, solvate or hydrate thereof. In addition, disclosed herein is a method for assisting decreasing food intake in an individual in need thereof, comprising measuring a creatinine clearance rate using the Cockcroft-Gault equation for the individual wherein a measurement of a creatinine clearance rate of greater than about 30 mL/minute using the Cockcroft-Gault equation indicates that the individual is suitable to receive administration of a therapeutically effective amount of (R)-8-chloro-1-methyl-2,3,4,5-tetrahydro-1H-3-benzazepine or a pharmaceutically acceptable salt, solvate or hydrate thereof.

Further disclosed herein is a method for assisting reducing the risk of an adverse event in an individual in need of decreasing food intake, comprising measuring the level of renal sufficiency of the individual, wherein a measurement of a level of renal sufficiency selected from the group consisting of: no renal impairment, mild renal impairment, and moderate renal impairment indicates that the individual is suitable for prescription of a therapeutically effective amount of (R)-8-chloro-1-methyl-2,3,4,5-tetrahydro-1H-3-benzazepine or a pharmaceutically acceptable salt, solvate or hydrate thereof. Also disclosed herein is a method for assisting reducing the risk of an adverse event in an individual in need of decreasing food intake, comprising measuring the level of renal sufficiency of the individual, wherein a measurement of a level of renal sufficiency selected from the group consisting of: no renal impairment, mild renal impairment, and moderate renal impairment indicates that the individual is suitable to receive administration of a therapeutically effective amount of (R)-8-chloro-1-methyl-2,3,4,5-tetrahydro-1H-3-benzazepine or a pharmaceutically acceptable salt, solvate or hydrate thereof.

Further disclosed herein is a method for assisting reducing the risk of an adverse event in an individual in need of decreasing food intake, comprising measuring the level of renal sufficiency of the individual, wherein a measurement of a level of renal sufficiency indicating renal impairment indicates that the individual is suitable for prescription of a reduced dosage regimen of (R)-8-chloro-1-methyl-2,3,4,5-tetrahydro-1H-3-benzazepine or a pharmaceutically acceptable salt, solvate or hydrate thereof. Also disclosed herein is a method for assisting reducing the risk of an adverse event in an individual in need of decreasing food intake, comprising measuring the level of renal sufficiency of the individual, wherein a measurement of a level of renal sufficiency indicating renal impairment indicates that the individual is suitable to receive administration of a reduced dosage regimen of (R)-8-chloro-1-methyl-2,3,4,5-tetrahydro-1H-3-benzazepine or a pharmaceutically acceptable salt, solvate or hydrate thereof.

Further disclosed herein is a method for assisting reducing the risk of an adverse event in an individual in need of decreasing food intake, comprising measuring an approximate serum creatinine concentration for the individual, wherein a measurement of an approximate serum creatinine concentration of:
  (i) less than 4.9 mg/dL for an 18-20 year old man,
  (ii) less than 3.5 mg/dL for an 18-20 year old woman,
  (iii) less than 4.5 mg/dL for a 21-30 year old man,
  (iv) less than 3.2 mg/dL for a 21-30 year old woman,
  (v) less than 4.1 mg/dL for a 31-40 year old man,
  (vi) less than 2.9 mg/dL for a 31-40 year old woman,
  (vii) less than 3.7 mg/dL for a 41-50 year old man,
  (viii) less than 2.7 mg/dL for a 41-50 year old woman,
  (ix) less than 3.3 mg/dL for a 51-60 year old man,
  (x) less than 2.4 mg/dL for a 51-60 year old woman,
  (xi) less than 3.0 mg/dL for a man over 60 years old, or
  (xii) less than 2.0 mg/dL for a woman over 60 years old
indicates that the individual is suitable for prescription of a therapeutically effective amount of (R)-8-chloro-1-methyl-2,3,4,5-tetrahydro-H-3-benzazepine or a pharmaceutically acceptable salt, solvate or hydrate thereof. Also disclosed herein is a method for assisting reducing the risk of an adverse event in an individual in need of decreasing food intake, comprising measuring an approximate serum creatinine concentration for the individual, wherein a measurement of an approximate serum creatinine concentration of:
  (i) less than 4.9 mg/dL for an 18-20 year old man,
  (ii) less than 3.5 mg/dL for an 18-20 year old woman,
  (iii) less than 4.5 mg/dL for a 21-30 year old man,
  (iv) less than 3.2 mg/dL for a 21-30 year old woman,
  (v) less than 4.1 mg/dL for a 31-40 year old man,
  (vi) less than 2.9 mg/dL for a 31-40 year old woman,
  (vii) less than 3.7 mg/dL for a 41-50 year old man,
  (viii) less than 2.7 mg/dL for a 41-50 year old woman,
  (ix) less than 3.3 mg/dL for a 51-60 year old man,
  (x) less than 2.4 mg/dL for a 51-60 year old woman,
  (xi) less than 3.0 mg/dL for a man over 60 years old, or
  (xii) less than 2.0 mg/dL for a woman over 60 years old
indicates that the individual is suitable to receive administration of a therapeutically effective amount of (R)-8-chloro-1-methyl-2,3,4,5-tetrahydro-1H-3-benzazepine or a pharmaceutically acceptable salt, solvate or hydrate thereof.

Further disclosed herein is a method for assisting selecting an individual for treatment with (R)-8-chloro-1-methyl-2,3,4,5-tetrahydro-1H-3-benzazepine or a pharmaceutically acceptable salt, solvate or hydrate thereof from a plurality of individuals in need of decreasing food intake, comprising measuring the level of renal sufficiency of the individual, wherein a measurement of a level of renal sufficiency selected from the group consisting of: no renal impairment, mild renal impairment, and moderate renal impairment indicates the individual is selected for treatment with (R)-8-chloro-1-methyl-2,3,4,5-tetrahydro-1H-3-benzazepine or a pharmaceutically acceptable salt, solvate or hydrate thereof. Also disclosed herein is a method for assisting selecting an individual for treatment with (R)-8-chloro-1-methyl-2,3,4,5-tetrahydro-1H-3-benzazepine or a pharmaceutically acceptable salt, solvate or hydrate thereof from a plurality of individuals in need of decreasing food intake, comprising measuring the level of renal sufficiency of the individual, wherein a measurement of an approximate serum creatinine concentration of
  (i) less than 4.9 mg/dL for an 18-20 year old man,
  (ii) less than 3.5 mg/dL for an 18-20 year old woman,
  (iii) less than 4.5 mg/dL for a 21-30 year old man,
  (iv) less than 3.2 mg/dL for a 21-30 year old woman,
  (v) less than 4.1 mg/dL for a 31-40 year old man,
  (vi) less than 2.9 mg/dL for a 31-40 year old woman,
  (vii) less than 3.7 mg/dL for a 41-50 year old man,
  (viii) less than 2.7 mg/dL for a 41-50 year old woman,
  (ix) less than 3.3 mg/dL for a 51-60 year old man,
  (x) less than 2.4 mg/dL for a 51-60 year old woman,
  (xi) less than 3.0 mg/dL for a man over 60 years old, or
  (xii) less than 2.0 mg/dL for a woman over 60 years old
indicates that the individual is selected for treatment with (R)-8-chloro-1-methyl-2,3,4,5-tetrahydro-1H-3-benzazepine or a pharmaceutically acceptable salt, solvate or hydrate thereof.

Further disclosed herein is a composition for use in a method of decreasing food intake in an individual, said composition comprising (R)-8-chloro-1-methyl-2,3,4,5-tetrahydro-1H-3-benzazepine or a pharmaceutically acceptable salt, solvate or hydrate thereof, wherein said individual has previously been determined to have a level of renal sufficiency selected from the group consisting of: no renal impairment, mild renal impairment, and moderate renal impairment.

Further disclosed herein is a low dosage formulation of a compound for use in a method of decreasing food intake in an individual, wherein said individual has previously been determined to have renal impairment; wherein said compound is (R)-8-chloro-1-methyl-2,3,4,5-tetrahydro-1H-3-benzazepine or a pharmaceutically acceptable salt, solvate or hydrate thereof. Also disclosed is a low dosage formulation of a compound for use in a method of decreasing food intake in an individual, wherein said low dosage reduces a toxic event in said individual to said compound, wherein said individual has previously been determined to have renal impairment; and wherein said compound is (R)-8-chloro-1-methyl-2,3,4,5-tetrahydro-1H-3-benzazepine or a pharmaceutically acceptable salt, solvate or hydrate thereof. In addition, disclosed is a low dosage formulation of a compound for use in a method of decreasing food intake in an individual, wherein said low dosage prevents a toxic event in said individual to said compound, wherein said individual has previously been determined to have renal impairment; and wherein said compound is R)-8-chloro-1-methyl-2,3,4,5-tetrahydro-1H-3-benzazepine or a pharmaceutically acceptable salt, solvate or hydrate thereof.

Further disclosed herein is a composition for use in a method of decreasing food intake in an individual in need thereof, comprising a therapeutically effective amount of R)-8-chloro-1-methyl-2,3,4,5-tetrahydro-1H-3-benzazepine or a pharmaceutically acceptable salt, solvate or hydrate thereof, wherein the individual has an approximate serum creatinine concentration of:
(i) less than 4.9 mg/dL for an 18-20 year old man,
(ii) less than 3.5 mg/dL for an 18-20 year old woman,
(iii) less than 4.5 mg/dL for a 21-30 year old man,
(iv) less than 3.2 mg/dL for a 21-30 year old woman,
(v) less than 4.1 mg/dL for a 31-40 year old man,
(vi) less than 2.9 mg/dL for a 31-40 year old woman,
(vii) less than 3.7 mg/dL for a 41-50 year old man,
(viii) less than 2.7 mg/dL for a 41-50 year old woman,
(ix) less than 3.3 mg/dL for a 51-60 year old man,
(x) less than 2.4 mg/dL for a 51-60 year old woman,
(xi) less than 3.0 mg/dL for a man over 60 years old, or
(xii) less than 2.0 mg/dL for a woman over 60 years old.

In addition, disclosed herein is a composition for use in a method of reducing the risk of an adverse event in an individual in need of decreasing food intake, comprising a therapeutically effective amount of R)-8-chloro-1-methyl-2,3,4,5-tetrahydro-1H-3-benzazepine or a pharmaceutically acceptable salt, solvate or hydrate thereof, wherein the individual has an approximate serum creatinine concentration of:
(i) less than 4.9 mg/dL for an 18-20 year old man,
(ii) less than 3.5 mg/dL for an 18-20 year old woman,
(iii) less than 4.5 mg/dL for a 21-30 year old man,
(iv) less than 3.2 mg/dL for a 21-30 year old woman,
(v) less than 4.1 mg/dL for a 31-40 year old man,
(vi) less than 2.9 mg/dL for a 31-40 year old woman,
(vii) less than 3.7 mg/dL for a 41-50 year old man,
(viii) less than 2.7 mg/dL for a 41-50 year old woman,
(ix) less than 3.3 mg/dL for a 51-60 year old man,
(x) less than 2.4 mg/dL for a 51-60 year old woman,
(xi) less than 3.0 mg/dL for a man over 60 years old, or
(xii) less than 2.0 mg/dL for a woman over 60 years old.

Further disclosed herein is a kit for use in a method of decreasing food intake in an individual in need thereof, comprising: a) a therapeutically effective amount of R)-8-chloro-1-methyl-2,3,4,5-tetrahydro-1H-3-benzazepine or a pharmaceutically acceptable salt, solvate or hydrate thereof, and b) instructions indicating that the compound is to be administered to an individual having an approximate serum creatinine concentration of:
(i) less than 4.9 mg/dL for an 18-20 year old man,
(ii) less than 3.5 mg/dL for an 18-20 year old woman,
(iii) less than 4.5 mg/dL for a 21-30 year old man,
(iv) less than 3.2 mg/dL for a 21-30 year old woman,
(v) less than 4.1 mg/dL for a 31-40 year old man,
(vi) less than 2.9 mg/dL for a 31-40 year old woman,
(vii) less than 3.7 mg/dL for a 41-50 year old man,
(viii) less than 2.7 mg/dL for a 41-50 year old woman,
(ix) less than 3.3 mg/dL for a 51-60 year old man,
(x) less than 2.4 mg/dL for a 51-60 year old woman,
(xi) less than 3.0 mg/dL for a man over 60 years old, or
(xii) less than 2.0 mg/dL for a woman over 60 years old.

Also disclosed herein is a kit for reducing the risk of an adverse event in an individual in need of decreasing food intake, comprising: a) a therapeutically effective amount of R)-8-chloro-1-methyl-2,3,4,5-tetrahydro-1H-3-benzazepine or a pharmaceutically acceptable salt, solvate or hydrate thereof, and b) instructions indicating that the compound is to be administered to an individual having an approximate serum creatinine concentration of:
(i) less than 4.9 mg/dL for an 18-20 year old man,
(ii) less than 3.5 mg/dL for an 18-20 year old woman,
(iii) less than 4.5 mg/dL for a 21-30 year old man,
(iv) less than 3.2 mg/dL for a 21-30 year old woman,
(v) less than 4.1 mg/dL for a 31-40 year old man,
(vi) less than 2.9 mg/dL for a 31-40 year old woman,
(vii) less than 3.7 mg/dL for a 41-50 year old man,
(viii) less than 2.7 mg/dL for a 41-50 year old woman,
(ix) less than 3.3 mg/dL for a 51-60 year old man,
(x) less than 2.4 mg/dL for a 51-60 year old woman,
(xi) less than 3.0 mg/dL for a man over 60 years old, or
(xii) less than 2.0 mg/dL for a woman over 60 years old.

In some embodiments, the individual in need of decreasing food intake is a patient with an initial body mass index $\geq 30$ kg/m$^2$. In some embodiments, the individual is a patient with an initial body mass index $\geq 27$ kg/m$^2$ in the presence of at least one weight related comorbid condition. In some embodiments, the individual is a patient with an initial body mass index $\geq 27$ kg/m$^2$ in the presence of at least one weight related comorbid condition selected from: hypertension, dyslipidemia, cardiovascular disease, glucose intolerance and sleep apnea. In some embodiments, the individual has an initial body mass index $\geq 30$ kg/m$^2$. In some embodiments, the individual has an initial body mass index $\geq 27$ kg/m$^2$. In some embodiments, the individual has an initial body mass index $\geq 27$ kg/m$^2$ in the presence of at least one weight related comorbid condition. In some embodiments, the individual has an initial body mass index $\geq 27$ kg/m$^2$ in the presence of at least one weight related comorbid condition selected from: hypertension, dyslipidemia, cardiovascular disease, glucose intolerance and sleep apnea. In some embodiments, the individual has an initial body mass index $\geq 25$ kg/m$^2$. In some embodiments, the individual has an initial body mass index $\geq 25$ kg/m$^2$ in the presence of at least one weight related comorbid condition. In some embodiments, the individual has an initial body mass index $\geq 25$ kg/m$^2$ in the presence of at least one weight related comorbid condition selected from: hypertension, dyslipidemia, cardiovascular disease, glucose intolerance and sleep apnea.

In some embodiments, the compositions or low dosage formulations characterized in the composition or formulation is administered in conjunction with phentermine to the individual. In some embodiments, a kit disclosed herein further comprises phentermine.

In some embodiments, the Cockcroft-Gault equation is used to determine the level of renal sufficiency of the individual. In some embodiments, the individual's ideal body weight is used in the equation and in other embodiments, the individual's actual body weight is used in the equation. In some embodiments, the individual's serum creatinine concentration is used to determine the level of renal sufficiency of the individual.

Further disclosed herein is a method for assisting inducing satiety in an individual in need thereof, comprising measuring the level of renal sufficiency of the individual, wherein a measurement of a level of renal sufficiency selected from the group consisting of: no renal impairment, mild renal impairment, and moderate renal impairment indicates that the individual is suitable for prescription of a therapeutically effective amount of (R)-8-chloro-1-methyl-2,3,4,5-tetrahydro-1H-3-benzazepine or a pharmaceutically acceptable salt, solvate or hydrate thereof. In addition, disclosed herein is a method for assisting inducing satiety in an individual in need thereof, comprising measuring the level of renal sufficiency of the individual, wherein a measurement of a level of renal sufficiency selected from the group consisting of: no renal impairment, mild renal impairment, and moderate renal impairment indicates that the individual is suitable to receive administration of a therapeutically effective amount of (R)-8-chloro-1-methyl-2,3,4,5-tetrahydro-1H-3-benzazepine or a pharmaceutically acceptable salt, solvate or hydrate thereof.

Further disclosed herein is a method for assisting inducing satiety in an individual in need thereof, comprising measuring the level of renal sufficiency of the individual, wherein a measurement of a level of renal sufficiency of severe renal impairment or ESRD indicates that the individual is suitable for prescription of a therapeutically effective amount of (R)-8-chloro-1-methyl-2,3,4,5-tetrahydro-1H-3-benzazepine or a pharmaceutically acceptable salt, solvate or hydrate thereof. In addition, disclosed herein is a method for assisting inducing satiety in an individual in need thereof, comprising measuring the level of renal sufficiency of the individual, wherein a measurement of a level of renal sufficiency of severe renal impairment or ESRD indicates that the individual is suitable to receive administration of a therapeutically effective amount of (R)-8-chloro-1-methyl-2,3,4,5-tetrahydro-1H-3-benzazepine or a pharmaceutically acceptable salt, solvate or hydrate thereof.

Further disclosed herein is a method for assisting inducing satiety in an individual in need thereof, comprising measuring the level of renal sufficiency of the individual, wherein a measurement of a level of renal sufficiency indicating renal impairment indicates that the individual is suitable for prescription of a reduced dosage regiment of (R)-8-chloro-1-methyl-2,3,4,5-tetrahydro-1H-3-benzazepine or a pharmaceutically acceptable salt, solvate or hydrate thereof. In addition, disclosed herein is a method for assisting inducing satiety in an individual in need thereof, comprising measuring the level of renal sufficiency of the individual, wherein a measurement of a level of renal sufficiency indicating renal impairment indicates that the individual is suitable to receive administration of a reduced dosage regiment of (R)-8-chloro-1-methyl-2,3,4,5-tetrahydro-1H-3-benzazepine or a pharmaceutically acceptable salt, solvate or hydrate thereof.

Further disclosed herein is a method for assisting inducing satiety in an individual in need thereof, comprising measuring an approximate serum creatinine concentration for the individual, wherein a measurement of an approximate serum creatinine concentration of:

(i) less than 4.9 mg/dL for an 18-20 year old man,
(ii) less than 3.5 mg/dL for an 18-20 year old woman,
(iii) less than 4.5 mg/dL for a 21-30 year old man,
(iv) less than 3.2 mg/dL for a 21-30 year old woman,
(v) less than 4.1 mg/dL for a 31-40 year old man,
(vi) less than 2.9 mg/dL for a 31-40 year old woman,
(viii) less than 2.7 mg/dL for a 41-50 year old woman,
(ix) less than 3.3 mg/dL for a 51-60 year old man,
(x) less than 2.4 mg/dL for a 51-60 year old woman,
(xi) less than 3.0 mg/dL for a man over 60 years old, or
(xii) less than 2.0 mg/dL for a woman over 60 years old
indicates that the individual is suitable for prescription of a therapeutically effective amount of (R)-8-chloro-1-methyl-2,3,4,5-tetrahydro-1H-3-benzazepine or a pharmaceutically acceptable salt, solvate or hydrate thereof. Also disclosed herein is a method for assisting inducing satiety in an individual in need thereof, comprising measuring an approximate serum creatinine concentration for the individual, wherein a measurement of an approximate serum creatinine concentration of:

(i) less than 4.9 mg/dL for an 18-20 year old man,
(ii) less than 3.5 mg/dL for an 18-20 year old woman,
(iii) less than 4.5 mg/dL for a 21-30 year old man,
(iv) less than 3.2 mg/dL for a 21-30 year old woman,
(v) less than 4.1 mg/dL for a 31-40 year old man,
(vi) less than 2.9 mg/dL for a 31-40 year old woman,
(viii) less than 2.7 mg/dL for a 41-50 year old woman,
(ix) less than 3.3 mg/dL for a 51-60 year old man,
(x) less than 2.4 mg/dL for a 51-60 year old woman,
(xi) less than 3.0 mg/dL for a man over 60 years old, or.
(xii) less than 2.0 mg/dL for a woman over 60 years old
indicates that the individual is suitable to receive administration of a therapeutically effective amount of (R)-8-chloro-1-methyl-2,3,4,5-tetrahydro-1H-3-benzazepine or a pharmaceutically acceptable salt, solvate or hydrate thereof.

Further disclosed herein is a method for assisting inducing satiety in an individual in need thereof, comprising measuring a creatinine clearance rate using the Cockcroft-Gault equation for the individual wherein a measurement of a creatinine clearance rate of greater than about 80 mL/minute using the Cockcroft-Gault equation indicates that the individual is suitable for prescription of a therapeutically effective amount of (R)-8-chloro-1-methyl-2,3,4,5-tetrahydro-1H-3-benzazepine or a pharmaceutically acceptable salt, solvate or hydrate thereof. In addition, disclosed herein is a method for assisting inducing satiety in an individual in need thereof, comprising measuring a creatinine clearance rate using the Cockcroft-Gault equation for the individual wherein a measurement of a creatinine clearance rate of greater than about 80 mL/minute using the Cockcroft-Gault equation indicates that the individual is suitable to receive administration of a therapeutically effective amount of (R)-8-chloro-1-methyl-2,3,4,5-tetrahydro-1H-3-benzazepine or a pharmaceutically acceptable salt, solvate or hydrate thereof.

Further disclosed herein is a method for assisting inducing satiety in an individual in need thereof, comprising measuring a creatinine clearance rate using the Cockcroft-Gault equation for the individual wherein a measurement of a creatinine clearance rate of greater than about 50 mL/minute using the Cockcroft-Gault equation indicates that the individual is suitable for prescription of a therapeutically effective amount of (R)-8-chloro-1-methyl-2,3,4,5-tetrahydro-1H-3-benzazepine or a pharmaceutically acceptable salt, solvate or hydrate thereof. In addition, disclosed herein is a method for assisting inducing satiety in an individual in need thereof, comprising measuring a creatinine clearance rate using the Cockcroft-Gault equation for the individual wherein a measurement of a creatinine clearance rate of greater than about 50 mL/minute using the Cockcroft-Gault equation indicates that the individual is suitable to receive administration of a therapeutically effective amount of (R)-8-chloro-1-methyl-2,3,4,5-tetrahydro-1H-3-benzazepine or a pharmaceutically acceptable salt, solvate or hydrate thereof.

Further disclosed herein is a method for assisting inducing satiety in an individual in need thereof, comprising measuring a creatinine clearance rate using the Cockcroft-Gault equation for the individual wherein a measurement of a creatinine clearance rate of greater than about 30 mL/minute using the Cockcroft-Gault equation indicates that the individual is suitable for prescription of a therapeutically effective amount of (R)-8-chloro-1-methyl-2,3,4,5-tetrahydro-1H-3-benzazepine or a pharmaceutically acceptable salt, solvate or hydrate thereof. In addition, disclosed herein is a method for assisting inducing satiety in an individual in need thereof, comprising measuring a creatinine clearance rate using the Cockcroft-Gault equation for the individual wherein a measurement of a creatinine clearance rate of greater than about 30 mL/minute using the Cockcroft-Gault equation indicates that the individual is suitable to receive administration of a therapeutically effective amount of (R)-8-chloro-1-methyl-2,3,4,5-tetrahydro-1H-3-benzazepine or a pharmaceutically acceptable salt, solvate or hydrate thereof.

Further disclosed herein is a method for assisting reducing the risk of an adverse event in an individual in need of inducing satiety, comprising measuring the level of renal sufficiency of the individual, wherein a measurement of a level of renal sufficiency selected from the group consisting of: no renal impairment, mild renal impairment, and moderate renal impairment indicates that the individual is suitable for prescription of a therapeutically effective amount of (R)-8-chloro-1-methyl-2,3,4,5-tetrahydro-1H-3-benzazepine or a pharmaceutically acceptable salt, solvate or hydrate thereof. Also disclosed herein is a method for assisting reducing the risk of an adverse event in an individual in need of inducing satiety, comprising measuring the level of renal sufficiency of the individual, wherein a measurement of a level of renal sufficiency selected from the group consisting of: no renal impairment, mild renal impairment, and moderate renal impairment indicates that the individual is suitable to receive administration of a therapeutically effective amount of (R)-8-chloro-1-methyl-2,3,4,5-tetrahydro-1H-3-benzazepine or a pharmaceutically acceptable salt, solvate or hydrate thereof.

Further disclosed herein is a method for assisting reducing the risk of an adverse event in an individual in need of inducing satiety, comprising measuring the level of renal sufficiency of the individual, wherein a measurement of a level of renal sufficiency indicating renal impairment indicates that the individual is suitable for prescription of a reduced dosage regimen of (R)-8-chloro-1-methyl-2,3,4,5-tetrahydro-1H-3-benzazepine or a pharmaceutically acceptable salt, solvate or hydrate thereof. Also disclosed herein is a method for assisting reducing the risk of an adverse event in an individual in need of inducing satiety, comprising measuring the level of renal sufficiency of the individual, wherein a measurement of a level of renal sufficiency indicating renal impairment indicates that the individual is suitable to receive administration of a reduced dosage regimen of (R)-8-chloro-1-methyl-2,3,4,5-tetrahydro-1H-3-benzazepine or a pharmaceutically acceptable salt, solvate or hydrate thereof.

Further disclosed herein is a method for assisting reducing the risk of an adverse event in an individual in need of inducing satiety, comprising measuring an approximate serum creatinine concentration for the individual, wherein a measurement of an approximate serum creatinine concentration of:
  (i) less than 4.9 mg/dL for an 18-20 year old man,
  (ii) less than 3.5 mg/dL for an 18-20 year old woman,
  (iii) less than 4.5 mg/dL for a 21-30 year old man,
  (iv) less than 3.2 mg/dL for a 21-30 year old woman,
  (v) less than 4.1 mg/dL for a 31-40 year old man,
  (vi) less than 2.9 mg/dL for a 31-40 year old woman,
  (vii) less than 3.7 mg/dL for a 41-50 year old man,
  (viii) less than 2.7 mg/dL for a 41-50 year old woman,
  (ix) less than 3.3 mg/dL for a 51-60 year old man,
  (x) less than 2.4 mg/dL for a 51-60 year old woman,
  (xi) less than 3.0 mg/dL for a man over 60 years old, or
  (xii) less than 2.0 mg/dL for a woman over 60 years old
indicates that the individual is suitable for prescription of a therapeutically effective amount of (R)-8-chloro-1-methyl-2,3,4,5-tetrahydro-H-3-benzazepine or a pharmaceutically acceptable salt, solvate or hydrate thereof. Also disclosed herein is a method for assisting reducing the risk of an adverse event in an individual in need of inducing satiety, comprising measuring an approximate serum creatinine concentration for the individual, wherein a measurement of an approximate serum creatinine concentration of:
  (i) less than 4.9 mg/dL for an 18-20 year old man,
  (ii) less than 3.5 mg/dL for an 18-20 year old woman,
  (iii) less than 4.5 mg/dL for a 21-30 year old man,
  (iv) less than 3.2 mg/dL for a 21-30 year old woman,
  (v) less than 4.1 mg/dL for a 31-40 year old man,
  (vi) less than 2.9 mg/dL for a 31-40 year old woman,
  (vii) less than 3.7 mg/dL for a 41-50 year old man,
  (viii) less than 2.7 mg/dL for a 41-50 year old woman,
  (ix) less than 3.3 mg/dL for a 51-60 year old man,
  (x) less than 2.4 mg/dL for a 51-60 year old woman,
  (xi) less than 3.0 mg/dL for a man over 60 years old, or
  (xii) less than 2.0 mg/dL for a woman over 60 years old
indicates that the individual is suitable to receive administration of a therapeutically effective amount of (R)-8-chloro-1-methyl-2,3,4,5-tetrahydro-1H-3-benzazepine or a pharmaceutically acceptable salt, solvate or hydrate thereof.

Further disclosed herein is a method for assisting selecting an individual for treatment, with (R)-8-chloro-1-methyl-2,3,4,5-tetrahydro-1H-3-benzazepine or a pharmaceutically acceptable salt, solvate or hydrate thereof from a plurality of individuals in need of inducing satiety, comprising measuring the level of renal sufficiency of the individual, wherein a measurement of a level of renal sufficiency selected from the group consisting of: no renal impairment, mild renal impairment, and moderate renal impairment indicates the individual is selected for treatment with (R)-8-chloro-1-methyl-2,3,4,5-tetrahydro-1H-3-benzazepine or a pharmaceutically acceptable salt, solvate or hydrate thereof. Also disclosed herein is a method for assisting selecting an individual for treatment with (R)-8-chloro-1-methyl-2,3,4,5-tetrahydro-1H-3-benzazepine or a pharmaceutically acceptable salt, solvate or hydrate thereof from a plurality of individuals in need of inducing satiety, comprising measuring the level of renal sufficiency of the individual, wherein a measurement of an approximate serum creatinine concentration of
  (i) less than 4.9 mg/dL for an 18-20 year old man,
  (ii) less than 3.5 mg/dL for an 18-20 year old woman,
  (iii) less than 4.5 mg/dL for a 21-30 year old man,
  (iv) less than 3.2 mg/dL for a 21-30 year old woman, (v) less than 4.1 mg/dL for a 31-40 year old man,
(vi) less than 2.9 mg/dL for a 31-40 year old woman,
(vii) less than 3.7 mg/dL for a 41-50 year old man,
(viii) less than 2.7 mg/dL for a 41-50 year old woman,
(ix) less than 3.3 mg/dL for a 51-60 year old man,
(x) less than 2.4 mg/dL for a 51-60 year old woman,
(xi) less than 3.0 mg/dL for a man over 60 years old, or
(xii) less than 2.0 mg/dL for a woman over 60 years old
indicates that the individual is selected for treatment with (R)-8-chloro-1-methyl-2,3,4,5-tetrahydro-1H-3-benzazepine or a pharmaceutically acceptable salt, solvate or hydrate thereof.

Further disclosed herein is a composition for use in a method of inducing satiety in an individual, said composition comprising (R)-8-chloro-1-methyl-2,3,4,5-tetrahydro-1H-3-benzazepine or a pharmaceutically acceptable salt, solvate or hydrate thereof, wherein said individual has previously been determined to have a level of renal sufficiency selected from the group consisting of: no renal impairment, mild renal impairment, and moderate renal impairment.

Further disclosed herein is a low dosage formulation of a compound for use in a method of inducing satiety in an individual, wherein said individual has previously been determined to have renal impairment; wherein said compound is (R)-8-chloro-1-methyl-2,3,4,5-tetrahydro-1H-3-benzazepine or a pharmaceutically acceptable salt, solvate or hydrate thereof. Also disclosed is a low dosage formulation of a compound for use in a method of inducing satiety in an individual, wherein said low dosage reduces a toxic event in said individual to said compound, wherein said individual has previously been determined to have renal impairment; and wherein said compound is (R)-8-chloro-1-methyl-2,3,4,5-tetrahydro-1H-3-benzazepine or a pharmaceutically acceptable salt, solvate or hydrate thereof. In addition, disclosed is a low dosage formulation of a compound for use in a method of inducing satiety in an individual, wherein said low dosage prevents a toxic event in said individual to said compound, wherein said individual has previously been determined to have renal impairment; and wherein said compound is (R)-8-chloro-1-methyl-2,3,4,5-tetrahydro-1H-3-benzazepine or a pharmaceutically acceptable salt, solvate or hydrate thereof.

Further disclosed herein is a composition for use in a method of inducing satiety in an individual in need thereof, comprising a therapeutically effective amount of (R)-8-chloro-1-methyl-2,3,4,5-tetrahydro-1H-3-benzazepine or a pharmaceutically acceptable salt, solvate or hydrate thereof, wherein the individual has an approximate serum creatinine concentration of:
(i) less than 4.9 mg/dL for an 18-20 year old man,
(ii) less than 3.5 mg/dL for an 18-20 year old woman,
(iii) less than 4.5 mg/dL for a 21-30 year old man,
(iv) less than 3.2 mg/dL for a 21-30 year old woman,
(v) less than 4.1 mg/dL for a 31-40 year old man,
(vi) less than 2.9 mg/dL for a 31-40 year old woman,
(vii) less than 3.7 mg/dL for a 41-50 year old man,
(viii) less than 2.7 mg/dL for a 41-50 year old woman,
(ix) less than 3.3 mg/dL for a 51-60 year old man,
(x) less than 2.4 mg/dL for a 51-60 year old woman,
(xi) less than 3.0 mg/dL for a man over 60 years old, or
(xii) less than 2.0 mg/dL for a woman over 60 years old.

In addition, disclosed herein is a composition for use in a method of reducing the risk of an adverse event in an individual in need of inducing satiety, comprising a therapeutically effective amount of R)-8-chloro-1-methyl-2,3,4,5-tetrahydro-1H-3-benzazepine or a pharmaceutically acceptable salt, solvate or hydrate thereof, wherein the individual has an approximate serum creatinine concentration of:
(i) less than 4.9 mg/dL for an 18-20 year old man,
(ii) less than 3.5 mg/dL for an 18-20 year old woman,
(iii) less than 4.5 mg/dL for a 21-30 year old man,
(iv) less than 3.2 mg/dL for a 21-30 year old woman,
(v) less than 4.1 mg/dL for a 31-40 year old man,
(vi) less than 2.9 mg/dL for a 31-40 year old woman,
(vii) less than 3.7 mg/dL for a 41-50 year old man,
(viii) less than 2.7 mg/dL for a 41-50 year old woman,
(ix) less than 3.3 mg/dL for a 51-60 year old man,
(x) less than 2.4 mg/dL for a 51-60 year old woman,
(xi) less than 3.0 mg/dL for a man over 60 years old, or
(xii) less than 2.0 mg/dL for a woman over 60 years old.

Further disclosed herein is a kit for use in a method of inducing satiety in an individual in need thereof, comprising: a) a therapeutically effective amount of R)-8-chloro-1-methyl-2,3,4,5-tetrahydro-1H-3-benzazepine or a pharmaceutically acceptable salt, solvate or hydrate thereof, and b) instructions indicating that the compound is to be administered to an individual having an approximate serum creatinine concentration of:
(i) less than 4.9 mg/dL for an 18-20 year old man,
(ii) less than 3.5 mg/dL for an 18-20 year old woman,
(iii) less than 4.5 mg/dL for a 21-30 year old man,
(iv) less than 3.2 mg/dL for a 21-30 year old woman,
(v) less than 4.1 mg/dL for a 31-40 year old man,
(vi) less than 0.2.9 mg/dL for a 31-40 year old woman,
(vii) less than 3.7 mg/dL for a 41-50 year old man,
(viii) less than 2.7 mg/dL for a 41-50 year old woman,
(ix) less than 3.3 mg/dL for a 51-60 year old man,
(x) less than 2.4 mg/dL for a 51-60 year old woman,
(xi) less than 3.0 mg/dL for a man over 60 years old, or
(xii) less than 2.0 mg/dL for a woman over 60 years old.

Also disclosed herein is a kit for reducing the risk of an adverse event in an individual in need of inducing satiety, comprising: a) a therapeutically effective amount of R)-8-chloro-1-methyl-2,3,4,5-tetrahydro-1H-3-benzazepine or a pharmaceutically acceptable salt, solvate or hydrate thereof, and b) instructions indicating that the compound is to be administered to an individual having an approximate serum creatinine concentration of:
(i) less than 4.9 mg/dL for an 18-20 year old man,
(ii) less than 3.5 mg/dL for an 18-20 year old woman,
(iii) less than 4.5 mg/dL for a 21-30 year old man,
(iv) less than 3.2 mg/dL for a 21-30 year old woman,
(v) less than 4.1 mg/dL for a 31-40 year old man,
(vi) less than 2.9 mg/dL for a 31-40 year old woman,
(vii) less than 3.7 mg/dL for a 41-50 year old man,
(viii) less than 2.7 mg/dL for a 41-50 year old woman,
(ix) less than 3.3 mg/dL for a 51-60 year old man,
(x) less than 2.4 mg/dL for a 51-60 year old woman,
(xi) less than 3.0 mg/dL for a man over 60 years old, or
(xii) less than 2.0 mg/dL for a woman over 60 years old.

In some embodiments, the individual in need of inducing satiety is a patient with an initial body mass index ≥30 kg/m$^2$. In some embodiments, the individual is a patient with an initial body mass index ≥27 kg/m$^2$ in the presence of at least one weight related comorbid condition. In some embodiments, the individual is a patient with an initial body mass index ≥27 kg/m$^2$ in the presence of at least one weight related comorbid condition selected from: hypertension, dyslipidemia, cardiovascular disease, glucose intolerance and sleep apnea. In some embodiments, the individual has an initial body mass index ≥30 kg/m$^2$. In some embodiments, the individual has an initial body mass index ≥27 kg/m². In some embodiments, the individual has an initial body mass index ≥27 kg/m² in the presence of at least one weight related comorbid condition. In some embodiments, the individual has an initial body mass index ≥27 kg/m² in the presence of at least one weight related comorbid condition selected from: hypertension, dyslipidemia, cardiovascular disease, glucose intolerance and sleep apnea. In some embodiments, the individual has an initial body mass index ≥25 kg/m². In some embodiments, the individual has an initial body mass index ≥25 kg/m² in the presence of at least one weight related comorbid condition. In some embodiments, the individual has an initial body mass index ≥25 kg/m² in the presence of at least one weight related comorbid condition selected from: hypertension, dyslipidemia, cardiovascular disease, glucose intolerance and sleep apnea.

In some embodiments, the compositions or low dosage formulations characterized in the composition or formulation is administered in conjunction with phentermine to the individual. In some embodiments, a kit disclosed herein further comprises phentermine.

In some embodiments, the Cockcroft-Gault equation is used to determine the level of renal sufficiency of the individual. In some embodiments, the individual's ideal body weight is used in the equation and in other embodiments, the individual's actual body weight is used in the equation. In some embodiments, the individual's serum creatinine concentration is used to determine the level of renal sufficiency of the individual.

Further disclosed herein is a method for assisting treatment of obesity in an individual in need thereof, comprising measuring the level of renal sufficiency of the individual, wherein a measurement of a level of renal sufficiency selected from the group consisting of: no renal impairment, mild renal impairment, and moderate renal impairment indicates that the individual is suitable for prescription of a therapeutically effective amount of (R)-8-chloro-1-methyl-2,3,4,5-tetrahydro-H-3-benzazepine or a pharmaceutically acceptable salt, solvate or hydrate thereof. In addition, disclosed herein is a method for assisting treatment of obesity in an individual in need thereof, comprising measuring the level of renal sufficiency of the individual, wherein a measurement of a level of renal sufficiency selected from the group consisting of: no renal impairment, mild renal impairment, and moderate renal impairment indicates that the individual is suitable to receive administration of a therapeutically effective amount of (R)-8-chloro-1-methyl-2,3,4,5-tetrahydro-1H-3-benzazepine or a pharmaceutically acceptable salt, solvate or hydrate thereof.

Further disclosed herein is a method for assisting treatment of obesity in an individual in need thereof, comprising measuring the level of renal sufficiency of the individual, wherein a measurement of a level of renal sufficiency of severe renal impairment or ESRD indicates that the individual is suitable for prescription of a therapeutically effective amount of (R)-8-chloro-1-methyl-2,3,4,5-tetrahydro-1H-3-benzazepine or a pharmaceutically acceptable salt, solvate or hydrate thereof. In addition, disclosed herein is a method for assisting treatment of obesity in an individual in need thereof, comprising measuring the level of renal sufficiency of the individual, wherein a measurement of a level of renal sufficiency of severe renal impairment or ESRD indicates that the individual is suitable to receive administration of a therapeutically effective amount of (R)-8-chloro-1-methyl-2,3,4,5-tetrahydro-1H-3-benzazepine or a pharmaceutically acceptable salt, solvate or hydrate thereof.

Further disclosed herein is a method for assisting treatment of obesity in an individual in need thereof, comprising measuring the level of renal sufficiency of the individual, wherein a measurement of a level of renal sufficiency indicating renal impairment indicates that the individual is suitable for prescription of a reduced dosage regiment of (R)-8-chloro-1-methyl-2,3,4,5-tetrahydro-1H-3-benzazepine or a pharmaceutically acceptable salt, solvate or hydrate thereof. In addition, disclosed herein is a method for assisting treatment of obesity in an individual in need thereof, comprising measuring the level of renal sufficiency of the individual, wherein a measurement of a level of renal sufficiency indicating renal impairment indicates that the individual is suitable to receive administration of a reduced dosage regiment of (R)-8-chloro-1-methyl-2,3,4,5-tetrahydro-1H-3-benzazepine or a pharmaceutically acceptable salt, solvate or hydrate thereof.

Further disclosed herein is a method for assisting treatment of obesity in an individual in need thereof, comprising measuring an approximate serum creatinine concentration for the individual, wherein a measurement of an approximate serum creatinine concentration of:

(i) less than 4.9 mg/dL for an 18-20 year old man,
(ii) less than 3.5 mg/dL for an 18-20 year old woman,
(iii) less than 4.5 mg/dL for a 21-30 year old man,
(iv) less than 3.2 mg/dL for a 21-30 year old woman,
(v) less than 4.1 mg/dL for a 31-40 year old man,
(vi) less than 2.9 mg/dL for a 31-40 year old woman,
(viii) less than 2.7 mg/dL for a 41-50 year old woman,
(ix) less than 3.3 mg/dL for a 51-60 year old man,
(x) less than 2.4 mg/dL for a 51-60 year old woman,
(xi) less than 3.0 mg/dL for a man over 60 years old, or
(xii) less than 2.0 mg/dL for a woman over 60 years old indicates that the individual is suitable for prescription of a therapeutically effective amount of (R)-8-chloro-1-methyl-2,3,4,5-tetrahydro-1H-3-benzazepine or a pharmaceutically acceptable salt, solvate or hydrate thereof. Also disclosed herein is a method for assisting treatment of obesity in an individual in need thereof, comprising measuring an approximate serum creatinine concentration, for the individual, wherein a measurement of an approximate serum creatinine concentration of:

(i) less than 4.9 mg/dL for an 18-20 year old man,
(ii) less than 3.5 mg/dL for an 18-20 year old woman,
(iii) less than 4.5 mg/dL for a 21-30 year old man,
(iv) less than 3.2 mg/dL for a 21-30 year old woman,
(v) less than 4.1 mg/dL for a 31-40 year old man,
(vi) less than 2.9 mg/dL for a 31-40 year old woman,
(viii) less than 2.7 mg/dL for a 41-50 year old woman,
(ix) less than 3.3 mg/dL for a 51-60 year old man,
(x) less than 2.4 mg/dL for a 51-60 year old woman,
(xi) less than 3.0 mg/dL for a man over 60 years old, or
(xii) less than 2.0 mg/dL for a woman over 60 years old indicates that the individual is suitable to receive administration of a therapeutically effective amount of (R)-8-chloro-1-methyl-2,3,4,5-tetrahydro-1H-3-benzazepine or a pharmaceutically acceptable salt, solvate or hydrate thereof.

Further disclosed herein is a method for assisting treatment of obesity in an individual in need thereof, comprising measuring a creatinine clearance rate using the Cockcroft-Gault equation for the individual wherein a measurement of a creatinine clearance rate of greater than about 80 mL/minute using the Cockcroft-Gault equation indicates that the individual is suitable for prescription of a therapeutically effective amount of (R)-8-chloro-1-methyl-2,3,4,5-tetrahydro-1H-3-benzazepine or a pharmaceutically acceptable salt, solvate or hydrate thereof. In addition, disclosed herein is a method for assisting treatment of obesity in an individual in need thereof, comprising measuring a creatinine clearance rate using the Cockcroft-Gault equation for the individual wherein a measurement of a creatinine clearance rate of greater than about 80 mL/minute using the Cockcroft-Gault equation indicates that the individual is suitable to receive administration of a therapeutically effective amount of (R)-8-chloro-1-methyl-2,3,4,5-tetrahydro-1H-3-benzazepine or a pharmaceutically acceptable salt, solvate or hydrate thereof.

Further disclosed herein is a method for assisting treatment of obesity in an individual in need thereof, comprising measuring a creatinine clearance rate using the Cockcroft-Gault equation for the individual wherein a measurement of a creatinine clearance rate of greater than about 50 mL/minute using the Cockcroft-Gault equation indicates that the individual is suitable for prescription of a therapeutically effective amount of (R)-8-chloro-1-methyl-2,3,4,5-tetrahydro-1H-3-benzazepine or a pharmaceutically acceptable salt, solvate or hydrate thereof. In addition, disclosed herein is a method for assisting treatment of obesity in an individual in need thereof, comprising measuring a creatinine clearance rate using the Cockcroft-Gault equation for the individual wherein a measurement of a creatinine clearance rate of greater than about 50 mL/minute using the Cockcroft-Gault equation indicates that the individual is suitable to receive administration of a therapeutically effective amount of (R)-8-chloro-1-methyl-2,3,4,5-tetrahydro-1H-3-benzazepine or a pharmaceutically acceptable salt, solvate or hydrate thereof.

Further disclosed herein is a method for assisting treatment of obesity in an individual in need thereof, comprising measuring a creatinine clearance rate using the Cockcroft-Gault equation for the individual wherein a measurement of a creatinine clearance rate of greater than about 30 mL/minute using the Cockcroft-Gault equation indicates that the individual is suitable for prescription of a therapeutically effective amount of (R)-8-chloro-1-methyl-2,3,4,5-tetrahydro-1H-3-benzazepine or a pharmaceutically acceptable salt, solvate or hydrate thereof. In addition, disclosed herein is a method for assisting treatment of obesity in an individual in need thereof, comprising measuring a creatinine clearance rate using the Cockcroft-Gault equation for the individual wherein a measurement of a creatinine clearance rate of greater than about 30 mL/minute using the Cockcroft-Gault equation indicates that the individual is suitable to receive administration of a therapeutically effective amount of (R)-8-chloro-1-methyl-2,3,4,5-tetrahydro-1H-3-benzazepine or a pharmaceutically acceptable salt, solvate or hydrate thereof.

Further disclosed herein is a method for assisting reducing the risk of an adverse event in an individual in need of treatment of obesity, comprising measuring the level of renal sufficiency of the individual, wherein a measurement of a level of renal sufficiency selected from the group consisting of: no renal impairment, mild renal impairment, and moderate renal impairment indicates that the individual is suitable for prescription of a therapeutically effective amount of (R)-8-chloro-1-methyl-2,3,4,5-tetrahydro-1H-3-benzazepine or a pharmaceutically acceptable salt, solvate or hydrate thereof. Also disclosed herein is a method for assisting reducing the risk of an adverse event in an individual in need of treatment of obesity, comprising measuring the level of renal sufficiency of the individual, wherein a measurement of a level of renal sufficiency selected from the group consisting of: no renal impairment, mild renal impairment, and moderate renal impairment indicates that the individual is suitable to receive administration of a therapeutically effective amount of (R)-8-chloro-1-methyl-2,3,4, 5-tetrahydro-1H-3-benzazepine or a pharmaceutically acceptable salt, solvate or hydrate thereof.

Further disclosed herein is a method for assisting reducing the risk of an adverse event in an individual in need of treatment of obesity, comprising measuring the level of renal sufficiency of the individual, wherein a measurement of a level of renal sufficiency indicating renal impairment indicates that the individual is suitable for prescription of a reduced dosage regimen of (R)-8-chloro-1-methyl-2,3,4,5-tetrahydro-1H-3-benzazepine or a pharmaceutically acceptable salt, solvate or hydrate thereof. Also disclosed herein is a method for assisting reducing the risk of an adverse event in an individual in need of treatment of obesity, comprising measuring the level of renal sufficiency of the individual, wherein a measurement of a level of renal sufficiency indicating renal impairment indicates that the individual is suitable to receive administration of a reduced dosage regimen of (R)-8-chloro-1-methyl-2,3,4,5-tetrahydro-1H-3-benzazepine or a pharmaceutically acceptable salt, solvate or hydrate thereof.

Further disclosed herein is a method for assisting reducing the risk of an adverse event in an individual in need of treatment of obesity, comprising measuring an approximate serum creatinine concentration for the individual, wherein a measurement of an approximate serum creatinine concentration of:
  (i) less than 4.9 mg/dL for an 18-20 year old man,
  (ii) less than 3.5 mg/dL for an 18-20 year old woman,
  (iii) less than 4.5 mg/dL for a 21-30 year old man,
  (iv) less than 3.2 mg/dL for a 21-30 year old woman,
  (v) less than 4.1 mg/dL for a 31-40 year old man,
  (vi) less than 2.9 mg/dL for a 31-40 year old woman,
  (vii) less than 3.7 mg/dL for a 41-50 year old man,
  (viii) less than 2.7 mg/dL for a 41-50 year old woman,
  (ix) less than 3.3 mg/dL for a 51-60 year old man,
  (x) less than 2.4 mg/dL for a 51-60 year old woman,
  (xi) less than 3.0 mg/dL for a man over 60 years old, or
  (xii) less than 2.0 mg/dL for a woman over 60 years old
  indicates that the individual is suitable for prescription of a therapeutically effective amount of (R)-8-chloro-1-methyl-2,3,4,5-tetrahydro-1H-3-benzazepine or a pharmaceutically acceptable salt, solvate or hydrate thereof. Also disclosed herein is a method for assisting reducing the risk of an adverse event in an individual in need of treatment of obesity, comprising measuring an approximate serum creatinine concentration for the individual, wherein a measurement of an approximate serum creatinine concentration of:
  (i) less than 4.9 mg/dL for an 18-20 year old man,
  (ii) less than 3.5 mg/dL for an 18-20 year old woman,
  (iii) less than 4.5 mg/dL for a 21-30 year old man,
  (iv) less than 3.2 mg/dL for a 21-30 year old woman,
  (v) less than 4.1 mg/dL for a 31-40 year old man,
  (vi) less than 2.9 mg/dL for a 31-40 year old woman,
  (vii) less than 3.7 mg/dL for a 41-50 year old man,
  (viii) less than 2.7 mg/dL for a 41-50 year old woman,
  (ix) less than 3.3 mg/dL for a 51-60 year old man,
  (x) less than 2.4 mg/dL for a 51-60 year old woman,
  (xi) less than 3.0 mg/dL for a man over 60 years old, or
  (xii) less than 2.0 mg/dL for a woman over 60 years old
  indicates that the individual is suitable to receive administration of a therapeutically effective amount of (R)-8-chloro-1-methyl-2,3,4,5-tetrahydro-1H-3-benzazepine or a pharmaceutically acceptable salt, solvate or hydrate thereof.

Further disclosed herein is a method for assisting selecting an individual for treatment with (R)-8-chloro-1-methyl-2,3,4,5-tetrahydro-1H-3-benzazepine or a pharmaceutically acceptable salt, solvate or hydrate thereof from a plurality of individuals in need of treatment of obesity, comprising measuring the level of renal sufficiency of the individual, wherein a measurement of a level of renal sufficiency selected from the group consisting of: no renal impairment, mild renal impairment, and moderate renal impairment indicates the individual is selected for treatment with (R)-8-chloro-1-methyl-2,3,4,5-tetrahydro-1H-3-benzazepine or a pharmaceutically acceptable salt, solvate or hydrate thereof. Also disclosed herein is a method for assisting selecting an individual for treatment with (R)-8-chloro-1-methyl-2,3,4,5-tetrahydro-1H-3-benzazepine or a pharmaceutically acceptable salt, solvate or hydrate thereof from a plurality of individuals in need of treatment of obesity, comprising measuring the level of renal sufficiency of the individual, wherein a measurement of an approximate serum creatinine concentration of (i) less than 4.9 mg/dL for an 18-20 year old man, (ii) less than 3.5 mg/dL for an 18-20 year old woman, (iii) less than 4.5 mg/dL for a 21-30 year old man, (iv) less than 3.2 mg/dL for a 21-30 year old woman, (v) less than 4.1 mg/dL for a 31-40 year old man, (vi) less than 2.9 mg/dL for a 31-40 year old woman, (vii) less than 3.7 mg/dL for a 41-50 year old man, (viii) less than 2.7 mg/dL for a 41-50 year old woman, (ix) less than 3.3 mg/dL for a 51-60 year old man, (x) less than 2.4 mg/dL for a 51-60 year old woman, (xi) less than 3.0 mg/dL for a man over 60 years old, or (xii) less than 2.0 mg/dL for a woman over 60 years old indicates that the individual is selected for treatment with (R)-8-chloro-1-methyl-2,3,4,5-tetrahydro-1H-3-benzazepine or a pharmaceutically acceptable salt, solvate or hydrate thereof.

Further disclosed herein is a composition for use in a method of treatment of obesity in an individual, said composition comprising (R)-8-chloro-1-methyl-2,3,4,5-tetrahydro-1H-3-benzazepine or a pharmaceutically acceptable salt, solvate or hydrate thereof, wherein said individual has previously been determined to have a level of renal sufficiency selected from the group consisting of: no renal impairment, mild renal impairment, and moderate renal impairment.

Further disclosed herein is a low dosage formulation of a compound for use in a method of treatment of obesity in an individual, wherein said individual has previously been determined to have renal impairment; wherein said compound is (R)-8-chloro-1-methyl-2,3,4,5-tetrahydro-1H-3-benzazepine or a pharmaceutically acceptable salt, solvate or hydrate thereof. Also disclosed is a low dosage formulation of a compound for use in a method of treatment of obesity in an individual, wherein said low dosage reduces a toxic event in said individual to said compound, wherein said individual has previously been determined to have renal impairment; and wherein said compound is (R)-8-chloro-1-methyl-2,3,4,5-tetrahydro-1H-3-benzazepine or a pharmaceutically acceptable salt, solvate or hydrate thereof. In addition, disclosed is a low dosage formulation of a compound for use in a method of treatment of obesity in an individual, wherein said low dosage prevents a toxic event in said individual to said compound, wherein said individual has previously been determined to have renal impairment; and wherein said compound is (R)-8-chloro-1-methyl-2,3,4,5-tetrahydro-1H-3-benzazepine or a pharmaceutically acceptable salt, solvate or hydrate thereof.

Further disclosed herein is a composition for use in a method of treatment of obesity in an individual in need thereof, comprising a therapeutically effective amount of (R)-8-chloro-1-methyl-2,3,4,5-tetrahydro-1H-3-benzazepine or a pharmaceutically acceptable salt, solvate or hydrate thereof, wherein the individual has an approximate serum creatinine concentration of:

(i) less than 4.9 mg/dL for an 18-20 year old man, (ii) less than 3.5 mg/dL for an 18-20 year old woman, (iii) less than 4.5 mg/dL for a 21-30 year old man, (iv) less than 3.2 mg/dL for a 21-30 year old woman, (v) less than 4.1 mg/dL for a 31-40 year old man, (vi) less than 2.9 mg/dL for a 31-40 year old woman, (vii) less than 3.7 mg/dL for a 41-50 year old man, (viii) less than 2.7 mg/dL for a 41-50 year old woman, (ix) less than 3.3 mg/dL for a 51-60 year old man, (x) less than 2.4 mg/dL for a 51-60 year old woman, (xi) less than 3.0 mg/dL for a man over 60 years old, or (xii) less than 2.0 mg/dL for a woman over 60 years old.

In addition, disclosed herein is a composition for use in a method of reducing the risk of an adverse event in an individual in need of treatment of obesity, comprising a therapeutically effective amount of R)-8-chloro-1-methyl-2,3,4,5-tetrahydro-1H-3-benzazepine or a pharmaceutically acceptable salt, solvate or hydrate thereof, wherein the individual has an approximate serum creatinine concentration of:

(i) less than 4.9 mg/dL for an 18-20 year old man, (ii) less than 3.5 mg/dL for an 18-20 year old woman, (iii) less than 4.5 mg/dL for a 21-30 year old man, (iv) less than 3.2 mg/dL for a 21-30 year old woman, (v) less than 4.1 mg/dL for a 31-40 year old man, (vi) less than 2.9 mg/dL for a 31-40 year old woman, (vii) less than 3.7 mg/dL for a 41-50 year old man, (viii) less than 2.7 mg/dL for a 41-50 year old woman, (ix) less than 3.3 mg/dL for a 51-60 year old man, (x) less than 2.4 mg/dL for a 51-60 year old woman, (xi) less than 3.0 mg/dL for a man over 60 years old, or (xii) less than 2.0 mg/dL for a woman over 60 years old.

Further disclosed herein is a kit for use in a method of treatment of obesity in an individual in need thereof, comprising: a) a therapeutically effective amount of R)-8-chloro-1-methyl-2,3,4,5-tetrahydro-1H-3-benzazepine or a pharmaceutically acceptable salt, solvate or hydrate thereof, and b) instructions indicating that the compound is to be administered to an individual having an approximate serum creatinine concentration of:

(i) less than 4.9 mg/dL for an 18-20 year old man, (ii) less than 3.5 mg/dL for an 18-20 year old woman, (iii) less than 4.5 mg/dL for a 21-30 year old man, (iv) less than 3.2 mg/dL for a 21-30 year old woman, (v) less than 4.1 mg/dL for a 31-40 year old man, (vi) less than 2.9 mg/dL for a 31-40 year old woman, (vii) less than 3.7 mg/dL for a 41-50 year old man, (viii) less than 2.7 mg/dL for a 41-50 year old woman, (ix) less than 3.3 mg/dL for a 51-60 year old man, (x) less than 2.4 mg/dL for a 51-60 year old woman, (xi) less than 3.0 mg/dL for a man over 60 years old, or (xii) less than 2.0 mg/dL for a woman over 60 years old.

Also disclosed herein is a kit for reducing the risk of an adverse event in an individual in need of treatment of obesity, comprising: a) a therapeutically effective amount of R)-8-chloro-1-methyl-2,3,4,5-tetrahydro-1H-3-benzazepine or a pharmaceutically acceptable salt, solvate or hydrate thereof, and b) instructions indicating that the compound is to be administered to an individual having an approximate serum creatinine concentration of:

(i) less than 4.9 mg/dL for an 18-20 year old man,
(ii) less than 3.5 mg/dL for an 18-20 year old woman,
(iii) less than 4.5 mg/dL for a 21-30 year old man,
(iv) less than 3.2 mg/dL for a 21-30 year old woman,
(v) less than 4.1 mg/dL for a 31-40 year old man,
(vi) less than 2.9 mg/dL for a 31-40 year old woman,
(vii) less than 3.7 mg/dL for a 41-50 year old man,
(viii) less than 2.7 mg/dL for a 41-50 year old woman,
(ix) less than 3.3 mg/dL for a 51-60 year old man,
(x) less than 2.4 mg/dL for a 51-60 year old woman,
(xi) less than 3.0 mg/dL for a man over 60 years old, or
(xii) less than 2.0 mg/dL for a woman over 60 years old.

In some embodiments, treatment of obesity comprises weight loss. In some embodiments, treatment of obesity comprises maintenance of weight loss. In some embodiments, treatment of obesity further comprises prescribing or administering a reduced-calorie diet. In some embodiments, treatment of obesity further comprises prescribing or administering a program of regular exercise. In some embodiments, treatment of obesity further comprises prescribing or administering both a reduced-calorie diet and a program of regular exercise.

In some embodiments, the individual in need of treatment of obesity is a patient with an initial body mass index ≥30 kg/m$^2$. In some embodiments, the individual is a patient with an initial body mass index ≥27 kg/m$^2$ in the presence of at least one weight related comorbid condition. In some embodiments, the individual is a patient with an initial body mass index ≥27 kg/m$^2$ in the presence of at least one weight related comorbid condition selected from: hypertension, dyslipidemia, cardiovascular disease, glucose intolerance and sleep apnea. In some embodiments, the individual has an initial body mass index ≥30 kg/m$^2$. In some some embodiments, the individual has an initial body mass index 27 kg/m$^2$. In some embodiments, the individual has an initial body mass index ≥27 kg/m$^2$ in the presence of at least one weight related comorbid condition. In some embodiments, the individual has an initial body mass index ≥27 kg/m$^2$ in the presence of at least one weight related comorbid condition selected from: hypertension, dyslipidemia, cardiovascular disease, glucose intolerance and sleep apnea.

In some embodiments, the compositions or low dosage formulations characterized in the composition or formulation is administered in conjunction with phentermine to the individual. In some embodiments, a kit disclosed herein further comprises phentermine.

In some embodiments, the Cockcroft-Gault equation is used to determine the level of renal sufficiency of the individual. In some embodiments, the individual's ideal body weight is used in the equation and in other embodiments, the individual's actual body weight is used in the equation. In some embodiments, the individual's serum creatinine concentration is used to determine the level of renal sufficiency of the individual.

Further disclosed herein is a method for assisting prevention of obesity in an individual in need thereof, comprising measuring the level of renal sufficiency of the individual, wherein a measurement of a level of renal sufficiency selected from the group consisting of: no renal impairment, mild renal impairment, and moderate renal impairment indicates that the individual is suitable for prescription of a therapeutically effective amount of (R)-8-chloro-1-methyl-2,3,4,5-tetrahydro-1H-3-benzazepine or a pharmaceutically acceptable salt, solvate or hydrate thereof. In addition, disclosed herein is a method for assisting prevention of obesity in an individual in need thereof, comprising measuring the level of renal sufficiency of the individual, wherein a measurement of a level of renal sufficiency selected from the group consisting of: no renal impairment, mild renal impairment, and moderate renal impairment indicates that the individual is suitable to receive administration of a therapeutically effective amount of (R)-8-chloro-1-methyl-2,3,4,5-tetrahydro-1H-3-benzazepine or a pharmaceutically acceptable salt, solvate or hydrate thereof.

Further disclosed herein is a method for assisting prevention of obesity in an individual in need thereof, comprising measuring the level of renal sufficiency of the individual, wherein a measurement of a level of renal sufficiency of severe renal impairment or ESRD indicates that the individual is suitable for prescription of a therapeutically effective amount of (R)-8-chloro-1-methyl-2,3,4,5-tetrahydro-1H-3-benzazepine or a pharmaceutically acceptable salt, solvate or hydrate thereof. In addition, disclosed herein is a method for assisting prevention of obesity in an individual in need thereof, comprising measuring the level of renal sufficiency of the individual, wherein a measurement of a level of renal sufficiency of severe renal impairment or ESRD indicates that the individual is suitable to receive administration of a therapeutically effective amount of (R)-8-chloro-1-methyl-2,3,4,5-tetrahydro-1H-3-benzazepine or a pharmaceutically acceptable salt, solvate or hydrate thereof.

Further disclosed herein is a method for assisting prevention of obesity in an individual in need thereof, comprising measuring the level of renal sufficiency of the individual, wherein a measurement of a level of renal sufficiency indicating renal impairment indicates that the individual is suitable for prescription of a reduced dosage regiment of (R)-8-chloro-1-methyl-2,3,4,5-tetrahydro-1H-3-benzazepine or a pharmaceutically acceptable salt, solvate or hydrate thereof. In addition, disclosed herein is a method for assisting prevention of obesity in an individual in need thereof, comprising measuring the level of renal sufficiency of the individual, wherein a measurement of a level of renal sufficiency indicating renal impairment indicates that the individual is suitable to receive administration of a reduced dosage regiment of (R)-8-chloro-1-methyl-2,3,4,5-tetrahydro-1H-3-benzazepine or a pharmaceutically acceptable salt, solvate or hydrate thereof.

Further disclosed herein is a method for assisting prevention of obesity in an individual in need thereof, comprising measuring an approximate serum creatinine concentration for the individual, wherein a measurement of an approximate serum creatinine concentration of:
(i) less than 4.9 mg/dL for an 18-20 year old man,
(ii) less than 3.5 mg/dL for an 18-20 year old woman,
(iii) less than 4.5 mg/dL for a 21-30 year old man,
(iv) less than 3.2 mg/dL for a 21-30 year old woman,
(v) less than 4.1 mg/dL for a 31-40 year old man,
(vi) less than 2.9 mg/dL for a 31-40 year old woman,
(viii) less than 2.7 mg/dL for a 41-50 year old woman,
(ix) less than 3.3 mg/dL for a 51-60 year old man,
(x) less than 2.4 mg/dL for a 51-60 year old woman,
(xi) less than 3.0 mg/dL for a man over 60 years old, or
(xii) less than 2.0 mg/dL for a woman over 60 years old
indicates that the individual is suitable for prescription of a therapeutically effective amount of (R)-8-chloro-1-methyl-2,3,4,5-tetrahydro-1H-3-benzazepine or a pharmaceutically acceptable salt, solvate or hydrate thereof. Also disclosed herein is a method for assisting prevention of obesity in an individual in need thereof, comprising measuring an approximate serum creatinine concentration for the individual, wherein a measurement of an approximate serum creatinine concentration of:

(i) less than 4.9 mg/dL for an 18-20 year old man,
(ii) less than 3.5 mg/dL for an 18-20 year old woman,
(iii) less than 4.5 mg/dL for a 21-30 year old man,
(iv) less than 3.2 mg/dL for a 21-30 year old woman,
(v) less than 4.1 mg/dL for a 31-40 year old man,
(vi) less than 2.9 mg/dL for a 31-40 year old woman,
(viii) less than 2.7 mg/dL for a 41-50 year old woman,
(ix) less than 3.3 mg/dL for a 51-60 year old man,
(x) less than 2.4 mg/dL for a 51-60 year old woman,
(xi) less than 3.0 mg/dL for a man over 60 years old, or
(xii) less than 2.0 mg/dL for a woman over 60 years old
indicates that the individual is suitable to receive administration of a therapeutically effective amount of (R)-8-chloro-1-methyl-2,3,4,5-tetrahydro-1H-3-benzazepine or a pharmaceutically acceptable salt, solvate or hydrate thereof.

Further disclosed herein is a method for assisting prevention of obesity in an individual in need thereof, comprising measuring a creatinine clearance rate using the Cockcroft-Gault equation for the individual wherein a measurement of a creatinine clearance rate of greater than about 80 mL/minute using the Cockcroft-Gault equation indicates that the individual is suitable for prescription of a therapeutically effective amount of (R)-8-chloro-1-methyl-2,3,4,5-tetrahydro-1H-3-benzazepine or a pharmaceutically acceptable salt, solvate or hydrate thereof. In addition, disclosed herein is a method for assisting prevention of obesity in an individual in need thereof, comprising measuring a creatinine clearance rate using the Cockcroft-Gault equation for the individual wherein a measurement of a creatinine clearance rate of greater than about 80 mL/minute using the Cockcroft-Gault equation indicates that the individual is suitable to receive administration of a therapeutically effective amount of (R)-8-chloro-1-methyl-2,3,4,5-tetrahydro-1H-3-benzazepine or a pharmaceutically acceptable salt, solvate or hydrate thereof.

Further disclosed herein is a method for assisting prevention of obesity in an individual in need thereof, comprising measuring a creatinine clearance rate using the Cockcroft-Gault equation for the individual wherein a measurement of a creatinine clearance rate of greater than about 50 mL/minute using the Cockcroft-Gault equation indicates that the individual is suitable for prescription of a therapeutically effective amount of (R)-8-chloro-1-methyl-2,3,4,5-tetrahydro-1H-3-benzazepine or a pharmaceutically acceptable salt, solvate or hydrate thereof. In addition, disclosed herein is a method for assisting prevention of obesity in an individual in need thereof, comprising measuring a creatinine clearance rate using the Cockcroft-Gault equation for the individual wherein a measurement of a creatinine clearance rate of greater than about 50 mL/minute using the Cockcroft-Gault equation indicates that the individual is suitable to receive administration of a therapeutically effective amount of (R)-8-chloro-1-methyl-2,3,4,5-tetrahydro-1H-3-benzazepine or a pharmaceutically acceptable salt, solvate or hydrate thereof.

Further disclosed herein is a method for assisting prevention of obesity in an individual in need thereof, comprising measuring a creatinine clearance rate using the Cockcroft-Gault equation for the individual wherein a measurement of a creatinine clearance rate of greater than about 30 mL/minute using the Cockcroft-Gault equation indicates that the individual is suitable for prescription of a therapeutically effective amount of (R)-8-chloro-1-methyl-2,3,4,5-tetrahydro-1H-3-benzazepine or a pharmaceutically acceptable salt, solvate or hydrate thereof. In addition, disclosed herein is a method for assisting prevention of obesity in an individual in need thereof, comprising measuring a creatinine clearance rate using the Cockcroft-Gault equation for the individual wherein a measurement of a creatinine clearance rate of greater than about 30 mL/minute using the Cockcroft-Gault equation indicates that the individual is suitable to receive administration of a therapeutically effective amount of (R)-8-chloro-1-methyl-2,3,4,5-tetrahydro-1H-3-benzazepine or a pharmaceutically acceptable salt, solvate or hydrate thereof.

Further disclosed herein is a method for assisting reducing the risk of an adverse event in an individual in need of prevention of obesity, comprising measuring the level of renal sufficiency of the individual, wherein a measurement of a level of renal sufficiency selected from the group consisting of: no renal impairment, mild renal impairment, and moderate renal impairment indicates that the individual is suitable for prescription of a therapeutically effective amount of (R)-8-chloro-1-methyl-2,3,4,5-tetrahydro-1H-3-benzazepine or a pharmaceutically acceptable salt, solvate or hydrate thereof. Also disclosed herein is a method for assisting reducing the risk of an adverse event in an individual in need of prevention of obesity, comprising measuring the level of renal sufficiency of the individual, wherein a measurement of a level of renal sufficiency selected from the group consisting of: no renal impairment, mild renal impairment, and moderate renal impairment indicates that the individual is suitable to receive administration of a therapeutically effective amount of (R)-8-chloro-1-methyl-2,3,4,5-tetrahydro-1H-3-benzazepine or a pharmaceutically acceptable salt, solvate or hydrate thereof.

Further disclosed herein is a method for assisting reducing the risk of an adverse event in an individual in need of prevention of obesity, comprising measuring the level of renal sufficiency of the individual, wherein a measurement of a level of renal sufficiency indicating renal impairment indicates that the individual is suitable for prescription of a reduced dosage regimen of (R)-8-chloro-1-methyl-2,3,4,5-tetrahydro-1H-3-benzazepine or a pharmaceutically acceptable salt, solvate or hydrate thereof. Also disclosed herein is a method for assisting reducing the risk of an adverse event in an individual in need of prevention of obesity, comprising measuring the level of renal sufficiency of the individual, wherein a measurement of a level of renal sufficiency indicating renal impairment indicates that the individual is suitable to receive administration of a reduced dosage regimen of (R)-8-chloro-1-methyl-2,3,4,5-tetrahydro-1H-3-benzazepine or a pharmaceutically acceptable salt, solvate or hydrate thereof.

Further disclosed herein is a method for assisting reducing the risk of an adverse event in an individual in need of prevention of obesity, comprising measuring an approximate serum creatinine concentration for the individual, wherein a measurement of an approximate serum creatinine concentration of:
(i) less than 4.9 mg/dL for an 18-20 year old man,
(ii) less than 3.5 mg/dL for an 18-20 year old woman,
(iii) less than 4.5 mg/dL for a 21-30 year old man,
(iv) less than 3.2 mg/dL for a 21-30 year old woman,
(v) less than 4.1 mg/dL for a 31-40 year old man,
(vi) less than 2.9 mg/dL for a 31-40 year old woman,
(vii) less than 3.7 mg/dL for a 41-50 year old man,
(viii) less than 2.7 mg/dL for a 41-50 year old woman,
(ix) less than 3.3 mg/dL for a 51-60 year old man,
(x) less than 2.4 mg/dL for a 51-60 year old woman,
(xi) less than 3.0 mg/dL for a man over 60 years old, or
(xii) less than 2.0 mg/dL for a woman over 60*years old
indicates that the individual is suitable for prescription of a therapeutically effective amount of (R)-8-chloro-1-methyl- 2,3,4,5-tetrahydro-1H-3-benzazepine or a pharmaceutically acceptable salt, solvate or hydrate thereof. Also disclosed herein is a method for assisting reducing the risk of an adverse event in an individual in need of prevention of obesity, comprising measuring an approximate serum creatinine concentration for the individual, wherein a measurement of an approximate serum creatinine concentration of:
 (i) less than 4.9 mg/dL for an 18-20 year old man,
 (ii) less than 3.5 mg/dL for an 18-20 year old woman,
 (iii) less than 4.5 mg/dL for a 21-30 year old man,
 (iv) less than 3.2 mg/dL for a 21-30 year old woman,
 (v) less than 4.1 mg/dL for a 31-40 year old man,
 (vi) less than 2.9 mg/dL for a 31-40 year old woman,
 (vii) less than 3.7 mg/dL for a 41-50 year old man,
 (viii) less than 2.7 mg/dL for a 41-50 year old woman,
 (ix) less than 3.3 mg/dL for a 51-60 year old man,
 (x) less than 2.4 mg/dL for a 51-60 year old woman,
 (xi) less than 3.0 mg/dL for a man over 60 years old, or
 (xii) less than 2.0 mg/dL for a woman over 60 years old
indicates that the individual is suitable to receive administration of a therapeutically effective amount of (R)-8-chloro-1-methyl-2,3,4,5-tetrahydro-1H-3-benzazepine or a pharmaceutically acceptable salt, solvate or hydrate thereof.

Further disclosed herein is a method for assisting selecting an individual for treatment with (R)-8-chloro-1-methyl-2,3,4,5-tetrahydro-1H-3-benzazepine or a pharmaceutically acceptable salt, solvate or hydrate thereof from a plurality of individuals in need of prevention of obesity, comprising measuring the level of renal sufficiency of the individual, wherein a measurement of a level of renal sufficiency selected from the group consisting of: no renal impairment, mild renal impairment, and moderate renal impairment indicates the individual is selected for treatment with (R)-8-chloro-1-methyl-2,3,4,5-tetrahydro-1H-3-benzazepine or a pharmaceutically acceptable salt, solvate or hydrate thereof. Also disclosed herein is a method for assisting selecting an individual for treatment with (R)-8-chloro-1-methyl-2,3,4,5-tetrahydro-1H-3-benzazepine or a pharmaceutically acceptable salt, solvate or hydrate thereof from a plurality of individuals in need of prevention of obesity, comprising measuring the level of renal sufficiency of the individual, wherein a measurement of an approximate serum creatinine concentration of
 (i) less than 4.9 mg/dL for an 18-20 year old man,
 (ii) less than 3.5 mg/dL for an 18-20 year old woman,
 (iii) less than 4.5 mg/dL for a 21-30 year old man,
 (iv) less than 3.2 mg/dL for a 21-30 year old woman,
 (v) less than 4.1 mg/dL for a 31-40 year old man,
 (vi) less than 2.9 mg/dL for a 31-40 year old woman,
 (vii) less than 3.7 mg/dL for a 41-50 year old man,
 (viii) less than 2.7 mg/dL for a 41-50 year old woman,
 (ix) less than 3.3 mg/dL for a 51-60 year old man,
 (x) less than 2.4 mg/dL for a 51-60 year old woman,
 (xi) less than 3.0 mg/dL for a man over 60 years old, or
 (xii) less than 2.0 mg/dL for a woman over 60 years old
indicates that the individual is selected for treatment with (R)-8-chloro-1-methyl-2,3,4,5-tetrahydro-1H-3-benzazepine or a pharmaceutically acceptable salt, solvate or hydrate thereof.

Further disclosed herein is a composition for use in a method of prevention of obesity in an individual, said composition comprising (R)-8-chloro-1-methyl-2,3,4,5-tetrahydro-1H-3-benzazepine or a pharmaceutically acceptable salt, solvate or hydrate thereof, wherein said individual has previously been determined to have a level of renal sufficiency selected from the group consisting of: no renal impairment, mild renal impairment, and moderate renal impairment.

Further disclosed herein is a low dosage formulation of a compound for use in a method of prevention of obesity in an individual, wherein said individual has previously been determined to have renal impairment; wherein said compound is (R)-8-chloro-1-methyl-2,3,4,5-tetrahydro-1H-3-benzazepine or a pharmaceutically acceptable salt, solvate or hydrate thereof. Also disclosed is a low dosage formulation of a compound for use in a method of prevention of obesity in an individual, wherein said low dosage reduces a toxic event in said individual to said compound, wherein said individual has previously been determined to have renal impairment; and wherein said compound is (R)-8-chloro-1-methyl-2,3,4,5-tetrahydro-1H-3-benzazepine or a pharmaceutically acceptable salt, solvate or hydrate thereof. In addition, disclosed is a low dosage formulation of a compound for use in a method of prevention of obesity in an individual, wherein said low dosage prevents a toxic event in said individual to said compound, wherein said individual has previously been determined to have renal impairment; and wherein said compound is (R)-8-chloro-1-methyl-2,3,4,5-tetrahydro-1H-3-benzazepine or a pharmaceutically acceptable salt, solvate or hydrate thereof.

Further disclosed herein is a composition for use in a method of prevention of obesity in an individual in need thereof, comprising a therapeutically effective amount of R)-8-chloro-1-methyl-2,3,4,5-tetrahydro-1H-3-benzazepine or a pharmaceutically acceptable salt, solvate or hydrate thereof, wherein the individual has an approximate serum creatinine concentration of:
 (i) less than 4.9 mg/dL for an 18-20 year old man,
 (ii) less than 3.5 mg/dL for an 18-20 year old woman,
 (iii) less than 4.5 mg/dL for a 21-30 year old man,
 (iv) less than 3.2 mg/dL for a 21-30 year old woman,
 (v) less than 4.1 mg/dL for a 31-40 year old man,
 (vi) less than 2.9 mg/dL for a 31-40 year old woman,
 (vii) less than 3.7 mg/dL for a 41-50 year old man,
 (viii) less than 2.7 mg/dL for a 41-50 year old woman,
 (ix) less than 3.3 mg/dL for a 51-60 year old man,
 (x) less than 2.4 mg/dL for a 51-60 year old woman,
 (xi) less than 3.0 mg/dL for a man over 60 years old, or
 (xii) less than 2.0 mg/dL for a woman over 60 years old.

In addition, disclosed herein is a composition for use in a method of reducing the risk of an adverse event in an individual in need of prevention of obesity, comprising a therapeutically effective amount of R)-8-chloro-1-methyl-2,3,4,5-tetrahydro-1H-3-benzazepine or a pharmaceutically acceptable salt, solvate or hydrate thereof, wherein the individual has an approximate serum creatinine concentration of:
 (i) less than 4.9 mg/dL for an 18-20 year old man,
 (ii) less than 3.5 mg/dL for an 18-20 year old woman,
 (iii) less than 4.5 mg/dL for a 21-30 year old man,
 (iv) less than 3.2 mg/dL for a 21-30 year old woman,
 (v) less than 4.1 mg/dL for a 31-40 year old man,
 (vi) less than 2.9 mg/dL for a 31-40 year old woman,
 (vii) less than 3.7 mg/dL for a 41-50 year old man,
 (viii) less than 2.7 mg/dL for a 41-50 year old woman,
 (ix) less than 3.3 mg/dL for a 51-60 year old man,
 (x) less than 2.4 mg/dL for a 51-60 year old woman,
 (xi) less than 3.0 mg/dL for a man over 60 years old, or
 (xii) less than 2.0 mg/dL for a woman over 60 years old.

Further disclosed herein is a kit for use in a method of prevention of obesity in an individual in need thereof, comprising: a) a therapeutically effective amount of R)-8- chloro-1-methyl-2,3,4,5-tetrahydro-1H-3-benzazepine or a pharmaceutically acceptable salt, solvate or hydrate thereof, and b) instructions indicating that the compound is to be administered to an individual having an approximate serum creatinine concentration of:
- (i) less than 4.9 mg/dL for an 18-20 year old man,
- (ii) less than 3.5 mg/dL for an 18-20 year old woman,
- (iii) less than 4.5 mg/dL for a 21-30 year old man,
- (iv) less than 3.2 mg/dL for a 21-30 year old woman,
- (v) less than 4.1 mg/dL for a 31-40 year old man,
- (vi) less than 2.9 mg/dL for a 31-40 year old woman,
- (vii) less than 3.7 mg/dL for a 41-50 year old man,
- (viii) less than 2.7 mg/dL for a 41-50 year old woman,
- (ix) less than 3.3 mg/dL for a 51-60 year old man,
- (x) less than 2.4 mg/dL for a 51-60 year old woman,
- (xi) less than 3.0 mg/dL for a man over 60 years old, or
- (xii) less than 2.0 mg/dL for a woman over 60 years old.

Also disclosed herein is a kit for reducing the risk of an adverse event in an individual in need of prevention of obesity, comprising: a) a therapeutically effective amount of R)-8-chloro-1-methyl-2,3,4,5-tetrahydro-1H-3-benzazepine or a pharmaceutically acceptable salt, solvate or hydrate thereof, and b) instructions indicating that the compound is to be administered to an individual having an approximate serum creatinine concentration of:
- (i) less than 4.9 mg/dL for an 18-20 year old man,
- (ii) less than 3.5 mg/dL for an 18-20 year old woman,
- (iii) less than 4.5 mg/dL for a 21-30 year old man,
- (iv) less than 3.2 mg/dL for a 21-30 year old woman,
- (v) less than 4.1 mg/dL for a 31-40 year old man,
- (vi) less than 2.9 mg/dL for a 31-40 year old woman,
- (vii) less than 3.7 mg/dL for a 41-50 year old man,
- (viii) less than 2.7 mg/dL for a 41-50 year old woman,
- (ix) less than 3.3 mg/dL for a 51-60 year old man,
- (x) less than 2.4 mg/dL for a 51-60 year old woman,
- (xi) less than 3.0 mg/dL for a man over 60 years old, or
- (xii) less than 2.0 mg/dL for a woman over 60 years old.

In some embodiments, the prevention of obesity comprises weight loss. In some embodiments, the prevention of obesity comprises maintenance of weight loss. In some embodiments, the prevention of obesity further comprises prescribing or administering a reduced-calorie diet. In some embodiments, the prevention of obesity further comprises prescribing or administering a program of regular exercise. In some embodiments, the prevention of obesity further comprises prescribing or administering both a reduced-calorie diet and a program of regular exercise.

In some embodiments, the individual in need of prevention of obesity is a patient with an initial body mass index ≥27 kg/m² in the presence of at least one weight related comorbid condition. In some embodiments, the individual is a patient with an initial body mass index ≥27 kg/m² in the presence of at least one weight related comorbid condition selected from: hypertension, dyslipidemia, cardiovascular disease, glucose intolerance and sleep apnea. In some embodiments, the individual has an initial body mass index ≥27 kg/m². In some embodiments, the individual has an initial body mass index ≥27 kg/m² in the presence of at least one weight related comorbid condition. In some embodiments, the individual has an initial body mass index ≥27 kg/m² in the presence of at least one weight related comorbid condition selected from: hypertension, dyslipidemia, cardiovascular disease, glucose intolerance and sleep apnea. In some embodiments, the individual has an initial body mass index ≥25 kg/m². In some embodiments, the individual has an initial body mass index ≥25 kg/m² in the presence of at least one weight related comorbid condition. In some embodiments, the individual has an initial body mass index ≥25 kg/m² in the presence of at least one weight related comorbid condition selected from: hypertension, dyslipidemia, cardiovascular disease, glucose intolerance and sleep apnea.

In some embodiments, the compositions or low dosage formulations characterized in the composition or formulation is administered in conjunction with phentermine to the individual. In some embodiments, a kit disclosed herein further comprises phentermine.

In some embodiments, the Cockcroft-Gault equation is used to determine the level of renal sufficiency of the individual. In some embodiments, the individual's ideal body weight is used in the equation and in other embodiments, the individual's actual body weight is used in the equation. In some embodiments, the individual's serum creatinine concentration is used to determine the level of renal sufficiency of the individual.

Further disclosed herein is a method of weight management, decreasing food intake, inducing satiety or treating or preventing obesity in an individual said method comprising administering (R)-8-chloro-1-methyl-2,3,4,5-tetrahydro-1H-3-benzazepine or a pharmaceutically acceptable salt, solvate or hydrate thereof to the individual and monitoring the individual for accumulation of a metabolite of (R)-8-chloro-1-methyl-2,3,4,5-tetrahydro-1H-3-benzazepine or a pharmaceutically acceptable salt, solvate or hydrate thereof. For example, disclosed herein is a method of weight management decreasing food intake, inducing satiety or treating or preventing obesity in an individual said method comprising administering (R)-8-chloro-1-methyl-2,3,4,5-tetrahydro-1H-3-benzazepine or a pharmaceutically acceptable salt, solvate or hydrate thereof to the individual and monitoring the individual for accumulation of a metabolite of (R)-8-chloro-1-methyl-2,3,4,5-tetrahydro-H-3-benzazepine or a pharmaceutically acceptable salt, solvate or hydrate thereof and discontinuing administration if said metabolite exceeds a predetermined safe level. A safe level can be determined, for example, by a health care practitioner or a regulatory agency. A metabolite of (R)-8-chloro-1-methyl-2,3,4,5-tetrahydro-1H-3-benzazepine or a pharmaceutically acceptable salt, solvate or hydrate thereof can be, for example, metabolite M1 (lorcaserin sulfamate) and/or M5 (N-carbamoyl glucuronide of lorcaserin).

Other uses of the disclosed methods will become apparent to those in the art based upon, inter alia, a review of this patent document.

EXAMPLES

The examples are provided to further define the disclosure without, however, limiting the disclosure to the specifics of these examples.

Example 1

Clinical Trial APD356-016. Pharmacokinetics of Lorcaserin in Renal Impairment

The interaction of renal insufficiency with the pharmacokinetics, tolerability and safety of lorcaserin were evaluated in a formal PK study in subjects with renal impairment and in the populations studied in phase 2 and phase 3 clinical studies.

The pharmacokinetic properties of lorcaserin in subjects with varying degrees of renal impairment were evaluated in clinical trial APD356-016. At the time of study conduct and analysis, subjects were assigned to renal impairment groups based on creatinine clearance calculated using IDEAL body weight (Table 1). This calculation was used to avoid overestimation of creatinine clearance due to the excess body weight (overweight and obese subjects were enrolled in the trial). Summaries of pharmacokinetic properties by group assignment using creatinine clearance calculated using ACTUAL body weights are also provided in the sections that follow.

TABLE 1

Group Assignments in APD356-016
Renal Impairment Study Group

| Description | Estimated Creatinine Clearance using Ideal Body Weight (mL/min) |
|---|---|
| Normal renal function | >80 mL/min |
| Mild renal impairment | 51-80 mL/min |
| Moderate renal impairment | 31-50 mL/min |
| Severe renal impairment not receiving dialysis | 5-30 mL/min |
| End stage renal disease requiring hemodialysis | ESRD |

Source: APD356-016 CSR, Table 1

Example 2

Lorcasein

Consistent with the metabolism of lorcaserin through multiple pathways, and the low renal excretion of lorcascrin demonstrated in clinical study APD356-006, lorcascrin exposure was not clearly affected by renal impairment. The 90% confidence interval for geometric mean ratios (GMR) of lorcaserin $AUC_{0-inf}$ in renal impairment relative to normal was slightly above the equivalence range in the mild and moderate impairment groups, but not in the severe impairment groups (Table 2, FIG. 1A, 1B).

TABLE 2

Geometric Mean Ratios of Lorcaserin Plasma Pharmacokinetic Parameters

| Pharmacokinetic Parameters | Geometric Mean Ratios of LSM (90% Confidence Intervals) of (R)-8-chloro-1-methyl-2,3,4,5-tetrahydro-1H-3-benzazepine Relative to Normal Renal Function Group (n = 8 per Group) | | |
|---|---|---|---|
| | Mild | Moderate | Severe |
| Using Ideal Body Weight (original CSR analysis) | | | |
| | N = 8 | N = 8 | N = 8 |
| $C_{max}$ | 0.991 (0.764, 1.29) | 0.697 (0.537, 0.904) | 0.686 (0.529, 0.891) |
| $AUC_{last}$ | 1.31 (1.01, 1.69) | 1.02 (0.791, 1.32) | 0.933 (0.723, 1.20) |
| $AUC_{0-inf}$ | 1.30 (1.01, 1.67) | 1.03 (0.806, 1.32) | 0.931 (0.727, 1.19) |
| Note: Group assignments based on ideal body weight Source: APD356-016 CSR, Table 14.2.1.3 | | | |
| Using Actual Body Weight | | | |
| | N = 10 | N = 8 | N = 1 |
| $C_{max}$ | 0.819 (0.652, 1.03) | 0.738 (0.579, 0.941) | 0.468 (0.267, 0.821) |
| $AUC_{last}$ | 0.912 (0.723, 1.15) | 0.868 (0.678, 1.11) | 0.861 (0.487, 1.52) |
| $AUC_{0-inf}$ | 0.921 (0.735, 1.15) | 0.869 (0.683, 1.11) | 0.861 (0.494, 1.50) |

Figure 2:
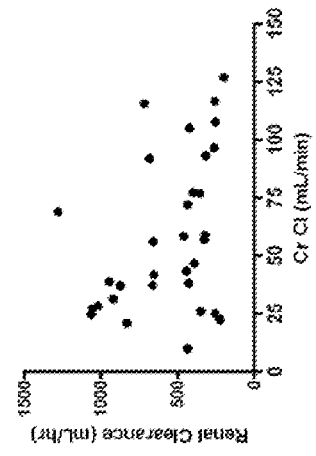
FIG. 2 shows renal clearance of lorcaserin as a function of creatinine clearance. The upper panel is for calculation uses ideal body weight and the lower panel is for calculation using actual body weight.
Figure 2:
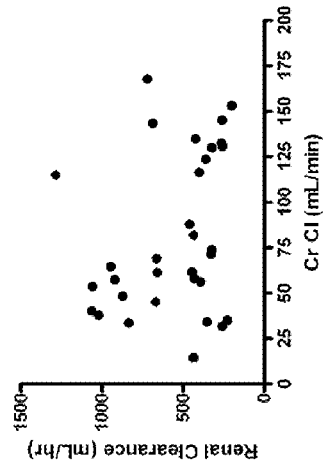

Group assignments based on ideal body weight were reported in the APD356-016 Clinical Study Report Source
LSM—Least-squares means
CSR—Clinical Study Report
$AUC_{last}$—area under the plasma concentration -time curve from time zero to the last time point
$AUC_{0-inf}$—area under the plasma concentration -time curve from time zero to infinity A weak negative correlation was observed between renal clearance of lorcaserin and calculated creatinine clearance using ideal body weight (FIG. 2), but no correlation was observed with creatinine clearance calculated using actual body weight (FIG. 2). The weak correlation is unlikely to be meaningful, given that renal clearance represents a small fraction of total lorcaserin clearance (fractional excretion 2.2% in subjects with normal renal function). Total lorcaserin clearance was not significantly correlated with creatinine clearance (FIG. 3). Lorcaserin was not removed by hemodialysis.

Reassignment of subjects to renal impairment groups based on creatinine clearance calculated using actual body weight instead of ideal body weight had little impact on the overall interpretation of the results for lorcaserin (Table 3).

TABLE 3

Mean Lorcaserin Pharmacokinetic Parameters after a 10 mg Dose of Lorcaserin:
Based in Renal Function Assignments using IDEAL or ACTUAL Body Weight

| PK Parameters[a] mean (SD) | GROUP ASSIGNMENTS USING IDEAL BODY WEIGHT | | | |
|---|---|---|---|---|
| | Normal N = 8 | Mild N = 8 | Moderate N = 8 | Severe N = 8 |
| $AUC_{0-t}$ (µg · hr/mL) | 0.482 (0.101) | 0.623 (0.088) | 0.515 (0.190) | 0.469 (0.172) |
| $AUC_{0-inf}$ (µg · hr/mL) | 0.501 (0.104) | 0.644 (0.089) | 0.538 (0.190) | 0.486 (0.179) |
| % $AUC_{0-inf}$ Extrapolated | 3.81 (1.57) | 3.36 (0.87) | 4.92 (2.68) | 3.59 (1.01) |
| $C_{max}$ (ng/mL) | 37.0 (8.7) | 36.3 (8.0) | 26.2 (8.3) | 26.4 (11.7) |
| $t_{max}$ (hr)[a] | 2.00 (1.00-3.00) | 4.50 (1.00-8.00) | 2.50 (2.00-3.00) | 3.00 (1.00-4.00) |
| Cl/F (L/hr) | 17.5 (3.4) | 13.3 (1.8) | 17.7 (6.6) | 19.7 (8.0) |
| $Cl_R$/F (L/hr) | 0.392 (0.202) | 0.533 (0.322) | 0.667 (0.228) | 0.657 (0.373) |
| $Cl_{NR}$/F (L/hr) | 17.1 (3.3) | 12.8 (1.6) | 17.0 (6.5) | 19.0 (7.8) |
| Vz/F (L) | 276 (53) | 248 (40) | 399 (132) | 401 (103) |
| $MRT_{inf}$ (hr) | 14.8 (2.2) | 18.0 (3.0) | 21.1 (2.8) | 21.7 (5.7) |
| $Ae_{0-120}$ (µg) | 185 (78) | 326 (156) | 327 (100) | 280 (140) |
| $fe_{0-120}$ | 0.0220 (0.0092) | 0.0386 (0.0185) | 0.0387 (0.0118) | 0.0332 (0.0166) |
| $T_{1/2z}$ (hr) | 11.0 (1.4) | 13.0 (1.9) | 15.9 (2.1) | 15.0 (3.6) |

| PK Parameters[a] mean (SD) | GROUP ASSIGNMENTS USING ACTUAL BODY WEIGHT | | | |
|---|---|---|---|---|
| | Normal N = 13 | Mild N = 10 | Moderate N = 8 | Severe N = 1 |
| $AUC_{0-t}$ (µg · hr/mL) | 0.549 (0.129) | 0.513 (0.164) | 0.497 (0.186) | 0.461 (NA) |
| $AUC_{0-inf}$ (µg · hr/mL) | 0.569 (0.132) | 0.535 (0.165) | 0.516 (0.191) | 0.478 (NA) |
| % $AUC_{0-inf}$ Extrapolated | 3.57 (1.31) | 4.54 (2.49) | 3.74 (1.16) | 3.70 (NA) |
| $C_{max}$ (ng/mL) | 36.0 (8.0) | 30.2 (10.4) | 27.6 (11.6) | 16.4 (NA) |
| $t_{max}$ (hr)[a] | 2.0 (1.00-8.00) | 2.5 (1.00-3.00) | 2.5 (1.00-4.00) | 4.0 (4.00-4.00) |
| Cl/F (L/hr) | 15.6 (3.7) | 17.3 (5.9) | 18.9 (8.4) | 17.6 (NA) |
| $Cl_R$/F (L/hr) | 0.468 (0.291) | 0.617 (0.275) | 0.663 (0.340) | 0.436 (NA) |
| $Cl_{NR}$/F (L/hr) | 15.1 (3.7) | 16.7 (5.7) | 18.2 (8.2) | 17.2 (NA) |
| Vz/F (L) | 266 (51) | 361 (130) | 381 (116) | 479 (NA) |
| $MRT_{inf}$ (hr) | 16.5 (3.3) | 19.3 (3.5) | 20.8 (4.4) | 30.8 (NA) |
| $Ae_{0-120}$ (µg) | 257 (152) | 297 (100) | 304 (142) | 204 (NA) |
| $fe_{0-120}$ | 0.0304 (0.0180) | 0.0352 (0.0118) | 0.0360 (0.0168) | 0.0242 (NA) |
| $T_{1/2z}$ (hr) | 12.1 (2.0) | 14.6 (2.7) | 14.9 (3.3) | 18.8 (NA) |

[a]Median (minimum-maximum)
Source: APD356-016 CSR: Tables 14.2.1.2.1, 14.2.1.2.2, 14.2.1.2.3, 14.2.1.2.4, 14.2.1.2.5, 14.2.1.2.6
$AUC_{0-t}$—area under the plasma concentration -time curve from time zero to time t
$t_{max}$—time to reach maximum plasma concentration
Cl/F—apparent clearance
$Cl_R$/f—apparent renal clearance
$Cl_{NR}$/F—apparent non-renal clearance
Vz/F—apparent volume of distribution
$MRT_{inf}$—mean residence time to infinity
$Ae_{0-120}$—amount excreted in the urine over 120 hours post dosing
$Fe_{0-120}$—fraction excreted in the urine over 120 hours post dosing
$T_{1/2z}$—elimination half-life Example 3

M1

In contrast to the parent compound lorcaserin, the pharmacologically inactive major circulating metabolite M1 (lorcascrin sulfamate) was significantly affected by renal impairment. Although M1 is a minor metabolite in urine, plasma exposure was increased in subjects with renal impairment (Table 4, FIGS. 1C, 1D). $AUC_{0-inf}$ of M1, but not $C_{max}$, was negatively correlated with creatinine clearance (Table 5). M1 was not removed by hemodialysis.

Similar results were obtained whether creatinine clearance was calculated using ideal body weight (as was done in the APD356-016 Clinical Study Report), or actual body weight (which can overestimate creatinine clearance, since creatinine is not produced by adipose tissue).

The highest mean M1 exposure ($AUC_{0-inf}$=23.6) was observed in the severe renal impairment group (Table 4). This relatively high value was largely driven by a single subject, 3285-009, who had an $AUC_{0-inf}$ value of 101 µg·hr/mL and a $C_{max}$ of 542 ng/mL. This subject's calculated creatinine clearance was 28.3 mL/min using ideal body weight, or 37.9 mL/min using actual body weight. As a result, when the study data were reanalyzed using group assignments according to actual body weight, subject 3285-009 was assigned to the moderate renal impairment group, driving the mean exposure higher in that group.

TABLE 4

Mean M1 Plasma and Urine Pharmacokinetic Parameters after a 10 mg Oral Dose of Lorcaserin

| PK Parameters[a] mean (SD) | GROUP ASSIGNMENTS USING IDEAL BODY WEIGHT | | | |
|---|---|---|---|---|
| | Normal N = 8 | Mild N = 8 | Moderate N = 8 | Severe N = 8 |
| $AUC_{0-t}$ (μg·hr/mL) | 0.482 (0.101) | 0.623 (0.088) | 0.515 (0.190) | 0.469 (0.172) |
| $AUC_{0-inf}$ (μg·hr/mL) | 0.501 (0.104) | 0.644 (0.089) | 0.538 (0.190) | 0.486 (0.179) |
| % $AUC_{0-inf}$ Extrapolated | 3.81 (1.57) | 3.36 (0.87) | 4.92 (2.68) | 3.59 (1.01) |
| $C_{max}$ (ng/mL) | 37.0 (8.7) | 36.3 (8.0) | 26.2 (8.3) | 26.4 (11.7) |
| $t_{max}$ (hr)[a] | 2.00 (1.00-3.00) | 4.50 (1.00-8.00) | 2.50 (2.00-3.00) | 3.00 (1.00-4.00) |
| Cl/F (L/hr) | 17.5 (3.4) | 13.3 (1.8) | 17.7 (6.6) | 19.7 (8.0) |
| $Cl_R$/F (L/hr) | 0.392 (0.202) | 0.533 (0.322) | 0.667 (0.228) | 0.657 (0.373) |
| $Cl_{NR}$/F (L/hr) | 17.1 (3.3) | 12.8 (1.6) | 17.0 (6.5) | 19.0 (7.8) |
| Vz/F (L) | 276 (53) | 248 (40) | 399 (132) | 401 (103) |
| $MRT_{inf}$ (hr) | 14.8 (2.2) | 18.0 (3.0) | 21.1 (2.8) | 21.7 (5.7) |
| $Ae_{0-120}$ (μg) | 185 (78) | 326 (156) | 327 (100) | 280 (140) |
| $fe_{0-120}$ | 0.0220 (0.0092) | 0.0386 (0.0185) | 0.0387 (0.0118) | 0.0332 (0.0166) |
| $T_{1/2z}$ (hr) | 11.0 (1.4) | 13.0 (1.9) | 15.9 (2.1) | 15.0 (3.6) |

| PK Parameters[a] mean (SD) | GROUP ASSIGNMENTS USING ACTUAL BODY WEIGHT | | | |
|---|---|---|---|---|
| | Normal N = 13 | Mild N = 10 | Moderate N = 8 | Severe N = 1 |
| $AUC_{0-t}$ (μg·hr/mL) | 0.549 (0.129) | 0.513 (0.164) | 0.497 (0.186) | 0.461 (NA) |
| $AUC_{0-inf}$ (μg·hr/mL) | 0.569 (0.132) | 0.535 (0.165) | 0.516 (0.191) | 0.478 (NA) |
| % $AUC_{0-inf}$ Extrapolated | 3.57 (1.31) | 4.54 (2.49) | 3.74 (1.16) | 3.70 (NA) |
| $C_{max}$ (ng/mL) | 36.0 (8.0) | 30.2 (10.4) | 27.6 (11.6) | 16.4 (NA) |
| $t_{max}$ (hr)[a] | 2.0 (1.00-8.00) | 2.5 (1.00-3.00) | 2.5 (1.00-4.00) | 4.0 (4.00-4.00) |
| Cl/F (L/hr) | 15.6 (3.7) | 17.3 (5.9) | 18.9 (8.4) | 17.6 (NA) |
| $Cl_R$/F (L/hr) | 0.468 (0.291) | 0.617 (0.275) | 0.663 (0.340) | 0.436 (NA) |
| $Cl_{NR}$/F (L/hr) | 15.1 (3.7) | 16.7 (5.7) | 18.2 (8.2) | 17.2 (NA) |
| Vz/F (L) | 266 (51) | 361 (130) | 381 (116) | 479 (NA) |
| $MRT_{inf}$ (hr) | 16.5 (3.3) | 19.3 (3.5) | 20.8 (4.4) | 30.8 (NA) |
| $Ae_{0-120}$ (μg) | 257 (152) | 297 (100) | 304 (142) | 204 (NA) |
| $fe_{0-120}$ | 0.0304 (0.0180) | 0.0352 (0.0118) | 0.0360 (0.0168) | 0.0242 (NA) |
| $T_{1/2z}$ (hr) | 12.1 (2.0) | 14.6 (2.7) | 14.9 (3.3) | 18.8 (NA) | b Median (minimum-maximum)
Source: APD356-016 CSR: Tables 14.2.1.2.1, 14.2.1.2.2, 14.2.1.2.3, 14.2.1.2.4, 14.2.1.2.5, 14.2.1.2.6

M1 exposure ($AUC_{0-inf}$) was significantly inversely correlated with creatinine clearance; $C_{max}$ was not correlated with creatinine clearance (Table 5, FIG. 4).

TABLE 5

Correlation Analysis: M1 Exposure as a Function of Creatinine Clearance

| Parameter | CrCl Calculated with Ideal BW | | CrCl Calculated with Actual BW | |
|---|---|---|---|---|
| | AUCinf | $C_{max}$ | AUCinf | $C_{max}$ |
| N | 32 | 32 | 32 | 32 |
| Spearman r | −0.8076 | −0.2051 | −0.7716 | −0.2282 |
| 95% CI | −0.9042 to −0.6322 | −0.5248 to 0.1652 | −0.8852 to −0.5714 | −0.5421 to 0.1416 |
| P value (two-tailed) | <0.0001 | 0.2601 | <0.0001 | 0.2090 |

Source: APD356-016 CSR, Tables 14.2.2.2.1. 14.2.2.2.2, 14.2.2.2.3, and 14.2.2.2.4; Listing 16.2.4; non-parametric (Spearman) correlation analysis generated using GraphPad Prism version 5.01 for Windows, GraphPad Software, San Diego California USA
Spearman r—Spearman's rank correlation coefficient
CI—confidence interval To better assess the potential implications of M1 levels in subjects with renal impairment, steady state M1 exposure following lorcaserin 10 mg BID administration was modeled using simulations and noncompartmental analysis based upon data from pharmacokinetic studies with once daily (QD) dosing. This modeling is discussed below in Example 5.

Example 4

M5

Figure 5:
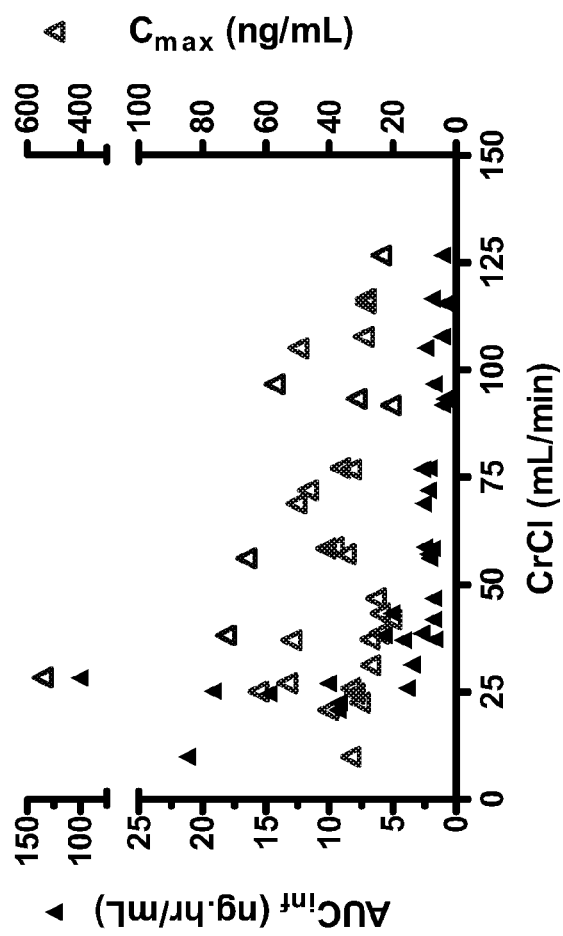
FIG. 5 shows M5 exposure as a function of creatinine clearance.

Plasma exposure of M5 (N-carbamoyl glucuronide of lorcaserin), the major urinary metabolite, was increased with increasing renal impairment. The fractional excretion of M5 ranged from 35% in severe renal impairment to 48% in normal renal function. Plasma exposure of M5 increased with decreasing creatinine clearance (FIG. 5, Table 6). M5 $AUC_{0-inf}$ but not $C_{max}$, was significantly correlated with creatinine clearance (Table 7). M5 was partially removed by hemodialysis, with an extraction ratio of 18.4%.

TABLE 6

Mean M5 Plasma and Urine Pharmacokinetic Parameters after a 10 mg Oral Dose of Lorcaserin

| Pharmacokinetic Parameters Mean (SD) | Mean Pharmacokinetic Parameters for M5 | | | | | |
|---|---|---|---|---|---|---|
| | Normal | Mild | Moderate | Severe | ESRD (Period 1) | ESRD (Period 2) |
| Group Assignments using IDEAL Body Weight | | | | | | |
| | N = 8 | N = 8 | N = 8 | N = 8 | N = 8 | N = 8 |
| $AUC_{0-t}$ (μg·hr/mL) | 0.345 (0.111) | 0.482 (0.136) | 0.944 (0.343) | 2.29 (1.70) | 9.53 (4.94) | 8.24 (4.02) |
| $AUC_{0-inf}$ (μg·hr/mL) | 0.475 (0.155) | 0.583 (0.146) | 1.10 (0.31) | 2.47 (1.72) | 11.2 (5.6) | 11.9 (6.0) |
| % AUC Extrapolated | 26.3 (51.6) | 17.7 (5.1) | 15.6 (10.7) | 8.46 (5.01) | 14.7 (7.3) | 26.9 (15.4) |
| $C_{max}$ (ng/mL) | 70.5 (22.3) | 62.4 (10.7) | 96.4 (23.7) | 153 (57) | 300 (139) | 231 (93) |
| $MRT_{inf}$ (hr) | 14.6 (10.9) | 13.5 (3.0) | 18.5 (4.6) | 20.0 (7.5) | 38.6 (9.5) | 59.1 (27.5) |
| $t_{max}$ (hr)$^a$ | 1.00 (1.00-2.00) | 2.00 (1.00-3.00) | 2.00 (1.00-3.00) | 2.50 (2.00-4.00) | 3.00 (2.00-6.00) | 3.10 (2.10-6.00) |
| $t_{1/2z}$ (hr) | 12.2 (9.3) | 10.7 (2.6) | 15.4 (4.8) | 14.9 (5.5) | 25.7 (7.2) | 40.5 (20.2) |
| Ae (μg) | 8540 (1722) | 7160 (1375) | 8000 (1975) | 6300 (1249) | NA | NA |
| $Fe_{0-120}$ | 0.476 (0.096) | 0.399 (0.077) | 0.446 (0.110) | 0.351 (0.070) | NA | NA |
| Group Assignments using ACTUAL Body Weight | | | | | | |
| | N = 13 | N = 10 | N = 8 | N = 1 | N = 8 | N = 8 |
| $AUC_{last}$ (μg·hr/mL) | 0.381 (0.104) | 0.914 (0.421) | 1.51 (0.676) | 6.31 | 9.53 (4.94) | 8.24 (4.02) |
| $AUC_{0-inf}$ (μg·hr/mL) | 0.498 (0.126) | 1.04 (0.407) | 1.70 (0.71) | 6.48 | 11.2 (5.6) | 11.9 (6.0) |
| % AUC Extrapolated | 23.1 (11.5) | 14.5 (9.8) | 12.1 (6.7) | 2.59 | 14.7 (7.3) | 26.9 (15.4) |
| $C_{max}$ (ng/mL) | 66.2 (19.3) | 91.9 (27.4) | 134 (57.5) | 214 | 300 (139) | 231 (93) |
| $MRT_{inf}$ (hr) | 14.2 (8.5) | 16.6 (5.1) | 18.5 (5.3) | 33.4 | 38.6 (9.5) | 59.1 (27.5) |
| $t_{max}$ (hr)$^a$ | 2 (1-3) | 2 (1-3) | 2 (2-4) | 4 | 3.00 (2.00-6.00) | 3.10 (2.10-6.00) |
| $t_{1/2z}$ (hr) | 11.7 (7.2) | 13.5 (5.2) | 14.4 (4.5) | 23.1 | 25.7 (7.2) | 40.5 (20.2) |
| Ae (μg) | 8210 (1391) | 7470 (2100) | 6480 (1554) | 6720 | NA | NA |
| $Fe_{0-120}$ | 0.458 (0.078) | 0.417 (0.117) | 0.361 (0.087) | 0.375 | NA | NA |

NA: Not applicable
c Median (minimum-maximum)
Source: APD356-016 CSR: Table 14.2.3.2.1, 14.2.3.2.2, 14.2.3.2.3, 14.2.3.2.4, 14.2.3.2.5, 14..2.3.2.6

TABLE 7

Correlation Analysis: M5 Clearance as a Function of Creatinine Clearance

| | CrCl Calculated with Ideal BW | | CrCl Calculated with Actual BW | |
|---|---|---|---|---|
| Parameter | $AUC_{inf}$ | $C_{max}$ | $AUC_{inf}$ | $C_{max}$ |
| N | 32 | 32 | 32 | 32 |
| Spearman r | −0.8076 | −0.2051 | −0.7716 | −0.2282 |
| 95% CI | −0.9042 to −0.6322 | −0.5248 to 0.1652 | −0.8852 to −0.5714 | −0.5421 to 0.1416 |
| P value (two-tailed) | <0.0001 | 0.2601 | <0.0001 | 0.2090 |

Abbreviations: CrCl = Creatinine clearance, BW = body weight
APD356-016 CSR, Tables 14.2.3.2.1. 14.2.3.2.2, 14.2.3.2.3, and 14.2.3.2.4; Listing 16.2.4; non-parametric (Spearman) correlation analysis generated using GraphPad Prism version 5.01 for Windows, GraphPad Software, San Diego California USA

Example 5

Discussion of M1 and M5 Exposure in Renal Impairment

M1 and M5 exposures increased in patients with moderate to severe renal impairment; lorcaserin did not. To better assess the potential implications of M1 and M5 levels, steady state exposures following lorcaserin 10 mg BID dosing were modeled using simulations and noncompartmental analysis based upon data from pharmacokinetic studies with once daily (QD) dosing. (PDR-09-151; Table 8). The predicted M1 $C_{max}$ values in subjects with normal and mild renal impairment are 130 ng/ml and 207 ng/ml, respectively, which are consistent with the mean M1 $C_{max}$ levels of 196 ng/mL observed in patients at Week 12 following lorcaserin 10 mg BID in APD356-009 study (APD356-009 CSR, Table 14.3.164). Based on the modeled values, subjects with moderate renal impairment are expected to achieve M1 $C_{max}$ levels of 414 ng/mL, while those with severe impairment will reach 1090 ng/mL. Total daily exposures ($AUC_{24}$) are predicted to be 9670 and 25,500 hr·ng/mL in moderate and severe renal impairment, respectively.

M1 exposures achieved in preclinical toxicology studies were well above the exposures observed in the APD356-016 clinical study (mean $AUC_{0-inf}$=23.6 μg·hr/mL in the severe renal impairment group; Table 9), or the modeled steady state exposures (Table 8). In monkeys dosed with 2 mg/kg/day lorcaserin (the no observable adverse event level (NOAEL)) for 52 weeks, the M1 $AUC_{0-inf}$ values of 41 and 62 μg·hr/mL (female and male) are 1.6-2.4 times the predicted daily exposure in a person with severe renal impairment. At the 10 mg/kg/day dose, the $AUC_{0-inf}$ exposure margin is about 12 fold. $C_{max}$ values of 4.58 and 5.01 μg/mL (females and males) are approximately 5 times the predicted $C_{max}$ in a person with severe renal impairment who takes lorcaserin 10 mg BID to steady state. At a dose of 10 mg/kg day in the monkey, the $C_{max}$ margin is approximately 20-25 times the predicted exposure in a person with severe renal impairment.

Predicted M5 exposure in a person with severe renal impairment is also well below the exposures in monkeys at the NOAEL. The predicted $C_{max}$ of 223 ng/mL in the human with severe renal impairment is 2.8-3.5 times less than the $C_{max}$ in monkeys at the NOAEL of 2 mg/kg/day. Exposure ($AUC_{0-inf}$) in monkeys at 2 mg/kg/day is approximately half the predicted daily exposure in severe renal impairment, and approximately equal to that in moderate renal impairment. At a dose of 10 mg/kg/day in monkeys, the exposure exceeds the predicted daily exposure in severe renal impairment by 1.5-3.2 times, and exceeds that predicted for moderate renal impairment by 3.0-6.3 times (Table 10).

TABLE 8

Modeled and Measured PK Parameters for Lorcaserin, M1, and M5 Following 10 mg BID Dosing

| Renal Function | Dose Regimen | Duration | Lorcaserin[a] | | | M1[b] | | | M5[c] | | |
|---|---|---|---|---|---|---|---|---|---|---|---|
| | | | $t_{1/2}$ (hr) | $C_{max}$ (ng/mL) | $AUC_{24\ hr}$ (hr · ng/mL) | $t_{1/2}$ (hr) | $C_{max}$ (ng/mL) | $AUC_{24\ hr}$ (hr · ng/mL) | $t_{1/2}$ (hr) | $C_{max}$ (ng/mL) | $AUC_{24\ hr}$ (hr · ng/mL) |
| Normal | QD Authentic | Day 1 | 11.0 | 37.0 | 482 | 36.2 | 33.6 | 1270 | 12.2 | 70.5 | 345 |
| | BID Simulation[d] | Steady State | 8.28 | 55.8 | 942 | 30.0 | 130 | 2790 | 6.11 | 77.3 | 765 |
| Mild | QD Authentic | Day 1 | 13.0 | 36.3 | 623 | 45.5 | 43.5 | 1940 | 10.7 | 62.4 | 482 |
| | BID Simulation | Steady State | 12.0 | 64.1 | 1270 | 34.6 | 207 | 4620 | 5.41 | 78.1 | 1090 |
| Moderate | QD Authentic | Day 1 | 15.9 | 26.2 | 515 | 70.8 | 34.1 | 2240 | 15.4 | 96.4 | 944 |
| | BID Simulation | Steady State | 11.5 | 49.5 | 935 | 109 | 414 | 9670 | 9.83 | 141 | 2150 |
| Severe | QD Authentic | Day 1 | 15.0 | 26.4 | 469 | 220 | 103 | 7850 | 14.9 | 153 | 2290 |
| | BID Simulation | Steady State | 12.8 | 40.9 | 835 | 99.2 | 1090 | 25500 | 11.0 | 223 | 4260 |
| ESRD | QD Authentic | Day 1 | 43.8 | 27.2 | 618 | UD | 67.6 | 3650 | 25.7 | 300 | 9530 |
| | BID Simulation | Steady State | 24.8 | 87.6 | 1860 | UD | — | — | 22.9 | 936 | 20100 |

Abbreviations: QD = once a day, BID = twice a day, ESRD = end stage renal disease

[d] 10 mg QD Authentic lorcaserin mean values were determined from the individual plasma concentration versus time profiles: source: APD356-016 CSR: Tables 14.2.1.2.1, 14.2.1.2.2, 14.2.1.2.3, 14.2.1.2.4, 14.2.1.2.5 e 10 mg QD Authentic M1 mean values were determined from the individual plasma concentration versus time profiles: source: APD356-016 CSR: Tables 14.2.2.2.1, 14.2.2.2.2, 14.2.2.2.3, 14.2.2.2.4, 14.2.2.2.5 f 10 mg QD Authentic M5 mean values were determined from the individual plasma concentration versus time profiles: source: APD356-016 CSR: Tables 14.2.3.2.1, 14.2.3.2.2, 14.2.3.2.3, 14.2.3.2.4, 14.2.3.2.5 g 10 mg lorcaserin BID Simulation steady state values were determined from Day 1 mean plasma concentration versus time profiles: simulation parameters are described in PDR-09-151

TABLE 9

M1 Pharmacokinetics after Oral Administration of Lorcaserin: Preclinical Toxicology

| Species | Duration | Dose (mg/kg/day) | $t_{max}$ (hr) | | $C_{max}$ (μg/mL) | | $AUC_{last}$ (μg · hr/mL) | | $AUC_{0-inf}$ (μg · hr/mL) | |
|---|---|---|---|---|---|---|---|---|---|---|
| | | | M | F | M | F | M | F | M | F |
| Mice | 52 wk | 5 | 0.5 | 0.5 | 10.8 | 14.4 | 59.7 | 74.4 | 61.2 | 75.2 |
| | | 25 | 0.5 | 0.5 | 25.4 | 39.8 | 223 | 217 | UD | 221 |
| | | 50 | 0.5 | 0.5 | 42.7 | 49.1 | 308 | 345 | 319 | 356 |
| Rats | 52 wk | 10 | 1.0 | 1.0 | 15.4 | 16.3 | 170 | 193 | 175 | 200 |
| | | 30 | 1.0 | 4.0 | 23.9 | 31.7 | 319 | 412 | 338 | 443 |
| | | 100 | 0.5 | 2.0 | 36.0 | 63.7 | 633 | 1050 | 927 | 1480 |
| Monkeys | 52 wk | 2[g] | 3.0 ± 1.2 | 1.5 ± 0.6 | 5.01 ± 2.16 | 4.58 ± 1.70 | 56.4 ± 14.3 | 39.3 ± 1.8 | 61.6 ± 15.4 | 40.9 ± 1.6 |
| | | 10 | 3.3 ± 1.5 | 2.5 ± 1.0 | 22.0 ± 7.6 | 27.5 ± 6.6 | 276 ± 74 | 269 ± 40 | 312 ± 79 | 307 ± 66 |
| | | 50 | 4.7 ± 1.6 | 5.2 ± 2.4 | 62.3 ± 14.1 | 56.3 ± 13.4 | 904 ± 228 | 771 ± 182 | 1060 ± 313 | 877 ± 221 |
| | | 125 | 3.7 ± 2.3 | 3.5 ± 2.5 | 106 ± 31 | 115 ± 24 | 1460 ± 269 | 1580 ± 501 | 2020 ± 856 | 1910 ± 865 |

UD, undefined terminal phase

Source: 2.6.4, Pharmacokinetics Written Summary, Table 16

M5 is pharmacologically inactive at all receptors, transporters and ion channels tested to date. The highest individual overall exposure in a subject not on hemodialysis was observed in subject 3140-010 (creatinine clearance 9.9 mL/min), with $AUC_{0-inf}$ of 6.48 µg·hr/mL. The highest exposure overall was observed in a subject with ESRD on hemodialysis, whose $AUC_{0-inf}$ was 20.8 µg·hr/mL. The highest observed $C_{max}$ in the clinical study was 520 ng/mL in a subject with ESRD (subject #3140-505). Consistent with the absence of detectable M5 pharmacological activity, neither of these subjects reported any adverse events. Similarly, M1 is pharmacologically inactive when tested at a concentration of 10 µM against a panel of receptors, ion channels and transporters.

TABLE 10

M5 Pharmacokinetics after Oral Administration of Lorcaserin: Preclinical Toxicology

| Species | Duration | Dose (mg/kg/day) | $t_{max}$ (hr) M | $t_{max}$ (hr) F | $C_{max}$ (µg/mL) M | $C_{max}$ (µg/mL) F | $AUC_{last}$ (µg·hr/mL) M | $AUC_{last}$ (µg·hr/mL) F | $AUC_{0-inf}$ (µg·hr/mL) M | $AUC_{0-inf}$ (µg·hr/mL) F |
|---|---|---|---|---|---|---|---|---|---|---|
| Mice | 52 weeks | 5 | 0.5 | 0.5 | 0.0983 | 0.100 | 0.134 | 0.184 | 0.178 | 0.201 |
|  |  | 25 | 0.5 | 0.5 | 0.590 | 0.431 | 1.84 | 1.21 | UD | UD |
|  |  | 50 | 0.5 | 0.5 | 1.00 | 0.824 | 3.42 | 3.23 | 3.47 | 3.26 |
| Rats | 52 weeks | 10 | 1.0 | 0.5 | 0.178 | 0.0538 | 0.550 | 0.273 | 0.602 | 0.349 |
|  |  | 30 | 0.5 | 1.0 | 0.559 | 0.337 | 3.07 | 1.62 | 3.1 | 1.96 |
|  |  | 100 | 0.5 | 2.0 | 2.03 | 1.20 | 14.9 | 11.1 | 16.5 | 12.8 |
| Monkeys | 52 weeks | 2 | 0.8 ± 0.3 | 0.5 ± 0.0 | 0.635 ± 0.310 | 0.771 ± 0.104 | 1.82 ± 0.57 | 1.76 ± 0.83 | 2.38 ± 0.29 | 2.13 ± 0.82 |
|  |  | 10 | 1.8 ± 0.5 | 1.0 ± 0.7 | 2.48 ± 1.14 | 1.67 ± 0..63 | 12.5 ± 6.1 | 6.14 ± 1.71 | 13.6 ± 5.0 | 6.52 ± 1.52 |
|  |  | 50 | 2.3 ± 1.9 | 3.2 ± 1.8 | 7.04 ± 2.05 | 3.60 ± 0.62 | 69.0 ± 25.8 | 38.7 ± 12.7 | 71.4 ± 26.6 | 40.4 ± 13.4 |
|  |  | 125 | 2.2 ± 1.9 | 2.7 ± 2.0 | 15.8 ± 3.7 | 19.7 ± 13.5 | 170 ± 64 | 134 ± 78 | 182 ± 77 | 140 ± 78 |

UD, undefined terminal phase
Source: 2.6.4, Pharmacokinetics Written Summary, Table 17

Given the predicted level of M1 and M5 in patients with severe renal impairment (creatinine clearance≤30 mL/min), including end stage renal disease on hemodialysis, lorcascrin should not be used in these patients pending further study. Lorcaserin should be used with caution in patients with moderate renal impairment, defined as creatinine clearance 30-50 mL/min.

Example 6

Adverse Events (AEs) in the Renal Impairment Clinical Study

The incidence of adverse events was not related to severity of renal impairment. Events considered possibly or probably related to lorcaserin included 1 event each of abdominal pain (moderate group), diarrhea (moderate group), dyspepsia (mild group), stomach discomfort (mild group), and worsening renal impairment (moderate group). Two events of dizziness (I in severe group, one in ESRD group) and 3 events of headache (2 normal, 1 moderate group) were considered possibly/probably related to study drug. A summary of the Treatment Emergent Adverse Events in the APD356-016 study by renal impairment groups and relationship to study drug are listed in Table 11.

TABLE 11

Summary of Treatment Emergent AEs in Clinical Study APD356-016 by Renal Impairment Group

|  | Normal (N = 8) | Mild (N = 8) | Moderate (N = 8) | Severe (N = 8) | End Stage (N = 8) |
|---|---|---|---|---|---|
| Number (%) of Subjects Reporting AEs | 4 (50.0%) | 2 (25.0%) | 5 (62.5%) | 3 (37.5%) | 1 (12.5%) |
| Number of AEs Reported[a] | 4 | 3 | 9 | 4 | 1 |
| Number (%) of Subjects Reporting AEs By Maximum Intensity[b] |  |  |  |  |  |
| Mild | 4 (50.0%) | 2 (25.0%) | 4 (50.0%) | 3 (37.5%) | 1 (12.5%) |
| Moderate | 0 (0.0%) | 0 (0.0%) | 1 (12.5%) | 0 (0.0%) | 0 (0.0%) |
| Severe | 0 (0.0%) | 0 (0.0%) | 0 (0.0%) | 0 (0.0%) | 0 (0.0%) |

TABLE 11-continued

Summary of Treatment Emergent AEs in Clinical
Study APD356-016 by Renal Impairment Group

|  | Normal (N = 8) | Mild (N = 8) | Moderate (N = 8) | Severe (N = 8) | End Stage (N = 8) |
|---|---|---|---|---|---|
| Number (%) of Subjects Reporting AEs By Most Direct Relationship to Study Treatment[b] | | | | | |
| Probable | 1 (12.5%) | 1 (12.5%) | 0 (0.0%) | 0 (0.0%) | 0 (0.0%) |
| Possible | 1 (12.5%) | 1 (12.5%) | 3 (37.5%) | 1 (12.5%) | 0 (0.0%) |
| Unlikely | 2 (25.0%) | 0 (0.0%) | 1 (12.5%) | 2 (25.0%) | 0 (0.0%) |
| Not Related | 0 (0.0%) | 0 (0.0%) | 1 (12.5%) | 0 (0.0%) | 1 (12.5%) |

[a]In counting the number of adverse events reported, an adverse event was defined as an event with a unique subject identification number, System Organ Class and preferred term.
[b]Subjects reporting one or more adverse events are counted once at the maximum intensity and most direct relationship of all adverse events.
Source: APD356-016 CSR, Table 14.3.1

No clear trends in vital signs, laboratory values, or ECG attributable to lorcaserin were noted in the renal impairment study.

Example 7

Analysis of Renal Impairment in Phase 2 and Pooled Phase 3 Clinical Trials

No patient in the APD356-004 phase 2b study had a creatinine greater than 1.3 mg/dL at any time during the trial, and no patient in the APD356-003 study had a creatinine higher than 1.5. Hence, the discussion of adverse events observed in patients with renal impairment is restricted to the pooled phase 3 trials.

Few patients in the APD356-009 trial developed creatinine values above or creatinine clearance values below normal (Table 12). At study entry, no patient had creatinine clearance less than 30 mL/min, and only 4 (1 randomized to lorcaserin, 3 to placebo) had values below 40 mL/min based on ideal body weight. In the APD356-011 study, 2 patients (1 placebo, 1 lorcaserin BID) had a creatinine clearance less than 30 mL/min (based on ideal body weight) at randomization. Given the small number of patients with moderate or greater renal impairment in the phase 3 studies, a meaningful evaluation of the relationship between adverse events and renal impairment is not possible. Lorcaserin did not, however, appear to affect renal function. Creatinine clearance at last measurement did not differ meaningfully among treatment groups (Table 12). Table 12. Summary of Creatinine and Creatinine Clearance Outside Predefined Limits during 52 Weeks in Pooled Phase 3 Studies

TABLE 12

Summary of Creatinine and Creatinine Clearance Outside Predefined Limits during 52 Weeks in Pooled Phase 3 Studies

| Laboratory Parameter | Limits of Change | Treatment Group | n/N[a] (%) |
|---|---|---|---|
| Creatinine | >Baseline or >ULN | Pooled Placebo | 1572/2918 (53.9) |
|  |  | Lorcaserin 10 mg QD | 431/754 (57.2) |
|  |  | Lorcaserin 10 mg BID Pooled | 1589/2992 (53.1) |
|  |  | Any Lorcaserin Dose | 2020/3746 (53.9) |
| Creatinine | >1.5x Baseline or >1.5x ULN | Pooled Placebo | 16/2918 (0.5) |
|  |  | Lorcaserin 10 mg QD | 5/754 (0.7) |
|  |  | Lorcaserin 10 mg BID Pooled | 15/2992 (0.5) |
|  |  | Any Lorcaserin Dose | 20/3746 (0.5) |
| Creatinine | >3x Baseline or >3x ULN | Pooled Placebo | 2/2918 (<0.1) |
|  |  | Lorcaserin 10 mg QD | 0/754 (0.0) |
|  |  | Lorcaserin 10 mg BID Pooled | 1/2992 (<0.1) |
|  |  | Any Lorcaserin Dose | 1/3746 (<0.1) |

| | N | Treatment Group | Mean (SD) |
|---|---|---|---|
| Creatinine Clearance at Baseline (Ideal Body Weight) | 2918 | Pooled Placebo | 83.85 (20.143) |
|  | 754 | Lorcaserin 10 mg QD | 85.24 (20.812) |
|  | 2992 | Lorcaserin 10 mg BID Pooled | 83.96 (19.769) |
|  | 3746 | Any Lorcaserin Dose | 84.22 (19.987) |

| | N | Treatment Group | Mean (SEM) Change from Baseline |
|---|---|---|---|
| Creatinine Clearance at Last Observation (Ideal Body Weight) | 2918 | Pooled Placebo | −0.28 (0.186) |
|  | 754 | Lorcaserin 10 mg QD | −0.67 (0.391) |
|  | 2992 | Lorcaserin 10 mg BID Pooled | 0.47 (0.181) |
|  | 3746 | Any Lorcaserin Dose | 0.25 (0.165) |

Abbreviations: BL = baseline; LLN = lower limit of normal; ULN = upper limit of normal.
Note:
Ideal body weight is used for creatinine clearance calculation to avoid confounding effect of weight loss
c Number of patients with baseline and at least one post baseline tests.
Source: Statistical Report for the Integrated Summary of Safety, Table S12.1, S13.1 and S14.0

Lorcaserin exposure was not meaningfully affected by renal impairment. Neither renal nor total lorcaserin clearance was correlated with renal function (creatinine clearance). Metabolites M1 and M5 were also evaluated. Of note, neither metabolite is active at serotonin receptors or at a panel of more than 60 GPCRs, transporters and ion channels. Exposure of M1, indicated by $AUC_{0-inf}$, was correlated with renal function. M5 is the major urinary metabolite of lorcaserin; accordingly, exposure ($AUC_{0-inf}$) was significantly correlated with renal function. Based on clinical findings and the current guidance provided by the Federal Drug Agency, no lorcaserin dose adjustment should be needed in patients with mild or moderate renal impairment. Given the predicted level of M1 and M5 in patients with severe renal impairment (creatinine clearance≤30 mL/min), lorcaserin should be used with caution in patients with moderate renal impairment (creatinine clearance 30-50 mL/min) and should not be used in patients with severe renal impairment (creatinine clearance≤30 mL/min) or end stage renal disease requiring hemodialysis.

Example 8

Individual Variation in HSO3-APD356 Metabolite (M1) $C_{max}$ in Severe Renal Impairment Group The modeled steady state $C_{max}$ for metabolite M1 is 1090 ng/mL—this is essentially an estimated mean value. As shown in Table 13, actual M1 levels were variable, with $C_{max}$ values ranging from about 25 to about 540 ng/mL at 4 hours on day 1. Maximum individual $C_{max}$ was more than five times the mean $C_{max}$ for the subjects studied. Hence, one might predict that some individuals would reach level of more than 5000 ng/mL (5 μg/mL) at steady state. This is approximately the $C_{max}$ in monkeys given a 2 mg/kg dose (the NOAEL dose, see Table 9 above). This provides no margin between anticipated exposures and exposures that may produce toxicity. The FDA expects a reasonable margin between anticipated exposures and exposures that may produce toxicity. A reasonable margin can vary depending on the expected toxicity, but generally is an order of magnitude (10 times), but can sometimes be less for mild toxicity.

TABLE 13

Summary of Plasma Concentration (ng/mL) of HSO3-APD356 Metabolite over Time by Group: Severe Renal Impairment Not Receiving Dialysis

| Subject ID | Day 1 | | | | | | | | | | Day 2 | | Day 3 | Day 4 | Day 5 | Day 6 |
|---|---|---|---|---|---|---|---|---|---|---|---|---|---|---|---|---|
| | Predose | 0.5 h | 1 h | 2 h | 3 h | 4 h | 6 h | 8 h | 12 h | 16 h | 24 h | 36 h | 48 h | 72 h | 96 h | 120 h |
| 3140-002 | 0.00 | 12.2 | 31.4 | 53.2 | 55.6 | 55.1 | 46.5 | 50.4 | 52.2 | 18.0 | 62.4 | 52.2 | 54.2 | 46.2 | 43.8 | 40.1 |
| 3140-010 | 0.00 | 0.00 | 4.30 | 13.3 | 20.9 | 25.4 | 26.1 | 25.8 | 25.4 | 28.0 | 31.6 | 30.6 | 33.3 | 30.2 | 32.3 | 28.6 |
| 3285-001 | 0.00 | 0.00 | 7.19 | 23.9 | 28.5 | 32.8 | 33.3 | 29.8 | 29.5 | 30.6 | 32.0 | 28.4 | 25.8 | 19.7 | 15.1 | 12.3 |
| 3285-003 | 0.00 | 0.00 | 2.43 | 12.9 | 25.2 | 30.3 | 28.5 | 25.8 | 28.2 | 25.4 | 27.1 | 27.8 | 26.7 | 21.2 | 19.1 | 18.5 |
| 3285-009 | 0.00 | 182 | 319 | 489 | 468 | 542 | 445 | 473 | 439 | 410 | 406 | 336 | 292 | 248 | 225 | 212 |
| 3286-004 | 0.00 | 2.66 | 22.8 | 42.2 | 52.4 | 53.3 | 51.9 | 49.7 | 45.9 | 46.9 | 51.1 | 45.5 | 47.2 | 40.2 | 36.0 | 30.4 |
| 3286-007 | 9.00 | 8.54 | 18.0 | 25.1 | 26.5 | 28.2 | 32.2 | 27.8 | 27.2 | 28.1 | 33.0 | 40.4 | 34.3 | 33.0 | 30.2 | 26.3 |
| 3286-009 | 0.00 | 0.00 | 0.00 | 6.08 | 17.6 | 28.6 | 29.8 | 29.2 | 27.3 | 27.5 | 31.9 | 30.6 | 31.0 | 27.9 | 28.5 | 25.2 |
| N | 8 | 8 | 8 | 8 | 8 | 8 | 8 | 8 | 8 | 8 | 8 | 8 | 8 | 8 | 8 | 8 |
| Mean | 1.13 | 25.7 | 50.6 | 83.2 | 86.8 | 99.5 | 86.7 | 88.9 | 84.3 | 76.8 | 84.4 | 73.9 | 68.1 | 58.3 | 53.8 | 49.2 |
| SD | 3.18 | 63.3 | 109.0 | 164.7 | 154.7 | 179.2 | 145.1 | 155.5 | 143.6 | 134.9 | 130.5 | 106.3 | 91.0 | 77.2 | 69.8 | 66.3 |
| Median | 0.00 | 1.33 | 12.6 | 24.5 | 27.5 | 31.6 | 32.8 | 29.5 | 28.9 | 28.1 | 32.5 | 35.5 | 33.8 | 31.6 | 31.3 | 27.5 |
| Min | 0.00 | 0.00 | 0.00 | 6.08 | 17.6 | 25.4 | 26.1 | 25.8 | 25.4 | 18.0 | 27.1 | 27.8 | 25.8 | 19.7 | 15.1 | 12.3 |
| Max | 9.00 | 182 | 319 | 489 | 468 | 542 | 445 | 473 | 439 | 410 | 406 | 336 | 292 | 248 | 225 | 212 |
| CV (%) [a] | 283 | 247 | 215 | 198 | 178 | 180 | 167 | 175 | 170 | 176 | 155 | 144 | 134 | 132 | 130 | 135 |

[a] % CV = Standard Deviation/Mean * 100.

Example 9

Serum Creatinine and Cockcroft-Gault Equation Creatinine Clearance Values for Individual Subjects Two individuals have been noted above with significantly higher $C_{max}$ values for either metabolite M1 or M5 (see Table 14). Subject number 328-009 was grouped in the severe renal impairment group and had the highest observed $C_{max}$ levels for metabolite M1. Subject number 3140-505 was on dialysis and grouped in the end stage renal disease group. This subject had the highest observed $C_{max}$ for metabolite M5.

TABLE 14

Individual Subject Data

| Subject ID Number | Age | Gender | Race | Renal Impairment Group | Serum Creatinine (mg/dL) | Cockcroft-Gault Creatinine Clearance (mL/min) (IDEAL body weight) |
|---|---|---|---|---|---|---|
| 3140-005 | 73 | MALE | White or Caucasian | 2 | 1.2 | 54.8 |
| 3285-004 | 71 | MALE | White or Caucasian | 2 | 1.2 | 56.3 |
| 3285-002 | 78 | MALE | White or Caucasian | 2 | 0.9 | 57.9 |
| 3140-006 | 50 | FEMALE | Black or African American | 2 | 1 | 58.1 |

TABLE 14-continued

| | | | | | | Cockcroft-Gault Creatinine |
| | | | | Renal | Serum | Clearance |
| Subject | | | | Impairment | Creatinine | (mL/min) (IDEAL |
| ID Number | Age | Gender | Race | Group | (mg/dL) | body weight) |
|---|---|---|---|---|---|---|
| 3286-003 | 50 | FEMALE | Black or African American | 2 | 0.9 | 68 |
| 3286-011 | 55 | MALE | Asian | 2 | 1.1 | 70.9 |
| 3140-004 | 35 | MALE | Black or African American | 2 | 1.2 | 74.7 |
| 3285-005 | 59 | FEMALE | White or Caucasian | 2 | 0.7 | 76.5 |
| 3285-008 | 68 | MALE | White or Caucasian | 3 | 1.9 | 30.9 |
| 3286-010 | 60 | MALE | Black or African American | 3 | 2.5 | 36.5 |
| 3140-003 | 75 | MALE | White or Caucasian | 3 | 1.5 | 37 |
| 3286-008 | 73 | FEMALE | White or Caucasian | 3 | 1.1 | 37.7 |
| 3285-011 | 72 | MALE | White or Caucasian | 3 | 1.5 | 38.1 |
| 3286-006 | 42 | MALE | Black or African American | 3 | 2.8 | 42 |
| 3286-002 | 62 | MALE | White or Caucasian | 3 | 2 | 42.7 |
| 3140-001 | 71 | MALE | White or Caucasian | 3 | 1.5 | 46.6 |
| 3140-010 | 62 | MALE | White or Caucasian | 4 | 7.5 | 9.7 |
| 3286-007 | 52 | MALE | White or Caucasian | 4 | 3.6 | 20.5 |
| 3285-003 | 42 | MALE | White or Caucasian | 4 | 3.7 | 22.3 |
| 3286-009 | 61 | FEMALE | White or Caucasian | 4 | 2.5 | 24.2 |
| 3140-002 | 75 | FEMALE | White or Caucasian | 4 | 1.9 | 24.9 |
| 3285-001 | 75 | FEMALE | White or Caucasian | 4 | 1.6 | 25.6 |
| 3286-004 | 36 | MALE | Black or African American | 4 | 3.3 | 26.7 |
| 3285-009 | 50 | MALE | Black or African American | 4 | 3.8 | 28 |
| 3140-501 | 44 | MALE | Black or African American | 5 | 13.6 | 0 |
| 3140-502 | 49 | MALE | Black or African American | 5 | 5.2 | 0 |
| 3140-503 | 39 | MALE | Black or African American | 5 | 7.8 | 0 |
| 3140-504 | 46 | MALE | Black or African American | 5 | 8.7 | 0 |
| 3140-507 | 57 | MALE | Black or African American | 5 | 10.6 | 0 |
| 3140-508 | 56 | MALE | Hispanic or Latino | 5 | 11.6 | 0 |
| 3140-505 | 44 | MALE | Black or African American | 5 | 10.4 | 0 |
| 3140-506 | 46 | FEMALE | Black or African American | 5 | 11.4 | 0 |

TABLE 14-continued

Individual Subject Data

| Subject ID Number | Age | Gender | Race | Renal Impairment Group | Serum Creatinine (mg/dL) | Cockcroft-Gault Creatinine Clearance (mL/min) (IDEAL body weight) |
|---|---|---|---|---|---|---|
| 3286-001 | 41 | MALE | White or Caucasian | 1 | 1.1 | 90.5 |
| 3285-006 | 23 | FEMALE | White or Caucasian | 1 | 0.8 | 92.1 |
| 3140-007 | 33 | MALE | Black or African American | 1 | 1 | 95.1 |
| 3286-005 | 22 | MALE | Black or African American | 1 | 1.1 | 103.5 |
| 3285-007 | 19 | MALE | Hispanic or Latino | 1 | 1.1 | 106.3 |
| 3285-010 | 45 | MALE | Black or African American | 1 | 0.9 | 113.9 |
| 3140-008 | 21 | MALE | White or Caucasian | 1 | 1 | 114.9 |
| 3140-009 | 25 | MALE | Hispanic or Latino | 1 | 0.9 | 125.5 |

Renal Impairment Groups: Normal (1), Mild (2), Moderate (3), Severe (4), End stage renal disease on dialysis (5).

Example 10

Use of Lorcaserin in Renal Impairment Population

The disposition of lorcaserin was studied in patients with varying degrees of renal function. Impaired renal function has little or no influence on lorcaserin pharmacokinetics. However, exposure of metabolites M1 (lorcaserin sulfamate) and M5 (N-carbamoyl glucuronide lorcaserin) is significantly correlated with creatinine clearance (CLcr). Exposure (Geometric Mean Ratio for $AUC_{inf}$) of metabolite M1 was increased in patients with impaired renal function by 1.6-fold in mild (CLcr=51-80 mL/min), 2.3-fold in moderate (CLcr=31-50 mL/min) and 16.7-fold in severe renal impairment (CLcr=5-30 mL/min) compared to normal subjects (CLcr>80 mL/min). Exposure (Geometric Mean Ratio for $AUC_{inf}$) of metabolite M5 was increased in patients with impaired renal function by 1.2-fold in mild (CLcr=51-80 mL/min), 2.3-fold in moderate (CLcr=31-50 mL/min) and 5.2-fold in severe renal impairment (CLcr=5-30 mL/min) compared to normal subjects (CLcr>80 mL/min). The terminal half-life of M1 is prolonged by 26%, 96%, and 508% in mild, moderate, and severe renal impairment, respectively. The terminal half-life of M5 is prolonged by 0%, 26%, and 22% in mild, moderate, and severe renal impairment, respectively. The metabolites M1 and M5 accumulate in patients with severely impaired renal function on chronic administration. The pharmacologic response is not affected by renal function. Approximately 18% of metabolite M5 in the body was cleared from the body during a standard 4-hour hemodialysis procedure. Lorcaserin and M1 were not cleared by hemodialysis. Lorcaserin is not recommended for patients with severe renal impairment (i.e., CLcr≤30 mL/min).

Patients with severe renal impairment can be identified using the table below—do not use lorcaserin if the serum creatinine exceeds the patient-appropriate value in Table 15.

TABLE 15

Identification of individuals with severe renal impairment

| Age Range | Approximate Serum Creatine (mg/dL) | |
|---|---|---|
| | Men | Women |
| 18-20 | >4.9 | >3.5 |
| 21-30 | >4.5 | >3.2 |
| 31-40 | >4.1 | >2.9 |
| 41-50 | >3.7 | >2.7 |
| 51-60 | >3.3 | >2.4 |
| >60 | >3.0 | >2.0 |

Example 11

Determination of NOAEL Doses

In the mouse, seizures occurred at single doses of 100 and 300 mg/kg lorcaserin, and death followed single doses of 1000 and 2000 mg/kg. In repeat dose studies in mice, mortality occurred at doses ≥200 mg/kg. A dose of 250 mg/kg/day produced exposure multiples of 25 and 27 times (males and females) the exposure achieved in humans at a dose of 10 mg BID. At this dose, decreased red blood cell mass, increased reticulocytosis, increased liver weight, centrilobular hepatocellular hypertrophy, increased extramedullary hematopoeisis, and thymic necrosis occurred. The NOAEL in mice was 50 mg/kg/day, which produced exposure multiples of 7.6 and 2.3 (males and females) times the exposure in humans at 10 mg BID.

In rats, a single 1000 mg/kg dose caused death. In 10-day repeat dose studies, no mortality was observed at doses ≤150 mg/kg/day. The highest dose tested in 28-day studies, 50 mg/kg/day, was associated with increased serum lipids, centrilobular hepatocellular hypertrophy, splenic extramedullary hematopoiesis, increased pigmented macrophages, and reticulocytosis, and increased kidney weights, with minimal renal tubular epithelial hyperplasia in males only. A 13-week study and a 6-month study gave similar findings except there was no renal tubular epithelial changes and increases in kidney weights were limited to the 3-month study; the NOAEL was 5 mg/kg/day, which produced exposure multiples of 1.2 and 2.8 (males and females) relative to human exposure at a dose of 10 mg BID. At the highest dose given for 6 months, 50 mg/kg/day, some mortality was observed in addition to the previously observed findings, except there were no increases in kidney weights or other renal findings; exposure multiples were 22 and 34 (males and females) times human exposure at a dose of 10 mg BID.

In cynomolgus monkeys, dose-limiting emesis occurred at 300 mg/kg single dose. In repeat dose studies, the maximum tolerated dose was 100-125 mg/kg/day, and was associated with emesis, decreased activity, and penile extension. In a 28-day repeat dose study, one male given 100 mg/kg/day experienced a seizure. Exposure multiples of 74 and 68 (males and females) relative to human exposure at 10 mg BID were reached at a dose of 100 mg/kg/day. Reduced weight gain and food consumption occurred in 28-day, 13-week and 12-month studies at doses ≥10 mg/kg/day. Cholesterol, LDL and HDL decreased at ≥10 mg/kg/day in the 12-month study. Focal tubular epithelial cell degeneration and/or regeneration were observed in the kidneys in 0/8, 1/8, 2/8, 3/8, and 6/8 animals given 0, 2, 10, 50, and 125 mg/kg lorcaserin, respectively. Cystic ovarian follicles were observed in the ovaries of 0/4, 0/4, 1/4, 1/4, and 3/4 females given 0, 2, 10, 50 or 125 mg/kg lorcaserin, respectively; the finding was reversible. The NOAEL was considered to be 2 mg/kg/day.

In rats but not mice, modest increases in kidney weights were reported at high dose (≥50 mg/kg) in the 10-day, 28-day and 3-month studies, but were without microscopic correlate except in the 28-day study, in which minimal renal tubular epithelial hypertrophy was reported in male rats. In the one year toxicology study in monkeys, minimal to moderate focal tubular epithelial degeneration and/or regeneration were observed. The potential clinical relevance of this finding was evaluated in two ways. First, two pathologists with expertise in human renal pathology (Helmut Rennke, M.D. and Stephen Bonsib, M.D.) independently reviewed all monkey kidney slides from the 1-year study in a blinded manner. Both reported the findings to be mild and focal, clinically unimportant, without dose relationship, and more likely related to aging, infection, or inflammation than to study drug. Secondly, renal function was monitored in clinical trials not only by measuring creatinine and BUN, but also by examining urine sediment and by calculating creatinine clearance. The urine sediment data are of limited value due to the preponderance of "dirty" urine specimens contaminated with epithelial cells and other external debris. Neither BUN nor creatinine was affected by lorcaserin. Creatinine clearance, which was calculated using both actual body weight and the preferred ideal body weight method, was also not affected by lorcaserin use of up to 2 years.

Example 12

Toxicity Study in Monkeys

Lorcaserin doses of 0, 2, 10, 50, and 125 mg/kg in a 5 mL/kg dose volume were administered by nasogastric intubation once daily for 12 months to cynomolgus monkeys (4 to 6/sex/group). Two animals/sex from the control, 50 and 125 mg/kg groups were continued on study without further dosing for an additional 4 weeks prior to termination. For the first 91 days of the study, dose solutions were prepared using anhydrous lorcaserin. Starting on Day 92 and continuing for the remainder of the study, dose solutions were prepared using lorcascrin hemihydrate to match the intended commercial form. The theoretical presumption of bioequivalence of the two forms was confirmed in a pharmacokinetic study, and by similar exposures on Day 91 and 92 in this study. Evaluations included clinical signs, food consumption, BW, electrocardiograms, ophthalmic exams, and clinical pathology indices. Blood samples were collected for TK analysis on Day 1, Week 4, Day 91, Day 92, and Week 52. A full necropsy was conducted on all animals, and tissues were collected, preserved, processed, and examined microscopically. Additional sections of heart were collected to allow comprehensive evaluation of all heart valves. Heart histopathologic evaluation included atria, ventricles, interventricular septum, both AV valves (mitral and tricuspid), and the aortic and pulmonic valves.

There were no lorcascrin-related deaths in this study; however, two animals died prior to study completion, both of apparent dosing intubation accidents. A seizure was observed in a single high dose male 42 min after the first dose on Day 1. This animal continued treatment on Day 2 and no further seizures were observed throughout the duration of the study. A dose-dependent decrease in activity and hunched appearance were noted in both sexes at doses ≥10 mg/kg. In addition, there was an increase in the incidence of tremors (females only) and emesis in the high dose group and these did not occur during the recovery period. A dose-dependent decrease in food consumption was measured which resulted in decreased weight gain for some animals that was more pronounced in females. Mild reticulocytosis without accompanying reductions in red cell mass were observed at the 125 mg/kg dose. A reduction in serum lipids (cholesterol, HDL, and LDL) was measured in both sexes treated with ≥10 mg/kg doses of lorcaserin. Reductions in total cholesterol and LDL occurred in some animals treated with 2 mg/kg as well. There was a dose-independent reduction in the mean triglyceride concentration in both sexes at ≥2 mg/kg. Mild increases in ALT occurred primarily in females at all dose levels and in one control animal. White blood cells in the urine of some females dosed at ≥50 mg/kg/day were thought to be associated with renal tubular changes noted histologically in three out of five cases.

There were no lorcaserin-related gross findings. Histologic changes were identified in the kidneys, ovaries, and possibly in the liver. Changes in the kidney consisted of focal or multifocal tubular epithelial cell degeneration, regeneration, and cellular casts. Minimal to mild tubular epithelial degeneration was observed in 6 of 8 animals in the high dose group (125 mg/kg). Minimal to mild epithelial regeneration was observed in the renal cortex of 0/8, 1/8, 2/8, 3/8 and 6/8 animals given 0, 2, 10, 50, and 125 mg/kg lorcaserin, respectively, and moderate regeneration was found in 1 additional high dose animal (7/8 with regeneration in the 125 mg/kg group). Cellular casts were observed in 1/4 males at 50 mg/kg and 4/4 animals at 125 mg/kg. The histologic renal changes attributed to lorcaserin were not associated with changes in serum chemistry or kidney function. A review of the renal findings was conducted by two expert human renal pathologists, each of whom independently read blinded slides and reached the same conclusion: the administration of lorcaserin to monkeys for 12 months was not associated with drug-related renal pathology. In their opinions, renal histopathologic findings were mild and focal, showed no relationship to study drug administration and were most consistent with aging, infection, or inflammation rather than lorcascrin effects. One of these pathologists attributed the potential finding of regeneration to a staining artifact resulting in a bluish cytoplasmic discoloration. Cystic ovarian follicles were observed in the ovaries of 0/4, 0/4, 1/4, 1/4, and 3/4 females given 0, 2, 10, 50 or 125 mg/kg lorcaserin, respectively. This change was reversible after a one month drug-free interval. Hepatic lipidosis had an uncertain relationship to lorcaserin administration. It was generally of minimal to mild severity and was observed in 2/8, 4/8, 2/8, 3/8, and 4/8 animals given 0, 2, 10, 50 and 250 mg/kg/day of lorcaserin, respectively. Alanine aminotransferase levels between control and lorcaserin-treated monkeys were generally comparable, indicating an uncertain relationship between increased ALT levels and hepatic lipidosis. The lipidosis was not present in animals sacrificed after a one month drug-free interval. No changes were identified by the study pathologist or the peer review pathologist in the heart, heart valves, pulmonary vessels or lungs of animals given lorcaserin compared to controls.

Lorcaserin plasma exposure on Day 1 in male and female monkeys was dose linear from 2 to 125 mg/kg. Plasma exposure of M1 was less than dose proportional while exposure for M5 was more than dose proportional for both sexes. Lorcaserin, M1, and M5 plasma exposures did not vary with the change in lorcaserin salt form (i.e., anhydrous vs. hemihydrate). Repeat dosing of lorcaserin over 358 days resulted in modest increases (1.0 to 1.8-fold) in plasma exposure compared to a single dose, independent of gender for doses of 2 and 50 mg/kg/day. At the 125 mg/kg/day dose, plasma exposure marginally decreased (~10% to ~40%) from Day 1 to Day 358 in both male and female monkeys. Lorcaserin sulfamate (M1) and M5 were detected in the plasma at the first time point collected at 0.5 h, indicating that both were rapidly formed after oral administration of lorcaserin. After single or multiple doses of lorcaserin, both M1 and M5 exposure was greater than that of the parent compound, ranging from 20 to 160-fold higher for M1 and up to 3-fold higher for M5 than the concomitant lorcaserin exposure. Study findings were consistent with previous studies conducted in monkeys. As in previous studies, no differences were observed between the heart valves or lungs of controls and lorcaserin-treated animals. A NOAEL of 2 mg/kg was determined by the conducting laboratory. The kidney finding potentially related to lorcaserin at the NOAEL, i.e., a single focus of minimal tubular regeneration in 1/8 animals, was not deemed adverse.

Renal Findings

In monkeys kidney changes were only observed in the 52-week study (2, 10, 50, and 125 mg/kg/day). Changes in the kidney consisted of focal tubular epithelial cell degeneration, regeneration, and cellular casts. Minimal to mild tubular epithelial degeneration was observed in 6 of 8 animals in the high dose group (125 mg/kg). Minimal to mild epithelial regeneration was observed in the renal cortex of 0/8, 1/8, 2/8, 3/8 and 6/8 animals given 0, 2, 10, 50, and 125 mg/kg lorcaserin, respectively. At the high dose, moderate epithelial regeneration was observed in 1/4 females. Cellular casts were observed in 1/4 males at 50 mg/kg and 1/4 males and 2/4 females at 125 mg/kg. These findings were not observed in previous monkey studies, and no similar kidney findings occurred in rodents. Renal findings were determined to be unrelated to lorcaserin treatment by two independent human renal pathologists after reviewing blinded slide sets. In their independent opinions, the findings were not dose related and were consistent with age and focal inflammation or infection. One pathologist attributed the findings of regeneration to a staining artifact, resulting in a bluish cytoplasmic discoloration. If tubular renal epithelial regeneration were artifactual, renal findings of the conducting laboratory would be limited to the high dose. At 2, 10, 50, and 125 mg/kg, the margins were 1.0 and 0.6, 8 and 5, 44 and 31, and 51 and 51 times human exposure at the MRD for males and females, respectively. Renal findings in rodents and monkeys were of uncertain relationship to lorcaserin. Substantial margins over human exposure exist for all renal finding in rodents, and in monkeys according to two expert human renal pathologists. Even assuming the renal findings in monkeys are drug related, the principal findings were focal or multifocal, minimal to mild (1 instance of moderate regeneration at the high dose) renal tubular epithelial regeneration and degeneration that would have had to have been much more severe and diffuse to be of clinical relevance. Based upon adverse events, clinical chemistry and urinalyses in an extensive phase 2 and phase 3 program, there is no evidence of a lorcaserin effect on the kidney in humans.

Example 13

Physical Properties of Compound 1 Hydrochloride Hemihydrate Form III

Compound 1 Hydrochloride Salt Hemihydrate

The physical properties of Form III of Compound 1 hydrochloride salt hemihydrate are summarized in Table 16 below.

TABLE 16

Figure 6:
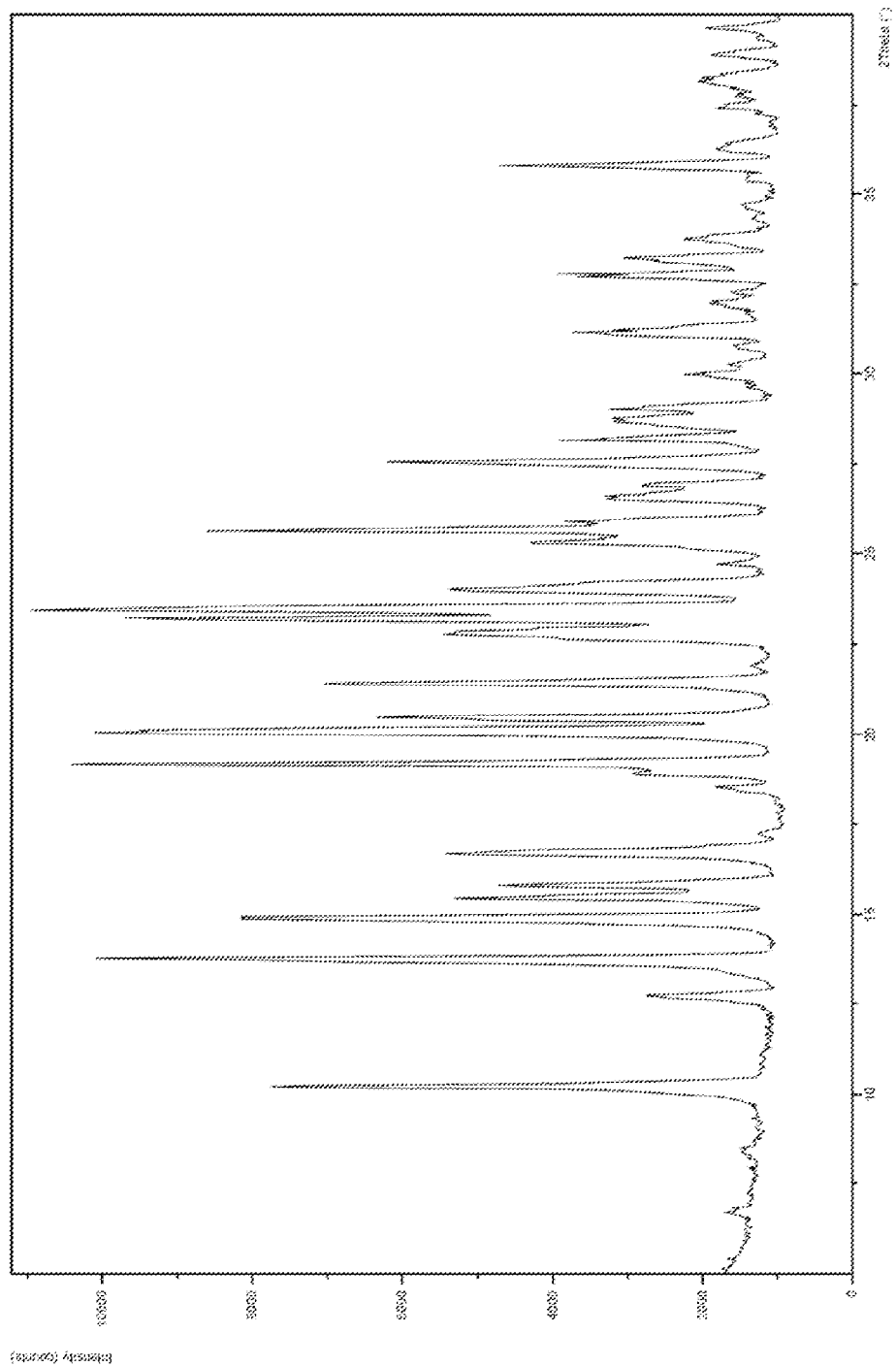
FIG. 6 shows powder X-ray diffraction pattern (PXRD) of Compound 1 Hydrochloride Hemihydrate, Form III.
Figure 7:
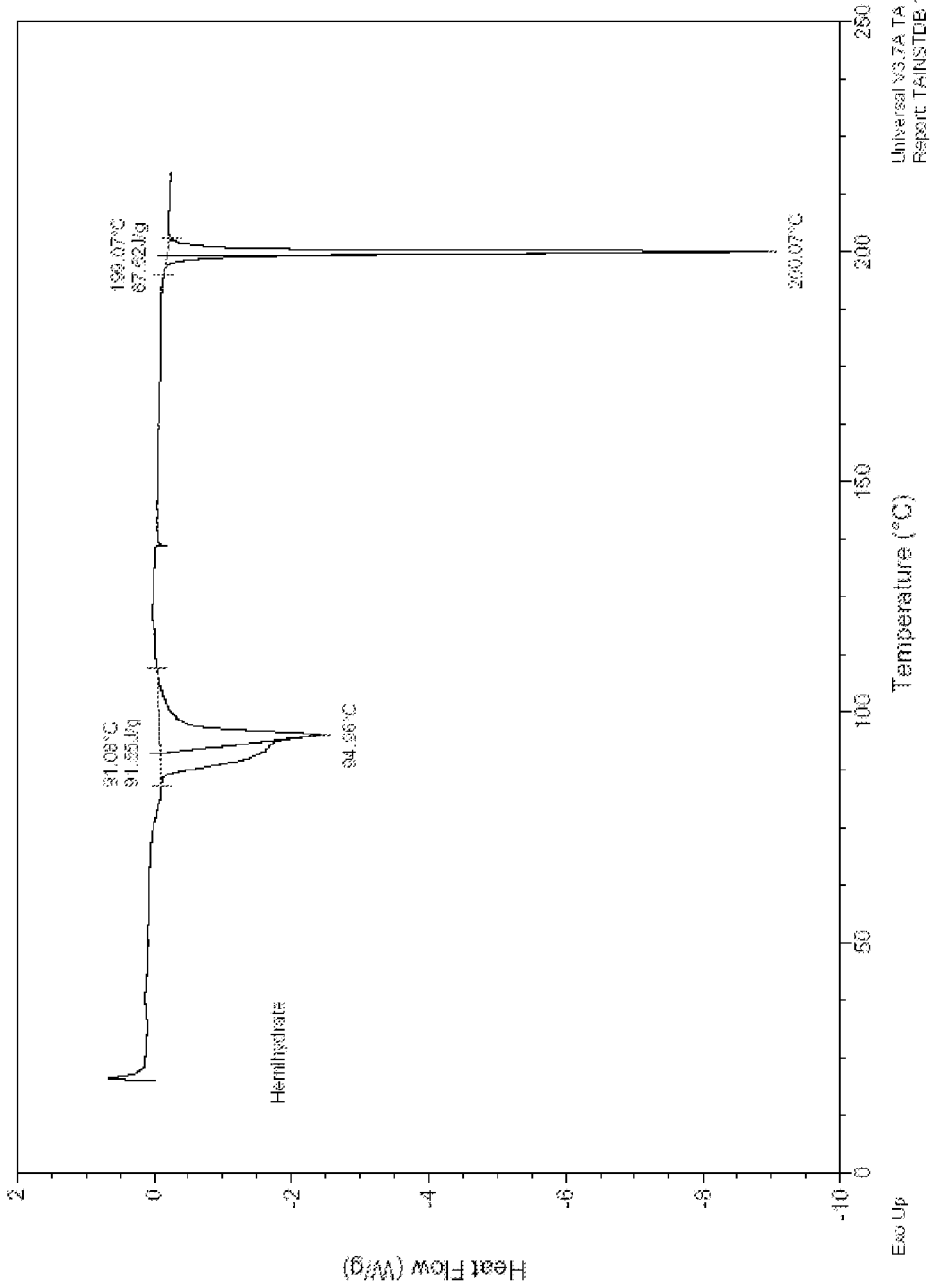
FIG. 7 shows differential scanning calorimetry (DSC) of Compound 1 Hydrochloride Hemihydrate, Form III.
Figure 8:
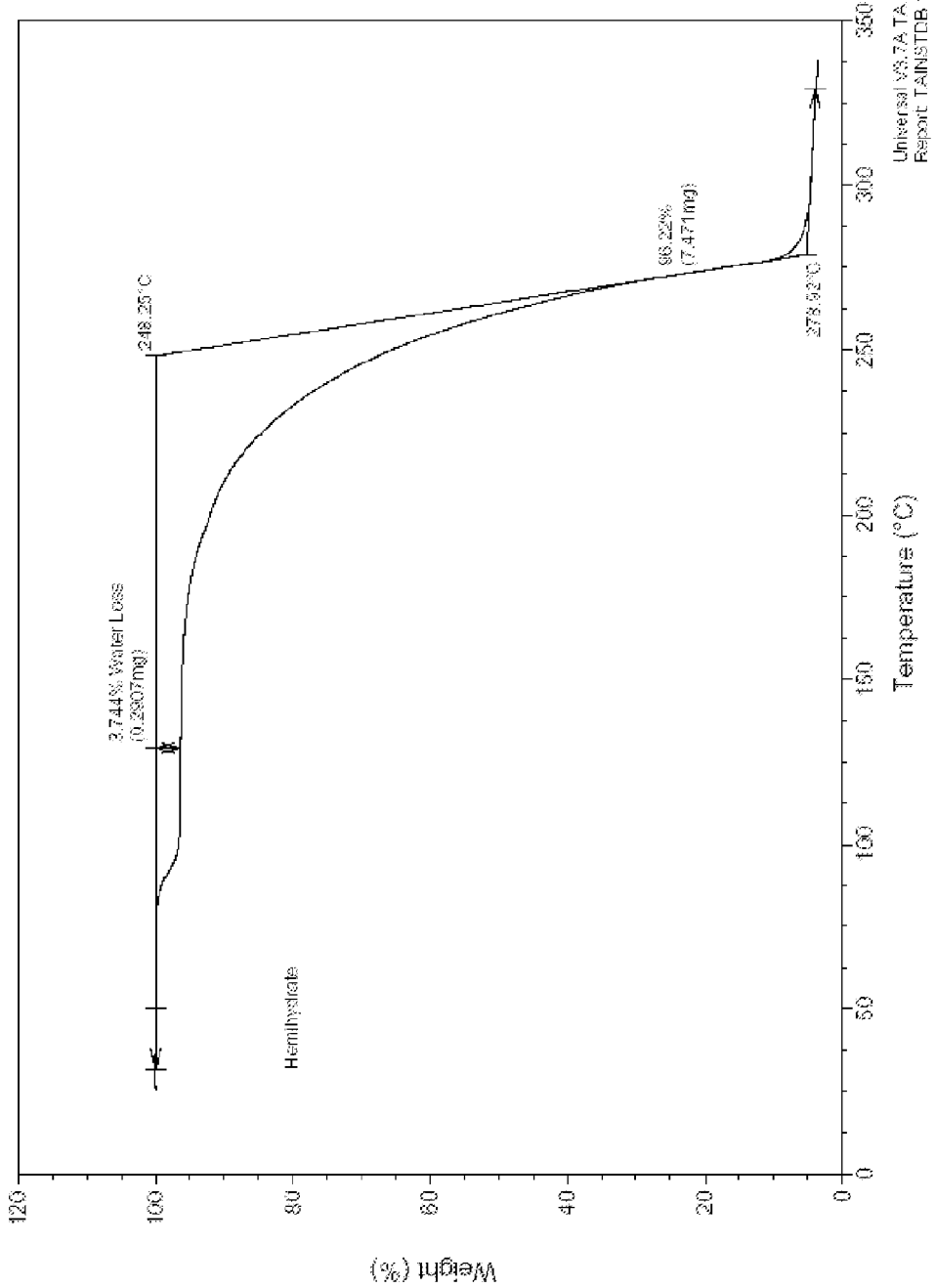
FIG. 8 shows thermogravimetric analysis (TGA) of Compound 1 Hydrochloride Hemihydrate, Form III.
Figure 9:
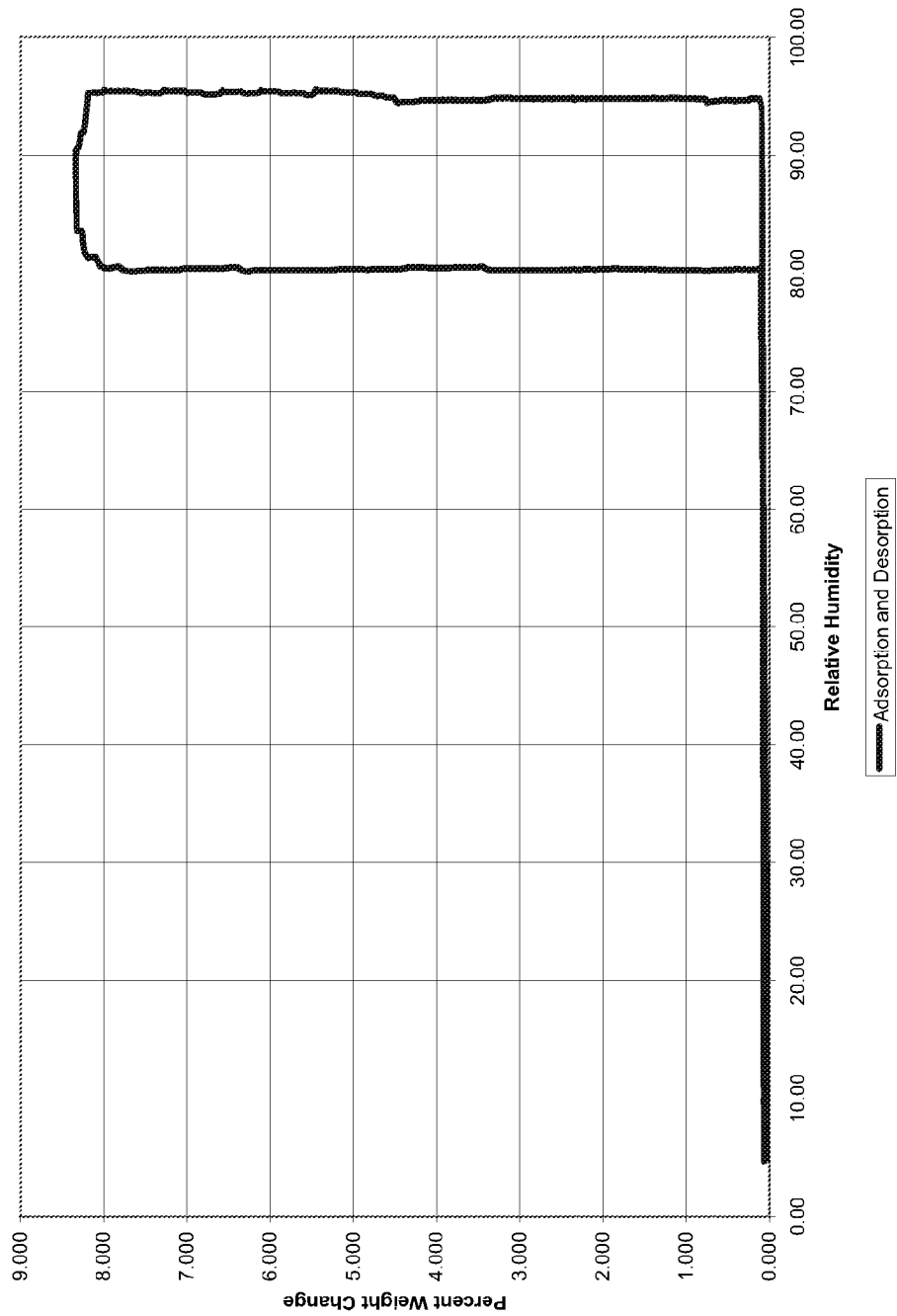
FIG. 9 shows DMS dynamic moisture sorption (also called dynamic vapor sorption) of Compound 1 Hydrochloride Hemihydrate, Form III.

| | Compound 1 Hydrochloride Salt Hemihydrate, Form III |
|---|---|
| PXRD | FIG. 6: Peaks at 13.7°, 14.9°, 15.4°, 15.8°, 16.7°, 18.9°2θ |
| DSC | FIG. 7: 95° C. (dehydration); 200° C. (melt) |
| TGA | FIG. 8: 3.7% water loss |
| DMS | FIG. 9: non-hygroscopic |

Compound 1 hydrochloride salt hemihydrate, Form III displays a dehydration feature calculated as a 3.7% weight loss which is consistent with the theoretical weight loss of 3.7% for a hemihydrate. Analysis by DSC further confirms the TGA results, where Compound 1 hydrochloride salt hemihydrate, Form III shows a dehydration event at about 95° C. and a melting/decomposition endotherm at about 200-201° C.

DVS data shows that Compound 1 hydrochloride salt hemihydrate, Form III is substantially non-hygroscopic, adsorbing less than 0.5 wt % water at 90% RH and the XRPD pattern showed no change in crystalline form after the DVS cycle.

Certain X-ray powder diffraction peaks for Compound 1 hydrochloride salt hemihydrate, Form III are shown in Table 17 below.

TABLE 17

| Pos. (°2θ) |
|---|
| 10.2 |
| 12.7 |
| 13.7 |
| 14.9 |
| 15.4 |
| 15.8 |
| 16.7 |
| 18.5 |
| 18.9 |
| 19.2 |
| 20.1 |
| 25.3 |

TABLE 17-continued

| Pos. (°2θ) |
|---|
| 25.7 |
| 26.0 |
| 26.5 |
| 26.9 |
| 27.6 |
| 28.2 |
| 20.5 |
| 21.4 |
| 22.8 |
| 23.2 |
| 23.5 |
| 24.0 |
| 24.2 |
| 24.7 |
| 29.0 |
| 30.0 |
| 30.3 |
| 30.8 |
| 31.1 |
| 32.0 |
| 32.3 |
| 32.7 |
| 33.3 |
| 33.8 |
| 35.8 |

Form III of Compound 1 hydrochloride salt hemihydrate can be prepared as described in Example 14.

Example 14

Preparation of (R)-8-Chloro-1-methyl-2,3,4,5-tetrahydro-1H-3-benzazepine Hydrochloride Hemihydrate, Form III Method 1

Step A: Preparation of 8-Chloro-1-methyl-2,3,4,5-tetrahydro-1H-3-benzazepine

2-Chloro-N-(4-chlorophenethyl)propan-1-amine hydrochloride (about 460 kg, 1.71 kmol, 1.00 eq.), aluminum chloride (about 336 kg, 2.52 kmol, 1.47 eq.), and 1,2-dichlorobenzene (about 1321 kg) are charged to a vessel vented to a caustic scrubber. The mixture is then stirred and heated at about 126° C. under nitrogen for about 16 h. The resulting Friedel-Crafts reaction mixture is then cooled. Silica gel and purified water (about 736 kg) are charged to a second vessel. The cooled Friedel-Crafts reaction mixture is then added to the aqueous silica gel slurry stirred and cooled in the second vessel. The stirred quench mixture is filtered at about 55° C., and the silica gel filter cake is washed with purified water (about 368 kg). Optionally, some or all of this purified water is used to rinse the quench vessel into the filter.

The mother and wash liquor filtrates are combined in a vessel and are cooled with stirring to about 22° C. Stirring is then stopped, and upon settling, three phases separate. The brown, lowest phase consists mostly of 1,2-dichlorobenzene and is drained. The lower of the remaining two phases, which is the middle phase of the original three-phase mixture, contains most of the product. The topmost phase is a turbid water phase containing a smaller amount of the product. These upper two phases are partitioned between cyclohexane (about 506 kg) and enough aqueous sodium hydroxide solution, approx. 30 wt %, to achieve an aqueous phase pH of at least 12. The cyclohexane phase is washed with water (at least 300 kg) at about 57° C. and then evaporated at reduced pressure to provide crude 8-chloro-1-methyl-2,3,4,5-tetrahydro-1H-3-benzazepine as an oil.

Step B: Preparation of (R)-s-Chloro-1-methyl-2,3,4,5-tetrahydro-1H-3-benzazepine Hemitartrate Acetone (about 848 kg) is added to the crude 8-chloro-1-methyl-2,3,4,5-tetrahydro-1H-3-benzazepine prepared in Step A. The vessel contents are stirred and heated to about 45° C. To the resulting solution is added a solution of L-(+)-tartaric acid (about 57.0 kg, 380 mol, 0.222 eq.) in purified water (about 98.0 kg) while the stirred vessel contents are maintained at about 45° C. Stirring is continued for about 20 min. (R)-8-chloro-1-methyl-2,3,4,5-tetrahydro-1H-3-benzazepine hemitartrate salt seed crystals are then optionally added to initiate nucleation. Stirring is continued, and more acetone is added. The resulting suspension is then cooled to about 2° C. The resulting precipitate is collected by centrifugation and washed with acetone (about 440 kg), a portion of which is optionally used to rinse the crystallization vessel into the centrifuge. The washed solid is discharged from the centrifuge, mixed with acetone (about 874 kg) and the mixture is stirred and heated to reflux. While reflux is maintained, purified water (at least 329 kg) is added until complete dissolution is achieved at reflux. The resulting mixture is stirred at reflux and then cooled to about 2° C. over about 2.5 hours. The resulting precipitate is collected by centrifugation and washed with acetone (about 184 kg), a portion of which is optionally used to rinse the crystallization vessel into the centrifuge. The washed solid is discharged from the centrifuge and dried at elevated temperature under reduced pressure to provide (R)-8-chloro-1-methyl-2,3,4,5-tetrahydro-1H-3-benzazepine hemitartrate. The yield range is 100 kg to 158 kg.

Step C: Preparation of (R)-4-Chloro-1-methyl-2,3,4,5-tetrahydro-1H-3-benzazepine Hydrochloride Hemihydrate Purified water (about 740 kg) is added to a stirred mixture of (R)-8-chloro-1-methyl-2,3,4,5-tetrahydro-1H-3-benzazepine hemitartrate from Step B (about 247 kg after correction for assay, 912 mol, 1.00 eq.), potassium carbonate (about 151 kg, 1093 mol, 1.20 eq.), and ethyl acetate (about 663 kg). The mixture is maintained at about 15° C. during the addition, after which it is stirred and then allowed to settle. The lower (aqueous) phase is drained to waste disposal. Purified water (about 740 kg) is added to the upper (organic) phase, and the resulting mixture is stirred at about 22° C. and then allowed to settle. The lower (aqueous) phase is drained to waste disposal.

Solvent is removed from the upper (organic) phase by vacuum distillation at about 40° C. to provide (R)-8-chloro-1-methyl-2,3,4,5-tetrahydro-1H-3-benzazepine as the distillation residue. Ethyl acetate (about 1050 kg) is added, and the mixture is stirred to achieve dissolution. If the water content of the resulting solution is found by Karl Fischer analysis to exceed 1.51 wt %, the procedure of this paragraph is repeated.

Through a polishing filter into a crystallization vessel is added purified water in the approximate amount calculated to provide a water concentration of 1.0 wt % in the (R)-8-chloro-1-methyl-2,3,4,5-tetrahydro-1H-3-benzazepine solution after the final ethyl acetate dilution. The solution is then filtered through the same polishing filter into the crystallization vessel. The vessel in which the (R)-8-chloro-1-methyl-2,3,4,5-tetrahydro-1H-3-benzazepine had been prepared is rinsed with additional fresh ethyl acetate (about 644 kg), and the rinse is filtered through the same polishing filter into the crystallization vessel.

The water content of the solution in the crystallization vessel is determined by Karl Fischer analysis. If the water content is about 0.8 wt % to about 1.2 wt % (0.5 wt % to 1.5 wt % non-critical range), then processing resumes at the beginning of the next paragraph. If the water content is too low, additional purified water is added through the polishing filter. If the water content is too high, then solvent is removed by vacuum distillation, purified water (about 18 kg) is added through the polishing filter, and ethyl acetate (about 1800 kg) is added through the polishing filter. In either case, the resulting solution is tested for water content.

As the contents of the crystallization vessel are stirred, hydrogen chloride gas (about 3.3 kg, 91 mol, 0.10 eq.) is added to the vessel head space. (R)-8-Chloro-1-methyl-2,3,4,5-tetrahydro-1H-3-benzazepine hydrochloride hemihydrate seed crystals are then added to initiate nucleation. Additional hydrogen chloride gas is then added to the vessel head space until the pH of the reaction mixture drops to and remains at about 5 or less. The precipitated product is collected by centrifugation and washed with filtered ethyl acetate (about 552 kg). The precipitate is dried under reduced pressure to provide the title compound. The yield range is 184 kg to 217 kg, which is 84% to 99% of theoretical uncorrected for seed charge and 83% to 98%, of theoretical corrected for seed charge.

Method 2

Step A: Preparation of 8-Chloro-1-methyl-2,3,4,5-tetrahydro-1H-3-benzazepine 1,2-Dichlorobenzene (about 1522 kg), 2-chloro-N-(4-chlorophenethyl)propan-1-amine hydrochloride (about 530 kg, 1.97 kmol, 1.00 eq.), and aluminum chloride (about 387 kg, 2.90 kmol, 1.47 eq.) are charged to a vessel vented to a caustic scrubber. The mixture is then stirred and heated at about 126° C. under nitrogen for about 16 h. The resulting Friedel-Crafts reaction mixture is then cooled. Purified or potable water (about 1060 kg) and silica gel are charged to a second vessel. The cooled Friedel-Crafts reaction mixture is then added to the aqueous silica gel slurry stirred and cooled in the second vessel. The stirred quench mixture is filtered at about 58° C., and the silica gel filter cake is washed with purified or potable water (about 212 kg). Optionally, some or all of this water may be used to rinse the quench vessel into the filter. The mother and wash liquor filtrates are combined in a vessel and are cooled with stirring to about 22° C. Stirring is then stopped, and upon settling, three phases separate. The brown lowest phase consists mostly of 1,2-dichlorobenzene and is drained to solvent regeneration. The lower of the remaining two phases, which is the middle phase of the original three-phase mixture, contains most of the product. The topmost phase is a turbid water phase containing a smaller amount of the product. These upper two phases are partitioned between cyclohexane (about 583 kg) and enough aqueous sodium hydroxide solution, approx. 30 wt %, to achieve an aqueous phase pH of at least about 13. The cyclohexane phase is washed with purified or potable water (about 1272 kg) at about 57° C. and then distilled at reduced pressure to remove solvent and provide crude title compound, an oil, as the distillation residue.

Step B: Preparation of (R)-8-Chloro-1-methyl-2,3,4,5-tetrahydro-1H-3-benzazepine Hemitartrate Acetone (about 977 kg) is added to the crude 8-chloro-1-methyl-2,3,4,5-tetrahydro-1H-3-benzazepine prepared in Step A. The vessel contents are stirred and heated to about 45° C. To the resulting solution is added a solution of L-(+)-tartaric acid (about 66 kg, 440 mol, 0.223 eq.) in purified or potable water (about 113 kg) while the stirred vessel contents are maintained at about 45° C. About half way through the tartaric acid addition, (R)-8-chloro-1-methyl-2,3,4,5-tetrahydro-1H-3-benzazepine hemitartrate seed crystals are added to the solution to achieve cloudiness and to initiate nucleation. Stirring is continued, and more acetone is added. The resulting suspension is then cooled to about 2° C. The resulting precipitate is collected by centrifugation and washed with acetone (about 508 kg), a portion of which is optionally used to rinse the crystallization vessel into the centrifuge. The washed solid is mixed with acetone (about 1007 kg) and the mixture is stirred and heated to reflux. While reflux is maintained, purified or potable water (at least about 392 kg) is added until complete dissolution is achieved at reflux. The resulting mixture is stirred at reflux and then cooled to about 2° C. over about 2.5 h. The resulting precipitate is collected by centrifugation and washed with acetone (about 212 kg), a portion of which is optionally used to rinse the crystallization vessel into the centrifuge. The washed solid is discharged from the centrifuge and dried at elevated temperature under reduced pressure to provide the title compound.

Step C: Preparation of (R)-8-Chloro-1-methyl-2,3,4,5-tetrahydro-1H-3-benzazepine Hydrochloride Hemihydrate Purified water (about 779 kg) is combined with (R)-8-chloro-1-methyl-2,3,4,5-tetrahydro-1H-3-benzazepine hemitartrate from Step B (about 260 kg after correction for assay, 960 mol, 1.00 eq.), potassium carbonate (about 159 kg, 1150 mol, 1.20 eq.), and ethyl acetate (about 698 kg) with stirring at about 15 TC. The resulting mixture is stirred and then allowed to settle. The lower (aqueous) phase is drained to waste disposal. Purified water (about 779 kg) is added to the upper (organic) phase, and the resulting mixture is stirred at about 22° C. and then allowed to settle. The lower (aqueous) phase is drained to waste disposal.

Solvent is removed from the upper (organic) phase by vacuum distillation with the jacket temperature increasing to about 60° C. (R)-8-chloro-1-methyl-2,3,4,5-tetrahydro-1H-3-benzazepine, an oil, is obtained as the distillation residue. Ethyl acetate (about 1105 kg) is added, and the mixture is stirred to achieve dissolution. If the water content of the resulting solution is found by Karl Fischer analysis to exceed 1.51 wt %, the procedure of this paragraph is repeated.

The solution in is then filtered through a polishing filter into a crystallization vessel. The vessel in which the (R)-8-chloro-1-methyl-2,3,4,5-tetrahydro-1H-3-benzazepine had been prepared is then rinsed with additional ethyl acetate (about 122 kg) through the same polishing filter into the crystallization vessel. To the crystallization vessel is then added purified water in the approximate amount calculated to provide a water concentration of 1.0 wt % in the solution after the final ethyl acetate dilution. Ethyl acetate (about 556 kg) is then added to the crystallization vessel, and the resulting mixture is stirred. The water content of the solution in the crystallization vessel is determined by Karl Fischer analysis. If the water content is about 0.8 wt % to about 1.2 wt % (0.5 wt % to 1.5 wt % qualified range), then processing resumes at the beginning of the next paragraph. If the water content is too low, additional purified water is added. If the water content is too high, then solvent is removed by vacuum distillation, and purified water and ethyl acetate are added. In either case, the resulting solution is retested for water content.

As the contents of the crystallization vessel are stirred, hydrogen chloride gas (about 3.5 kg, 96 mol, 0.10 eq.) is added to the vessel head space. (R)-8-chloro-1-methyl-2,3,4,5-tetrahydro-1H-3-benzazepine hydrochloride hemihydrate seed crystals are then added to initiate nucleation. Additional hydrogen chloride gas is then added to the vessel head space until the pH of the reaction mixture drops to and remains at about 3 or less. The precipitated product is collected by centrifugation and washed with ethyl acetate (about 580 kg) to provide the title compound (about 221 kg), which is dried in a tray or tumble dryer (such as a double cone dryer) under reduced pressure at a jacket temperature of about 26° C.

Method 3

Step A: Preparation of 8-Chloro-1-methyl-2,3,4,5-tetrahydro-1H-3-benzazepine

To a reactor equipped with overhead agitation, jacket temperature control, a nitrogen inlet, and a caustic scrubber vent were charged, in the specified order, 2-chloro-N-(4-chlorophenethyl)propan-1-amine hydrochloride (1.00 kg, 3.72 mol), aluminum chloride (0.745 kg, 5.58 mol), and 1,2-dichlorobenzene (2.88 kg). The stirred reactor contents were heated to 125-130° C., and stirring was continued at that temperature for 14-18 h. At 60-70° C., a dark colored solution was obtained. After reaction completion (<1.0% starting material by HPLC peak area) had been verified, the stirred reactor contents were cooled to 30-35° C. To a second reactor vented to a caustic scrubber was charged purified water (1.60 L) and silica gel (0.160 kg). The Friedel-Crafts reaction mixture was transferred from the first reactor to the second reactor sufficiently slowly to maintain the stirred contents of the second reactor at <60° C. After the transfer is completed, the next step may be executed without any hold period. The silica gel was filtered on a medium to coarse filter element at 55-60° C., and the filtered solids were subsequently washed with purified water (800 mL) preheated to 50-60° C. The combined mother and wash liquor filtrates were cooled to 20-25° C. with vigorous agitation. Then the stirring was stopped, and the phases were allowed to separate at 20-25° C. (Process volume peaked at this point at 5.68 L). Three phases separated after 1-2 hours of standing. The lowest layer was drained to waste disposal. This dark layer consisted mostly of 1,2-dichlorobenzene (1.64 kg, 1.33 L) at pH 3-4. About 1% of the product was lost to this layer. The remaining two phases were allowed to stand without agitation for another 2-4 h. The lower layer was drained and saved (Layer A). This light colored phase (2.64 kg, 2.00 L, pH 2-3) contained ~90% 8-chloro-1-methyl-2,3,4,5-tetrahydro-1H-benzazepine. The upper layer (2.24 kg of a turbid water phase at pH 0-1) contains ~1-4% 8-chloro-1-methyl-2,3,4,5-tetrahydro-1H-benzazepine and remained in the reactor for back-extraction. The reactor was charged with cyclohexane (1.10 kg) and then 30% aqueous NaOH (2.44 kg, 18.3 mol). The resulting mixture (5.60 L) was stirred vigorously for 30 min at room temperature. The stirring was stopped, and the phases were allowed to separate for 25-40 min. If the pH of the lower (aqueous) phase was ≥13, it was drained to waste disposal. Otherwise, more 30% aqueous NaOH was added, and this extraction was repeated. At pH 14, the aqueous phase contains <0.1% 8-chloro-1-methyl-2,3,4,5-tetrahydro-1H-benzazepine free base. The remaining upper (organic) phase from the reactor was drained and saved (Layer B). The reactor was rinsed with purified water and followed by a suitable organic solvent to remove residual salts. The lower, light-colored product phase (the middle of the original three phases, Layer A) and the upper phase (organic, Layer B) were returned to the reactor. To the stirred reactor contents was added 30% aqueous NaOH (1.60 kg, 12.0 mol). The reactor contents were stirred vigorously for 0.5 hours. The stirring was discontinued and the phases were allowed to separate over 15-30 minutes. The lower (aqueous) layer was drained to waste disposal. To the upper (organic) phase remaining in the reactor was added purified water (2.40 kg). The reactor contents were stirred vigorously at 60-65° C. for 0.5 h. The stirring was discontinued, and the phases were allowed to separate at 60-65° C. over 1.5-2 h. The lower (aqueous) layer was drained to waste disposal. With a reactor jacket temperature of 55-60° C., solvent from the upper (organic) layer was removed by vacuum distillation at pressures starting at 115-152 torr and falling to 40 torr. The crude product, 8-chloro-1-methyl-2,3,4,5-tetrahydro-1H-benzazepine as the free base, was obtained as a yellow to brown oil distillation residue.

Step B: Preparation of (R)-8-Chloro-1-methyl-2,3,4,5-tetrahydro-1H-3-benzazepine Hemitartrate The distillation residue from Step A (crude 8-chloro-1-methyl-2,3,4,5-tetrahydro-1H-benzazepine as the free base) was dissolved in acetone (0.400 kg). The resulting solution was drained and weighed to assay the 8-chloro-1-methyl-2,3,4,5-tetrahydro-1H-benzazepine content by HPLC. Results of the assay were used to calculate charges of acetone, L-tartaric acid, and water. The quantities indicated below are typical for achievement of the target 8-chloro-1-methyl-2,3,4,5-tetrahydro-1H-benzazepine:acetone:L-tartaric acid:water mole ratio of 1.00:9.6:0.25:3.6 prior to addition of seed crystals. More acetone (1.415 kg) was added to the reactor and the stirred reactor contents were heated to 47-52° C. To the resulting solution was added a solution of L-tartaric acid (0.1223 kg, 0.815 mol) in purified water (0.211 kg) at a steady rate over 5-15 min. A thin suspension formed during the addition but then redissolved when the mixture temperature was reestablished at 50° C. Hemitartrate seed crystals (0.80 g) were added to the 50° C. solution to achieve cloudiness and to initiate nucleation. Nucleation was allowed to continue for 2-3 h with agitation at 47-52° C. Acetone (0.473 kg) was added to the reactor while the stirred reactor contents were maintained at 50° C. The resulting suspension was cooled to 0-5° C. slowly over 3-5 h. Stirring was continued at 0° C. for another 1-3 h. The resulting white precipitate was collected on a medium-to-fine filter element and then washed with a mixture of acetone (0.900 kg) and purified water (0.054 kg). The enantiomeric excess (ee) of the wet cake was determined.

If the ee was <98%, the wet cake was transferred back into the reactor and reslurried in a mixture of acetone (1.90 kg) and purified water (0.400 kg) at 55-60° C. for 0.5-1 h. If dissolution had not been achieved after one h, then water (approximately 0.160 kg) was added until a clear solution was achieved. The resulting mixture was then cooled to 0-5° C. slowly over 2-3 h. Stirring at 0° C. was continued for another 3-5 h. The resulting white precipitate was collected on a medium-to-fine filter element and then washed with acetone (0.400 kg) at 0-4° C.

The washed solid product (296 g wet) was dried at 60-65° C. under full vacuum for 15-20 hours. The yield of (R)-8-chloro-1-methyl-2,3,4,5-tetrahydro-1H-3-benzazepine hemitartrate, with about 99.7% ee and 7.5 wt. % water content, was 295 g (27.1% based on racemic 2-chloro-N-(4-chlorophenethyl)propan-1-amine hydrochloride and corrected for product water content).

Step C: Preparation of (R)-8-Chloro-1-methyl-2,3,4,5-tetrahydro-1H-3-benzazepine Hydrochloride Hemihydrate, Form III To a reactor equipped with overhead agitation and a nitrogen inlet was charged, in the specified order, (R)-8-chloro-1-methyl-2,3,4,5-tetrahydro-1H-3-benzazepine hemitartrate (1.00 kg containing 7.5 wt % water, 1.71 mol), potassium carbonate (0.508 kg, 3.68 moles), ethyl acetate (2.68 kg), and purified water (2.68 kg). The resulting mixture was stirred at 20-25° C. for 30-40 min, and then the phases were allowed to separate over 0.5-1 h. The lower (aqueous) phase was drained to waste disposal. Purified water (2.68 kg) was added to the reactor, and the resulting mixture was vigorously stirred for 10-20 min. The phases were allowed to separate over 1-1.5 h. The lower (aqueous) phase was drained to waste disposal. With the reactor contents at a temperature of 40-45° C., the solvent was removed by vacuum distillation at pressures falling from 153 torr to 46 tort. The residue was cooled to 20-25 TC. Ethyl acetate (3.81 kg) was charged to the reactor, and the distillation residue was dissolved with stirring. The water content of the resulting solution was verified by Karl Fischer analysis to be <0.8 wt. %. The solution was filtered through a polishing filter. The reactor was rinsed through the filter with ethyl acetate (2.33 kg) previously verified by Karl Fischer analysis to have <0.05 wt. % water content. Both the solution and rinse filtrates were charged back into the reactor. Purified water (39.9 g) was added to the reactor. The stirred reactor contents were cooled to 0-5° C., and then HCl gas (19.0 g, 0.521 mol) was added while the stirred reactor contents were maintained at 0-5° C. (R)-8-Chloro-1-methyl-2,3,4,5-tetrahydro-1H-3-benzazepine hemihydrate seed crystals (1.33 g) were added to the stirred reactor contents to initiate nucleation at 0-5° C. The remaining HCl gas (107.6 g, 2.95 mol) was charged to the reactor at a steady rate over at least 1.5-2 h while the stirred reactor contents were maintained at 0-5° C. The resulting suspension was stirred at 0-5° C. for 2 h. The resulting white precipitate was collected on a medium-to-fine filter element. The reactor and then the filtered solid product were washed with ethyl acetate (1.33 kg). The wet cake (ca. 867 g) was dried at full vacuum and 33-37° C. for 20 h or until the cake temperature had been stable for 4 hours, whichever occurred first. The resulting (R)-8-chloro-1-methyl-2,3,4,5-tetrahydro-1H-3-benzazepine hydrochloride hemihydrate (3.7 wt. % water content, 14.7% chloride content, <0.01% ROI, >99.6% ee, >99% HPLC purity, and <0.1% wrong isomer content) was obtained in a yield of about 741 g (89.9%).

Those skilled in the art will recognize that various modifications, additions, substitutions, and variations to the illustrative examples set forth herein can be made without departing from the spirit of the disclosure and are, therefore, considered within the scope of the disclosure.

We claim:

1. A method for weight management, comprising:
administering to an individual having moderate renal impairment and in need of said weight management a therapeutically effective amount of (R)-8-chloro-1-methyl-2,3,4,5-tetrahydro-1H-3-benzazepine hydrochloride or a hydrated form thereof,
wherein said moderate renal impairment is a creatinine clearance from 31 mL/min to 50 mL/min in said individual determined by the Cockcroft-Gault equation using ideal body weight.

2. The method of claim 1, wherein the therapeutically effective amount is about 10 mg of (R)-8-chloro-1-methyl-2,3,4,5-tetrahydro-1H-3-benzazepine hydrochloride or a hydrated form thereof administered orally twice daily.

3. The method of claim 1, wherein the therapeutically effective amount is about 20 mg administered orally once daily.

4. A method for weight management, comprising:
administering to an individual having moderate renal impairment and in need of said weight management a dose of about 20 mg of (R)-8-chloro-1-methyl-2,3,4,5-tetrahydro-1H-3-benzazepine hydrochloride or a hydrated form thereof,
wherein said moderate renal impairment is a creatinine clearance from 31 mL/min to 50 mL/min in said individual determined by the Cockcroft-Gault equation using ideal body weight.

5. The method of claim 4, wherein the dose is administered as about 10 mg of (R)-8-chloro-1-methyl-2,3,4,5-tetrahydro-1H-3-benzazepine hydrochloride or a hydrated form thereof orally twice daily.

6. The method of claim 4, wherein the dose is administered orally once daily.

* * * * *